US009988683B2

(12) United States Patent
Adorjan et al.

(10) Patent No.: US 9,988,683 B2
(45) Date of Patent: *Jun. 5, 2018

(54) METHOD AND NUCLEIC ACIDS FOR THE ANALYSIS OF COLON CELL PROLIFERATIVE DISORDERS

(75) Inventors: Peter Adorjan, Berlin (DE); Matthias Burger, Berlin (DE); Sabine Maier, Princeton, NJ (US); Ralf Lesche, Berlin (DE); Susan Cottrell, Seattle, WA (US); Suzanne Mooney, Seattle, WA (US)

(73) Assignee: EPIGENOMICS AG, Berlin (DE)

( * ) Notice: Subject to any disclaimer, the term of this patent is extended or adjusted under 35 U.S.C. 154(b) by 717 days.

This patent is subject to a terminal disclaimer.

(21) Appl. No.: 12/794,449

(22) Filed: Jun. 4, 2010

(65) Prior Publication Data

US 2011/0046005 A1 Feb. 24, 2011

Related U.S. Application Data

(63) Continuation of application No. 10/506,089, filed as application No. PCT/EP03/02034 on Feb. 27, 2003, now abandoned.

(30) Foreign Application Priority Data

Feb. 27, 2002 (EP) .................................. 02004551

(51) Int. Cl.
*C12Q 1/68* (2018.01)
(52) U.S. Cl.
CPC ..... *C12Q 1/6886* (2013.01); *C12Q 2600/154* (2013.01); *Y10T 436/143333* (2015.01)
(58) Field of Classification Search
None
See application file for complete search history.

(56) References Cited

U.S. PATENT DOCUMENTS

| | | | |
|---|---|---|---|
| 5,565,552 A | 10/1996 | Magda et al. |
| 5,567,810 A | 10/1996 | Weis et al. |
| 5,574,142 A | 11/1996 | Meyer, Jr. et al. |
| 5,580,722 A | 12/1996 | Foulkes et al. |
| 5,585,481 A | 12/1996 | Arnold, Jr. et al. |
| 5,587,371 A | 12/1996 | Sessler et al. |
| 5,597,696 A | 1/1997 | Linn et al. |
| 5,786,146 A | 7/1998 | Herman |
| 5,837,832 A | 11/1998 | Chee et al. |
| 5,958,773 A | 9/1999 | Monia |
| 6,017,704 A | 1/2000 | Herman et al. |
| 6,265,171 B1 | 7/2001 | Herman et al. |
| 6,331,393 B1 | 12/2001 | Laird et al. |
| 7,118,868 B2 | 10/2006 | Berlin |

FOREIGN PATENT DOCUMENTS

| | | |
|---|---|---|
| EP | 02004551.4 | 2/2002 |
| WO | WO 1991/008230 | 6/1991 |
| WO | WO 1995/000669 | 1/1995 |
| WO | WO 1995/015373 | 6/1995 |
| WO | WO 1997/046705 | 12/1997 |
| WO | 1998/032849 A2 | 7/1998 |
| WO | WO 1999/028498 | 6/1999 |
| WO | WO 2000/026401 | 5/2000 |
| WO | WO 2001/007647 | 2/2001 |
| WO | WO 2001/009183 | 2/2001 |
| WO | WO 2001/068911 | 9/2001 |
| WO | WO 2001/068912 | 9/2001 |
| WO | 2002/000926 A2 | 1/2002 |
| WO | WO 2002/000928 | 1/2002 |
| WO | WO 2002/074079 | 9/2002 |
| WO | WO 2002/088381 | 11/2002 |
| WO | WO 2003/064700 | 8/2003 |

OTHER PUBLICATIONS

Ushijima (Nature Reviews. 2005. 5: 223-231).*
Benner et al (Trends in Genetics (2001) vol. 17, pp. 414-418).*
Grunau et al ( Nucleic Acids Research (2001) vol. 29, e65).*
Walsh et al teaches (Genes & Development (1999) vol. 13, pp. 26-36).*
Cottrell S.E., "Molecular diagnostic applications of DNA methylation technology", *Clin. Biochem.*, 37(7):595-604 (2004).
Database Biosis [Online], Biosciences Information Service, Philadelphia, PA, US; Mar. 1998 (Mar. 1998), Ho Coty et al., "Hypermethylation of the versican gene promoter in colorectal tumors", Database accession No. PREV199800197539 XP002265914 & *Proceedings of the American Association for Cancer Research Annual*, vol. 39, Mar. 1998 (Mar. 1998), pp. 539-540, 89th Annual Meeting of the American Association for Cancer Research, New Orleans, Louisiana, USA; Mar. 28-Apr. 1, 1998, Mar. 1998 ISSN: 0197-016X.
Ehrlich, M., "DNA methylation in cancer: too much, but also too little", *Oncogene*, 21(35):5400-5413 (2002).
Griffin and Smith, "Single-nucleotide polymorphism analysis by MALDI-TOF mass spectrometry", *Trends Biotechnol.*, 18(2):77-84 (2000).
Hiltunen et al., "Hypermethylation of the WT1 and Calcitonin Gene Promoter Regions at chromosome 11P in Human Colorectal Cancer", *British Journal of Cancer*, 76(9):1124-1130 (1997).
Kuismanen et al., "Epigenetic phenotypes distinguish microsatellite-stable and -unstable colorectal cancers", *PNAS U.S.A.*, 96(22):12661-12666 (1999).
Mills et al., "Increasing methylation of the calcitonin gene during disease progression in sequential samples from CML patients", *Leukemia Research*, 20(9):771-775 (1996).
NCBI Website. Genbank Accession No. AC026696, Dec. 12, 2001.
Olek and Walter, "The pre-implantation ontogeny of the H19 methylation imprint", *Nat. Genet.*, 17(3):275-276 (1997).

(Continued)

*Primary Examiner* — Katherine D Salmon
(74) *Attorney, Agent, or Firm* — Lathrop Gage LLP; James H. Velema, Esq.; Sean M. Coughlin, Esq.

(57) ABSTRACT

Provided are methods and nucleic acids for detecting, differentiating or distinguishing between colon cell proliferative disorders by analysis of one or more of the genes Versican, TPEF, H-Cadherin, Calcitonin, and EYA4. Further provided are novel nucleic acid sequences useful for the cell proliferative disorder specific analysis of said genes as well as methods, assays and kits thereof.

35 Claims, 23 Drawing Sheets

(56) References Cited

OTHER PUBLICATIONS

Olek et al., "A modified and improved method for bisulphite based cytosine methylation analysis", Nucleic Acids Res., 24(24):5064-5066 (1996).
Pienkos et al., "Molybdenum cofactors from molybdoenzymes and in vitro reconstitution of nitrogenase and nitrate reductase", Proc. Natl. Acad. Sci. U.S.A., 74(12):5468-71 (1977).
Rein et al., "Identifying 5-methylcytosine and related modifications in DNA genomes", Nucl. Acids Res., 26(10):2255-2264 (1998).
Sanger et al., "DNA sequencing with chain-terminating inhibitors", Proc. Natl. Acad. Sci. U.S.A., 74(12):5463-5467 (1977).
Silverman et al., "Abnormal methylation of the calcitonin gene in human colonic neoplasms", Cancer Res., 49(13):3468-3473 (1989).
Toyota et al., "Identification of differentially methylated sequences in colorectal cancer by methylated CpG island amplification", Cancer Research, 59(10): 2307-2312 (1999).
van der Krol et al., "Modulation of eukaryotic gene expression by complementary RNA or DNA sequences", BioTechniques, 6(10):958-976 (1988).
Wayne et al., "Mutations in the transcriptional activator EYA4 cause late-onset deafness at the DFNA10 locus", Hum. Mol. Genet., 10(3):195-200 (2001).
Xiong and Laird , "COBRA: a sensitive and quantitative DNA methylation assay", Nucleic Acids Res., 25(12):2532-2534 (1997).
Yates et al., "Methylational urinalysis: a prospective study of bladder cancer patients and age stratified benign controls", Oncogene, 25:1984-1988 (2006).
Yu et al., "Specific inhibition of PCR by non-extendable oligonucleotides using a 5' to 3' exonuclease-deficient DNA polymerase", Bio Techniques, 23(4):714-720 (1997).
Zeschnigk et al., "Asingle-tubePCR test for the diagnosis of Angelman and Prader—Willi syndrome based on allelic methylation differences at the SNRPN locus", Eur. J. Hum. Genet., 5(2):94-98 (1997).
Zeschnigk et al., "Imprinted segments in the human genome: different DNA methylation patterns in the Prader-Willi/Angelman syndrome region as determined by the genomic sequencing method", Hum. Mol. Genet., 6(3):387-395 (1997).
Zon G., "Oligonucleotide analogues as potential chemotherapeutic agents", Pharm. Res., 5(9):539-549 (1988).
Adany et al. (1990) "Altered Methylation of Versican Proteoglycan Gene in Human Colon Carcinoma," Biochemical and Biophysical Research Communications. 171(3):1402-1413.
Eads et al. (1999) "CpG Island Hypermethylation in Human Colorectal Tumors Is Not Associated with DNA Methyltransferase Overexpression," Cancer Research. 59:2302-2306.
Eads et al. (2001) "Epigenetic Patterns in the Progression of Esophageal Adenocarcinoma," Cancer Research. 61:3410-3418.
Feil et al. (1994) "Methylation analysis on individual chromosomes: improved protocol for bisulphite genomic sequencing," Nucleic Acids Research. 22(4):695-696.
Gonzalgo et al. (1997) "Rapid quantitation of methylation differences at specific sites using methylation-sensitive single nucleotide primer extension (Ms-SNuPE)," Nucleic Acids Research. 25(12):2529-2531.
Gonzalgo et al. (1997) "Identification and Characterization of Differentially Methylated Regions of Genomic DNA by Methylation-sensitive Arbitrarily Primed PCR," Cancer Research. 57:594-599.
Grigg et al. (1994) "Sequencing 5-Methylcytosine Residues in Genomic DNA," BioEssays. 16(6):431-436.
Gut et al. (1995) "DNA and Matrix Assisted Laser Desorption Ionization Mass Spectrometry," In; Molecular Biology: Current Innovations and Future Trends. Horizon Scientific Press. Wymondham, United Kingdom. pp. 147-157.
Gut et al. (1995) "A procedure for selection DNA alkylation and detection by mass spectrometry," Nucleic Acids Research. 23(8):1367-1373.

Heid et al. (1996) "Real Time Quantitative PCR," Genome Research. 6:986-994.
Herman et al. (1996) "Methylation-specific PCR: A novel PCR assay for methylation status of CpG islands," Proc. Natl. Acad. Sci. USA 93:9821-9826.
Issa et al. (2001) "Accelerated Age-related CpG Island Methylation in Ulcerative Colitis," Cancer Research. 61:3573-3577.
Karas et al. (1988) "Laser Desorption Ionization of Proteins with Molecular Masses Exceeding 10 000 Daltons," Analytical Chemistry. 60(20):2299-2301.
Liang et al. (2000) "The Gene for a Novel Transmembrane Protein Containing Epidermal Growth Factor and Follistatin Domains Is Frequently Hypermethylated in Human Tumor Cells," Cancer Research. 60:4907-4912.
Martin et al. (1995) "Genomic sequencing indicates a correlation between DNA hypomethylation in the 5' region of the pS2' gene and its expression in human breast cancer cell lines," Gene. 157:261-265.
Model et al. (2001) "Feature selection for DNA methylation based cancer classification," Bioinformatics. 17(Suppl 1): S157-S164.
Ausubel (1995) Hybridization Analysis of DNA Blots, Unit 2.10 in; Current Protocols in Molecular Biology. John Wiley & Sons. New York, New York. pp. 2.10.1-2.10.16.
Basset, Jr. et al. (1999) "Gene expression informatics—its all in your mine," Nat. Genetics. 21(Suppl 1):51-55.
Bowtell (1999) "Options available—from start to finish—for obtaining expression data by microarray," Nat. Genetics. 21(Suppl 1):25-32.
Brown et al. (1999) "Exploring the new world of the genome with DNA microarrays," Nat. Genetics. 21(Suppl 1):33-37.
Chakravarti (1999) "Population genetics-making sense out of sequence," Nat. Genetics. 21(Suppl 1):56-60.
Cheung et al. (1999) "Making and reading microarrays," Nat Genetics. 21(Suppl 1):15-19.
Cole et al. (1999) "The genetics of cancer-a 3D model," Nat Genetics. 21(Suppl 1):38-41.
Collins (1999) "Microarrays and macroconsequences," Nat Genetics. 21(Suppl 1):2.
Debouck et al. (1999) "DNA microarrays in drug discovery and development" Nat Genetics. 21(Suppl 1):48-50.
Duggan et al. (1999) "Expression profiling using cDNA microarrays," Nat. Genetics. 21(Suppl 1):10-14.
Genbank Database [online] (Jun. 25, 2016) "Homo sapiens versican (VCAN), transcript variant 1, mRNA," Accession No. NM_004385. Accessible on the Internet at URL: https://www.ncbi.nlm.nih.gov/nuccore/NM_004385. [Last Accessed Oct. 6, 2016].
Genbank Database [online] (Sep. 5, 2016) "Homo sapiens transmembrane protein with EGF like and two follistatin like domains 2 (TMEFF2), transcript variant 1, mRNA," Accession No. NM_016192. Accessible on the Internet at URL: https://www.ncbi.nlm.nih.gov/nuccore/NM_016192. [Last Accessed Oct. 6, 2016].
Genbank Database [online] (Sep. 9, 2016) "Homo sapiens cadherin 13 (CDH13), transcript variant 1, mRNA," Accession No. NM_001257. Accessible on the Internet at URL: https://www.ncbi.nlm.nih.gov/nuccore/NM_001257. [Last Accessed Oct. 6, 2016].
Hacia (1999) "Resequencing and mutational analysis using oligonucleotide microarrays," Nat. Genetics. 21(Suppl 1):42-47.
Lander (1999) "Array of hope," Nat Genetics. 21(Suppl 1):3-4.
Lipshutz et al. (1999) "High density synthetic oligonucleotide arrays," Nat Genetics. 21(Suppl 1):20-24.
Phimister (1999) "Going global," Nat Genetics. 21(Suppl 1):1.
Southern et al. (1999) "Molecular interactions on microarrays," Nat. Genetics. 21(Suppl 1):5-9.
International Preliminary Report on Patentability corresponding to International Patent Application No. PCT/EP2003/002034, completed Jun. 9, 2004.

\* cited by examiner

SEQUENCE LISTING

```
<160> NUMBER OF SEQ ID NOS: 110

<210> SEQ ID NO 1
<211> LENGTH: 965
<212> TYPE: DNA
<213> ORGANISM: Homo Sapiens

<400> SEQUENCE: 1
gatcaattaa gggcatctta gaagttaggc gttcccgctg cctcctttga gcacggaggc      60
caccaacccc taggggaag agatgtagcg cgaggcaggg gtgtcgtgct aagaaatttc      120
gacgcttctg gggactgagg acaaaggtgc ggacacgacc ccggggtacc tggagttccg      180
tgactcgcgc cacggacggc acacctaggg gctaatttct gctctgcctc aaagaacctc      240
```

| | |
|---|---|
| aagctagagt ccttgcctcc gcccacagcc ccgggatgcc gctgctgcgc tcaccgcaca | 300 |
| ggcagcgccc ggaccggctg cagcagatcg cgcgctgcgc gttccaccgg gagatggtgg | 360 |
| agacgctgaa aagcttcttt cttgccactc tggacgctgt gggcggcaag cgccttagtc | 420 |
| cctacctctg ctgagctgaa cgctcaggca cagtggaact gaaacccggt tccctacctc | 480 |
| tgctgagctg aacgctcagg cacagtggaa ctgaaacccg ttctgcggg atgtgagagc | 540 |
| tgttgaggtc acgcgtaatt gggtgtgatg gagggcgcct gttcgtgatg tgtgcaggtt | 600 |
| tgatgcaagc aggtcatcgt cgtgcgagtg tgtggatgcg accgcccgag agactcggag | 660 |
| gcaggcttgg gacacgtttg agtgaacacc tcaggatact cttctggcca gtatctgttt | 720 |
| tttagtgtct gtgattcaga gtgggcacat gttgggagac agtaatgggt ttgggtgtgt | 780 |
| gtaaatgagt gtgaccggaa gcgagtgtga gcttgatcta ggcagggacc acacagcact | 840 |
| gtcacacctg cctgctcttt agtagaggac tgaagtgcgg gggtggggt acggggccgg | 900 |
| aatagaatgt ctctgggaca tcttggcaaa cagcagccgg aagcaagggg gcagctgtgc | 960 |
| aaacg | 965 |

<210> SEQ ID NO 2
<211> LENGTH: 16579
<212> TYPE: DNA
<213> ORGANISM: Homo Sapiens

<400> SEQUENCE: 2

| | |
|---|---|
| tgttttttaa aatgatgtct agctgaacca gccaatggag acaaaatat ttatatataa | 60 |
| ttttcctcta agttcactag tcattttata gatcagttat aactttggct actccaatga | 120 |
| gttaatttct ttctagagac attataaact ccttaaagat ggaaataat tgttactttt | 180 |
| ttgaataatg cctactatct aaaacaatgc acataaaagc tgctcaataa acttttgttg | 240 |
| aattgagaga aaatataaaa aattgaaagc agtctgtttg taataagtgt ttgctaagtc | 300 |
| ttacagatct tctctttttt ttggaattat tgcaacaaat atttgacctt tgatttgtag | 360 |
| gattaaaatg tgatttctca tattttaata ggagcaagca ttagtcctgc aattcttttt | 420 |
| gtcaatagaa taaaaatgga atgtatgctt gctgcttcta catgccggtt gatacccatg | 480 |
| ctgaacactt ttcttacaac gcagaggttt ccttgttttc tgtcttgcgt tctaccttg | 540 |
| ctcaccacag agacattaat gatgccatgt gtcttttgc accatcagtg cagcagcttt | 600 |
| cattatgctc cttgtctcgg tcccactgta gtctaattaa ataaatggaa acgggtagtc | 660 |
| actgaaaata aacagcaact gcaaaagttt tgcctcttaa gaaaccttct gcattgtatt | 720 |
| ccgcccctgcc tcattgattc taagatctct accgcttcct tgtgttcaga aaccagactc | 780 |
| ttcagttttgt cttgcttcag tcagacaaat gcttttataa aatgacctat atttttcaga | 840 |
| ctgtggggag agaagaaaaa gactttgaga aagtgactaa ggagggagta agagtgatac | 900 |
| aatctttgat tcaatttagt tggactgtgt tctttatgcc ttcatctttt tcttataaa | 960 |
| aaagatagcg ttttttgatgc tctgctccag gcagcctccc agggtgagtg cagatgtgct | 1020 |
| gagccatttg gctgccttga ggaccggctc agagagcctc tcttctcact aatgaagtca | 1080 |
| tctcctctcg gcagcccggc ctctcccatc actccatgtt ggaacttggc tttggcttgc | 1140 |
| atagttctgt cgtgatgtag atggtctttc agttaagttc tagagaaatc tgctcaacca | 1200 |
| tgaacaggac atttacagca caggagaaaa aaaatttat taaaacaaat attttactgt | 1260 |
| aacatttgaa tttgggggtt ggagagcaaa aactcaatat ctgatgtctg ggaaaatct | 1320 |
| aatgttttat ggctttctaa ggaaatttgt ctgtgtttaa tttatcagag caatttatat | 1380 |

```
acttcgggtt aaagcacaat gagattgcca ccatcacttt gccttttgca agatttcttt    1440
tttaagaata aaagaaggc aataaagacc ttatatttct gcctttccta gaaagccaaa    1500
gagaattcaa agtgctggat gaaatgtctg tccctaattt gcagtgtttt atttaaaaaa    1560
aaaattatga cacaatctta gaggataggc ttccttttc cagggtcttt gaaagttaaa    1620
agtacatttt taatctgtag cattactgta tcatccagtg aggataattt gcttagttgt    1680
gcctaggacc agtcagatca aggagttgaa actaagctct ttctgaattt gaatgggact    1740
ggaatcttgt catccctaga gcagcaatag atgatgccat gtctaagaac acttcacctg    1800
atcaataaaa aaggagaagt ctgaaatgta atcctaaaga acctcagaag gaggtttaga    1860
tgaagataat aaaattccct ggagacacat ctgccatcta cacctttcct ctccaagtca    1920
ttggcttgct gccctgagc tcagccaaat tcccaaagac aagatcaaag caaggaagca    1980
aggcacatag cttctggctt atggtttctt ttagacacaa gcattgtgaa tgaagatctt    2040
gctttattta tacctgggat cttggagttt tcacaaagaa tatccccagt acaaggatgt    2100
gatttaaagg gggactcaca gaataatatt ttaattactg tttgattcat acttgagtgt    2160
aatggacaaa taaatacaat tttagttata aaacctgaaa aatatatatt ttcccattca    2220
aaaacttctg atagttttgt caggcattgg agaatcagaa ataaatgctc tctcattttc    2280
tttctcttga tgaaggaaag tcattaaaaa cagttacata gaataataa tacaactgta    2340 gactctattc taaatatagc tggtatgttt tcctttttct tttttatcca ttctccattt    2400
tagacagcta gaggggaaag tctgccctag agatagaaag aagatatcca tggggtataa    2460
tttcatttta gttatctgat agcctgaaga agtatttaat tttctgaata ataatgttac    2520
aagtcaaaga agagaaaaga caggcagttt aaagcttttc aacattgtgc atattctaat    2580
tccttaagtc agccctgaga aagtgccttt gtcctgtaga agtatttggt caagtgttgt    2640
gaagtctatt ggcattaaaa gaaactaaaa attttggagg attagagaat caaatttggc    2700
aacataaatg aaaacatctc agaatgtaaa aagtatctaa cccatcactt tcaatcatgt    2760
tccattatat acagatggca ttatttatag tgaatgttaa ctattaacat ttccctaaaa    2820
atgggcatta atctgctatt agttgcttgt ttctgatcta gttctccttt gttgaaaggt    2880
tttacttaac tgtatcataa agggacaaaa gggtaaaaga taataagctt ttcagactgg    2940
cagatctgtc acttacaaaa tggccttggg caggttactt gaactctttg aaactcaact    3000
agatttactc aaatttaaga atgagaatac aaatccacat cttgaagtgt ttcacagaaa    3060
ggtctatctt aatgtctgga gtatatattt caatgaacat tcattttatt ttatttctct    3120
ccattcctga atcaagcaat cttgaatcta aagttgctat gattagcact gaaaagacca    3180
ctggactatt aattgtgtga ctttgggaca gtaacttct gcaccttagt ttgtttacat    3240
gttatacatg aaggttgaag tctgattctg ctctgtgact atcattctaa acatctgatg    3300
aaatcaaatt tcagtgtttg gaatggtagt acaataaatt tactaagaat aaataattca    3360
ctgcaaaaac acattgattt ccaaatgatg taactgacag ttatattact gcagagggct    3420
gataaataac aaaagaaatg aaagatgcac atggtgagaa ctgaaattat cctgacaagt    3480
cttctacctg tttatcactt aaaatcaatg accatgctga atgcctacaa attacaaaat    3540 ataaagaaa tcttataaat gcgcatgtac aggagtctaa gttactaaaa gttttaaagc    3600
ataagtttaa accaaactaa tcaaagaagt tgagaggaaa aattggcttt catctttaat    3660
cactactgtt ttgaggtcct atgttaata taattttcta agtagaggct tcagagagaa    3720
```

```
gagttgtgag gatactttca tatttgtgta gaaggaaaag tttgccatcc attctagtat   3780
ccctagtgtt atactgatgt gcaccttgga tttattttgt tcctattgta taaactcata   3840
cttgacttca agaaaagga aaatccaaag tccctctttt ctaagggac agaaatcctt    3900
tgtgtcaact gtttgaccct tttctctgta aggtcctatt ggaaatcttt tgtaacacaa   3960
tgcaggggac tcttccatgt gttgatgctg tttacacagt ggggtgggcc tgactgaaga   4020
aaaaaaatcg catatacgca tgaaagatta tggtcttatt ccggaaagc atgaaaggtg    4080
attgatactt ccaagaagtc cctgttactc aggaaaatta tcaaatattc tactcagaga   4140
tacttggaaa gactgaagga aaggaagaac gaagaaagca gaatctagac ttatgtgggg   4200
agagatttgt ggcagaggaa aagtattctc tttgaatccg acaagggatt tgcctggggg   4260
aatttcctgt ccagccttt attaccaggg tcttttgaag ccgggctccc cattgggcag    4320
ttccctggga gtgcagtggg gaattcttac actttccctc taggtccccg aaggatctcg   4380
ttttctcagt gtctctttca ggttggcagg agccttgagc ctgacacttc cctttgatgg   4440
gacaggcaag ctctgtgggc gcgtaaacac gctgtaacca agttctttgc tgattttaca   4500
gttttgtgtg ctcccgagaa gaagtgatcg tactcaattg tctattgctg gcctgccccc   4560
taagagcctg ggggctcctt tcccctaacc cagaactagc tgcacggggg gcggggaagt   4620
gggggtgggg aaggagtggg agggcagtgg tttccgcgag cagagcgatg ttactgagtg   4680
agtccctgaa tggggagcgc tgctgtcccc aagccgattg gtacttcttg tcaggaagaa   4740
acgccaagag gtgggagtgc ctggggaggg aggcaggcgg tccctaccgc aggcgcgggg   4800
agctgccttt ccgcccctcc gcctgctttc caagcctgga ctcttaggag tggctgaagc   4860
tgcggagcgc ttttggagcc tgtgaatgaa ccctcctcct ctcctcctc cttcttctcg    4920
ctgagtctcc tcctcggctc tgacggtaca gtgatataat gatgatgggt gtcacaaccc   4980
gcatttgaac ttgcaggcga gctgccccga gcctttctgg ggaagaactc caggcgtgcg   5040
gacgcaacag ccgagaacat taggtgttgt ggacaggagc tgggaccaag atcttcggcc   5100
agccccgcat cctcccgcat cttccagcac cgtcccgcac cctccgcatc cttccccggg   5160
ccaccacgct tcctatgtga cccgcctggg caacgccgaa cccagtcgcg cagcgctgca   5220
gtgaattttc cccccaaact gcaataagcc gccttccaag gtaatcacgt ttctttgtt    5280
cccccttaa aaacaaaaa caaaaaactt atagaaaaaa acccgcgagc ttagaaaaa     5340
gaagcaattg gtagaaggct ttaattaagg caaagagctg taaggcgaag ttaagaaaat   5400
gtaggcactt aaaaaatgca ggtaactttc ataaaggctt ttggggagag gcatacagag   5460
ggaccttggt gttgaaaaag attcagacaa agaaaccca gggtggggtg ggggtaaaat    5520
gactaacgga attggggaa gggagggaat aaattgtaaa gaaatcatag aaaagtggtg    5580
ggttcttgag ctggagagaa gagagggacc tttggcactt tgatttttt gttgttgttg    5640
ttcttaacac gctcgaggca aaagtttgaa tggggactac caagacttgc cacagacaag   5700
tccccgaagc cgccttggtg caggccacct ggtttcccag cccctggtgt gtggtcagtg   5760
cctggtgttc ctggaaagcc actcccgggc agctcctgac agtgcgaccc ggcgcccaag   5820
cagcctggga ccttgcgcgg acctgacccc ttcagaccgc aggcagtctg ggaggaggtc   5880
cggccggggg aggtgcagga tccccgccgt gtctctttga cgacttgggg actgtcacgg   5940
ttctctcccg gcgcccctgg gttctttttgt cctgcacgcg gtgcgaaggg gccagcaggg   6000
aaggagcaga ggatgggggg tggggttgtt ggagcccgc ggaggtctgg gaggcccctg    6060
ggcgggaaaa gcctgttctg aatcggcagg gatgtgcaac aatttttctc accctgaaga   6120
```

```
gtgaaatagg gtctgtcgct cccatctcaa caagcaaacc ggcacccaga gcgcactgca    6180
gacaaaggtg gctcggggac ccgaatcagg ggcctctggg tcagtcctct cgcccagact    6240
acaggagtcc tccgtttcct tacatattcc ccaccctctc ctagttctcc gctctagttg    6300
agcaacttta ctggcaggtc tagcggcagc ggcgcgcgcg tgtgccggga gccccggggg    6360
acgtcctcgg ctggagcgcc ccaccgtcct gcagaggcgt gggcgctgta gggcgacatc    6420
cctggtgcgt gcagacctag ggcatccggg ttgttctggc ccgcggtctg tgtcactggg    6480
cgtggagcgg tctgggtgtt aggcagagga gagcggggta gaaaaatagt gtcatagcct    6540
aaactatttg ctctccaatc caactgcgtc tcggcaagtc ctgcatgtcc ctgggagatg    6600
ctgcgggaag ggggagaaat ctacacggcg cctggagagt tgtcctgccg cgcgcacacc    6660
cgcggcagag tctctctggg tcgcgttcct catctttgtg tctccctctg tctccatctt    6720
ctctgcctcc cttcccctct cccagcctct gttctctctc tctagcttct gcgtcccctc    6780
ccccacagct gacaaatgaa tggctagtgt gaaatccctg cctttcccgt gctccaaggc    6840
agcagggagg gaggagcgag ggaggcggtg cgctccttcg gatctgcccc cagttcagct    6900
cacaagactt gcagaaccta gatgtctagg aattgggagt tttgcggcgg gtgtgggcgc    6960
cccctgatgg agaagtcccg cacaggcgga gaaaaacaag ccccccagac caagcgtgca    7020
tctttcacaa ccttgtgttc aaggatggaa ggccctagtt ttcccttaag tcattcattt    7080
tgcactccac aatctgcggc gtacatctag gagtttggag gaccctgaaa aaaggtcttg    7140
gtctgtgcaa agtgcagaga tgccttctcg cgagtcggct ggaacgcacg cggcgccctg    7200
ggtccagttc gccgcttagt ggacgaacgc acatggccgg ggtggagcca ggtttcggag    7260
gtctagacgc gccaccctgg gcgtctttaa gaaagataat acacataccg tgctctcaaa    7320
acccatgacc acttgaaccc aacggtaggg ccccgcccca ggatattgca aaagaagggc    7380
tcctaatcca aaacttaaac ttcctcaact tcagggcggg cgtcgacggg gaaagtggag    7440
agaaggcggg cagtgggagg aaaaaagaaa gggaaggaag ggaagtggaa ggaaagagga    7500
ccgtggaggg gaggaaaagg agaaaggaac ggagatgggg cagatggcat tcaaacagcc    7560
aggaacggac cggaagggtt cgtttcgggg tttgggtctg aatttcgaga ctcgttttag    7620
gatactcttt tccctttccc agcggcaaca aatgtgactg cagaggcgtg ccgggatgga    7680
agggtgggaa agaactagac aagcggaggt ggtccagccc cgcccaaagg ggctgggtct    7740
ggggcccgcc cccactcgct cacctcgcgc caagggagga cccgcaacgg gcgctccccg    7800
cagcggctgt gttagccagc cgccacgtgg gttggcgctt cggctcccag ccgagacggg    7860
tgtgacttcc tgggctcaga gactgcagta cagccgcaca ggcggccggc gcagccgagg    7920
cccccaccca ccgaggccaa tggggcgggg cggggaagg cagggcccag cttaaccgag    7980
agagccgagt ggcctcgccc ccgggattcg gggccggctg cttctggagc tgacccgagt    8040
tccatccaga cagcgctgaa cactcttatt aaaaggctat ttaagtttta ttttatttta    8100
ttttattttt gcttgcttct tgggagtggt aggaggggca tcgtgctttt gttttgaggc    8160
aggggagagg ttaaaattta ctccaagcaa acttttttgtc agaaaaatga gactttatac    8220
cgtattccat ttgttgactt tttaaataca ttcaggtcac tctaaagccc attcttagtc    8280
aattaacaga ttaatttcgt tccagactgt cataaagagt tcgcctggaa tggcaaatac    8340
tgccattcga caagactaat agaatttcat gggggcaaac atggaagggc tgcgagtgta    8400
actgaggttc ctgtgcctca atgaggaacc ttagcgggga cctggcgggg actggaagct    8460
```

```
cagcacctat ttagggagtg actgagctgg aaacctggag aagcttggtg cagacgagac    8520
ggtgcttctt agagctgcat tttaagtcct cccattttgc tgcatattgg aagaactgga    8580
ttttaaagat cttttccatc acctcagatt ctgtagctaa cagccacgtc ttttctttt     8640 tgtctgctga aagctgtgac ctaattgttt taagcacttc ttgacaattt cgccaaaccc    8700
atcctgaaaa tattcacata aagtcctaaa ataggatgtt gtgagtgtaa tataaaata    8760 ggaaggtacc aatggaagca acaattagtg ttctgagata gaagcggttc ccagtttgta    8820
acttggaaat gttaagagca gtacatcagg gagaaggtct ccaagagtct gacttcttgt    8880
tctgagctct gagtaaagaa agaaatatgt tagaattgta ttgtctgccc gcagtaatat    8940
tgtaaagggt tccaatggat tccaatgtga ttgagcaatt acttcctcca gcaccaagtc    9000
cacagtcctt aatcttcttg tgagaagatt aggtaggaag cgggatgaga ttcaagacaa    9060
tcatttagga tttatgtcag aattcaaagt tttgattctt ttggtagata aaaacagagt    9120
tggttttaaa ttgtatttcc tgcttttcaaa aaaacgaggt ttgaaaggaa tcccctaga   9180 tttacatagg tttacagatg taagtttctt cttttccct gtgtttgcaa actggaggga    9240
gatgcctttg atattccaga atacctgtat ctatacactt gtaaattctg ctaggaaagg    9300
acctaaacag ctaaaccaaa ggtgaccatg attaatgtta aagatactac ccattgttct    9360
ctcttttgtt gtattattag gcttaaatac tttggagtta atgattggtc acttaattga    9420
gtaacagagc ctttgagagc gcaaagatca actaactctg tctcccaaag tctggcaact    9480
aagccctcct ttcctggtga gatttaaaca tttttgttga cgtcattcat ggacaaacat    9540
cggtaaacac tgtatttaaa atgggatatt gccctgtgat ggagcagaac ttctcaagac    9600
acatggttct tttgaaagaa agaattaatg actgtagtaa ggtattttt caccacccac     9660 gtagagaaac cagttaggac tgacaaacac tcattgttgg gagttacttg ctctggtctg    9720
agaaaatatg ctgattgtta cataggtctg tattttacca gaaaacacaa agcatgtact    9780
ctccctgatt tggaatcaga aaaggggat tagatatgga tgtcttggcc aagctccatt    9840
tcaattagtg aattttgcc agtttcctct tgtagcctag acttggtaaa ttacatatat     9900
ataaagtctg tgtgtgtgtg tggggtgcgt gtgtgtgtgt atgtatacag gttttttaaa    9960
cactgctaag ttcttaccat tgaatgtgtt agaggtggtt gtatttcaga ggtcagtaca   10020
aagaatcttt gtttaatgtg tcagttctgt ttcctgaaac acacctctgg gtagatttac   10080
caactataaa aggatacaaa tgtatatact ttccacatct gtatacatcc tacctcattc   10140
ttctaaggat tttaagaggt gtttatgtct ataaaatgag attacatatt ttacaataaa   10200
catatttgat aaattataat cttttatta ttaaattatt gatttgatat tacttgaggt    10260
atagtggaat gagcactaga cttggaatca gaaagtttga gttggactca ctagctgaga   10320
aaaccaagca aagatattac ttttggacct ttagtgtcat aatctattaa atgaatatgc   10380
agttataaag atcaaagag taagtacttt gaaaaactat acaaaaagg gatgataata    10440 tattatgtct tgggattcat attgatctaa ttctataatt ttaataataa ctgcattacc   10500
caagccatgt agtttctact gaatctataa aataaatcag agagggcat attgttttaa    10560 aaattgttta gtttcattaa tcagaagaca gattacagaa attgactcca atgaagttgg   10620
acattcagtg gaaaggaaga attattcaat aaatggtttc aggacaattg atgggtccat   10680
gcaaaataag aatcagtctc tacctgattt ctcatcctaa agaaatata agatgaatca    10740 aatatgaaat gtagggaata acttttaca aaatgataaa agaaaatcat gggattaaaa    10800
aaaataagtt aggaatagag aaacctgttc taagcaaaac ataaaaccca gtgccattct  10860
```

```
aggaaatact gataggtctg actaagtaaa aattacacaa aagcaaataa tatatttgga    10920
aaacatctac gacatttgag agacaaaaag ctaataactc ttgatattcc atggactttt    10980
atgaataact ttgaaaagtc cacatctatc aaaaatgag caaaaattat gtacaggtag    11040
tggcagaaag agacatagag ttttaaaatt atagaaaaaa tcgctcagcc tcatctgtaa    11100
ttaaataaat agtaattaaa acaccaatga tatgctacac cattttttca ccaatcagag    11160
gagtaacaaa aaaaaataat ttttttcttt tttttttttt ttgagatgga gtctgttact    11220
caggttggag tgcagtggca cgatctcagc tcactgcaac ctccgccttc caggttcaag    11280
caattctcct gtgtcagcct ccctagtagc tgggattatg ggcacccacc accatgcttg    11340
gctaattttc gtgttttttag tagagtgggg tttcaccatg ttggccatgg cagttgatct    11400
tgaactcctg acctcaagtg attcacccac ctcagcctcc caaagtgctg ggattacagg    11460
catgagccac tgtgcctggc aaaaatgaaa ttaaaaagtt tgatgcaagt tgtgttggc    11520
caggttgtgg agaaactggg tctctcatat actgttgtat gaaagtaaat aggttcctct    11580
acttcaaaaa ataatttggc aatcactttt ttttgattct ttatcaaaag ttttttaaaag    11640
atgtatatac tctttgattc agcaattcca cttctcgaca ttattatatg gatggatatt    11700
ggtaccaata tcacccaaga caaatggaca aggatgttct ttgcagcatt gcttctaaga    11760
gcaaatatct ggaacagtg taacaggctc atcatagga accattttaaa taaaagttgc    11820
tgtatccacc taatggaaaa ctatgcagct gtcaaaaata acatggaaaa attgtatttg    11880
ctgatttgga acattctcca aaatatattg tattctaagt gaaaaaattg atagataaaa    11940
ctgagtatat attatacatc taattatgta aaatgggtgt atattcattc ttttaacaaa    12000
tatttactga gtgttctagg cattgtggat acaggagtga acaaaacatc aaagactgct    12060
ctgttggaac ttttactatg gtaggtagag aaaggcaatt cccaatcaca tatgcaaaat    12120
ggtgatatgt gctaggatga aaatagagca tgggaaaggg aatagagtac agtatgtctt    12180
aggtagagta atgagaaagg agttcaccag gcagagaaca gaggagtgct aagggcgac    12240
aatgtgaaaa agcttagcca agtccaggtt caggaattca catgatgcta ttacttgtat    12300
gaagtaaatt catgaaattt cgcacctaaa tcacgtgatt tctctctgct gtacaatgat    12360
tctttctgtg agaaagaacc agtgagcaat atgatatgtg atgctcatta catccactttt    12420
gtagctgaag tatcctagaa agttggttgt ctagggtacc taattagcag aatggtggac    12480
aaaaccaccg tgtctctgtc cttaagtcac cccttgtcag ctgagcttcc ccaaaatcaa    12540
gggagaatac taaatatcta tttaatagaa tcttggcttt ctctcggagg ctgcccatcc    12600
ctggtgtgtc ccttatcctc cctgcagaca tttctcatgg ataggagttc cattgaccttt    12660
gtcttttatg tctcccaggc aattaaacag tctcagtacc ctgtacctgg attgttcaat    12720
gactttcttc ccttctcatt gacttcactg gagtagaagg ctaaatatag gcattcactc    12780
tcatatctct caggtctttc catgcagaca gagttgttat cactagtaga cggtgcttat    12840
aagagagaca tggaaaagtg gaagaatgga aataggggatt tggagtggtg ctaaaaacaa    12900
agaaagaggc ttctgaaagc tttccattta atatgatcaa acatagaaga caaaagatgt    12960
aacttaatga ccaaggatag ggacatagcc ttgagaaaat tacagaagtg gaatgaacgt    13020
cttggactcc aaagaagagg gaatggaaat gcagttctga ggcagctaaa gtcaataaag    13080
ccctctgata tatttactgt agaaataaat gatcatcttt taattcaagg tttgcaaact    13140
taggtgacta caggggcgag gcatggagtg gaaatgggta agagactaag tgggggcagt    13200
```

```
aatggccttg agcacacaga cttaagggga gagactgctg cttggttaat gctcatgatc   13260
agccagctga aatatagact tagtgttgct agaccttctg attttttgaa agaagttaga   13320
gattttatat ttagtgtaaa cagtctaatt tttaaattga gtaacttatt caaacatatt   13380
tatgcaactt attcaaatgt atttagagca tgtctgatct cctccttgta ttcttaccta   13440
gtcttagggg taatcttaag gaaagtgatg cgtatacttg ttgtacctat gtagatggag   13500
gaccattctc ctctcccaa caaaagacac ttttataagg attgagtgtg cacaaagag    13560 ttcgattttt agtatttaaa ttgagtagga aactcaaata cagaagatcc tttcctgggt   13620
cacacctttg gttttttaa atgagatttg actctctaga tattgacaaa catcatatta    13680
ttgggtcatg gtaaatcttc aagtggactg attcaaaagt gttcaaaagt atttcaggtg   13740
ttaaggaatt gttggcacgg agtttcaaag gtgtttctgc ataagaaata gaggcgttga   13800
tcatgtattt gatctacaaa cattcctcaa ggatatacc tgaacctggc aatgaagaaa     13860
tattgtggga attattaagt tgaataaagt actagctctg ccttccagaa gcctactgtt   13920
ctacagagga gattagacat gtttacagat aatttgaagt acatagcaat aaattatagg   13980
atgatttatt ccaagcataa agtgtatatt gctactatag tggtaaccta ggttataatt   14040
ttcaaatgta agagccccaa atactattct ttttactctt agtgatatga aactatgtta   14100
gaacatctgc agaaagtctg aattagtaat tttaataata aatattgagt actgatatat   14160
tgtatatcac tgagatttat tttatataca ttattttatc aattcctatg atcacttcgg   14220
taagtactaa ttttcacaac taagtagtga cagaaaatga ggtttagaga gatatagtat   14280
tttacccaaa gtcacagaat ataagtagag aatgcagaac ttgcattctg ggctatttga   14340
cagtggagcc cagactttta aaattaggct tataaagatt tcctgaaaa aaagaaaaat    14400 aaaaaataga gaacaaattt tcctgaagaa agtaggaaa ttattattta taagtataat    14460
taaagagaga tctttaattt cttttttttt ttttttttg agacggagtc tcgctctgtc    14520
gcccaggcgc aatctcagct cactgcaacc tccacctccc gggttcatgc cataaagaaa   14580
gtttctattt gattggtccg acctgattgt ctactagaac ataggctttc cagtagggtt   14640
aacaagtcat aacagttcta gtgatataag ataaatacaa actaataata aggttaattt   14700
agaattatca acatatgttt ttcattgtga attatcagtt ggtctataga tggaaaatat   14760
aagatatata atgtattagc ttaaaaaatg ctccttcagag agtgtctaga attatagaat   14820
ttaaaatttt tgttttgaaa aggtctaatt cttatttcaa aatatataaa gaaatcaaat   14880
gcaaaaaaat taagagaaaa ggtcttaatt aattaaatgc tgtacaactc caagccctat   14940
ttatgttcaa gatcagtttt gtaatttatg actaatttca gcattagctt gttttcaatc   15000
taggtttgct aaataatata gaatttcttt tccaatgaag ttttttcaggg tcccagctga    15060 aaaatatata ccagttagga tgctttcaac tgtaaggaac aaaaagtcac gatttttattg   15120 ggtttaaaca ataatgacat ttataatctc atataaaatg aagttcaaag gcatggtcca    15180
ctctaggtct aatccttaag gacttacgcc ttgcctttgc tgattctttc tcagcttcat    15240
ttccagaggt atctcactta ctcatggatg caaaatccct acaacagttc cagcagaaag   15300
attccagcat gataatgtcc agggaagaaa actgaccacc tcttcctttg ttctcttctc   15360
aggatgaatc tatctttccc agggacccctt cactggagga agagatcccc tcacatctca   15420
ctggccaaaa ctatattata tactgttcca aatccaatca ttggaaaagg gaatggtacc    15480
tctataattg acttaggata tcaggatcat cccttgggct ggggtttgac ccaggattct    15540
ccaaagtatg tgactgaggg taggcactag aatggaacca gagttgtgtt agaaaggaga    15600
```

```
aacgcatggc tattatagaa tagttctaaa tgctaccgag gagggcacaa ctgtaaaaac    15660
caaataatct tttgccattc ttttgaagtt ggcactttga tttctagatg gttccccaac    15720
acaggttctt ctcctcctca tcattatagc tgccttgaaa tttgagctgg aagggaacat    15780
tctgagaccc agattgttaa atgtcttttc caaagtcatg caataaatta aatggcaaag    15840
ccagggcagt tcttgactc agtacagggt attttctttc attctttact cttgagactt     15900
tagaactgtt ggtactgctt taaaattcat ggcaagaact ggtcacttt gtaattaaca     15960 cctccttata atacatttgt tttgtttgct tagccagcta gaaactacat ggagtctgtg    16020 cttttaaaaag cctgccgaag tccttattct ctgttttggt attatgtgca tgaaccacca   16080
attggttcct tctcacctta cacttgatga agatgccttt ctttcaacat ctttctctat    16140
tgctccccat cttctcttgc tctatttatg atcagctgtc tgtttctaaa tagactttgt    16200
ggtcacccat ttcttttgt gccagctcct atccactagt tacttgaact gtggtctcta    16260
ttgttcttca tacagcctac tcacttgtgg ttgtcacaca catccacatt gttatatgtt    16320
cccaaactgt attctggaat gattttggta atggctgcat tggatgagat tcaaactaat    16380
aattaaagca ttgagatagc ttctgctatt acaagtttac tcctgttttt atagtccaag    16440
aggagctact tcttctactc ttattactta atgcttaata ctacccttat tacatacaat    16500
gcacaaaaag catgtgattt atgacccact ttaaacctga atgcttgtga tttactttgt    16560
gtttttcttc atttctagg                                                16579

<210> SEQ ID NO 3
<211> LENGTH: 3000
<212> TYPE: DNA
<213> ORGANISM: Homo Sapiens

<400> SEQUENCE: 3
acatttaaat tgcatatttg gcttgtaata tattacatat ttaaaagaat tactattttt       60
ctgaatacca ttaatactaa taatagcatc acagtgacta agagtggact taaataaagg      120
ctggcttgaa actcaggtct gccatttatt agcaagcttc taaaaattct gagcccttag      180
ttttctcaca tgtgaaatgg agaaaataaa tctgcaaaat taattaaatc tgtccattca      240 tattttctc tccagtgtat attaactggc attcctcgtt aggccagaat gtgctctcaa       300
ccatgctcca aatccgcttt gtgccaaccc cactgccaga acccttctta ccttgagaac     360
cagaaaagga acattatgc ctggcaatgc ctacaccctc caaaataaat ctgcaggaaa       420
gaacacccag taagtgatga gagcagcaac gactgccttt atcatttaa atttacaaca      480 ccaccttttc tagagcctct taagcattgt agataattcc ccactcatta aaaataaat      540 tgtaaccata agtattcagg gttgatactg cttttgaatt agacagtgct catatcagtt     600
gcataagacc aacctaaagt agaggatgaa atctttttc tgaaccttt tcagaacgta      660 acttagtgaa tatattaaaa ctaaactttc tttgaatggg agtaatttct acggattaat     720
ctgtaatctc ttagaccaca cctaaggtaa tgtagaggtt gttgtatcat aggctttgtg    780
attagagacc actggatttg tctttggaaa agtcactcat gattcttggg ctttggttt    840 cctcatcttt tataccggct taataatgac caccgtagag ttgtcatgga agttaaatga    900
actcatgtac cataagtgac caatacaatg attgacactc agtgatttat caataaatta   960
aaacatttat tatcaatatg acagagaagg tgccgctaaa atagacaata ggttttggaa   1020
agaggtgatt aaatggatgc aaaatttatg gattgtttat tccgtctacc tttgctgtgt   1080
```

| | |
|---|---|
| cccctggttg tggcatacac acgtgtgggt ataaaatcgt aaatcctatg tagtcgcgta | 1140 |
| gtgcatgcgc agaaggctta gacacgaaat gtcatttcag caatgtgcct agagaagctc | 1200 |
| tgacgccgcc ttggaagtaa gtcgttgctg cctgaccttt gggcgtctgg gacggatgcc | 1260 |
| tatacctgca cccagcagca ctggaagggg cccaggccct tcgcagcaca gcctatcccc | 1320 |
| agaccgctta gtccttcata acatatatct ccacggaaaa gggtatttcc tcccgtcaga | 1380 |
| aaaagcgccc cagtctggtc tgggttggtt tttatttcac gttgttgcaa gtaggcgaag | 1440 |
| tcccttctgt ctcctccctt ggggtaagtg gaaaggagtc cggcaggggg cccgcagtgg | 1500 |
| cctgcacagg ggaactgggt agcgagagag ttccaggcaa ttccggggc tgccccacag | 1560 |
| aagcaggtgg ggatcgacag tggctctccg gcccaggag gagagcgcgg tcgcgggtcc | 1620 |
| ctcccctcag cctggaggct gcagccgctc gagtcggccc gggtggggc ggggtggggg | 1680 |
| cggcgcggag ggcacggaga ttacggcggc gccacccggg acatccaggg ccccgaggcc | 1740 |
| ctgggcggtc cccacgcgag atcgcaaacc atgacaatag gcagtcaccc gaggtcaaat | 1800 |
| aaaaacggag tgggtccccc gcgcgccgcc gcccccgcg tccctggcgg cctccccga | 1860 |
| ggccccggc ggcctcacga gcccgcagta gccggtggcg acgtcgcccc cgccccacct | 1920 |
| ccctgcgcaa gtgcgaggct gccggcagcg cggcgcacgc tccggccgtt cccggcttcc | 1980 |
| gcgcaaaact tccatcctgt ccacgtgaag ttgtcgctgc cttagagagg gggaaagagc | 2040 |
| tgcgggaaaa gccggggagt gacgactgcg gcggctgggc gcgctctctc attttctttt | 2100 |
| cttctccttt ccccctgtc gcagtccgga gttttggctc ctctcctttc ctcctcccc | 2160 |
| tcggagccgc cttctcccctc cgccccgctt ctccccgct tgtgtacgct atttgttgtg | 2220 |
| gggtggccga aggggatgtc ctgttttcac cagaggcaca gcgcgaaggg gaaacttcga | 2280 |
| cactggaagg aacgagaata aatacttaat tacggacgca ctgaaccgcg gctgggacag | 2340 |
| acacttcggg aacccgaggc ggaccgggcg acgaggtgag tgaccccttc ttccaacccc | 2400 |
| cgccccaggg ctcccggggg agcctgagtt gagagaaccc ccaaactttc cgggaaagtg | 2460 |
| cgcgaggctc cgccggggac gccgagcgct gggtactgag gacgcgcagc tggacggtgc | 2520 |
| gtgggcgcct gcgtccccgg ggggcgcttg gaggccgggt gccccacgcc tgagggcccg | 2580 |
| ggccgctcgg accgcagcgg tgctctctgc cctagaagac gtccccaagc cccaagggtc | 2640 |
| ccttccgagc ctgcctgtcc cttccggggt cggcgcggag cctgcgcgta acggagttca | 2700 |
| tccagcagtc cagcgcgcgg cttctacctg caccccgcct ccacctggca gaggcgcgag | 2760 |
| catcggggtc tcccccacat ctttcttatg acgtgtatta ctttctgatg accccctaga | 2820 |
| tggtccaggc gcgaggatgc tgacccagag tccttcggag ggtcacaggc gcctgggctt | 2880 |
| tcccggtgcc gggtgcgtgt gtactttaaa ggctcgcgtt ctaatctcca ggcactgatc | 2940 |
| gggcttttca actgcggcga tcccacttta atagttttta tgtggcgtgg actgaatgtc | 3000 |

```
<210> SEQ ID NO 4
<211> LENGTH: 1984
<212> TYPE: DNA
<213> ORGANISM: Homo Sapiens
<220> FEATURE:
<221> NAME/KEY: unsure
<222> LOCATION: (9, 17, 18, 33, 41, 49, 50, 52, 54, 62, 80, 84, 127,
      157, 159)
<223> OTHER INFORMATION: unknown base
<220> FEATURE:
<221> NAME/KEY: unsure
<222> LOCATION: (175, 207..209, 214, 1181)
<223> OTHER INFORMATION: unknown base
```

<400> SEQUENCE: 4

```
agcttcagnc atcactnnca tctttatcaa tgnccttggg nccacaggnn gngnccttct        60
gnccaaacag cagccaatgn aggnatctta aaaggcacat cactttatat ttattcagtg       120
gttatgncat cacttaatcc tcaccacaac cttgtgngnt cagtacaatt tgtgntttca       180
ttttatctgt gaacaaatgg aggcagnnnt ttgngtaatt tacaagtaag tggcagatcc       240
ggggctgtg cctagacaat gtggctccag actccttgcc cctccctgcc ttctgctgca        300
tcttgattga gtctagccat ctatttcttt aacacacact aattgctgtc tccatgttcc       360
aggccctgtg ccagatgcta gaaatacatc cccatccact ggatcttggc atggtccatt       420
gctcagtgtc ctgctatgtt acgtgttaca taatgcattt attccggtat ttagcccatg       480
gaaaataatg ctgaaagaca ttgtatgcat gtttctacaa caaaactatg taacttatgt       540
ttctttattt gctttggcta tcaggaagct cttatccaaa tcagagcaaa tacattagaa       600
tttgggcttg tcatttcagt ttgctgaact tttccttctg gcccagattt tctattttgg       660
ttcataaatt ctattgcaca aatgtccttt attgtaaaac accttaaatt ctttctaagg       720
gaaggctgca tggaaatgat acagtaaggt cttccctgca ttttcttaga ttcctattag       780
ggaaggcaga cctagatgtc cctcttaccc tcagtcccaa agcccccat ttataaaatc        840
ccttaagcag tgactactgc tgttctgagt acctggaggt agttcagagc ttctgaaagg       900
taaaatccat atacaaaaag aagttccttc cgatccagat cccagctttg gtgccagatg       960
cacatttgag gagtaggtgg ctagtcagac tctcacctga gcagttaata aaatctattg      1020
cccccttaatg gaatttttc tgcaagctcg aattgatctg tcatctttgt gatttgtgag      1080
atggcaggga agcaccaaac accatcatga cttgggccac agtggtggga aaaaaggaaa      1140
aaagaaaaaa aaaatccact gccaagcctt gccaggcgta naagggctg gaactgctgg       1200
ggccatttta tctgatttat tggaaataga gtggatctta ttaacatttt aataaagaga      1260
atctttttgc actaggctgg aagtggccgc cagtcccccg tgcaattcca ttctctggaa      1320
aagtggaatc agctggcatt gcccagcgtg atttgtgagg ctgagcccca acagtccaaa      1380
gaagcaaatg ggatgccacc tccgcggggc tcgctcctcg cgaggtgctc accccgtatc      1440
tgccatgcaa aacgagggag cgttaggaag gaatccgtct tgtaaagcca ttggtcctgg      1500
tcatcagcct ctacccaatg ctttcgtgat gctgctgctg atctatttgg gaagttggct      1560
ggctggcgag gcagagcctc tcctcaaagc ctggctccca cggaaaatat gctcagtgca      1620
gccgcgtgca tgaatgaaaa cgccgccggg cgcttctagt cggacaaaat gcagccgaga      1680
actccgctcg ttctgtgcgt tctcctgtcc caggtaggga agaggggctg ccgggcgcgc      1740
tctgcgcccc gtttctgcat tcggatcgcc cggcacgggc agggtgaggg ggctttcggg      1800
gggtcggggc ctccggtcgc ggcggcgaag acagatcggg gctcggtagg gaggtcattc      1860
cgagcccaga gatcctaggc accccccaca cacaggctcc cactctggcg tgcgtgcgtg      1920
tgtgtgtgtg tgtgtgtgtg tgtgtgtgtg tgtgtgtgtg tgtgtacgtt cgttaacggg      1980
agga                                                                   1984
```

<210> SEQ ID NO 5
<211> LENGTH: 7833
<212> TYPE: DNA
<213> ORGANISM: Homo Sapiens

<400> SEQUENCE: 5

```
gtctttggtg agatatgtgt tttacaagtt ttaatggaga aaaatgtaag tatttttacct       60
```

```
cctgaaactt ggctatttga gtaatgagaa aatagtcact ttccccagga cagtggttct    120
caatcatggc tatgtgtttc tccaggaaaa ctttaaaaat atatatatac caatgcttct    180
gtgtcacttc tagggattcc aagtctttga atacgaactc tgcatcagta ttctttaatt    240
atccaggtga ttgtgatgtg aaatcatgac tgagccccac tgctctaaga tgaaataaac    300
tttcctcagc actgaaatca caaacttaaa ctaccaaaat taattaaggg catgggaatc    360
aataaggcat agggaagctt ttacattata aaattatttc tttaaatcac agctcattgt    420
ttatatgtta tttgccattg tagaaaaggg tgaaaaaata gcaaatttaa ttactctcag    480
tttgaaaaat tatccagaaa tgaagatgac gactctgaaa cattgtcaat atcatttgac    540
ctataaataa tgttctaata catttactac acactgatag atacttttc atatgaatat     600 tatacattaa aactaaggca ataatgcatt tagaacattc tatctatatc tatgtatctt    660
aagtaggcta gaaattaaga tatgagttat taagtatgag atgttaaggt gtggggttag    720
aaattatact gtacttcatt atcaataatc aacatatact tcaatatcac atacatttaa    780
ctttaatttg tacatcttta actattttta attatgtgta taaatataag tacacacatc    840
tttatgtatt tatttattca tacctccatt cacttattta tagggggat ccccccaaat     900 ccactaccat taaaccatac attttttattt taatctttag aacaagccca ggaggcaggt   960
attgttatta ctcacatttt acaaatgagg aaattgtcta cagtcacaaa gttactgtgt   1020
cagacatatt agaagcttaa tacatatttg gtgaacatat gcataaaaac agagagacag   1080
acatgtacaa cagctcatct ttacactgag taaaagcttt taacctgtct cagaaacctc   1140
tctgtgaaaa ctgagcaaaa atcgaggtat cctttcattt gtcatatagg tataggtggt   1200
accttacttc tccaacaagg atgaatattg aaatgtggat cccaaggccc aactccagat   1260
tttctgaatc cctgatagtg ggacttggaa tttgtctatt gtttcaaagt ttctcaagga   1320
attcatatga tcaaccaggt tcagaaatca ctggatctta ttgccgaagt ttgagaatta   1380
aagtttgggc cttactgcgg ctccacagaa agggcaaatg aagtatcatg gacagaactg   1440
atacgttccc agttagtttc ccctctcaga agctaacagg cagcaataca gcagaaatta   1500
gtgacttatg tcttgtgctc tgaagtcagg cagaatttca cagagtccca gcagtgtcac   1560
tgacgagatt tgtttcttgg ggcaagttgc ctgatgcttt caaagccata ttccttttat   1620
ataaaatgag ataatattct ttgtctcata ggggtgtttt aaagattaaa taaaaataac   1680
atgttctatc ctacatggca caatgcctga cacctaagaa gcaaaggata catcttacct   1740
ttattgaagc aatcagaaag tatgaaatca tgaaggagat aagagttctg attggcagtg   1800
tatcttattt tcccaggttc atttatttat cttaaactat tcttgttgga gataactcc    1860 caagccccct acttaagctg tgagtaatct cacactttat aatgatgttc tttccatgag   1920
aaaaaaaaat gttcttaagt tttctggaga aaatatatct gcactatttc tactgaaaaa   1980
tctaacaact ggactctgct cctctgcatc aattctagag tgtatatgcc acaaataaag   2040
tgttctagct caagaagatt gaaagtaaat atggtatagt attttaaaat aagaattttg   2100
caaatacatg gtatgattgt gtcatattac tagcaatcat atgatacgca atgcaaagta   2160
cagttcatag acttaaattt aattctaata agtaaactga ttttgccttg ctggggaaaa   2220
gttaaagcac taatccaatt gctaatgcag tcttgtctac ttctttggta cctagtgaca   2280
agtctaaata atgtatatat ttttatttac atattcagta atacaattct ctgctcaatg   2340
agtgatgttc ttctgccact tggtggtgct tgccagtttc agaatttgtt tcttggtggc   2400
```

```
actataacac taagtacaga gtaagtgcaa caaaattgca gcattcccat tgaaaaggct    2460
ttgcttcaaa ctgtttaata atttaaagga cctctgtgga agcaaccgca tttgttaacc    2520
agttacaacc agtaattaac tcctttggag ttttaactta cttttggcaa aacgtcttag    2580
gaagagcata tattattaga aagtatgcca aaaatttact tagcagaaaa ttcaaaaaca    2640
gttttcctct gctaagaggt tctctaaaat tctacttaca tagccaaact ctgaaatcct    2700
agcaggtcct gtttcattat cataattact gcataaacac ttttaaggac tttgccttta    2760
gtttcaagca tgacttattt tcataagcct gattagttac cacaccagcc ttgctatgga    2820
aaatgacatg ttctcattct ctgctgtaga gttgttaaat cttgatctat atttatgttg    2880
ccttctctgc tgaaagcctg tagcgaaaga aatttctaat tccttgtttt gcaatattag    2940
ttggcagctc tatctaatgg gtattctgtt tccttaaaga atttagctgc tctgtctaga    3000
agccgatttt ctgatgcctc caacgtctgg tctaattgat ctgttttaat ggagtcttcg    3060
tcggtgagga gcgagatgcc accgactaga atgctgggat ctgctgctta attgccagga    3120
gtgagagaca ctgagattca gaaatctttg gaggtgggag gggagaggga cagtctcgga    3180
cggaggcgga gatgtaagat aaagggatgg atttcacaca ggaaaaaaaa aaagatttcg    3240
ttgaggcact gaggtgctgc acgatcacat ctctcaaagg agaagttaaa aagcaaggaa    3300
gtgggaggag gttggaggtt aaagtactta aaaggattac tcgggtacaa tttgtttttc    3360
tgctggtgtc tgcaaaggat agatagtccc gttttcaaag tatatgaatg cctcttttaa    3420
gtgattggga atggacacta attgcctgtt aaatgttatc aaatgctctc ctaaattcag    3480
gggacacaga aagaggggca caaaggagaa atttaaatag aaaaagggag gatccggagg    3540
cttttgaaag cggggggaga agaaggagga gggataacag agaggaatag agaaggagag    3600
cggagagaag ataaacaaaa acaaaaacag gaatcactga ataatcacac accaaaaaga    3660
aagctcttcc ctatggggca tccaaaacac tgagactgca atagtgaccc cggtcatgga    3720
agaaagatgt tcctctccac ccttgtcccc gaaagctctt ggtcccgtta ctggcgacta    3780
aaattccatt aggctaaaga gtgtgtctaa ctgcctgaag aatgcagcag acggaaggcg    3840
ggtcccgcta tgccgtttgc ccttcccgct ggagagaatg aaagaaacgc gcagagccag    3900
agactcctgc cgagttagac cttctctcgt cgccccaggt caccggccat ccggcaaaga    3960
cccgagtaag gaacgcaggg tcactgcctg ggccaacaaa tggagcccgc tctcccttc    4020 ccggacgccg ctgcccggcc gatgctcccg gcaacccacc cgcggcgtat gcagaggagc    4080 cttcctctt ctctcagacc acttgtcccg accaatctga ccttccaaac acatctgacc    4140
gcacctccca ggtggacaca ctaataggct acgggctgga gaggagcggg tgatgaggag    4200
agggattcaa acctgcgaac gcttgggctg ggtcggagct gcgggggcc tgggaggaga    4260 gagggagaa gagagaagga aggagagcgc ctgccgggat ggctgagctg cctcggcgag    4320
cagccttggg gttgcacgct cttgtgggag atgctgctgt tgcttccagg tcggcaagag    4380
cggttctaac accatcgcct ctcaccctct ttcctgtaaa tccctagaga aacgtccctg    4440
gcctctccgc cgcgacattc ccagcctgca tcccctaca gcctaggcgg cgcgctcccg    4500
cacgctggag cgccggtcgc cagcaggacg ccctctcccg cgccgactcg cccctctctg    4560
ccctgctgct gctgctcctc tgacacctcc gcccccacca tctccagctc ggagagacgc    4620
cacccagccg cggcccgcac tcgcggcccg gggtcacgcg cggaagaggg gcgctagtcc    4680
ggaccccgcc ttcggtaggg ggcgtcctgg agcggagagt gaggcgaatg gtatatgagt    4740
gtgcgggtag cccaccctga agcccgagct tctcatttga gccatgcccc gcctagcccc    4800
```

```
actcgggcca gcgcctggcg agcgagccca tctgtggctt ccgcggccgc ctcctccttg    4860
catccttgca cctactcgtc gacccctccc tcccgggacc tgcatcctgc tccaccaatc    4920
agagcccgac tgcctcttcc cacgtgaccc cgggcgggct gaggacctgc tgcttcccaa    4980
acgccagagg gatgcgggcg gcagagctcg agaggcggct gccgggctgc ggggcgcctt    5040
gactctccct ccaccctgcc tcctcgggct ccactcgtct gccccctggac tcccgtctcc    5100 tcctgtcctc cggcttccca gagctccctc cttatggcag cagcttcccg cgtctccggc    5160
gcagcttctc agcggacgac cctctcgctc cggggctgag cccagtccct ggatgttgct    5220
gaaactctcg agatcatgcg cgggtttggc tgctgcttcc ccgccgggtg ccactgccac    5280
cgccgccgcc tctgctgccg ccgtccgcgg gatgctcagt agcccgctgc ccggcccccg    5340
cgatcctgtg ttcctcggaa gccgtttgct gctgcagagt tgcacgaact agtcatggtg    5400
ctgtgggagt ccccgcggca gtgcagcagc tggacacttt gcgagggctt ttgctggctg    5460
ctgctgctgc ccgtcatgct actcatcgta gcccgcccgg tgaagctcgc tgctttccct    5520
acctccttaa gtgactgcca aacgcccacc ggctggaatt gctctggtaa gtccagaacc    5580
cccgtccccg accctttaac tccgcagaag aacacgcgta tccagcacag accagcctac    5640
cctagcgcgc tcctcagcc cctcacctcc tactgcccta gacccctaat accacccacc    5700
tctatccaga gaaacaaggg gaactgttgc aggcccgggg gtgaggggtg gttctgggat    5760
gggcagaaag tgcaggtgta gcaggaaacc tttgcatgct tgcgcttaca ttggagctgc    5820
gaggattttg agaaatatta acgggatgg ttttctgggt tcactgtttt gaaagagcac    5880
caatcctagg ggaaacactg aaacagaagc tttgtcatca ttaaagaaaa aagtcttact    5940
aggatgagga gaaataaact ttatgagaaa gaatgagcga gaaagcaata aatcaaatgg    6000
tgactgcagg ggaatcgctg attcctggca aaggtgccat gaggtcgcac tggtctcccg    6060
ttgaagacca ggtcacacag attctagagg agctgggttt caatagaatt tctctctctc    6120
tctctctctc tctctctctc tctctctctc tctctctatc tatctatctc tctctctctc    6180
tcattccctt ctctcctagg cggcaaaaga cattggtttt gcagtccaga tatgcccctc    6240
tctttgcttc cctaagcttc aaggtagtac aggggagttg agaaaaagaa cactttgcgg    6300
gtctcccagg ccggagtggg catgactgag gctggtcagg ctccatgtag gcgagccgag    6360
ggcggaaccg acttcagtgg gcgctgactc ctccatttct ggacaggctt ctgtggagtg    6420
ggtcaggcac tcttcttgct cgctcgggtt ccttcagatt ctgacggcga acgcttggca    6480
ggcttcgctc tgctgaagct tcctaattaa atagggccag aggatgggag ttgctgcact    6540
cctagctggc atagcattcg gtttgacagc ctgtagtata gggtgtatgt aattttttcat    6600 cttctgtgaa tataattttg ctgtagttaa atctggctct gaataaagtg tctttcaaag    6660
atgtatataa gctgaagtgt atgtaacttt agagaggagg gaatgaccaa ctgtaactca    6720
gggtgaaagc ctgtatagtt cctagttatt actgatgtaa atgccaaaag gaaaattatt    6780
atgcatcatt ctaatttatc ctttacaaag acaagttgag atatgcaacc ctattagatt    6840
tgggtcaata gattgttctc ttttttggca gtttctaaat ttggcatttt aataaaactc    6900
aacatgtttc tataacttct tgattcatgc gtacatgtgt gttgttttg aaagaataag    6960 tttcactttg ctattgccta atcacttttt agatgcttta ttatggtaat aattatgagc    7020
ctgcaaaaac aatttttgga aatgttgatg gcttgtagt ccaacacaga ctggtttgct    7080
tcattcctag cccttgcatt gttttaggaa ataactaact taaatgtgaa gttgacattt    7140
```

| | |
|---|---|
| gcaatcaaga aattacatat ttaccagata tttaaaggg gactgcataa actaaagaga | 7200 |
| ataaactggt tttgcagata ggttgtcaag aacttggcac cccgcttcca cccctgttaa | 7260 |
| cttagaggtg atcaatcttc atttgagcca aacagaccat cacagaaaac actgtgcctg | 7320 |
| tttatcttta ttattgaggc tttgtttcct ctttgtctgg atacatttca ataaggggt | 7380 |
| tgtttcagtc gttgaagcaa agaacaatt aaagatgggg aaatggtaaa agggtattca | 7440 |
| gagatcatca ctagctcttt tccaaaatgt ggagttttgt ggtcataaat attgtccacc | 7500 |
| taatgagcaa aaataaaaa taaaaaaaaa acaggaagca aatgttaagc tttcattcac | 7560 |
| cactgtcagt attaacgcaa gctttaaaaa atagcactat cagaaaagga tactaaagga | 7620 |
| gaattgacta gaaaagaatt gtggaaaatg gaaacgaata ttgatcactt aactagattt | 7680 |
| tgaggttatc agtagacagt gaccttgcag tacagctata gttgttggat ttaaaattta | 7740 |
| ggacaagtat tttaaagctt caaagtagtg cttttttttg ttaaaaatct gtaagatgtt | 7800 |
| ttaatgactg gagtgttctc tttgaatttg agg | 7833 |

<210> SEQ ID NO 6
<211> LENGTH: 965
<212> TYPE: DNA
<213> ORGANISM: Artificial Sequence
<220> FEATURE:
<223> OTHER INFORMATION: chemically treated genomic DNA (Homo sapiens)

<400> SEQUENCE: 6

| | |
|---|---|
| gattaattaa gggtatttta gaagttaggc gttttcgttg ttttttttga gtacggaggt | 60 |
| tattaatttt taggggaag agatgtagcg cgaggtaggg gtgtcgtgtt aagaaatttc | 120 |
| gacgttttg gggattgagg ataaaggtgc ggatacgatt tcggggtatt tggagtttcg | 180 |
| tgattcgcgt tacggacggt atatttaggg gttaatttt gttttgtttt aaagaatttt | 240 |
| aagttagagt ttttgttttc gtttatagtt tcgggatgtc gttgttgcgt ttatcgtata | 300 |
| ggtagcgttc ggatcggttg tagtagatcg cgcgttgcgc gttttatcgg agatggtgg | 360 |
| agacgttgaa aagtttttt ttgttatttt tggacgttgt gggcggtaag cgttttagtt | 420 |
| tttatttttt ttgagttgaa cgtttaggta tagtggaatt gaaattcggt tttttatttt | 480 |
| tgttgagttg aacgtttagg tatagtggaa ttgaaattcg gttttgcggg atgtgagagt | 540 |
| tgttgaggtt acgcgtaatt gggtgtgatg gagggcgttt gttcgtgatg tgtgtaggtt | 600 |
| tgatgtaagt aggttatcgt cgtgcgagtg tgtggatgcg atcgttcgag agattcggag | 660 |
| gtaggtttgg gatacgtttg agtgaatatt ttaggatatt tttttggtta gtatttgttt | 720 |
| tttagtgttt gtgatttaga gtgggtatat gttgggagat agtaatgggt ttgggtgtgt | 780 |
| gtaaatgagt gtgatcggaa gcgagtgtga gtttgattta ggtagggatt atatagtatt | 840 |
| gttatatttg tttgtttttt agtagaggat tgaagtgcgg gggtgggggt acgggtcgg | 900 |
| aatagaatgt ttttgggata tttttggtaaa tagtagtcgg aagtaaaggg gtagttgtgt | 960 |
| aaacg | 965 |

<210> SEQ ID NO 7
<211> LENGTH: 965
<212> TYPE: DNA
<213> ORGANISM: Artificial Sequence
<220> FEATURE:
<223> OTHER INFORMATION: chemically treated genomic DNA (Homo sapiens)

<400> SEQUENCE: 7

| | |
|---|---|
| cgtttgtata gttgttttt tgtttttcggt tgttgtttgt taagatgttt tagagatatt | 60 |

```
ttatttcggt ttcgtatttt tattttcgta ttttagttttt ttattaaaga gtaggtaggt      120
gtgatagtgt tgtgtggttt tgtttagat taagtttata ttcgttttcg gttatattta       180
tttatatata tttaaattta ttattgtttt ttaatatgtg tttattttga attatagata      240
ttaaaaaata gatattggtt agaagagtat tttgaggtgt ttatttaaac gtgttttaag     300
tttgttttcg agttttcgg gcggtcgtat ttatatattc gtacgacgat gatttgtttg       360
tattaaattt gtatatatta cgaataggcg ttttttatta tatttaatta cgcgtgattt      420
taatagtttt tatatttcgt agaatcgggt tttagttttta ttgtgtttga gcgtttagtt    480
tagtagaggt agggaatcgg gttttagttt tattgtgttt gagcgtttag tttagtagag    540
gtagggatta aggcgtttgt cgtttatagc gtttagagtg gtaagaaaga agttttttag    600 cgttttatt attttttcggt ggaacgcgta gcgcgcgatt tgttgtagtc ggttcgggcg     660
ttgtttgtgc ggtgagcgta gtagcggtat ttcggggttg tgggcggagg taaggatttt    720
agtttgaggt ttttttgaggt agagtagaaa ttagttttta ggtgtgtcgt tcgtggcgcg    780
agttacggaa ttttaggtat ttcggggtcg tgttcgtatt tttgttttta gtttttagaa     840
gcgtcgaaat tttttagtac gatattttg tttcgcgtta tattttttt ttttaggggt       900 tggtggtttt cgtgtttaaa ggaggtagcg ggaacgttta attttaaga tgtttttaat       960 tgatt                                                                      965

<210> SEQ ID NO 8
<211> LENGTH: 16579
<212> TYPE: DNA
<213> ORGANISM: Artificial Sequence
<220> FEATURE:
<223> OTHER INFORMATION: chemically treated genomic DNA (Homo sapiens)

<400> SEQUENCE: 8
tgttttttaa aatgatgttt agttgaatta gttaatggag ataaaaatat ttatatataa       60 tttttttta agtttattag ttattttata gattagttat aatttggtt attttaatga       120 gttaattttt tttagagat attataaatt ttttaaagat ggaaataat tgttattttt       180 ttgaataatg tttattattt aaaataatgt atataaaagt tgtttaataa attttttgttg   240 aattgagaga aaatataaaa aattgaaagt agtttgtttg taataagtgt tgttaagtt     300 ttatagattt ttttttttt ttggaattat tgtaataaat atttgatttt tgatttgtag    360
gattaaaatg tgatttttta tattttaata ggagtaagta ttagttttgt aattttttt     420 gttaatagaa taaaaatgga atgtatgttt gttgttttta tatgtcggtt gatatttatg   480
ttgaatattt ttttttataac gtagaggttt ttttgttttt tgtttgcgt tttattttttg   540 tttattatag agatattaat gatgttatgt gttttttgt attattagtg tagtagtttt    600
tattatgttt tttgtttcgg ttttattgta gtttaattaa ataaatggaa acgggtagtt    660
attgaaaata aatagtaatt gtaaaagttt tgttttttaa gaaattttt gtattgtatt     720 tcgtttttgtt ttattgattt taagattttt atcgttttt tgtgtttaga aattagattt    780
tttagtttgt tttgtttag ttagataaat gttttataaa aatgatttat attttttaga   840
ttgtggggag agaagaaaaa gattttgaga aagtgattaa ggagggagta agagtgatat    900
aatttttgat ttaatttagt tggattgtgt ttttatgtt tttattttt ttttataaa      960 aaagatagcg ttttttgatgt tttgttttag gtagttttt agggtgagtg tagatgtgtt   1020
gagttatttg gttgttttga ggatcggttt agagagtttt ttttttatt aatgaagtta    1080
```

```
tttttttttcg gtagttcggt tttttttatt attttatgtt ggaatttggt tttggtttgt    1140
atagttttgt cgtgatgtag atggttttt agtaagttt tagagaaatt tgtttaatta      1200
tgaataggat atttatagta taggagaaaa aaaaatttat taaaataaat attttattgt    1260 aatatttga tttgggggtt ggagagtaaa aatttaatat ttgatgtttg ggaaaaattt     1320
aatgttttat ggttttttaa ggaaatttgt ttgtgtttaa tttattagag taatttatat   1380
atttcgggtt aaagtataat gagattgtta ttattatttt gttttttgta agatttttt     1440 tttaagaata aaagaaggt aataaagatt ttatatttt gttttttta gaaagttaaa       1500 gagaatttaa agtgttggat gaaatgtttg ttttaattt gtagtgtttt atttaaaaaa    1560
aaaattatga tataattta gaggataggt ttttttttt tagggttttt gaaagttaaa      1620
agtatatttt taatttgtag tattattgta ttatttagtg aggataattt gtttagttgt   1680
gtttaggatt agttagatta aggagttgaa attaagtttt ttttgaattt gaatgggatt   1740
ggaattttgt tatttttaga gtagtaatag atgatgttat gtttaagaat atttattg     1800 attaataaaa aaggagaagt ttgaaatgta atttaaaga attttagaag gaggtttaga   1860
tgaagataat aaaattttt ggagatatat ttgttattta tattttttt ttttaagtta     1920 ttggttttgtt gttttgagt ttagttaaat ttttaaagat aagattaaag taaggaagta   1980
aggtatatag tttttggttt atggtttttt ttagatataa gtattgtgaa tgaagattt   2040 gttttattta tatttgggat tttggagttt ttataaagaa atttttagt ataaggatgt     2100 gatttaaagg gggatttata gaataatatt ttaattattg tttgatttat atttgagtgt    2160
aatggataaa taaatataat tttagttata aaatttgaaa aatatatatt ttttattta     2220 aaaattttg atagttttgt taggtattgg agaattagaa ataaatgttt ttttattttt    2280
ttttttttga tgaaggaaag ttattaaaaa tagttatata gaaataataa tataattgta   2340
gatttatttt taaatatagt tggtatgttt tttttttttt tttttattta tttttattt     2400 tagatagtta gagggaaag tttgtttag agatagaaag aagatattta tggggtataa    2460
ttttatttta gttatttgat agtttgaaga agtatttaat tttttgaata ataatgttat    2520
aagttaaaga agagaaaaga taggtagttt aaagttttt aatattgtgt atattttaat   2580
tttttaagtt agttttgaga aagtgttttt gttttgtaga agtatttggt taagtgttgt   2640
gaagtttatt ggtattaaaa gaaattaaaa attttggagg attagagaat taaatttggt    2700
aatataaatg aaaatatttt agaatgtaaa aagtatttaa tttattattt ttaattatgt   2760
tttattatat atagatggta ttatttatag tgaatgttaa ttattaatat ttttttaaaa   2820
atgggtatta atttgttatt agttgtttgt ttttgattta gttttttttt gttgaaaggt   2880
tttatttaat tgtattataa agggataaaa gggtaaaaga taataagttt tttagattgg   2940
tagatttgtt atttataaaa tggttttggg taggttattt gaattttttg aaatttaatt   3000
agatttattt aaatttaaga atgagaatat aaatttatat tttgaagtgt tttatagaaa   3060
ggtttatttt aatgttggaa gtatatattt taatgaatat ttattttatt ttattttttt   3120
ttatttttga attaagtaat tttgaattta agttgttat gattagtatt gaaaagatta   3180
ttggattatt aattgtgtga ttttgggata gtaattttt gtattttagt ttgtttatat   3240
gttatatatg aaggttgaag tttgattttg ttttgtgatt attattttaa atatttgatg    3300
aaattaaatt ttagtgtttg gaatggtagt ataataaatt tattaagaat aaataattta   3360
ttgtaaaaat atattgattt ttaaatgatg taattgatag ttatattatt gtagagggtt   3420
gataaataat aaaagaaatg aaagatgtat atggtgagaa ttgaaattat tttgataagt   3480
```

```
tttttatttg tttattattt aaaattaatg attatgttga atgtttataa attataaaat    3540
ataaaagaaa ttttataaat gcgtatgtat aggagtttaa gttattaaaa gttttaaagt    3600
ataagtttaa attaaattaa ttaaagaagt tgagaggaaa aattggtttt tatttttaat    3660
tattattgtt ttgaggtttt atgtttaata taattttttta agtagaggtt ttagagagaa    3720
gagttgtgag gatatttta tatttgtgta gaaggaaaag tttgttattt attttagtat    3780
ttttagtgtt atattgatgt gtattttgga tttattttgt ttttattgta taaatttata    3840
tttgatttta aagaaaagga aaatttaaag ttttttttt ttaagggggat agaaatttt    3900
tgtgttaatt gtttgatttt ttttttgta aggtttatt ggaaatttt tgtaatataa    3960
tgtaggggat ttttttatgt gttgatgttg tttatatagt ggggtgggtt tgattgaaga    4020
aaaaaaatcg tatatacgta tgaaagatta tggttttatt ttcggaaagt atgaaaggtg    4080
attgatattt ttaagaagtt tttgttattt aggaaaatta ttaaatattt tatttagaga    4140
tatttggaaa gattgaagga aaggaagaac gaagaaagta gaatttagat ttatgtgggg    4200
agagatttgt ggtagaggaa aagtatttt ttgaattcg ataagggatt tgtttggggg    4260
aatttttgt ttagtttttt attattaggg ttttttgaag tcgggttttt tattgggtag    4320
tttttttggga gtgtagtggg gaatttttat atttttttt taggttttcg aaggatttcg    4380
tttttttagt gttttttta ggttggtagg agttttgagt ttgatattt tttttgatgg    4440
gataggtaag ttttgtgggc gcgtaaatac gttgtaatta agtttttgt tgatttata    4500
gttttgtgtg ttttcgagaa gaagtgatcg tatttaattg tttattgttg gtttgttttt    4560
taagagtttg ggggttttt tttttaatt tagaattagt tgtacggggg gcggggaagt    4620
ggggggtgggg aaggagtggg agggtagtgg ttttcgcgag tagagcgatg ttattgagtg    4680
agttttgaa tggggagcgt tgttgttttt aagtcgattg gtatttttg ttaggaagaa    4740
acgttaagag gtgggagtgt ttggggaggg aggtaggcgg ttttttatcgt aggcgcgggg    4800
agttgttttt tcgtttttc gtttgttttt taagtttgga ttttaggag tggttgaagt    4860
tgcggagcgt ttttggagtt tgtgaatgaa ttttttttt tttttttt tttttttcg    4920
ttgagttttt ttttcggtt tgacggtata gtgatataat gatgatgggt gttataattc    4980
gtatttgaat ttgtaggcga gttgtttcga gttttttgg ggaagaattt taggcgtgcg    5040
gacgtaatag tcgagaatat taggtgttgt ggataggagt tgggattaag attttcggtt    5100
agtttcgtat ttttcgtat tttttagtat cgtttcgtat ttttcgtatt tttttcggg    5160
ttattacgtt ttttatgtga ttcgtttggg taacgtcgaa tttagtcgcg tagcgttgta    5220
gtgaattttt tttttaaatt gtaataagtc gtttttaag gtaattacgt ttttttgtt    5280
ttttttaa aaataaaaa taaaaattt atagaaaaa attcgcgagt ttagaaaaaa    5340
gaagtaattg gtagaaggtt ttaattaagg taaagagttg taaggcgaag ttaagaaaat    5400
gtaggtattt aaaaaatgta ggtaatttt ataaaggttt ttggggagag gtatatagag    5460
ggattttggt gttgaaaaag atttagataa aagaaattta gggtggggtg ggggtaaaat    5520
gattaacgga attgggggaa gggagggaat aaattgtaaa gaattatag aaaagtggtg    5580
ggttttttgag ttggagagaa gagagggatt tttggtattt tgatttttt gttgttgttg    5640
tttttaatac gttcgaggta aaagtttgaa tggggattat taagatttgt tatagataag    5700
ttttcgaagt cgtttggtg taggttattt ggttttttag ttttggtgt gtggttagtg    5760
tttggtgttt ttggaaagtt attttcgggt agttttgat agtgcgattc ggcgtttaag    5820
```

```
tagtttggga ttttgcgcgg atttgatttt tttagatcgt aggtagtttg ggaggaggtt    5880
cggtcgggga aggtgtagga ttttcgtcgt gttttttga cgatttgggg attgttacgg    5940
tttttttcg gcgttttgg gttttttgt tttgtacgcg gtgcgaaggg gttagtaggg    6000
aaggagtaga ggatggggg tggggttgtt ggagtttcgc ggaggtttgg gaggtttttg    6060
ggcgggaaaa gtttgttttg aatcggtagg gatgtgtaat aattttttt attttgaaga    6120
gtgaaatagg gtttgtcgtt tttattttaa taagtaaatc ggtatttaga gcgtattgta    6180
gataaaggtg gttcggggat tcgaattagg ggttttggg ttagtttttt cgtttagatt    6240
ataggagttt ttcgttttt tatatatttt ttattttttt ttagttttc gtttagttg    6300
agtaatttta ttggtaggtt tagcggtagc ggcgcgcgcg tgtgtcggga gtttcggggg    6360
acgttttcgg ttggagcgtt ttatcgtttt gtagaggcgt gggcgttgta gggcgatatt    6420
tttggtgcgt gtagatttag ggtattcggg ttgttttggt tcgcgtttg tgttattggg    6480
cgtggagcgg tttgggtgtt aggtagagga gagcggggta gaaaaatagt gttatagttt    6540
aaattatttg tttttaatt taattgcgtt tcggtaagtt ttgtatgttt ttgggagatg    6600
ttgcgggaag gggagaaat ttatacggcg tttggagagt tgttttgtcg cgcgtatatt    6660
cgcggtagag ttttttggg tcgcgtttt tattttgtg ttttttttg tttttatttt    6720
tttgttttt tttttttt ttagttttt gtttttttt tttagttttt gcgttttttt    6780
tttatagtt gataaatgaa tggttagtgt gaaattttg ttttttcgt gttttaaggt    6840
agtagggagg gaggagcgag ggaggcggtg cgttttttcg gatttgtttt tagtttagtt    6900
tataagattt gtagaattta gatgtttagg aattgggagt tttgcggcgg gtgtgggcgt    6960
tttttgatgg agaagtttcg tataggcgga gaaaaataag ttttttagat taagcgtgta    7020
tttttttataa ttttgtgttt aaggatggaa ggttttagtt ttttttaag ttatttattt    7080
tgtattttat aatttgcggc gtatatttag gagtttggag gattttgaaa aaaggttttg    7140
gtttgtgtaa agtgtagaga tgttttttcg cgagtcggtt ggaacgtacg cggcgttttg    7200
ggtttagttc gtcgtttagt ggacgaacgt atatggtcgg ggtggagtta ggtttcggag    7260
gtttagacgc gttatttgg gcgttttaa gaaagataat atatatatcg tgttttaaa    7320
atttatgatt atttgaattt aacggtaggg tttcgtttta ggatattgta aaagaagggt    7380
ttttaattta aaatttaaat ttttttaatt ttagggcggg cgtcggacgg gaaagtggag    7440
agaaggcggg tagtgggagg aaaaagaaa gggaaggaag ggaagtggaa ggaaagagga    7500
tcgtggaggg gaggaaaagg agaaaggaac ggagatgggg tagatggtat ttaaatagtt    7560
aggaacggat cggaagggtt cgtttcgggg tttgggtttg aatttcgaga ttcgttttag    7620
gatatttttt tttttttt agcggtaata aatgtgattg tagaggcgtg tcgggatgga    7680
agggtgggaa agaattagat aagcggaggt ggtttagttt cgtttaaagg ggttgggttt    7740
ggggttcgtt tttattcgtt tatttcgcgt taagggagga ttcgtaacgg gcgttttcg    7800
tagcggttgg gttagttagt cgttacgtgg gttggcgttt cggttttag tcgagacggg    7860
tgtgattttt tgggtttaga gattgtagta tagtcgtata ggcggtcggc gtagtcgagg    7920
ttttatttta tcgaggttaa tggggcggg gcgggaagg tagggtttag tttaatcgag    7980
agagtcgagt ggtttcgttt tcgggattcg gggtcggttg ttttggagt tgattcgagt    8040
tttatttaga tagcgttgaa tatttttatt aaaaggttat ttaagttta ttttatttta    8100
tttattttt gtttgtttt tgggagtggt aggagggta tcgtgttttt gttttgaggt    8160
agggagagg ttaaaattta ttttaagtaa atttttttgtt agaaaaatga gattttatat    8220
```

```
cgtattttat ttgttgattt tttaaatata tttaggttat tttaaagttt attttttagtt      8280 aattaataga ttaatttcgt tttagattgt tataaagagt tcgtttggaa tggtaaatat      8340
tgttattcga taagattaat agaattttat ggggtaaat atggaagggt tgcgagtgta       8400
attgaggttt ttgtgtttta atgaggaatt ttagcgggga tttggcgggg attggaagtt     8460
tagtatttat ttagggagtg attgagttgg aaatttggag aagtttggtg tagacgagac     8520 ggtgttttt agagttgtat tttaagtttt tttattttgt tgtatattgg aagaattgga      8580
ttttaaagat ttttttatt attttagatt ttgtagttaa tagttacgtt ttttttttt       8640 tgtttgttga aagttgtgat ttaattgttt taagtattt ttgataattt cgttaaattt      8700
attttgaaaa tatttatata aagttttaaa ataggatgtt gtgagtgtaa tataaaaata    8760
ggaaggtatt aatggaagta ataattagtg ttttgagata gaagcggttt ttagtttgta   8820
atttggaaat gttaagagta gtatattagg gagaaggttt ttaagagttt gatttttttgt  8880 tttgagtttt gagtaaagaa agaaatatgt tagaattgta ttgtttgttc gtagtaatat  8940
tgtaaagggt tttaatggat tttaatgtga ttgagtaatt atttttttta gtattaagtt    9000
tatagttttt aatttttttg tgagaagatt aggtaggaag cgggatgaga tttaagataa  9060
ttatttagga tttatgttag aatttaaagt tttgattttt ttggtagata aaaatagagt   9120
tggttttaaa ttgtatttttt tgttttttaaa aaacgaggt ttgaaaggaa ttttttttaga 9180 tttatatagg tttatagatg taagtttttt tttttttttt gtgtttgtaa attggaggga   9240 gatgttttg atattttaga atatttgtat ttatatattt gtaaattttg ttaggaaagg  9300
atttaaatag ttaaattaaa ggtgattatg attaatgtta aagatattat ttattgtttt 9360 ttttttttgtt gtattattag gtttaaatat tttggagtta atgattggtt atttaattga    9420
gtaatagagt ttttgagagc gtaaagatta attaattttg tttttttaaag tttggtaatt  9480 aagttttttt tttttggtga gatttaaata ttttttgtta cgttatttat ggataaaatat   9540 cggtaaatat tgtatttaaa atgggatatt gttttgtgat ggagtagaat tttttaagat    9600
atatggtttt tttgaaagaa agaattaatg attgtagtaa ggtatttttt tattatttac   9660
gtagagaaat tagttaggat tgataaatat ttattgttgg gagttatttg ttttggtttg   9720
agaaaatatg ttgattgtta tataggtttg tatttatta gaaaatataa agtatgtatt   9780 tttttttgatt tggaattaga aaagggggat tagatatgga tgtttttggtt aagttttatt 9840 ttaattagtg aattttttgtt agttttttttt tgtagtttag atttggtaaa ttatatatat  9900 ataagtttg tgtgtgtgtg tggggtgcgt gtgtgtgtgt atgtatatag ggttttttaaa   9960 tattgttaag ttttttattat tgaatgtgtt agaggtggtt gtattttaga ggttagtata  10020
aagaattttt gtttaatgtg ttagttttgt tttttgaaat atattttttgg gtagatttat  10080 taattataaa aggatataaa tgtatatatt ttttatattt gtatatattt tatttttattt 10140 ttttaaggat tttaagaggt gtttatgttt ataaaatgag attatatatt ttataataaa   10200
tatatttgat aaattataat tttttttatta ttaaattatt gatttgatat tatttgaggt   10260
atagtggaat gagtattaga tttggaatta gaaagtttga gttggattta ttagttgaga  10320
aaattaagta aagatattat ttttggattt ttagtgttat aatttattaa atgaatatgt   10380
agttataaag attaaaagag taagtattttt gaaaaattat ataaaaaagg gatgataata 10440
tattatgttt tgggatttat attgatttaa ttttataatt ttaataataa ttgtattatt     10500
taagttatgt agttttttatt gaattataa aataaattag agaggggtat attgttttaa  10560
```

```
aaattgttta gttttattaa ttagaagata gattatagaa attgatttta atgaagttgg    10620
atatttagtg gaaaggaaga attatttaat aaatggtttt aggataattg atgggtttat    10680
gtaaaataag aattagtttt tatttgattt tttattttaa aagaaatata agatgaatta    10740
aatatgaaat gtagggaata attttttata aaatgataaa agaaaattat gggattaaaa    10800
aaaataagtt aggaatagag aaattgtttt taagtaaaat ataaaattta gtgttatttt    10860
aggaaatatt gataggtttg attaagtaaa aattatataa aagtaaataa tatatttgga    10920
aaatatttac gatatttgag agataaaaag ttaataattt ttgatatttt atggattttt    10980
atgaataatt ttgaaaagtt tatatttatt aaaatatgag taaaaattat gtataggtag    11040
tggtagaaag agatatagag ttttaaaatt atagaaaaaa tcgtttagtt ttatttgtaa    11100
ttaaataaat agtaattaaa atattaatga tatgttatat tatttttta ttaattagag     11160 gagtaataaa aaaaaataat ttttttttt tttttttttt ttgagatgga gtttgttatt    11220
taggttggag tgtagtggta cgattttagt ttattgtaat tttcgttttt taggtttaag    11280 taatttttt gtgttagttt ttttagtagt tgggattatg ggtatttatt attatgtttg     11340
gttaattttc gtgttttag tagagtgggg ttttattatg ttggttatgg tagttgattt     11400 tgaattttg attttaagtg atttatttat tttagttttt taaagtgttg ggattatagg     11460
tatgagttat tgtgtttggt aaaaatgaaa ttaaaaagtt tgatgtaagt ttgtgttggt    11520
taggttgtgg agaaattggg ttttttatat attgttgtat gaaagtaaat aggttttttt    11580
attttaaaaa ataatttggt aattattttt ttttgatttt ttattaaaag ttttaaaag    11640 atgtatatat ttttgattt agtaatttta ttttcgata ttattatatg gatggatatt     11700
ggtattaata ttatttaaga taaatggata aggatgtttt ttgtagtatt gtttttaaga    11760
gtaaatattt ggaaatagtg taataggttt attatagga attatttaaa taaaagttgt    11820
tgtatttatt taatggaaaa ttatgtagtt gttaaaaata atatggaaaa attgtatttg    11880
ttgatttgga atattttta aaatatattg tattttaagt gaaaaaattg atagataaaa    11940
ttgagtatat attatatatt taattatgta aaatgggtgt atatttattt ttttaataaa    12000
tatttattga gtgttttagg tattgtggat ataggagtga ataaaatatt aaagattgtt    12060
ttgttggaat ttttattatg gtaggtagag aaaggtaatt tttaattata tatgtaaaat    12120
ggtgatatgt gttaggatga aaatagagta tgggaaaggg aatagagtat agtatgtttt    12180
aggtagagta atgagaaagg agtttattag gtagagaata gaggagtgtt aagggggcgat    12240 aatgtgaaaa agtttagtta agtttaggtt taggaattta tatgatgtta ttatttgtat    12300
gaagtaaatt tatgaaattt cgtatttaaa ttacgtgatt tttttttgtt gtataatgat    12360 ttttttgtg agaaagaatt agtgagtaat atgatatgtg atgtttatta tatttatttt     12420
gtagttgaag tattttagaa agttggttgt ttagggtatt taattagtag aatggtggat    12480
aaaattatcg tgttttgtt tttaagttat ttttgttag ttgagttttt ttaaaattaa     12540
gggagaatat taaatattta tttaatagaa ttttggtttt tttcggagg ttgtttattt     12600 ttggtgtgtt tttatttt ttgtagata tttttatgg ataggagttt tattgatttt       12660
gttttttatg ttttttaggt aattaaatag tttagtatt ttgtatttgg attgtttaat     12720
gatttttttt ttttttatt gatttattg gagtagaagg ttaaatatag gtatttattt     12780 ttatatttt taggtttttt tatgtagata gagttgttat tattagtaga cggtgtttat     12840
aagagagata tggaaaagtg gaagaatgga aatagggatt tggagtggtg ttaaaaataa    12900
agaaagaggt ttttgaaagt tttttatttta atatgattaa atatagaaga taaaagatgt    12960
```

```
aatttaatga ttaaggatag ggatatagtt ttgagaaaat tatagaagtg gaatgaacgt    13020
tttggatttt aaagaagagg gaatggaaat gtagttttga ggtagttaaa gttaataaag    13080 tttttttgata tatttattgt agaaataaat gattatttt taatttaagg tttgtaaatt    13140
taggtgatta taggggcgag gtatggagtg gaaatgggta agagattaag tggggtagt     13200 aatggttttg agtatataga tttaagggga gagattgttg tttggttaat gtttatgatt    13260
agttagttga aatatagatt tagtgttgtt agatttttg attttttgaa agaagttaga     13320
gattttatat ttagtgtaaa tagtttaatt tttaaattga gtaatttatt taaatatatt    13380
tatgtaattt atttaaatgt atttagagta tgtttgattt tttttttgta ttttttattta   13440 gttttagggg taattttaag gaaagtgatg cgtatatttg ttgtatttat gtagatggag    13500
gattattttt tttttttaa taaaagatat tttataagg attgagtgtg gtataaagag      13560 ttcgatttt agtatttaaa ttgagtagga aatttaaata tagaagatt tttttgggt       13620 tatattttg gttttttaa atgagatttg attttttaga tattgataaa tattatatta      13680
ttgggttatg gtaaatttt aagtggattg atttaaagt gtttaaaagt attttaggtg      13740
ttaaggaatt gttggtacgg agttttaaag gtgttttgt ataagaaata gaggcgttga     13800 ttatgtatt gattatataa tattttttaa ggatatattt tgaatttggt aatgaagaaa     13860
tattgtggga attattaagt tgaataaagt attagttttg tttttagaa gtttattgtt     13920 ttatagagga gattagatat gtttatagat aatttgaagt atatagtaat aaattatagg    13980
atgatttatt ttaagtataa agtgtatatt gttattatag tggtaattta ggttataatt    14040
tttaaatgta agagttttaa atattatttt ttttatttt agtgatatga aattatgtta    14100
gaatatttgt agaaagtttg aattagtaat tttaataata atattgagt attgatatat    14160 tgtatattat tgagatttat tttatatata ttatttatt aattttatg attatttcgg     14220 taagtattaa tttttataat taagtagtga tagaaaatga ggtttagaga gatatagtat    14280
tttatttaaa gttatagaat ataagtagag aatgtagaat ttgtatttg ggttatttga    14340 tagtggagtt tagatttta aaattaggtt tataaagatt ttttggaaaa aagaaaat      14400 aaaaaataga gaataaattt ttttgaagaa aagtaggaaa ttattattta taagtataat    14460
taaagagaga tttttaattt tttttttttt ttttttttg agacggagtt tcgttttgtc     14520
gtttaggcgt aattttagtt tattgtaatt tttattttc gggtttatgt tataaagaaa     14580 gttttatt gattggttcg atttgattgt ttattagaat ataggttttt tagtagggtt     14640
aataagttat aatagtttta gtgatataag ataaatataa attaataata aggttaattt    14700
agaattatta atatatgttt tttattgtga attattagtt ggtttataga tggaaaatat    14760
aagatatata atgtattagt ttaaaaaatg ttttttagag agtgtttaga attatagaat    14820
ttaaaatttt tgttttgaaa aggtttaatt tttattttaa aatatataaa gaattaaat    14880 gtaaaaaaat taagagaaaa ggttttaatt aattaaatgt tgtataattt taagtttat     14940 ttatgtttaa gattagtttt gtaatttatg attaatttta gtattagttt gttttaatt    15000 taggtttgtt aaataatata gaatttttt tttaatgaag tttttaggg ttttagttga     15060 aaaatatata ttagttagga tgtttttaat tgtaaggaat aaaaagttac gatttattg     15120 ggtttaaata ataatgatat ttataattt atataaaatg aagtttaaag gtatggttta    15180
ttttaggttt aatttttaag gatttacgtt ttgttttgt tgatttttt ttagttttat     15240 ttttagaggt atttattta tttatggatg taaaattttt ataatagttt tagtagaaag    15300
```

```
attttagtat gataatgttt agggaagaaa attgattatt tttttttttg tttttttttt    15360
aggatgaatt tattttttt agggatttt tattggagga agagattttt ttatatttta      15420
ttggttaaaa ttatattata tattgtttta aatttaatta ttggaaaagg gaatggtatt    15480
tttataattg atttaggata ttaggattat ttttggttt ggggtttgat ttaggatttt     15540
ttaaagtatg tgattgaggg taggtattag aatggaatta gagttgtgtt agaaaggaga    15600
aacgtatggt tattatagaa tagttttaaa tgttatcgag gagggtataa ttgtaaaaat    15660
taaataattt tttgttattt ttttgaagtt ggtattttga tttttagatg gttttttaat    15720
ataggttttt tttttttta ttattatagt tgttttgaaa tttgagttgg aagggaatat     15780
tttgagattt agattgttaa atgttttttt taaagttatg taataaatta aatggtaaag    15840
ttagggtagt tttttgattt agtataggt attttttttt atttttatt tttgagattt      15900 tagaattgtt ggtattgttt taaaatttat ggtaagaatt ggttattttt gtaattaata    15960 ttttttata atatatttgt tttgttgtt tagttagtta gaaattatat ggagtttgtg      16020
ttttaaaaag tttgtcgaag tttttatttt ttgttttggt attatgtgta tgaattatta    16080
attggttttt tttattttta tatttgatga agatgttttt tttttaatat ttttttttat   16140 tgtttttat tttttttgt tttatttatg attagttgtt tgtttttaaa tagatttgt       16200 ggttatttat tttttttgt gttagttttt atttattagt tatttgaatt gtggttttta     16260 ttgttttta tatagtttat ttatttgtgg ttgttatata tatttatatt gttatatgtt     16320
tttaaattgt attttggaat gattttggta atggttgtat tggatgagat ttaaattaat    16380
aattaaagta ttgagatagt tttttgttatt ataagtttat ttttgttttt atagtttaag   16440
aggagttatt ttttttattt ttattattta atgtttaata ttattttat tatatataat     16500 gtataaaaag tatgtgattt atgatttatt ttaaatttga atgtttgtga tttatttgt     16560 gttttttttt attttagg                                                  16579
```

<210> SEQ ID NO 9
<211> LENGTH: 16579
<212> TYPE: DNA
<213> ORGANISM: Artificial Sequence
<220> FEATURE:
<223> OTHER INFORMATION: chemically treated genomic DNA (Homo sapiens)

<400> SEQUENCE: 9

```
tttagaaatg aagaaaaata taaagtaaat tataagtatt taggtttaaa gtgggttata     60
aattatatgt tttttgtgta ttgtatgtaa taagggtagt attaagtatt aagtaataag    120
agtagaagaa gtagttttt ttggattata aaaataggag taaatttgta atagtagaag     180 ttatttaat gttttaatta ttagtttgaa ttttatttaa tgtagttatt attaaaatta     240
ttttagaata tagtttggga atatataata atgtggatgt gtgtgataat tataagtgag    300
taggttgtat gaagaataat agagattata gtttaagtaa ttagtggata ggagttggta    360 taaaagaaa tgggtgatta taagtttat ttagaaatag atagttgatt ataaatagag      420
taagagaaga tggggagtaa tagagaaaga tgttgaaaga aaggtatttt tattaagtgt    480
aaggtgagaa ggaattaatt ggtggttat gtatataata ttaaaataga gaataaggat     540
ttcggtaggt tttttaaagt atagatttta tgtagttttt agttggttaa gtaaataaaa    600
taaatgtatt ataaggaggt gttaattata aaagtgatta gttttttgtta tgaatttta    660 agtagtatta atagttttaa agttttaaga gtaaagaatg aaagaaaata ttttgtattg    720
agttaagaaa ttgttttggt tttgttatt aatttattgt atgattttgg aaaagatatt     780
```

```
taataatttg ggttttagaa tgttttttt tagtttaaat tttaaggtag ttataatgat      840
gaggaggaga agaatttgtg ttggggaatt atttagaaat taaagtgtta aattttaaaag     900 aatggtaaaa gattatttgg tttttatagt tgtgtttttt tcggtagtat ttagaattat     960
tttataatag ttatgcgttt ttttttttta atataatttt ggttttatt tagtgtttat     1020 ttttagttat atattttgga gaattttggg ttaaatttta gtttaaggga tgattttgat    1080 atttaagtt aattatagag gtattatttt tttttttaat gattggattt ggaatagtat    1140
ataatatagt tttggttagt gagatgtgag gggattttt ttttagtga agggttttg      1200 ggaaagatag atttattttg agaagagaat aaaggaagag gtggttagtt ttttttttg    1260 gatattatta tgttggaatt tttttgttgg aattgttgta gggattttgt atttatgagt    1320
aagtgagata ttttggaaa tgaagttgag aaagaattag taaaggtaag gcgtaagttt    1380
ttaaggatta gatttagagt ggattatgtt tttgaatttt atttatatg agattataaa    1440 tgttattatt gttaaattt aataaaatcg tgattttttg ttttttatag ttgaaagtat    1500
tttaattggt atatatttt tagttgggat tttgaaaaat tttattggaa agaaatttt    1560 atattattta gtaaatttag attgaaaata agtaatgtt gaaattagtt ataaattata    1620
aaattgattt tgaatataaa tagggtttgg agttgtatag tatttaatta attaagattt    1680
ttttttttaa tttttttgta tttgattttt ttatatattt tgaaataaga attagatttt    1740
tttaaaataa aatttttaaa ttttataatt ttagatattt tttgaagagt attttttaag    1800
ttaatatatt atatattta tatttttat ttatagatta attgataatt tataatgaaa    1860
aatatatgtt gataatttta aattaatttt attattagtt tgtatttatt ttatattatt    1920
agaattgtta tgatttgtta attttattgg aaagtttatg ttttagtaga taattaggtc    1980
ggattaatta aatagaaatt tttttatgg tatgaattcg ggaggtggag gttgtagtga    2040
gttgagattg cgtttgggcg atagagcgag atttcgtttt aaaaaaaaaa aaaaaaaga    2100 aattaaagat ttttttttaa ttatatttat aaataataat tttttatttt tttttaggaa    2160
aatttgtttt ttatttttta tttttttt tttttaggaa atttttataa gtttaatttt    2220
aaaagtttgg gtttattgt taaatagttt agaatgtaag ttttgtattt tttattata    2280 ttttgtgatt tgggtaaaa tattatattt ttttaaattt tattttttgt tattatttag    2340
ttgtgaaaat tagtatttat cgaagtgatt ataggaattg ataaaataat gtatataaa    2400 taaattttag tgatatata tatattagta tttaatattt attattaaaa ttattaattt    2460
agattttttg tagatgtttt aatatagttt tatattatta agagtaaaaa gaatagtatt    2520
tggggttttt atatttgaaa attataattt aggttattat tatagtagta atatatattt    2580
tatgtttgga ataaattatt ttataattta ttgttatgta ttttaaatta tttgtaaata    2640
tgtttaattt ttttttgtaga atagtaggtt tttggaaggt agagttagta ttttattaa    2700 tttaataatt tttataatat tttttattg ttaggtttag ggtatatttt tgaggaatgt    2760
ttgtagatta aatatatgat taacgttttt atttttatg tagaaatatt tttgaaattt    2820
cgtgttaata attttttaat atttgaaata ttttgaata ttttgaatt agtttatttg    2880 aagatttatt atgatttaat aatatgatgt ttgttaatat ttagagagtt aaattttatt    2940
taaaaaaatt aaaggtgtga tttaggaaag gatttttttgt atttgagttt tttatttaat    3000
ttaaatatta aaatcgaat tttttgtgtt atatttaatt tttataaaag tgtttttgt    3060 tggggagagg agaatggttt tttatttata taggtataat aagtatacgt attatttttt    3120
```

```
ttaagattat ttttaagatt aggtaagaat ataaggagga gattagatat gttttaaata    3180
tatttgaata agttgtataa atatgtttga ataagttatt taatttaaaa attagattgt    3240
ttatattaaa tataaaattt ttaattttt ttaaaaaatt agaaggttta gtaatattaa     3300
gtttatattt tagttggttg attatgagta ttaattaagt agtagttttt ttttttaagt    3360
ttgtgtgttt aaggttatta ttgttttat ttagttttt atttatttt attttatgtt      3420
tcgtttttgt agttatttaa gtttgtaaat tttgaattaa aagatgatta tttattttta   3480
tagtaaatat attagagggt tttattgatt ttagttgttt tagaattgta tttttatttt   3540
ttttttttg gagtttaaga cgtttatttt atttttgtaa ttttttttaag gttatgtttt   3600
tattttggt tattaagtta tatttttgt tttttatgtt tgattatatt aaatggaaag     3660
ttttagaag ttttttttt tgttttagt attatttaa attttatttt ttatttttt        3720
attttttat gttttttta taagtatcgt ttattagtga taataatttt gtttgtatgg     3780
aaagatttga gagatatgag agtgaatgtt tatatttagt tttttatttt agtgaagtta   3840
atgagaaggg aagaaagtta ttgaataatt taggtatagg gtattgagat tgtttaattg   3900
tttgggagat ataaaagata aggttaatgg aattttatt tatgagaaat gtttgtaggg    3960
aggataaggg atatattagg gatgggtagt tttcgagaga aagttaagat tttattaaat   4020
agatatttag tatttttttt tgattttggg gaagtttagt tgataagggg tgatttaagg   4080
atagagatac ggtggttttg tttattattt tgttaattag gtattttaga taattaattt   4140
tttaggatat tttagttata aagtggatgt aatgagtatt atatattata ttgtttattg   4200
gttttttttt atagaaagaa ttattgtata gtagagagaa attacgtgat ttaggtgcga   4260
aattttatga atttatttta tataagtaat agtattatgt gaattttga atttggattt    4320
ggttaagttt ttttatattg tcgttttta gtattttttt gtttttgtt tggtgaattt     4380
ttttttatt attttattta agatatattg tatttattt tttttttat gtttatttt      4440
tatttagta tatattatta ttttgtatat gtgattggga attgtttttt tttatttatt   4500
atagtaaaag ttttaataga gtagttttg atgttttgtt tattttgta tttataatgt    4560
ttagaatatt tagtaaatat ttgttaaaag aatgaatata tatttatttt atataattag   4620
atgtataata tatatttagt tttatttatt aattttttta tttagaatat aatatatttt   4680
ggagaatgtt ttaaattagt aaatataatt ttttatgtt attttgata gttgtatagt     4740
tttttattag gtggatatag taattttat ttaaatggtt tttatgatg agtttgttat     4800
attgttttta gatatttgtt tttagaagta atgttgtaaa gaatattttt gtttatttgt   4860
tttgggtgat attggtatta atatttattt atataataat gtcgagaagt ggaattgttg   4920
aattaaagag tatatatatt ttttaaaaat ttttgataaa gaattaaaaa aaagtgattg   4980
ttaaattatt ttttgaagta gaggaattta tttattttta tataatagta tatgagagat   5040
ttagtttttt tataatttgg ttaatataaa tttgtattaa attttttaat tttatttttg   5100
ttaggtatag tggtttatgt ttgtaatttt agtattttgg gaggttgagg tgggtgaatt   5160
atttgaggtt aggagtttaa gattaattgt tatggttaat atggtgaaat tttatttat    5220
taaaaatacg aaaattagtt aagtatggtg gtgggtgttt ataatttag ttattaggga    5280
ggttgatata ggagaattgt ttgaatttgg aaggcggagg ttgtagtgag ttgagatcgt   5340
gttattgtat tttaatttga gtaatagatt ttattttaaa aaaaaaaaa aagaaaaaaa   5400
ttattttttt ttgttatttt tttgattggt gaaaaatgg tgtagtatat tattggtgtt    5460
ttaattatta tttatttaat tatagatgag gttgagcgat ttttttttata attttaaaat  5520
```

```
tttatgtttt tttttgttat tatttgtata taattttttgt ttatattttg atagatgtgg    5580 atttttttaaa gttatttata aaagtttatg gaatattaag agttattagt ttttttgtttt   5640 ttaaatgtcg tagatgtttt ttaaatatat tatttgtttt tgtgtaattt ttatttagtt    5700
agatttatta gtatttttta gaatggtatt gggtttatg ttttgtttag aataggtttt     5760 tttatttttta atttattttt ttaattttta tgatttttttt ttattattttt gtaaaaagtt  5820 attttttata ttttatattt gatttatttt atattttttt taggatgaga aattaggtag    5880
agattgattt ttattttgta tggatttatt aattgttttg aaattattta ttgaataatt    5940 ttttttttttt attgaatgtt taatttttatt ggagttaatt tttgtaattt gttttttgat   6000
taatgaaatt aaataatttt taaaataata tgttttttttt tgatttatttt tatagattta  6060 gtagaaatta tatggtttgg gtaatgtagt tattattaaa attatagaat tagattaata   6120
tgaattttaa gatataatat attattattt ttttttttgta tagttttta aagtatttat    6180 tttttttgatt tttataattg tatatttatt taatagatta tgatattaaa ggtttaaaag  6240 taatatttttt gtttggtttt tttagttagt gagtttaatt taaatttttt gattttaagt   6300
ttagtgttta ttttattata ttttaagtaa tattaaatta ataatttaat aataaaaaga    6360 ttataaattta ttaaatatgt ttattgtaaa atatgtaatt ttattttata gatataaata  6420 tttttttaaaa tttttagaag aatgaggtag gatgtatata gatgtggaaa gtatatatat   6480
ttgtattttt ttatagttgg taaatttatt tagaggtgtg ttttaggaaa tagaattgat   6540
atattaaata aagattttttt gtattgattt ttgaaatata attattttta atatatttaa    6600
tggtaagaat ttagtagtgt ttaaaaattt tgtatatata tatatatata cgtattttat    6660
atatatatat agatttttata tatatgtaat ttattaagtt taggttataa gaggaaattg   6720
gtaaaaattt attaattgaa atggagtttg gttaagatat ttatatttaa tttttttttt    6780
ttgattttaa attagggaga gtatatgtttt tgtgtttttt ggtaaaatat agatttatgt   6840
aataattagt atattttttt agattagagt aagtaatttt taataatgag tgtttgttag   6900
ttttaattgg ttttttttacg tgggtggtga aaaaatatttt tattatagtt attaattttt    6960
ttttttaaaa gaattatgtg ttttgagaag ttttgtttta ttatagggta atatttttatt   7020 ttaaatatag tgtttatcga tgtttgttta tgaatgacgt taataaaaat gtttaaattt   7080
tattaggaaa ggagggttta gttgttagat tttgggagat agagttagtt gattttttgcg   7140 ttttttaaagg ttttgttatt taattaagtg attaattatt aattttaaag tatttaagtt   7200
taataatata ataaaagaga gaataatggg tagtatttttt aatattaatt atggttattt   7260
ttggtttagt tgtttaggtt ttttttttagt agaatttata agtgtataga tataggtatt   7320
ttggaatatt aaaggtattt tttttttagtt tgtaaatata gggaaaaaga agaaatttat    7380
atttgtaaat ttatgtaaat ttagggggat ttttttttaaa tttcgtttttt ttgaaagtag   7440 gaaatataat ttaaaattaa ttttgttttt tatttattaaa agaattaaaaa ttttgaatttt   7500 tgatataaat tttaaatgat tgttttgaat ttttatttcgt tttttatttta attttttttat    7560 aagaagatta aggattgtgg atttggtgtt ggaggaagta attgtttaat tatattggaa   7620
tttattggaa ttttttatata tattattgcg ggtagataat ataattttaa tatattttttt    7680 tttttattta gagtttagaa taagaagtta gattttttgga gatttttttttt ttgatgtatt    7740 gttttttaata ttttttaagtt ataaaattggg aatcgtttttt attttagaat attaattgtt   7800
gtttttattg gtattttttt attttttatat tatatttata atatttttatt ttaggatttt   7860
```

```
atgtgaatat ttttaggatg ggtttggcga aattgttaag aagtgtttaa aataattagg    7920 ttatagttttt tagtagataa aaagaaaaag acgtggttgt tagttataga atttgaggtg    7980
atggaaaaga ttttttaaaat ttagttttttt taatatgtag taaaatggga ggatttaaaa    8040
tgtagtttta agaagtatcg tttcgtttgt attaagtttt tttaggtttt tagtttagtt    8100
attttttaaa taggtgttga gttttttagtt ttcgttaggt tttcgttaag gttttttatt    8160
gaggtatagg aattttagtt atattcgtag ttttttttatg tttgttttta tgaaattttta    8220 ttagttttgt cgaatggtag tatttgttat tttaggcgaa ttttttatga tagtttggaa    8280
cgaaattaat ttgttaattg attaagaatg ggttttagag tgatttgaat gtatttaaaa    8340
agttaataaa tggaatacgg tataaagttt tatttttttg ataaaaagtt tgtttggagt    8400
aaattttaat ttttttttttg ttttaaaata aaagtacgat gtttttttta ttattttttaa    8460 gaagtaagta aaataaaaat aaaataaaat aaaatttaaa tagttttttta ataagagtgt    8520 ttagcgttgt ttggatggaa ttcgggttag ttttagaagt agtcggtttc gaatttcggg    8580
ggcgaggtta ttcggttttt tcggttaagt tgggttttgt ttttttcgtt tcgttttttat    8640 tggtttcggt gggtggggggt ttcggttgcg tcggtcgttt gtgcggttgt attgtagttt    8700
ttgagtttag gaagttatat tcgtttcggt tgggagtcga agcgttaatt tacgtggcgg    8760
ttggttaatt tagtcgttgc ggggagcgtt cgttgcgggt ttttttttttgg cgcgaggtga    8820 gcgagtgggg gcgggtttta gatttagttt ttttgggcgg ggttggatta ttttcgtttg    8880
tttagttttt ttttattttt ttatttcggt acgttttttgt agttatattt gttgtcgttg    8940
ggaaagggaa aagagtattt taaaacgagt ttcgaaattt agatttaaat ttcgaaacga    9000
attttttcgg ttcgttttttg gttgtttgaa tgttatttgt tttattttcg tttttttttt    9060
tttttttttt ttttttacggt ttttttttttt tttattttttt tttttttttt tttttttttt    9120
tttttattgt tcgttttttt tttattttttt cgttcgacgt tcgttttgaa gttgaggaag    9180
tttaagtttt ggattaggag tttttttttt gtaatatttt ggggcggggt tttatcgttg    9240
ggtttaagtg gttatgggtt ttgagagtac ggtatgtgta ttattttttt taaagacgtt    9300
tagggtggcg cgtttagatt ttcgaaattt ggttttattt cggttatgtg cgttcgttta    9360
ttaagcggcg aattggattt agggcgtcgc gtgcgtttta gtcgattcgc gagaaggtat    9420
ttttgtattt tgtatagatt aagattttttt tttagggttt tttaaattttt tagatgtacg    9480 tcgtagattg tggagtgtaa aatgaatgat ttaagggaaa attagggttt tttattttttg    9540 aatataaggt tgtgaaagat gtacgtttgg ttttgggggt ttgttttttt tcgtttgtgc    9600 gggattttttt tattaggggg cgtttatatt cgtcgtaaaa ttttttaattt ttagatatttt    9660 aggttttgta agttttgtga gttgaattgg gggtagattc gaaggagcgt atcgttttttt    9720 tcgttttttt tttttttgttg ttttggagta cgggaaaggt agggatttta tattagttat    9780
ttatttgtta gttgtggggg aggggacgta gaagttagag agagagaata gaggttggga    9840
gaggggaagg gaggtagaga agatggagat agagggagat ataaagatga ggaacgcgat    9900
ttagagagat tttgtcgcgg gtgtgcgcgc ggtaggataa tttttttaggc gtcgtgtaga    9960 tttttttttt ttttcgtagt attttttagg gatatgtagg atttgtcgag acgtagtggg    10020
attggagagt aaatagtttta ggttatgata ttatttttttt atttcgtttt tttttgttta    10080
atatttagat cgttttacgt ttagtgatat agatcgcggg ttagaataat tcggatgttt    10140
taggtttgta cgtattaggg atgtcgtttt atagcgtttta cgttttttgta ggacggtggg    10200 gcgttttagt cgaggacgtt tttcggggtt ttcggtatac gcgcgcgtcg ttgtcgttag    10260
```

```
atttgttagt aaagttgttt aattagagcg gagaattagg agagggtggg gaatatgtaa    10320
ggaaacggag gattttttgta gtttgggcga gaggattgat ttagaggttt ttgattcggg    10380
ttttcgagtt attttttgttt gtagtgcgtt ttgggtgtcg gtttgtttgt tgagatggga    10440
gcgatagatt ttattttatt ttttagggtg agaaaaattg ttgtatattt ttgtcgattt    10500
agaataggtt ttttttcgttt aggggttttt tagattttcg cggggttttta ataattttat    10560
ttttatttt ttgtttttttt tttgttggtt ttttcgtatc gcgtgtagga taaaagaatt    10620
taggggcgtc gggagagaat cgtgatagtt tttaagtcgt taaagagata cggcggggat    10680
tttgtatttt tttcggtcgg attttttttt agattgtttg cggtttgaag gggttaggtt    10740
cgcgtaaggt tttaggttgt ttgggcgtcg ggtcgtattg ttaggagttg ttcgggagtg    10800
gttttttagg aatattaggt attgattata tattaggggt tgggaaatta ggtggttttgt    10860
attaaggcgg tttcggggat ttgtttgtgg taagtttttgg tagtttttat ttaaattttt    10920
gtttcgagcg tgttaagaat aataataata aaaaaattaa agtgttaaag gttttttttt    10980
ttttttttagt ttaagaattt attattttttt tatgattttt ttataattta ttttttttttt    11040
tttttttaatt tcgttagtta ttttatttttt attttatttt gggttttttt tgtttgaatt    11100
tttttttaata ttaaggtttt tttgtatgtt ttttttttaaa agttttttatg aaagttatttt    11160
gtattttta agtgtttata tttttttaat ttcgttttat agtttttttgt tttaattaaa    11220
gttttttatt aattgttttt ttttttttaag ttcgcgggtt ttttttttata agtttttttgt    11280
ttttgttttt taaggggggga ataaaagaaa cgtgattatt ttggaaggcg gtttattgta    11340
gtttgggggg aaaatttatt gtagcgttgc gcgattgggt tcggcgttgt ttaggcgggt    11400
tatataggaa gcgtggtggt tcggggaagg atgcggaggg tgcgggacgg tgttggaaga    11460
tgcgggagga tgcggggttg gtcgaagatt ttggttttag ttttttgttta taatatttaa    11520
tgttttcggt tgttgcgttc gtacgttggg agttttttttt tagaaaggtt cggggtagtt    11580
cgtttgtaag tttaaatgcg ggttgtgata tttattatta ttatattatt gtatcgttag    11640
agtcgaggag gagatttagc gagaagaagg aggagggaga ggaggagggt ttatttatag    11700
gttttaaaag cgtttcgtag ttttagttat tttaagagt ttaggtttgg aaagtaggcg    11760
gaggggcgga aagtagtttt ttcgcgtttg cggtagggat cgtttgtttt ttttttttagg    11820
tattttatt ttttggcgtt tttttttgat aagaagtatt aatcggtttg gggatagtag    11880
cgttttttat ttagggattt attagtaat atcgttttgt tcgcggaaat tattgttttt    11940
ttattttttt ttattttta ttttttcgtt ttcgtgtag ttagtttttgg gttaggggaa    12000
aggagttttt aggttttttag ggggtaggtt agtaatagat aattgagtac gattattttt    12060
tttcgggagt atataaaatt gtaaaattag taaagaattt ggttatagcg tgtttacgcg    12120
tttatagagt ttgtttgttt tattaaaggg aagtgttagg tttaaggttt ttgttaattt    12180
gaaagagata ttgagaaaac gagattttttc ggggatttag agggaaagtg taagaatttt    12240
ttattgtatt tttagggaat tgtttaatgg ggagttcggt tttaaaagat tttggtaata    12300
aaaggttgga taggaaattt ttttaggtaa attttttgtc ggatttaaag agaatatttt    12360
tttttgtta taaatttttt tttatataag tttgatttt gttttttttcg ttttttttttt    12420
ttttttagttt ttttaagtat ttttgagtag aatatttgat aatttttttg agtaataggg    12480
attttttgga agtattaatt attttttatg ttttcggaa ataagattat aatttttat    12540
gcgtatatgc gattttttttt ttttagttag gtttatttta ttgtgtaaat agtattaata    12600
```

```
tatggaagag ttttttgtat tgtgttataa aagatttttta ataggatttt atagagaaaa   12660
gggttaaata gttgatataa aggattttg ttttttaga aaagagggat tttggatttt     12720
tttttttttt gaagttaagt atgagtttat ataataggaa taaaataaat ttaaggtgta   12780
tattagtata atattaggga tattagaatg gatggtaaat ttttttttt atataaatat    12840
gaaagtattt ttataatttt ttttttgaa gttttttattt agaaaattat attaaatata  12900
ggatttttaaa atagtagtga ttaaagatga aagttaattt ttttttttaa tttttttgat  12960
tagtttggtt taaatttatg ttttaaaatt tttagtaatt tagatttttg tatatgcgta   13020
tttataagat tttttttata ttttgtaatt tgtaggtatt tagtatggtt attgattta    13080
agtgataaat aggtagaaga tttgttagga taattttagt ttttattatg tgtattttt    13140
atttttttg ttatttatta gttttttgta gtaatataat tgttagttat attatttgga   13200
aattaatgtg tttttgtagt gaattattta tttttagtaa atttattgta ttattattt    13260
aaatattgaa atttgatttt attagatgtt tagaatgata gttatagagt agaattagat   13320
tttaatttt atgtataata tgtaaataaa ttaaggtgta gaaagttatt gttttaaagt    13380
tatataatta atagtttagt ggttttttta gtgttaatta tagtaattt agatttaaga   13440
ttgtttgatt taggaatgga gagaaataaa ataaaatgaa tgtttattga aatatatatt   13500
ttagatatta agatagattt ttttgtgaaa tattttaaga tgtggatttg tattttttatt 13560
tttaaatttg agtaaattta gttgagtttt aaagagttta agtaatttgt ttaaggttat   13620
tttgtaagtg atagatttgt tagtttgaaa agtttattat ttttatttt tttgttttttt  13680
tatgatatag ttaagtaaaa tttttaata aaggagaatt agattagaaa taagtaatta   13740
atagtagatt aatgtttatt tttagggaaa tgttaatagt taatatttat tataaataat   13800
gttatttgta tataatggaa tatgattgaa agtgatgggt tagatatttt ttatattttg   13860
agatgttttt atttatgttg ttaaatttga ttttttaatt ttttaaaatt tttagttttt   13920
tttaatgtta atagatttta taatatttga ttaaatatt ttataggata aaggtatttt    13980
tttagggttg atttaaggaa ttagaatatg tataatgttg aaaagtttta aattgtttgt   14040
tttttttttt ttttgatttg taatattatt atttagaaaa ttaaatatt ttttaggtta   14100
ttagataatt aaaatgaaat tatattttat ggatattttt tttttatttt tagggtagat  14160
tttttttttt agttgtttaa aatggagaat ggataaaaaa gaaaaaggaa aatatattag   14220
ttatatttag aatagagttt atagttgtat tattatttt atgtaattgt ttttaatgat   14280
ttttttttat taagagaaag aaaatgagag agtatttatt tttgattttt taatgtttga   14340
taaaattatt agaagttttt gaatgggaaa atatatattt tttaggtttt ataattaaaa  14400
ttgtatttat ttgtttatta tatttaagta tgaattaaat agtaattaaa atattatttt  14460
gtgagtttt ttttaaatta tattttgta ttggggatat ttttgtgaa aattttaaga    14520
ttttaggtat aaataaagta agattttat ttataatgtt tgtgtttaaa agaaattata   14580
agttagaagt tatgtgttt gttttttgt tttgatttg tttttgggaa tttggttgag    14640
tttaggggta gtaagttaat gatttggaga ggaaaggtgt agatggtaga tgtgtttta   14700
gggaattta ttatttttat ttaaattttt ttttgaggtt ttttaggatt atatttaga   14760
tttttttttt tttattgatt aggtgaagtg ttttagata tggtattatt tattgttgtt  14820
ttagggatga taagatttta gttttatta aatttagaaa gagtttagtt taattttttt  14880
gatttgattg gttttaggta taattaagta aattattttt attggatgat atagtaatgt  14940
tatagattaa aaatgtattt ttaattttta aagattttgg aaaaaggaag tttatttttt  15000
```

```
aagattgtgt tataattttt tttttaaata aaatattgta aattagggat agatatttta    15060
tttagtattt tgaattttt ttggttttt aggaaaggta gaaatataag gtttttattg    15120
tttttttttt attttaaaa aagaaatttt gtaaaaggta aagtgatggt ggtaattta    15180 ttgtgtttta attcgaagta tataaattgt tttgataaat taaatataga taaatttttt    15240
tagaaagtta taaaatatta gattttttt agatattaga tattgagttt tgttttta    15300 attttaaat taaaatgtta tagtaaaata tttgttttaa taattttt ttttttgt    15360 gttgtaaatg ttttgtttat ggttgagtag attttttag aatttaattg aaagattatt    15420
tatattacga tagaattatg taagttaaag ttaagttta atatggagtg atgggagagg    15480
tcgggttgtc gagaggagat gattttatta gtgagaagag aggttttg agtcggtttt    15540 taaggtagtt aaatggttta gtatatttgt atttattttg ggaggttgtt tggagtagag    15600
tattaaaaac gttatttttt ttataaagaa aaagatgaag gtataagaa tatagtttaa    15660 ttaaattgaa ttaagattg tattatttt atttttttt tagttatttt tttaaagttt    15720
tttttttttt ttttatagt ttgaaaaata taggttattt ttataaagta tttgtttgat    15780
tgaagtaaga taaattgaag agtttggtt ttgaatataa ggaagcggta gagattttag    15840
aattaatgag gtagggcgga atataatgta gaaggtttt taagaggtaa aattttgta    15900 gttgttgttt atttttagtg attattcgtt tttatttatt taattagatt atagtgggat    15960
cgagataagg agtataatga aagttgttgt attgatggtg taaaagata tatggtatta    16020 ttaatgtttt tgtggtgagt aaaggtagaa cgtaagatag aaaataagga aatttttgcg    16080
ttgtaagaaa agtgtttagt atgggtatta atcggtatgt agaagtagta agtatatatt    16140 ttattttta tttattgata aaagaattg taggattaat gttgtttttt attaaaatat    16200
gagaaattat attttaattt tataaattaa aggttaaata tttgttgtaa taattttaaa    16260 aaaagagaa gattgtaag atttagtaaa tatttattat aaatagattg ttttaatttt    16320
tttatatttt ttttaatttt aataaaagtt tattgagtag tttttatgtg tattgttta    16380 gatagtaggt attatttaaa aaagtaataa ttattttta tttttaagga gtttataatg    16440
tttttagaaa gaaattaatt tattggagta gttaaagtta taattgattt ataaaatgat    16500
tagtgaattt agaggaaaat tatatataaa tattttgtt tttattggtt ggtttagtta    16560
gatattattt taaaaaata                                                 16579

<210> SEQ ID NO 10
<211> LENGTH: 3000
<212> TYPE: DNA
<213> ORGANISM: Artificial Sequence
<220> FEATURE:
<223> OTHER INFORMATION: chemically treated genomic DNA (Homo sapiens)

<400> SEQUENCE: 10
atatttaaat tgtatatttg gtttgtaata tattatatat ttaaaagaat tattatttt      60 ttgaatatta ttaatattaa taatagtatt atagtgatta agagtggatt taaataaagg    120
ttggtttgaa atttaggttt gttatttatt agtaagtttt taaaaatttt gagttttag    180 ttttttata tgtgaaatgg agaaaataaa tttgtaaaat taattaaatt tgtttattta    240
tatttttttt tttagtgtat attaattggt attttcgtt aggttagaat gtgttttaa    300 ttatgtttta aattcgtttt gtgttaattt tattgttaga atttttttta ttttgagaat    360
tagaaaagga aatattatgt ttggtaatgt ttatattttt taaaataaat tgtaggaaa    420
```

```
gaatatttag taagtgatga gagtagtaac gattgttttt attattttaa atttataata    480
ttatttttt  tagagtttt  taagtattgt agataatttt ttatttatta aaaaataaat    540
tgtaattata agtatttagg gttgatattg tttttgaatt agatagtgtt tatattagtt    600
gtataagatt aatttaaagt agaggatgaa attttttttt tgaattttt  ttagaacgta    660
atttagtgaa tatattaaaa ttaaattttt tttgaatggg agtaattttt acggattaat    720
ttgtaattt  ttagattata tttaaggtaa tgtagaggtt gttgtattat aggttttgtg    780
attagagatt attggatttg ttttggaaa  agttatttat gattttttgg gttttggttt    840
ttttatttt  tatatcggtt taataatgat tatcgtagag ttgttatgga agttaaatga    900
atttatgtat tataagtgat taatataatg attgatattt agtgatttat taataaatta    960
aaatatttat tattaatatg atagagaagg tgtcgttaaa atagataata ggttttggga   1020
agaggtgatt aaatggatgt aaaatttatg gattgtttat ttcgtttatt tttgttgtgt   1080
tttttggttg tggtatatat acgtgtgggt ataaaatcgt aaattttatg tagtcgcgta   1140
gtgtatgcgt agaaggttta gatacgaaat gttatttag  taatgtgttt agagaagttt   1200
tgacgtcgtt ttggaagtaa gtcgttgttg tttgatttt  gggcgtttgg gacggatgtt   1260
tatatttgta tttagtagta ttggaagggg tttaggtttt tcgtagtata gtttattttt   1320
agatcgttta gtttttata  atatatattt ttacggaaaa gggtatttt  tttcgttaga   1380
aaaagcgttt tagtttggtt tgggttggtt ttatttac   gttgttgtaa gtaggcgaag   1440
ttttttttgt ttttttttt  ggggtaagtg gaaaggagtt cggtaggggg ttcgtagtgg   1500
tttgtatagg ggaattgggt agcgagagag ttttaggtaa tttcggggt  tgttttatag   1560
aagtaggtgg ggatcgatag tggtttttcg gtttagggag gagagcgcgg tcgcgggttt   1620
ttttttttag tttggaggtt gtagtcgttc gagtcggttc gggtgggggc ggggtggggg   1680
cggcgcggag ggtacggaga ttacggcggc gttattcggg atatttaggg tttcgaggtt   1740
ttgggcggtt tttacgcgag atcgtaaatt atgataatag gtagttattc gaggttaaat   1800
aaaaacggag tgggtttttc gcgcgtcgtc gtttttcgcg ttttttggcg ttttttttcga  1860
ggttttcggc ggttttacga gttcgtagta gtcggtggcg acgtcgtttt cgttttattt   1920
ttttgcgtaa gtgcgaggtt gtcggtagcg cggcgtacgt ttcggtcgtt ttcggttttc   1980
gcgtaaaatt tttattttgt ttacgtgaag ttgtcgttgt tttagagagg gggaaagagt   2040
tgcgggaaaa gtcggggagt gacgattgcg gcggttgggc gcgtttttt  attttttttt   2100
tttttttttt tttttttgtc gtagttcgga gtttggttt  tttttttttt tttttttttt   2160
tcggagtcgg tttttttttt cgtttcgttt tttttcgtt  tgtgtacgtt atttgttgtg   2220
gggtggtcga aggggatgtt ttgttttat  tagaggtata gcgcgaaggg gaaatttcga   2280
tattggaagg aacgagaata aatatttaat tacggacgta ttgaatcgcg gttgggatag   2340
atatttcggg aattcgaggc ggatcgggcg acgaggtgag tgatttttt  ttttaattt    2400
cgttttaggg ttttcggggg agtttgagtt gagagaattt ttaaattt   cgggaaagtg   2460
cgcgaggttt cgtcggggac gtcgagcgtt gggtattgag gacgcgtagt tggacggtgc   2520
gtgggcgttt gcgttttcgg ggggcgtttg gaggtcgggt gttttacgtt tgagggttcg   2580
ggtcgttcgg atcgtagcgg tgtttttgt  tttagaagac gttttaagt  tttaagggtt   2640
ttttcgagt  ttgtttgttt tttcggggt  cggcgcggag tttgcgcgta acggagttta   2700
tttagtagtt tagcgcgcgg tttttatttg tatttcgttt ttatttggta gaggcgcgag   2760
tatcggggtt ttttttatat tttttttatg acgtgtatta ttttttgatg attttttaga   2820
```

```
tggtttaggc gcgaggatgt tgatttagag tttttcggag ggttataggc gtttgggttt    2880
tttcggtgtc gggtgcgtgt gtattttaaa ggttcgcgtt ttaattttta ggtattgatc    2940 gggttttta attgcggcga ttttatttta atagttttta tgtggcgtgg attgaatgtt    3000

<210> SEQ ID NO 11
<211> LENGTH: 3000
<212> TYPE: DNA
<213> ORGANISM: Artificial Sequence
<220> FEATURE:
<223> OTHER INFORMATION: chemically treated genomic DNA (Homo sapiens)

<400> SEQUENCE: 11
gatatttagt ttacgttata taaaaattat taaagtggga tcgtcgtagt tgaaaagttc      60
gattagtgtt tggagattag aacgcgagtt tttaaagtat atacgtattc ggatcgggga     120
aagtttaggc gtttgtgatt tttcgaagga ttttgggtta gtattttcgc gtttggatta    180
tttaggggga tattgaaaag taatatacgt tataagaaag atgtggggga gatttcgatg    240
ttcgcgtttt tgttaggtgg aggcggggtg taggtagaag tcgcgcgttg gattgttgga    300
tgaatttcgt tacgcgtagg tttcgcgtcg atttcggaag ggataggtag gttcggaagg    360
gattttgggg gtttggggac gttttttagg gtagagagta tcgttgcggt tcgagcggtt    420
cgggttttta ggcgtggggt attcggtttt taagcgtttt tcggggacgt aggcgtttac    480 gtatcgtttta gttgcgcgtt tttagtattt agcgttcggc gttttcggcg gagtttcgcg    540 tatttttttcg gaaagtttgg ggggttttttt aatttaggtt ttttcgggag ttttggggcg    600
ggggttggaa aagggggtta tttatttcgt cgttcggttc gtttcgggtt ttcgaagtgt    660
ttgttttagt cgcggtttag tgcgttcgta attaagtatt tatttttcgtt tttttttagtg    720 tcgaagtttt tttttcgcgt tgtgtttttg gtgaaaatag gatattttttt tcggttatttt    780 tataataaat agcgtatata agcgggggag aagcggggcg gagggagaag tcggtttcga    840 ggggaggag gaaaggagag gagttaaaat ttcggattgc gataggggg aaaggagaag    900 aaagagaaat gagagagcgc gtttagtcgt cgtagtcgtt attttccggt tttttttcgta    960 gtttttttttt ttttttttaag gtagcgataa ttttacgtgg ataggatgga agttttgcgc   1020
ggaagtcggg aacggtcgga gcgtgcgtcg cgttgtcggt agtttcgtat ttgcgtaggg   1080 aggtgggggcg gggggcgacgt cgttatcggt tattgcgggt tcgtgaggtc gtcgggggtt   1140
tcgggggagg tcgttaggga cgcggggggc ggcggcgcgc gggggattta tttcgttttt   1200 atttgattttc gggtgattgt ttattgttat ggtttgcgat ttcgcgtggg gatcgtttag   1260
ggtttcgggg ttttggatgt ttcgggtggc gtcgtcgtaa ttttcgtgtt tttcgcgtcg   1320
tttttatttc gttttttattc gggtcgattc gagcggttgt agtttttagg ttgagggggag   1380 ggattcgcga tcgcgttttt ttttttgggt cggagagtta ttgtcgattt ttatttgttt   1440
ttgtggggta gttttcggaa ttgtttggaa tttttttcgtt atttagtttt tttgtgtagg   1500
ttattgcggg tttttttgtcg gattttttttt tatttatttt aagggaggag atagaaggga   1560
tttcgtttat ttgtaataac gtgaaataaa aattaattta gattagattg gggcgttttt   1620
tttgacggga ggaaatattt ttttttcgtgg agatatatgt tatgaaggat taagcggttt   1680
ggggataggt tgtgttgcga agggtttggg ttttttttag tgttgttggg tgtaggtata   1740
ggtattcgtt ttagacgttt aaaggttagg tagtaacgat ttatttttaa ggcggcgtta   1800
gagttttttt aggtatattg ttgaaatgat atttcgtgtt taagtttttt gcgtatgtat   1860
```

-continued

| | |
|---|---|
| tacgcgatta tataggattt acgattttat atttatacgt gtgtatgtta taattagggg | 1920 |
| atatagtaaa ggtagacgga ataaataatt tataaatttt gtatttattt aattattttt | 1980 |
| tttaaaaatt tattgtttat tttagcggta ttttttttgt tatattgata ataaatgttt | 2040 |
| taatttattg ataaattatt gagtgttaat tattgtattg gttatttatg gtatatgagt | 2100 |
| ttatttaatt tttatgataa ttttacggtg gttattatta agtcggtata aaagatgagg | 2160 |
| aaattaaagt ttaaagaatt atgagtgatt tttttaaaga taaatttagt ggttttttaat | 2220 |
| tataaagttt atgatataat aatttttata ttattttagg tgtggtttaa gagattatag | 2280 |
| attaattcgt agaaattatt tttatttaaa gaaagtttag ttttaatata tttattaagt | 2340 |
| tacgttttga aaaaggttta gaaaaaagat tttatttttt attttaggtt ggttttatgt | 2400 |
| aattgatatg agtattgttt aatttaaaag tagtattaat tttgaatatt tatggttata | 2460 |
| atttatttt taatgagtgg ggaattattt ataatgttta agaggtttta gaaaaggtgg | 2520 |
| tgttgtaaat ttaaaatgat aaaggtagtc gttgttgttt ttattattta ttgggtgttt | 2580 |
| ttttttgtag atttattttg gagggtgtag gtattgttag gtataatgtt ttttttttg | 2640 |
| gtttttaagg tagaaagggt tttggtagtg gggttggtat aaagcggatt tggagtatgg | 2700 |
| ttgagagtat attttggttt aacgaggaat gttagttaat atatattgga gagaaaaata | 2760 |
| tgaatggata gatttaatta attttgtaga tttatttttt ttattttata tgtgagaaaa | 2820 |
| ttaagggttt agaatttta gaagtttgtt aataaatggt agatttgagt tttaagttag | 2880 |
| tttttattta agtttatttt tagttattgt gatgttatta ttagtattaa tggtatttag | 2940 |
| aaaaatagta attttttaa atatgtaata tattataagt taaatatgta atttaaatgt | 3000 |

<210> SEQ ID NO 12
<211> LENGTH: 1984
<212> TYPE: DNA
<213> ORGANISM: Artificial Sequence
<220> FEATURE:
<223> OTHER INFORMATION: chemically treated genomic DNA (Homo sapiens)
<220> FEATURE:
<221> NAME/KEY: unsure
<222> LOCATION: (9, 17, 18, 33, 41, 49, 50, 52, 54, 62, 80, 84, 127,
      157, 159)
<223> OTHER INFORMATION: unknown base
<220> FEATURE:
<221> NAME/KEY: unsure
<222> LOCATION: (175, 207..209, 214, 1181)
<223> OTHER INFORMATION: unknown base

<400> SEQUENCE: 12

| | |
|---|---|
| agttttagnt attattnnta tttttattaa tgnttttggg nttataggnn gngnttttt | 60 |
| gnttaaatag tagttaatgn aggnattta aaaggtatat tattttatat ttatttagtg | 120 |
| gttatgntat tatttaatt ttattataat tttgtgngnt tagtataatt tgtgnttta | 180 |
| ttttatttgt gaataaatgg aggtagnnnt ttgngtaatt tataagtaag tggtagattc | 240 |
| gggggttgtg tttagataat gtggttttag attttttgtt ttttttgtt tttgttgta | 300 |
| ttttgattga gtttagttat ttattttttt aatatatatt aattgttgtt tttatgtttt | 360 |
| aggttttgtg ttagatgtta gaaatatatt tttatttatt ggattttggt atggtttatt | 420 |
| gtttagtgtt ttgttatgtt acgtgttata taatgtattt atttcggtat ttagtttatg | 480 |
| gaaaataatg ttgaaagata ttgtatgtat gttttataa taaaattatg taatttatgt | 540 |
| ttttttttatt gttttggtta ttaggaagtt ttattaaa ttgagtaaa tatattgaaa | 600 |
| tttgggttg ttatttagt ttgttgaatt tttttttttg gttagatttt ttatttggg | 660 |

```
tttataaatt ttattgtata aatgttttt  attgtaaaat attttaaatt ttttttaagg    720
gaaggttgta tggaaatgat atagtaaggt tttttttgta tttttttaga ttttattag     780 ggaaggtaga tttagatgtt tttttattt  ttagttttaa agttttttat ttataaaatt    840
ttttaagtag tgattattgt tgttttgagt atttggaggt agtttagagt ttttgaaagg    900
taaaatttat atataaaaag aagttttttt cgatttagat tttagttttg gtgttagatg    960
tatatttgag gagtaggtgg ttagttagat ttttatttga gtagttaata aaatttattg   1020 tttttaatg  gaatttttt  tgtaagttcg aattgatttg ttatttttgt gatttgtgag   1080
atggtaggga agtattaaat attattatga tttgggttat agtggtggga aaaaaggaaa   1140
aaagaaaaaa aaaatttatt gttaagtttt gttaggcgta naaagggttg gaattgttgg   1200 ggttattta  tttgatttat tggaaataga gtggatttta ttaatatttt aataaagaga   1260 attttttgt  attaggttgg aagtggtcgt tagttttcg  tgtaattta  tttttggaa    1320 aagtggaatt agttggtatt gtttagcgtg atttgtgagg ttgagttta  atagtttaaa   1380 gaagtaaatg ggatgttatt ttcgcggggt tcgttttcg  cgaggtgttt atttcgtatt   1440
tgttatgtaa aacgagggag cgttaggaag gaattcgttt tgtaaagtta ttggttttgg   1500
ttattagttt ttatttaatg ttttcgtgat gttgttgttg atttatttgg gaagttggtt   1560
ggttggcgag gtagagtttt tttttaaagt ttggttttta cggaaaatat gtttagtgta   1620
gtcgcgtgta tgaatgaaaa cgtcgtcggg cgttttagt  cggataaaat gtagtcgaga   1680
atttcgttcg ttttgtgcgt tttttgttt  taggtaggga agaggggttg tcgggcgcgt   1740
tttgcgtttc gttttgtat  tcggatcgtt cggtacgggt agggtgaggg ggttttcggg   1800
gggtcggggt tttcggtcgc ggcggcgaag atagatcggg gttcggtagg gaggttattt   1860
cgagtttaga gattttaggt attttttata tataggtttt tattttggcg tgcgtgcgtg   1920
tgtgtgtgtg tgtgtgtgtg tgtgtgtgtg tgtgtgtgtg tgtacgtt   cgttaacggg   1980 agga                                                                1984
```

<210> SEQ ID NO 13
<211> LENGTH: 1984
<212> TYPE: DNA
<213> ORGANISM: Artificial Sequence
<220> FEATURE:
<223> OTHER INFORMATION: chemically treated genomic DNA (Homo sapiens)
<220> FEATURE:
<221> NAME/KEY: unsure
<222> LOCATION: (804, 1771, 1776..1778, 1810, 1826, 1828, 1858, 1901, 1905)
<223> OTHER INFORMATION: unknown base
<220> FEATURE:
<221> NAME/KEY: unsure
<222> LOCATION: (1923, 1931, 1933, 1935, 1936, 1944, 1952, 1967, 1968, 1976)
<223> OTHER INFORMATION: unknown base

<400> SEQUENCE: 13

```
ttttttcgtt aacgaacgta tatatatata tatatatata tatatatata tatatatata     60
tatatacgta cgtacgttag agtgggagtt tgtgtgtggg gggtgtttag gattttggg     120 ttcggaatga tttttttatc gagtttcgat ttgttttcgt cgtcgcgatc ggaggtttcg    180 attttttcgaa agttttttta ttttgttcgt gtcgggcgat tcgaatgtag aaacggggcg    240
tagagcgcgt tcggtagttt ttttttttta tttgggatag gagaacgtat agaacgagcg    300
gagttttcgg ttgtattttg ttcgattaga agcgttcggc ggcgttttta tttatgtacg    360
cggttgtatt gagtatattt ttcgtgggag ttaggttttg aggagaggtt tgtttcgtt    420
```

| | |
|---|---|
| agttagttaa tttttaaat agattagtag tagtattacg aaagtattgg gtagaggttg | 480 |
| atgattagga ttaatggttt tataagacgg attttttttt aacgttttt cgttttgtat | 540 |
| ggtagatacg gggtgagtat ttcgcgagga gcgagtttcg cggaggtggt attttatttg | 600 |
| ttttttttgga ttgttggggt ttagttttat aaattacgtt gggtaatgtt agttgatttt | 660 |
| atttttttag aaatggaat tgtacggggg attggcggtt attttagtt tagtgtaaaa | 720 |
| agattttttt tattaaaatg ttaataagat ttattttatt tttaataaat tagataaaat | 780 |
| ggttttagta gttttagttt tttntacgtt tggtaaggtt tggtagtgga tttttttttt | 840 |
| tttttttttt tttttttat tattgtggtt taagttatga tggtgtttgg tgttttttg | 900 |
| ttatttata aattataaag atgatagatt aattcgagtt tgtagaaaaa attttattaa | 960 |
| ggggtaatag attttattaa ttgtttaggt gagagtttga ttagttattt attttttaaa | 1020 |
| tgtgtatttg gtattaaagt tgggatttgg atcggaagga atttttttt gtatatggat | 1080 |
| tttatttttt agaagttttg aattattttt aggtatttag aatagtagta gttattgttt | 1140 |
| aagggatttt ataaatgggg ggttttggga ttgagggtaa gagggatatt taggtttgtt | 1200 |
| ttttttaata ggaatttaag aaaatgtagg gaagattta ttgtattatt tttatgtagt | 1260 |
| ttttttttag aaagaattta aggtgttta taataaagga tatttgtgta atagaattta | 1320 |
| tgaattaaaa tagaaaattt gggttagaag gaaaagttta gtaaattgaa atgataagtt | 1380 |
| taaattttaa tgtatttgtt ttgatttgga taagagtttt ttgatagtta aagtaataaa | 1440 |
| agaaatataa gttatatagt tttgttgtag aaatatgtat ataatgtttt ttagtattat | 1500 |
| tttttatggg ttaaatatcg gaataaatgt attatgtaat acgtaatata gtaggatatt | 1560 |
| gagtaatgga ttatgttaag atttagtgga tggggatgta tttttagtat ttggtatagg | 1620 |
| gtttggaata tggagatagt aattagtgtg tgttaaagaa atagatggtt agatttaatt | 1680 |
| aagatgtagt agaaggtagg gaggggtaag gagtttggag ttatattgtt taggtatagt | 1740 |
| tttcggatt gttatttatt tgtaaattat ntaaannntt gttttattt gtttatagat | 1800 |
| aaaatgaaan tataaattgt attgantnta taaggttgtg gtgaggatta agtgatgnta | 1860 |
| taattattga ataaatataa agtgatgtgt ttttaagat ntttntattg gttgttgttt | 1920 |
| ggntagaagg ntntnntttg tggntttaag gntattgata aagatgnnag tgatgnttga | 1980 |
| agtt | 1984 |

<210> SEQ ID NO 14
<211> LENGTH: 7833
<212> TYPE: DNA
<213> ORGANISM: Artificial Sequence
<220> FEATURE:
<223> OTHER INFORMATION: chemically treated genomic DNA (Homo sapiens)

<400> SEQUENCE: 14

| | |
|---|---|
| gttttggtg agatatgtgt ttataagtt ttaatggaga aaaatgtaag tattttattt | 60 |
| tttgaaattt ggttatttga gtaatgagaa aatagttatt ttttttagga tagtggtttt | 120 |
| taattatggt tatgtgtttt tttaggaaaa ttttaaaaat atatatatat taatgttttt | 180 |
| gtgttatttt tagggatttt aagttttga atacgaattt tgtattagta ttttttaatt | 240 |
| atttaggtga ttgtgatgtg aaattatgat tgagttttat tgtttaaga tgaaataaat | 300 |
| tttttttagt attgaaatta taaatttaaa ttattaaaat taattaaggg tatgggaatt | 360 |
| aataaggtat agggaagttt ttatattata aaattatttt tttaaattat agtttattgt | 420 |

```
ttatatgtta tttgttattg tagaaaaggg tgaaaaaata gtaaatttaa ttatttttag    480
tttgaaaaat tatttagaaa tgaagatgac gattttgaaa tattgttaat attatttgat    540
ttataaataa tgttttaata tatttattat atattgatag atattttttt atatgaatat    600
tatatattaa aattaaggta ataatgtatt tagaatattt tatttatatt tatgtatttt    660
aagtaggtta gaaattaaga tatgagttat taagtatgag atgttaaggt gtggggttag    720
aaattatatt gtattttatt attaataatt aatatatatt ttaatattat atatatttaa    780
ttttaatttg tatattttta attatttta attatgtgta taaatataag tatatatatt    840
tttatgtatt tatttattta tatttttatt tatttattta tagggggat ttttttaaat    900 ttattattat taaattatat attttttattt taatttttag aataagttta ggaggtaggt    960
attgttatta tttatatttt ataaatgagg aaattgttta tagttataaa gttattgtgt   1020
tagatatatt agaagtttaa tatatatttg gtgaatatat gtataaaaat agagagatag   1080
atatgtataa tagtttattt ttatattgag taaaagtttt taatttgttt tagaaatttt   1140
tttgtgaaaa ttgagtaaaa atcgaggtat tttttttattt gttatatagg tataggtggt   1200
attttatttt tttaataagg atgaatattg aaatgtggat tttaaggttt aattttagat   1260
tttttgaatt tttgatagtg ggatttggaa tttgttattt gttttaaagt tttttaagga   1320
atttatatga ttaattaggt ttagaaatta ttggattta ttgtcgaagt ttgagaatta   1380
aagtttgggt tttattgcgg ttttatagaa agggtaaatg aagtattatg gatagaaattg   1440 atacgttttt agttagtttt ttttttttaga agttaatagg tagtaatata gtagaaatta   1500
gtgatttatg ttttgtgttt tgaagttagg tagaattttta tagagtttta gtagtgttat   1560
tgacgagatt tgttttttgg ggtaagttgt ttgatgtttt taaagttata tttttttttat   1620 ataaaatgag ataatatttt ttgttttata ggggtgtttt aaagattaaa taaaatatat   1680
atgttttatt ttatatggta taatgtttga tatttaagaa gtaaaggata tatttttattt   1740 ttattgaagt aattagaaag tatgaaatta tgaaggagat aagagttttg attggtagtg   1800 tatttttattt ttttaggttt attttattttat tttaaattat ttttgttgga gaataatttt   1860
taagtttttt atttaagttg tgagtaattt tatatttttat aatgatgttt ttttttatgag   1920 aaaaaaaaat gttttttaagt ttttttggaga aaatatattt gtattatttt tattgaaaaa   1980
tttaataatt ggattttgtt ttttttgtatt aatttttagag tgtatatgtt ataaataaag   2040
tgttttagtt taagaagatt gaaagtaaat atggtatagt attttaaaat aagaattttg   2100
taaatatatg gtatgattgt gttatattat tagtaatatt atgatacgta atgtaaagta   2160
tagtttatag atttaaattt aattttaata agtaaattga ttttgttttg ttggggaaaa   2220
gttaaagtat taatttaatt gttaatgtag ttttgtttat ttttttggta tttagtgata   2280
agtttaaata atgtatatat ttttatttat atatttagta ataattttt tgtttaatg   2340 agtgatgttt ttttgttatt tggtggtgtt tgttagtttt agaatttgtt ttttggtggt   2400
attataatat taagtataga gtaagtgtaa taaaattgta gtattttttat tgaaaaggtt   2460 ttgttttaaa ttgttttaata attttaaagga ttttttgtgga agtaatcgta tttgttaatt   2520
agttataatt agtaattaat tttttttgag ttttaattta ttttttggtaa aacgttttag   2580 gaagagtata tattattaga aagtatgtta aaaatttattt tagtagaaaa tttaaaaata   2640
gttttttttt gttaagaggt tttttaaaat tttatttata tagttaaatt ttgaaatttt   2700
agtaggtttt gttttattat tataattatt gtataaaatat ttttaaggat tttgttttta   2760
gttttaagta tgatttatttt ttataagttt gattagttat tatattagtt ttgttatgga   2820
```

```
aaatgatatg tttttatttt ttgttgtaga gttgttaaat tttgatttat atttatgttg   2880 tttttttgt tgaaagtttg tagcgaaaga aatttttaat tttttgtttt gtaatattag   2940
ttggtagttt tatttaatgg gtattttgtt tttttaaaga atttagttgt tttgtttaga   3000
agtcgatttt ttgatgtttt taacgtttgg tttaattgat ttgttttaat ggagttttcg   3060
tcggtgagga gcgagatgtt atcgattaga atgttgggat ttgttgttta attgttagga   3120
gtgagagata ttgagattta gaaatttttg gaggtgggag gggagaggga tagtttcgga   3180
cggaggcgga gatgtaagat aaagggatgg attttatata ggaaaaaaaa aaagatttcg   3240
ttgaggtatt gaggtgttgt acgattatat tttttaaagg agaagttaaa aagtaaggaa   3300
gtgggaggag gttggaggtt aaagtattta aaaggattat tcgggtataa tttgtttttt   3360
tgttggtgtt tgtaaaggat agatagtttc gttttttaaag tatatgaatg tttttttttaa  3420 gtgattggga atggatatta attgtttgtt aaatgttatt aaatgttttt ttaaatttag   3480
gggatataga aagaggggta taaaaggaga atttaaatag aaaaaggag gattcggagg    3540 tttttgaaag cggggggaga agaaggagga gggataatag agaggaatag agaaggagag   3600
cggagagaag ataaataaaa ataaaaatag gaattattga ataattatat attaaaaaga   3660
aagttttttt ttatggggta tttaaaatat tgagattgta atagtgattt cggttatgga   3720
agaaagatgt tttttttat ttttgttttc gaaagtttt ggtttcgtta ttggcgatta    3780
aaattttatt aggttaaaga gtgtgtttaa ttgtttgaag aatgtagtag acggaaggcg   3840
ggtttcgtta tgtcgtttgt tttttttcgtt ggagagaatg aaagaaacgc gtagagttag  3900 agattttgt cgagttagat tttttttcgt cgttttaggt tatcggttat tcggtaaaga   3960
ttcgagtaag gaacgtaggg ttattgtttg ggttaataaa tggagttcgt tttttttttt   4020
tcggacgtcg ttgttcggtc gatgttttcg gtaatttatt cgcggcgtat gtagaggagt   4080
tttttttttt tttttagatt atttgtttcg attaatttga ttttttaaat atatttgatc   4140 gtattttta ggtggatata ttaataggtt acgggttgga gaggagcggg tgatgaggag    4200
agggatttaa atttgcgaac gtttggggtg ggtcggagtt gcgggggggtt tgggaggaga  4260 gaggggagaa gagagaagga aggagagcgt ttgtcgggat ggttgagttg tttcggcgag   4320
tagttttggg gttgtacgtt tttgtgggag atgttgttgt tgtttttagg tcggtaagag   4380
cggttttaat attatcgttt tttattttt tttttgtaaa tttttagaga aacgttttg    4440 gtttttcgt cgcgatattt ttagtttgta ttttttata gtttaggcgg cgcgttttcg    4500
tacgttggag cgtcggtcgt tagtaggacg ttttttttcg cgtcgattcg tttttttttg   4560
ttttgttgtt gttgtttttt tgatattttc gttttatta tttttagttc ggagagacgt    4620
tatttagtcg cggttcgtat tcgcggttcg gggttacgcg cggaagaggg gcgttagttc   4680
ggatttcgtt ttcggtaggg ggcgtttttgg agcggagagt gaggcgaatg gtatatgagt   4740
gtgcgggtag tttattttga agttcgagtt tttatttga gttatgtttc gtttagtttt     4800
attcgggtta gcgtttggcg agcgagtta tttgtggttt tcgcggtcgt ttttttttg   4860 tattttgta tttattcgtc gattttttttt tttcgggatt tgtatttgt tttattaatt   4920 agagttcgat tgtttttttt tacgtgattt cgggcgggtt gaggatttgt tgtttttttaa  4980 acgttagagg gatgcgggcg gtagagttcg agaggcggtt gtcgggttgc ggggcgtttt   5040 gattttttt ttattttgtt ttttcgggtt ttattcgttt gttttttggat tttcgttttt    5100 ttttgttttt cggttttta gagttttttt tttatggtag tagttttcg cgtttcggc     5160
```

```
gtagttttttt agcggacgat ttttcgttt cggggttgag tttagttttt ggatgttgtt    5220
gaaattttcg agattatgcg cgggtttggt tgttgttttt tcgtcgggtg ttattgttat    5280
cgtcgtcgtt tttgttgtcg tcgttcgcgg gatgtttagt agttcgttgt tcggttttcg    5340
cgattttgtg tttttcggaa gtcgtttgtt gttgtagagt tgtacgaatt agttatggtg    5400
ttgtgggagt tttcgcggta gtgtagtagt tggatatttt gcgagggttt ttgttggttg    5460
ttgttgttgt tcgttatgtt atttatcgta gttcgttcgg tgaagttcgt tgttttttttt   5520
attttttttaa gtgattgtta aacgtttatc ggttggaatt gttttggtaa gtttagaatt    5580
ttcgttttcg atttttttaat ttcgtagaag aatacgcgta tttagtatag attagtttat    5640
tttagcgcgt tttttttagtt ttttatttttt tattgtttta gattttttaat attatttatt   5700
tttatttaga gaaataaggg gaattgttgt aggttcgggg gtgaggggtg gttttgggat    5760
gggtagaaag tgtaggtgta gtaggaaatt tttgtatgtt tgcgtttata ttggagttgc    5820
gaggattttg agaaatatta aacgggatgg ttttttgggt ttattgtttt gaaagagtat    5880
taattttagg ggaaatattg aaatagaagt tttgttatta ttaaagaaaa aagttttatt    5940
aggatgagga agaaataatt ttatgagaaa gaatgagcga gaaagtaata aattaaatgg    6000
tgattgtagg ggaatcgttg atttttggta aaggtgttat gaggtcgtat tggttttttcg    6060
ttgaagatta ggttatatag attttagagg agttgggttt taatagaatt tttttttttt    6120
tttttttttt tttttttttt tttttttttt tttttttatt tattttattttt tttttttttt   6180
ttatttttttt tttttttagg cggtaaaaga tattggtttt gtagtttaga tatgtttttt    6240
tttttgtttt tttaagttttt aaggtagtat aggggagttg agaaaaagaa tattttgcgg    6300
gtttttttagg tcggagtggg tatgattgag gttggttagg ttttatgtag gcgagtcgag    6360
ggcggaatcg attttagtgg gcgttgattt ttttatttttt ggataggttt ttgtggagtg    6420
ggttaggtat tttttttttgtt cgttcggggtt tttttagatt ttgacggcga acgtttggta    6480
ggtttcgttt tgttgaagtt ttttaattaa ataggggttag aggatgggag ttgttgtatt    6540
tttagttggt atagtattcg gtttgatagt ttgtagtata gggtgtatgt aatttttttat   6600
tttttgtgaa tataattttg ttgtagttaa atttggtttt gaataaagtg ttttttaaag    6660
atgtatataa gttgaagtgt atgtaatttt agagaggagg gaatgattaa ttgtaatttta   6720
gggtgaaagt ttgtatagtt tttagttatt attgatgtaa atgttaaaag gaaaattatt    6780
atgtattatt ttaattttatt tttttataaag ataagttgag atatgtaatt ttattagatt   6840
tgggttaata gattgttttt tttttttggta gtttttaaat ttggtatttt aataaaattt    6900
aatatgttttt tataattttt tgatttatgc gtatatgtgt gttgtttttg aaagaataag    6960
ttttattttg ttattgttta attattttttt agatgtttta ttatggtaat aattatgagt    7020
ttgtaaaaat aattttttgga aatgttgatg gttttgtagt ttaatataga ttggtttgtt    7080
ttatttttag tttttttgtatt gtttttaggaa ataattaatt taaatgtgaa gttgatatttt   7140
gtaattaaga aattatatat ttattagata ttttaaaggg gattgtataa attaaagaga    7200
ataaattggt tttgtagata ggttgttaag aatttggtat ttcgttttta ttttttgttaa    7260
tttagaggtg attaattttt atttgagtta aatagattat tatagaaaat attgtgtttg    7320
tttatttttta ttattgaggt tttgttttttt ttttgtttgg atatattttta aataagggt    7380
tgttttagtc gttgaagtaa aagaataatt aaagatgggg aaatggtaaa agggtattta    7440
gagattatta ttagtttttt ttttaaaatgt ggagtttgtt ggttataaat attgtttatt    7500
taatgagtaa aaaataaaaa taaaaaaaaa ataggaagta aatgttaagt ttttatttat    7560
```

-continued

```
tattgttagt attaacgtaa gttttaaaaa atagtattat tagaaaagga tattaaagga      7620
gaattgatta gaaagaatt gtggaaaatg gaaacgaata ttgattattt aattagattt       7680
tgaggttatt agtagatagt gattttgtag tatagttata gttgttggat ttaaaattta     7740
ggataagtat tttaaagttt taaagtagtg tttttttttg ttaaaaattt gtaagatgtt     7800
ttaatgattg gagtgttttt tttgaatttg agg                                  7833
```

<210> SEQ ID NO 15
<211> LENGTH: 7833
<212> TYPE: DNA
<213> ORGANISM: Artificial Sequence
<220> FEATURE:
<223> OTHER INFORMATION: chemically treated genomic DNA (Homo sapiens)

<400> SEQUENCE: 15

```
ttttaaattt aaagagaata ttttagttat taaatatttt tatagatttt taataaaaaa       60
aagtattatt ttgaagtttt aaaatatttg ttttaaattt taaatttaat aattatagtt      120
gtattgtaag gttattgttt attgataatt ttaaaattta gttaagtgat taatattcgt      180
ttttattttt tataattttt ttttagttaa tttttttta gtattttttt ttgatagtgt       240 tatttttaa agtttgcgtt aatattgata gtggtgaatg aaagtttaat atttgttttt       300 tgttttttt ttatttttat ttttttgttta ttaggtggat aatatttatg attataaaat     360
tttatatttt ggaaaagagt tagtgatgat ttttgaatat ttttttatta ttttttatt      420 tttaattgtt ttttttgtttt aacgattgaa ataattttt atttgaaatg tatttagata     480
aagaggaaat aaagttttaa taataaagat aaataggtat agtgtttttt gtgatggttt     540
gtttggttta aatgaagatt gattattttt aagttaatag gggtggaagc ggggtgttaa     600
gtttttgata atttatttgt aaaattagtt tatttttttt agtttatgta gttttttta     660 aaatatttgg taaatatgta atttttttgat tgtaaatgtt aatttatat ttaagttagt    720 tattttttaa aataatgtaa gggttaggaa tgaagtaaat tagtttgtgt tggattataa    780
agttattaat attttttaaaa attgtttttg taggttata attattatta taataaagta    840
tttaaaaagt gattaggtaa tagtaaagtg aaatttattt ttttaaaaat aatatatatg    900
tacgtatgaa ttaagaagtt atagaaatat gttgagtttt attaaaatgt taaatttaga    960
aattgttaaa aaagagaata atttattgat ttaaatttaa tagggttgta tattttaatt    1020 tgttttttgta aaggataaat tagaatgatg tataataatt ttttttttgg tatttatatt   1080
agtaataatt aggaattata taggttttta ttttgagtta tagttggtta ttttttttt    1140 tttaaagtta tatatatttt agtttatata tattttgaa agatatttta tttagagtta    1200
gatttaatta tagtaaaatt atatttatag aagatgaaaa attatatata ttttatatta   1260
taggttgtta aatcgaatgt tatgttagtt aggagtgtag taatttttat ttttttggttt   1320 tatttaatta ggaagttta gtagagcgaa gtttgttaag cgttcgtcgt tagaatttga    1380
aggaattcga gcgagtaaga agagtgtttg attttattta tagaagtttg tttagaaatg   1440
gaggagttag cgtttattga agtcggtttc gttttcggtt cgtttatatg gagttttgatt   1500 agttttagtt atgtttattt cggtttggga gattcgtaaa gtgttttttt ttttaatttt   1560
tttgtattat tttgaagttt agggaagtaa agagaggggt atatttggat tgtaaaatta   1620
atgttttttg tcgtttagga gagaagggaa tgagagagag agagatag atagatagag     1680 agagagagag agagagagag agagagagag agagagagag agaaattttta ttgaaattta   1740
```

```
gtttttttag aatttgtgtg atttggtttt taacgggaga ttagtgcgat tttatggtat    1800
ttttgttagg aattagcgat tttttttgtag ttattatttg atttattgtt ttttcgttta   1860
ttttttttta taaagttatt ttttttttat tttagtaaga ttttttttt taatgatgat     1920 aaagttttg tttagtgtt tttttagga ttggtgtttt tttaaaatag tgaatttaga        1980
aaattatttc gtttaatatt ttttaaaatt ttcgtagttt taatgtaagc gtaagtatgt    2040
aaagtttttt tgttatattt gtatttttg ttttattttag aattatttttt tatttttcggg  2100 tttgtaatag ttttttttgt ttttttggat agaggtgggt ggtattaggg gtttagggta    2160
gtaggaggtg aggggttgag gaggcgcgtt agggtaggtt ggtttgtgtt ggatacgcgt    2220 gttttttgc ggagttaaag ggtcggggac gggggttttg gatttattag agtaatttta     2280
gtcggtgggc gtttggtagt tatttaagga ggtagggaaa gtagcgagtt ttatcgggcg    2340
ggttacgatg agtagtatga cgggtagtag tagtagttag taaaagttttt cgtaaagtgt   2400 ttagttgttg tattgtcgcg gggattttta tagtattatg attagttcgt gtaattttgt    2460
agtagtaaac ggttttcgag gaatatagga tcgcggggggt cgggtagcgg gttattgagt   2520
atttcgcgga cggcggtagt agaggcggcg gcggtggtag tggtattcgg cggggaagta    2580
gtagttaaat tcgcgtatga tttcgagagt tttagtaata tttagggatt gggtttagtt    2640
tcggagcgag agggtcgttc gttgagaagt tgcgtcggag acgcgggaag ttgttgttat    2700 aaggaggag ttttgggaag tcggaggata ggaggagacg ggagtttagg ggtagacgag     2760
tggagttcga ggaggtaggg tggagggaga gttaaggcgt ttcgtagttc ggtagtcgtt    2820
tttcgagttt tgtcgttcgt atttttttgg cgtttgggaa gtagtaggtt tttagttcgt    2880
tcggggttac gtgggaagag gtagtcgggt tttgattggt ggagtaggat gtaggtttcg    2940
ggagggaggg gtcgacgagt aggtgtaagg atgtaaggag gaggcggtcg cggaagttat    3000
agatgggttc gttcgttagg cgttggttcg agtgggggtta ggcggggtat ggtttaaatg   3060
agaagttcgg gttttagggt gggttattcg tatatttata tattattcgt tttatttttc    3120
gttttaggac gttttttatc gaaggcgggg ttcggattag cgttttttttt tcgcgcgtga   3180 tttcgggtcg cgagtgcggg tcgcggttgg gtggcgtttt ttcgagttgg agatggtggg    3240
ggcggaggtg ttagaggagt agtagtagta gggtagagag gggcgagtcg gcgcgggaga   3300 gggcgtttg ttggcgatcg gcgttttagc gtgcgggagc gcgtcgttta ggttgtaggg    3360
ggatgtaggt tgggaatgtc gcggcggaga ggttagggac gttttttttag ggatttatag   3420 gaaagagggt gagaggcgat ggtgttgaaa tcgtttttgt cgatttggaa gtaatagtag   3480
tattttttat aagagcgtgt aattttaagg ttgttcgtcg aggtagttta gttatttcgg    3540
taggcgtttt tttttttttt tttttttttt tttttttttt ttaggttttt cgtagtttcg    3600
atttagttta agcgttcgta ggtttgaatt tttttttta ttattcgttt tttttagtt      3660 cgtagtttat tagtgtgttt atttgggagg tgcggttaga tgtgtttgga aggttagatt    3720
ggtcgggata agtggtttga gagaaagaga aaggttttt tgtatacgtc gcgggtgggt    3780
tgtcgggagt atcggtcggg tagcggcgtt cgggaagggg agagcgggtt ttatttgttg    3840
gtttaggtag tgattttgcg ttttttattc gggttttgt cggatggtcg gtgatttggg     3900
gcgacgagag aaggtttaat tcggtaggag ttttttggttt tgcgcgtttt ttttattttt   3960
tttagcggga agggtaaacg gtatagcggg attcgttttt cgtttgttgt attttttagg    4020
tagttagata tatttttag tttaatggaa ttttagtcgt tagtaacggg attaagagtt     4080 ttcgggggata agggtggaga ggaatatttt tttttttatga tcggggttat tattgtagtt  4140
```

```
ttagtgtttt ggatgtttta tagggaagag tttttttttt ggtgtgtgat tatttagtga    4200
tttttgtttt tgttttttgtt tattttttttt tcgttttttt tttttatttt tttttgttat   4260
tttttttttt tttttttttt tcgttttttaa aagttttcgg attttttttt tttttattta    4320
aatttttttt ttgtgttttt tttttttgtgt ttttttgaatt taggagagta tttgataata   4380
tttaataggt aattagtgtt tatttttaat tatttaaaag aggtatttat atattttgaa    4440
aacgggatta tttattttt gtagatatta gtagaaaaat aaattgtatt cgagtaattt     4500
ttttaagtat tttaatttt aatttttttt tatttttttg ttttttaatt tttttttttga    4560 gagatgtgat cgtgtagtat tttagtgttt taacgaaatt tttttttttt ttttgtgtga    4620
aatttatttt tttatttttat attttcgttt tcgttcgaga ttgtttttttt tttttttttat 4680 ttttaaagat ttttgaattt tagtgttttt tatttttggt aattaagtag tagatttttag  4740 tattttagtc ggtggtattt cgttttttat cgacgaagat tttattaaaa tagattaatt   4800
agattagacg ttggaggtat tagaaaatcg gttttttagat agagtagtta aattttttaa   4860
ggaaatagaa tatttattag atagagttgt taattaatat tgtaaaataa ggaattagaa    4920
atttttttcg ttataggttt ttagtagaga aggtaatata aatatagatt aagatttaat    4980
aattttatag tagagaatga gaatatgtta tttttttatag taaggttggt gtggtaatta  5040
attaggttta tgaaaataag ttatgtttga aattaaaggt aaagttttta aaagtgttta   5100
tgtagtaatt atgataatga aataggattt gttaggattt tagagtttgg ttatgtaagt   5160 agaatttttag agaatttttt agtagaggaa aattgttttt gaatttttttg ttaagtaaat 5220 ttttggtata ttttttaata atatatgttt tttttaagac gttttgttaa aagtaagtta   5280 aaatttttaaa ggagttaatt attggttgta attggttaat aaatgcggtt gtttttatag  5340 aggttttta aattattaaa tagtttgaag taaagttttt ttaatgggaa tgttgtaatt    5400
ttgttgtatt tatttttgtat ttagtgttat agtgttatta agaaataaat tttgaaattg  5460
gtaagtatta ttaagtggta gaagaatatt atttattgag tagagaattg tattattgaa   5520
tatgtaaata aaaatatata tattatttag atttgttatt aggtattaaa gaagtagata   5580
agattgtatt agtaattgga ttagtgtttt aattttttttt tagtaaggta aaattagttt   5640
atttattaga attaaattta agtttatgaa ttgtattttg tattgcgtat tatatgattg   5700
ttagtaatat gatataatta tattatgtat ttgtaaaatt tttattttaa aatattatat   5760
tatatttatt tttaattttt ttgagttaga atattttatt tgtggtatat atattttaga   5820
attgatgtag aggagtagag tttagttgtt agattttta gtagaaatag tgtagatata   5880
ttttttttag aaaatttaag aatatttttt tttttatgg aaagaatatt attataaagt   5940
gtgagattat ttatagtttta agtaggggggt ttgggagtta ttttttaata agaatagttt 6000
aagataaata aatgaatttg ggaaaataag atatattgtt aattagaatt tttattttt    6060 ttatgatttt atattttttg attgttttaa taaaggtaag atgtattttt tgtttttttag  6120 gtgttaggta ttgtgttatg taggatagaa tatgttattt ttatttaatt tttaaaatat   6180
ttttatgaga taaagaatat tatttttattt tatataaaag gaatatggtt ttgaaagtat  6240
taggtaattt gttttaagaa ataaatttcg ttagtgatatt tgttgggatt ttgtgaaatt  6300
ttgtttgatt ttagagtata agatataagt tattaattttt tgttgtattg ttgtttgtta  6360 gttttttgaga ggggaaatta attgggaacg tattagtttt gttatgata ttttattttgt   6420 ttttttttgtg gagtcgtagt aaggtttaaa ttttaatttt taaatttcgg taataagatt  6480
```

```
tagtgatttt tgaatttggt tgattatatg aatttttga gaaattttga aataatagat      6540
aaattttaag ttttattatt agggattag aaaattgga gttgggtttt gggatttata      6600
ttttaatatt tatttttgtt ggagaagtaa ggtattattt atatttatat gataaatgaa      6660
aggatatttc gattttttgtt tagttttat agagaggttt tgagatagg ttaaaagttt      6720 ttatttagtg taaagatgag ttgttgtata tgtttgtttt tttgttttta tgtatatgtt      6780
tattaaatat gtattaagtt tttaatatgt ttgatatagt aattttgtga ttgtagataa      6840 ttttttttatt tgtaaaatgt gagtaataat aatatttgtt ttttgggttt gttttaaaga      6900
ttaaaataaa aatgtatggt ttaatggtag tggatttggg gggatttttt atataaataa      6960
gtgaatggag gtatgaataa ataaatatat aaagatgtgt gtatttatat ttatatatat      7020
aattaaaaat agttaaagat gtaaaatta agttaaatg tatgtgatat tgaagtatat      7080
gttgattatt gataatgaag tatagtataa ttttaatttt tatattttaa tatttatat      7140 ttaataattt atattttaat ttttagttta tttaagatat atagatatag atagaatgtt      7200
ttaaatgtat tattgtttta gttttaatgt ataaatttta tatgaaaaag tatttattag      7260
tgtgtagtaa atgtattaga atatatttta taggttaaat gatattgata atgttttaga      7320
gtcgttattt ttatttttgg ataattttt aaattgagag taattaaatt tgttattttt      7380 ttatttttt ttataatggt aaataatata taaataatga gttgtgattt aaagaaataa      7440
ttttataatg taaaagttttt tttatgtttt attgattttt atgttttaa ttaatttgg      7500 tagtttaagt ttgtgatttt agtgttgagg aaagtttatt ttatttaga gtagtggggt      7560 ttagttatga ttttatatta taattattg gataattaaa gaatattgat gtagagttcg      7620
tatttaaaga tttggaattt ttagaagtga tatagaagta ttggtatata tatattttta      7680
aagttttttt ggagaaatat atagttatga ttgagaatta ttgttttggg gaaagtgatt      7740 attttttat tatttaaata gttaagtttt aggaggtaaa atatttatat tttttttat      7800 taaaatttgt aaaatatata ttttattaaa gat                                  7833

<210> SEQ ID NO 16
<211> LENGTH: 965
<212> TYPE: DNA
<213> ORGANISM: Artificial Sequence
<220> FEATURE:
<223> OTHER INFORMATION: chemically treated genomic DNA (Homo sapiens)

<400> SEQUENCE: 16
gattaattaa gggtattta gaagttaggt gttttgttg ttttttttga gtatggaggt        60
tattaatttt tagggggaag agatgtagtg tgaggtaggg gtgttgtgtt aagaaatttt      120 gatgttttg gggattgagg ataaaggtgt ggatatgatt ttggggtatt tggagttttg      180
tgatttgtgt tatggatggt atatttaggg gttaattttt gttttgtttt aaagaatttt      240
aagttagagt ttttgttttt gttatagtt ttgggatgtt gttgttgtgt ttattgtata      300
ggtagtgttt ggattggttg tagtagattg tgtgttgtgt gttttattgg gagatggtgg      360
agatgttgaa aagttttttt tttgttattt tggatgttgt gggtggtaag tgttttagtt      420 tttattttg ttgagttgaa tgtttaggta tagtggaatt gaaatttggt ttttatttt      480 tgttgagttg aatgtttagg tatagtggaa ttgaaatttg gttttgtggg atgtgagagt      540
tgttgaggtt atgtgtaatt gggtgtgatg gagggtgttt gtttgtgatg tgtgtaggtt      600
tgatgtaagt aggttattgt tgtgtgagtg tgtggatgtg attgtttgag agatttggag      660
gtaggtttgg gatatgtttg agtgaatatt ttaggatatt tttttggtta gtatttgttt      720
```

```
tttagtgttt gtgatttaga gtgggtatat gttgggagat agtaatgggt ttgggtgtgt    780
gtaaatgagt gtgattggaa gtgagtgtga gtttgattta ggtagggatt atatagtatt    840
gttatatttg tttgttttt  agtagaggat tgaagtgtgg gggtgggggt atggggttgg    900
aatagaatgt ttttgggata ttttggtaaa tagtagttgg aagtaaaggg gtagttgtgt    960
aaatg                                                                 965

<210> SEQ ID NO 17
<211> LENGTH: 965
<212> TYPE: DNA
<213> ORGANISM: Artificial Sequence
<220> FEATURE:
<223> OTHER INFORMATION: chemically treated genomic DNA (Homo sapiens)

<400> SEQUENCE: 17
tgtttgtata gttgttttt  tgtttttggt tgttgtttgt taagatgttt tagagatatt     60
ttattttggt tttgtatttt tattttgta  ttttagtttt ttattaaaga gtaggtaggt    120
gtgatagtgt tgtgtggttt tgtttagat  taagtttata tttgttttg  gttatattta    180 tttatatata tttaaattta ttattgtttt taatatgtg  tttattttga attatagata    240
ttaaaaaata gatattggtt agaagagtat tttgaggtgt ttatttaaat gtgttttaag    300 tttgttttg  agttttttgg gtggttgtat ttatatattt gtatgatgat gatttgtttg    360
tattaaattt gtatatatta tgaataggtg tttttatta  tatttaatta tgtgtgattt    420
taatagtttt tatattttgt agaattgggt tttagtttta ttgtgtttga gtgtttagtt    480
tagtagaggt agggaattgg gttttagttt tattgtgttt gagtgtttag tttagtagag    540
gtagggatta aggtgtttgt tgtttatagt gtttagagtg gtaagaaaga agtttttag    600 tgtttttatt attttttggt ggaatgtgta gtgtgtgatt tgttgtagtt ggtttgggtg    660
ttgtttgtgt ggtgagtgta gtagtggtat tttggggttg tgggtggagg taaggatttt    720
agtttgaggt ttttttgaggt agagtagaaa ttagtttta  ggtgtgttgt ttgtggtgtg    780
agttatggaa ttttaggtat tttggggttg tgtttgtatt tttgttttta gttttttagaa    840 gtgttgaaat ttttagtat  gatattttg  ttttgtgtta tatttttttt ttttaggggt    900
tggtggtttt tgtgtttaaa ggaggtagtg ggaatgttta attttaaga  tgttttaat     960 tgatt                                                                 965

<210> SEQ ID NO 18
<211> LENGTH: 16579
<212> TYPE: DNA
<213> ORGANISM: Artificial Sequence
<220> FEATURE:
<223> OTHER INFORMATION: chemically treated genomic DNA (Homo sapiens)

<400> SEQUENCE: 18 tgtttttaa  aatgatgttt agttgaatta gttaatggag ataaaaatat ttatatataa     60 ttttttta   agtttattag ttattttata gattagttat aattttggtt attttaatga    120
gttaattttt ttttagagat attataaatt ttttaaagat ggaaataat  tgttatttt     180 ttgaataatg tttattattt aaaataatgt atataaaagt tgtttaataa attttgttg    240 aattgagaga aaatataaaa aattgaaagt agtttgtttg taataagtgt tgttaagtt    300 ttatagattt ttttttttt  ttggaattat tgtaataaat atttgatttt tgatttgtag    360
gattaaaatg tgatttttta tattttaata ggagtaagta ttagtttttgt aattttttt     420
```

```
gttaatagaa taaaaatgga atgtatgttt gttgttttta tatgttggtt gatatttatg    480
ttgaatattt tttttataat gtagaggttt ttttgttttt tgtttgtgt tttatttttg     540 tttattatag agatattaat gatgttatgt gtttttttgt attattagtg tagtagtttt    600
tattatgttt tttgttttgg ttttattgta gtttaattaa ataaatggaa atgggtagtt    660
attgaaaata aatagtaatt gtaaaagttt tgttttttaa gaaatttttt gtattgtatt    720
ttgttttgtt ttattgattt taagattttt attgttttttt tgtgtttaga aattagattt   780
tttagtttgt tttgttttag ttagataaat gttttataaa aatgatttat atttttttaga  840 ttgtggggag agaagaaaaa gattttgaga aagtgattaa ggagggagta agagtgatat    900 aattttgat ttaatttagt tggattgtgt tttttatgtt tttatttttt tttttataaa    960
aaagatagtg tttttgatgt tttgttttag gtagtttttt agggtgagtg tagatgtgtt   1020
gagttatttg gttgttttga ggattggttt agagagtttt ttttttatt aatgaagtta    1080 ttttttttg gtagtttggt ttttttatt attttatgtt ggaatttggt tttggtttgt     1140
atagttttgt tgtgatgtag atggttttt agttaagttt tagagaaatt tgtttaatta    1200
tgaataggat atttatagta taggagaaaa aaaaattat taaaataaat attttattgt    1260 aatatttttga tttgggggtt ggagagtaaa aatttaaatat ttgatgtttg ggaaaaattt  1320
aatgttttat ggttttttaa ggaaatttgt ttgtgtttaa tttattagag taatttatat   1380
attttgggtt aaagtataat gagattgtta ttattattttt gttttttgta agattttttt  1440
tttaagaata aaaagaaggt aataaagatt ttatatttt gttttttttta gaaagttaaa   1500 gagaattta agtgttggat gaaatgtttg tttttaattt gtagtgtttt atttaaaaaa    1560
aaaattatga tataatttta gaggataggt tttttttttt tagggttttt gaaagttaaa   1620 agtatattt taatttgtag tattattgta ttatttagtg aggataattt gtttagttgt    1680
gtttaggatt agttagatta aggagttgaa attaagtttt ttttgaattt gaatgggatt   1740
ggaattttgt tattttaga gtagtaatag atgatgttat gtttaagaat atttattttg    1800
attaataaaa aaggagaagt ttgaaatgta attttaaaga attttagaag gaggtttaga   1860
tgaagataat aaaattttt ggagatatat ttgttatta tattttttttt ttttaagtta   1920 ttggtttgtt gtttttgagt ttagttaaat tttaaagat aagattaaag taaggaagta    1980
aggtatatag ttttggttt atggttttttt ttagatataa gtattgtgaa tgaagatttt   2040 gtttattta tatttgggat tttggagttt ttataaagaa tattttagt ataaggatgt     2100 gatttaaagg gggattata gaataatatt ttaattattg tttgatttat atttgagtgt    2160
aatggataaa taaatataat tttagttata aaatttgaaa aatatatatt ttttattta    2220 aaaatttttg atagttttgt taggtattgg agaattagaa ataaatgttt ttttattttt   2280 tttttttga tgaaggaaag ttattaaaaa tagttatata gaaataataa tataattgta    2340 gatttattt taaatatagt tggtatgttt tttttttttt ttttttattta tttttttattt  2400 tagatagtta gagggaaaag tttgttttag agatagaaag aagatattta tggggtataa   2460
ttttatttta gttatttgat agtttgaaga agtatttaat ttttgaata ataatgttat    2520 aagtaaaga agagaaaaga taggtagttt aaagttttttt aatattgtgt atatttttaat  2580 tttttaagtt agttttgaga aagtgttttt gttttgtaga agtatttggt taagtgttgt   2640
gaagtttatt ggtattaaaa gaaattaaaa attttggagg attagagaat taaatttggt   2700
aatataaatg aaaatatttt agaatgtaaa aagtatttaa tttattattt ttaattatgt   2760
tttattatat atagatggta ttatttatag tgaatgttaa ttattaatat tttttaaaa    2820
```

```
atgggtatta atttgttatt agttgtttgt ttttgattta gttttttttt gttgaaaggt    2880
tttatttaat tgtattataa agggataaaa gggtaaaaga taataagttt tttagattgg    2940
tagatttgtt atttataaaa tggttttggg taggttattt gaattttttg aaatttaatt    3000
agatttattt aaatttaaga atgagaatat aaatttatat tttgaagtgt tttatagaaa    3060
ggtttatttt aatgtttgga gtatatattt taatgaatat ttattttatt ttattttttt    3120
ttatttttga attaagtaat tttgaattta agttgttat gattagtatt gaaagatta    3180 ttggattatt aattgtgtga ttttgggata gtaattttt gtatttagt ttgtttatat    3240 gttatatatg aaggttgaag tttgattttg ttttgtgatt attattttaa atatttgatg    3300
aaattaaatt ttagtgtttg aatggtagt ataataaatt tattaagaat aaataattta    3360
ttgtaaaaat atattgattt ttaaatgatg taattgatag ttatattatt gtagagggtt    3420
gataaataat aaaagaaatg aaagatgtat atggtgagaa ttgaaattat tttgataagt    3480
tttttatttg tttattattt aaaattaatg attatgttga atgtttataa attataaaat    3540
ataaaagaaa ttttataaat gtgtatgtat aggagtttaa gttattaaaa gttttaaagt    3600
ataagtttaa attaaattaa ttaaagaagt tgagaggaaa aattggtttt tattttaat    3660 tattattgtt ttgaggtttt atgtttaata taattttta agtagaggtt ttagagagaa    3720
gagttgtgag gatattttta tatttgtgta gaaggaaaag tttgttattt attttagtat    3780
ttttagtgtt atattgatgt gtattttgga tttattttgt ttttattgta taaatttata    3840
tttgatttta aagaaaagga aaatttaaag tttttttttt ttaagggat agaaattttt    3900 tgtgttaatt gtttgatttt tttttttgta aggttttatt ggaaattttt tgtaatataa    3960
tgtaggggat tttttatgt gttgatgttg tttatatagt ggggtgggtt tgattgaaga    4020
aaaaaaattg tatatatgta tgaaagatta tggttttatt tttggaaagt atgaaaggtg    4080
attgatattt ttaagaagtt tttgttattt aggaaaatta ttaaatattt tatttagaga    4140
tatttggaaa gattgaagga aaggaagaat gaagaaagta gaatttagat ttatgtgggg    4200
agagatttgt ggtagaggaa aagtattttt tttgaatttg ataagggatt tgtttggggg    4260
aattttttgt ttagttttt attattaggg tttttttgaag ttgggttttt tattgggtag    4320
ttttttggga gtgtagtggg gaattttat atttttttt taggttttg aaggattttg    4380 tttttttagt gttttttta ggttggtagg agttttgagt ttgatatttt tttttgatgg    4440
gataggtaag ttttgtgggt gtgtaaatat gttgtaatta agtttttgt tgattttata    4500 gttttgtgtg ttttgagaa gaagtgattg tatttaattg tttattgttg gtttgttttt    4560
taagagtttg ggggttttt tttttaatt tagaattagt tgtatggggg gtgggaagt    4620 ggggtgggg aaggagtggg agggtagtgg ttttgtgag tagagtgatg ttattgagtg    4680 agttttgaa tggggagtgt tgttgttttt aagttgattg gtattttttg ttaggaagaa    4740
atgttaagag gtgggagtgt ttgggagggg aggtaggtgg tttttattgt aggtgtgggg    4800
agttgttttt ttgttttttt gtttgttttt taagtttgga ttttaggag tggttgaagt    4860 tgtggagtgt ttttggagtt tgtgaatgaa tttttttttt tttttttttt tttttttttg    4920
ttgagttttt ttttttggttt tgatggtata gtgatataat gatgatgggt gttataattt    4980
gtatttgaat ttgtaggtga ttgtttga gttttttgg ggaagaattt taggtgtgtg    5040
gatgtaatag ttgagaatat taggtgttgt ggataggagt tgggattaag attttggtt    5100 agttttgtat tttttgtat ttttagtat tgttttgtat ttttgtatt tttttggg    5160
```

```
ttattatgtt ttttatgtga tttgtttggg taatgttgaa tttagttgtg tagtgttgta    5220
gtgaattttt tttttaaatt gtaataagtt gttttttaag gtaattatgt ttttttttgtt   5280
ttttttttaa aaaataaaaa taaaaaattt atagaaaaaa atttgtgagt ttagaaaaaa    5340
gaagtaattg gtagaaggtt ttaattaagg taaagagttg taaggtgaag ttaagaaaat    5400
gtaggtattt aaaaaatgta ggtaattttt ataaaggttt ttggggagag gtatatagag    5460
ggattttggt gttgaaaaag atttagataa aagaaattta gggtggggtg ggggtaaaat   5520
gattaatgga attgggggaa gggagggaat aaattgtaaa gaaattatag aaaagtggtg    5580
ggttttttgag ttggagagaa gagagggatt tttggtatttt tgatttttttt gttgttgttg 5640
tttttaatat gtttgaggta aaagtttgaa tggggattat taagatttgt tatagataag    5700
tttttgaagt tgttttggtg taggttattt ggttttttag tttttggtgt gtggttagtg    5760
tttggtgttt ttggaaagtt attttttgggt agttttttgat agtgtgatttt ggtgtttaag 5820
tagtttggga ttttgtgtgg atttgatttt tttagattgt aggtagtttg ggaggaggtt    5880
tggttggggg aggtgtagga tttttgttgt gttttttttga tgatttgggg attgttatgg   5940
ttttttttttg gtgtttttgg gttttttttgt tttgtatgtg gtgtgaaggg gttagtaggg 6000
aaggagtaga ggatgggggg tggggttgtt ggagttttgt ggaggtttgg gaggtttttg   6060
ggtgggaaaa gtttgttttg aattggtagg gatgtgtaat aatttttttt attttgaaga   6120
gtgaaatagg gtttgttgtt tttattttaa taagtaaatt ggtatttaga gtgtattgta   6180
gataaaggtg gtttgggggat ttgaattagg ggttttttggg ttagtttttt tgtttagatt 6240
ataggagttt tttgtttttt tatatatttt ttattttttt ttagtttttt gttttagttg    6300
agtaattttta ttggtaggtt tagtggtagt ggtgtgtgtg tgtgttggga gttttggggg  6360
atgttttttgg ttggagtgtt ttattgtttt gtagaggtgt gggtgttgta gggtgatatt  6420
tttggtgtgt gtagatttag ggtatttggg ttgttttggt ttgtggtttg tgttattggg   6480
tgtggagtgg tttgggtgtt aggtagagga gagtggggta gaaaaatagt gttatagttt   6540
aaattatttg tttttttaatt taattgtgtt ttggtaagtt ttgtatgttt ttgggagatg   6600
ttgtgggaag ggggagaaat ttatatggtg tttggagagt tgttttgttg tgtgtatatt   6660
tgtggtagag ttttttttggg ttgtgttttt tatttttgtg ttttttttttg ttttatttt   6720
ttttgttttt tttttttttt tttagttttt gtttttttttt tttagttttt gtgttttttt   6780
tttatagttt gataaatgaa tggttagtgt gaaattttttg tttttttttgt gttttaaggt 6840
agtagggagg gaggagtgag ggaggtggtg tgttttttttg gatttgtttt tagtttagtt  6900
tataagattt gtagaattta gatgtttagg aattgggagt tttgtggtgg gtgtgggtgt    6960
ttttttgatgg agaagttttg tataggtgga gaaaaataag tttttttagat taagtgtgta 7020
tttttttataa ttttgtgttt aaggatggaa ggttttagtt tttttttaag ttatttatttt 7080
tgtatttttat aatttgtggt gtatatttag gagtttggag gattttgaaa aaaggttttg   7140
gtttgtgtaa agtgtagaga tgttttttttg tgagttggtt ggaatgtatg tggtgttttg   7200
ggtttagttt gttgtttagt ggatgaatgt atatggttgg ggtggagtta ggttttggag    7260
gtttagatgt gttattttgg gtgttttttaa gaaagataat atatatattg tgtttttaaa   7320
atttatgatt atttgaattt aatggtaggg ttttgttttta ggatattgta aaagaagggt   7380
ttttaatttta aaatttaaat tttttttaatt ttagggtggg tgttggatgg gaaagtggag  7440
agaaggtggg tagtgggagg aaaaaagaaa gggaaggaag ggaagtggaa ggaaagagga   7500
ttgtggaggg gaggaaaagg agaaaggaat ggagatgggg tagatggtat ttaaatagtt    7560
```

-continued

```
aggaatggat tggaagggtt tgttttgggg tttgggtttg aattttgaga tttgttttag    7620
gatattttt ttttttttt agtggtaata aatgtgattg tagaggtgtg ttgggatgga     7680
agggtgggaa agaattagat aagtggaggt ggtttagttt tgtttaaagg ggttgggttt    7740
ggggtttgtt tttatttgtt tattttgtgt taagggagga tttgtaatgg gtgttttttg    7800
tagtggttgg gttagttagt tgttatgtgg gttggtgttt tggttttag ttgagatggg    7860
tgtgattttt tgggtttaga gattgtagta tagttgtata ggtggttggt gtagttgagg    7920
ttttattta ttgaggttaa tgggggtggg gtggggaagg tagggtttag tttaattgag    7980
agagttgagt ggttttgttt ttgggatttg gggttggttg tttttggagt tgatttgagt   8040
tttatttaga tagtgttgaa tattttatt aaaaggttat ttaagtttta tttattta     8100
ttttatttt gtttgttttt tgggagtggt aggagggta ttgtgtttt gttttgaggt     8160
aggggagagg ttaaaattta ttttaagtaa attttttgtt agaaaatga gattttatat   8220
tgtatttat ttgttgattt tttaaatata tttaggttat tttaaagttt attttagtt    8280
aattaataga ttaattttgt tttagattgt tataaagagt ttgtttggaa tggtaaatat   8340
tgttatttga taagattaat agaattttat gggggtaaat atggaagggt tgtgagtgta   8400
attgaggttt ttgtgttta atgaggaatt ttagtgggga tttggtgggg attggaagtt   8460
tagtatttat ttagggagtg attgagttgg aaatttggag aagttggtg tagatgagat    8520
ggtgttttt agagttgtat tttaagtttt tttatttgt tgtatattgg aagaattgga    8580
ttttaaagat ttttttatt attttagatt ttgtagttaa tagttatgtt ttttttttt    8640
tgtttgttga agttgtgat ttaattgttt taagtatttt ttgataattt tgttaaattt   8700
atttgaaaa tatttatata aagttttaaa ataggatgtt gtgagtgtaa tataaaata    8760
ggaaggtatt aatggaagta ataattagtg ttttgagata gaagtggttt ttagtttgta   8820
atttggaaat gttaagagta gtatattagg gagaaggttt ttaagagttt gattttttgt   8880
tttgagtttt gagtaaagaa agaaatatgt tagaattgta ttgtttgttt gtagtaatat   8940
tgtaaaggt tttaatggat tttaatgtga ttgagtaatt attttttta gtattaagtt    9000
tatagtttt aattttttg tgagaagatt aggtaggaag tgggatgaga tttaagataa    9060
ttatttagga tttatgttag aatttaaagt tttgattttt ttggtagata aaaatagagt   9120
tggttttaaa ttgtattttt tgttttaaa aaaatgaggt ttgaaaggaa ttttttaga    9180
tttatatagg tttatagatg taagtttttt tttttttttt gtgtttgtaa attggaggga   9240
gatgttttg atatttaga atatttgtat ttatatattt gtaaatttg ttaggaaagg    9300
atttaaatag ttaaattaaa ggtgattatg attaatgtta aagatattat ttattgtttt   9360
tttttttgtt gtattattag gtttaaatat tttggagtta atgattggtt atttaattga   9420
gtaatagagt ttttgagagt gtaaagatta attaattttg ttttttaaag tttggtaatt   9480
aagttttttt tttttggtga gatttaaata ttttgttga tgttatttat ggataaatat   9540
tggtaaatat tgtatttaaa atgggatatt gttttgtgat ggagtagaat tttttaagat   9600
atatggtttt tttgaaagaa agaattaatg attgtagtaa ggtatttttt tattatttat   9660
gtagagaaat tagttaggat tgataaatat ttattgttgg gagttatttg ttttggtttg   9720
agaaaatatg ttgattgtta tataggtttg tatttattta gaaaatataa agtatgtatt   9780
ttttttgatt tggaattaga aaaggggggat tagatatgga tgtttggtt aagtttatt    9840
ttaattagtg aattttttgtt agttttttttt tgtagtttag atttggtaaa ttatatatat  9900
```

```
ataaagtttg tgtgtgtgtg tggggtgtgt gtgtgtgtgt atgtatatag ggttttttaaa    9960
tattgttaag ttttttattat tgaatgtgtt agaggtggtt gtattttaga ggttagtata   10020
aagaattttt gtttaatgtg ttagttttgt tttttgaaat atattttttgg gtagatttat   10080
taattataaa aggatataaa tgtatatatt tttttatattt gtatatattt tatttttattt   10140
ttttaaggat tttaagaggt gtttatgttt ataaaatgag attatatatt ttataataaa   10200
tatatttgat aaattataat ttttttatta ttaaattatt gatttgatat tatttgaggt   10260
atagtggaat gagtattaga tttggaatta gaaagtttga gttggatttta ttagttgaga   10320
aaattaagta aagatattat ttttggattt ttagtgttat aatttattaa atgaatatgt   10380
agttataaag attaaaagag taagtatttt gaaaaattat ataaaaaagg gatgataata   10440
tattatgttt tgggatttat attgatttaa ttttataatt ttaataataa ttgtattatt   10500
taagttatgt agtttttatt gaattataaa ataaaattag agagggtat attgttttaa    10560
aaattgttta gtttttattaa ttagaagata gattatagaa attgattttta atgaagttgg   10620
atatttagtg gaaaggaaga attatttaat aaatggtttt aggataattg atgggtttat   10680
gtaaaataag aattagttttt tatttgattt tttattttaa aagaaatata agatgaatta   10740
aatatgaaat gtagggaata attttttata aaatgataaa agaaaattat gggattaaaa   10800
aaaataagtt aggaatagag aaatttgttt taagtaaaat ataaaattta gtgttatttt   10860
aggaaatatt gataggtttg attaagtaaa aattatataa aagtaaataa tatatttgga   10920
aaatatttat gatatttgag agataaaaag ttaataattt ttgatatttt atggattttt   10980
atgaataatt ttgaaaagtt tatatttatt aaaatatgag taaaaattat gtataggtag   11040
tggtagaaag agatatagag ttttaaaatt atagaaaaaa ttgtttagtt ttatttgtaa   11100
ttaaataaat agtaattaaa atattaatga tatgttatat tatttttta ttaattagag    11160
gagtaataaa aaaaaataat tttttttttt tttttttttt ttgagatgga gtttgttatt   11220
taggttggag tgtagtggta tgattttagt ttattgtaat ttttgttttt taggtttaag   11280
taattttttt gtgttagttt tttagtagt tgggattatg ggtatttatt attatgtttg    11340
gttaattttt gtgtttttag tagagtgggg ttttattatg ttggttatgg tagttgattt   11400
tgaattttg atttttaagtg atttatttat tttagttttt taaagtgttg ggattatagg   11460
tatgagttat tgtgtttggt aaaaatgaaa ttaaaaagtt tgatgtaagt ttgtgttggt   11520
taggttgtgg agaaattggg tttttttatat attgttgtat gaaagtaaat aggttttttt   11580
atttttaaaaa ataatttggt aattattttt ttttgatttt ttattaaaag ttttttaaaag   11640
atgtatatat ttttttgattt agtaattttta ttttttgata ttattatatg gatggatatt   11700
ggtattaata ttatttaaga taaatggata aggatgtttt ttgtagtatt gttttttaaga   11760
gtaaatattt ggaaatagtg taataggttt attatagggga attatttaaa taaaagttgt    11820
tgtatttatt taatggaaaa ttatgtagtt gttaaaaata atatgaaaa attgtatttg    11880
ttgatttgga atatttttta aaatatattg tattttaagt gaaaaaattg atagataaaa   11940
ttgagtatat attatatatt taattatgta aaatgggtgt atatttatttt ttttaataaa   12000
tatttattga gtgtttttagg tattgtggat ataggagtga ataaaatatt aaagattgtt   12060
ttgttggaat ttttattatg gtaggtagag aaaggtaatt tttaattata tatgtaaaat   12120
ggtgatatgt gttaggatga aaatagagta tgggaaaggg aatagagtat agtatgtttt   12180
aggtagagta atgagaaagg agtttattag gtagagaata gaggagtgtt aagggggtgat   12240
aatgtgaaaa agtttagtta agtttaggtt taggaattta tatgatgtta ttatttgtat   12300
```

```
gaagtaaatt tatgaaattt tgtatttaaa ttatgtgatt ttttttttgtt gtataatgat   12360 tttttttgtg agaaagaatt agtgagtaat atgatatgtg atgtttatta tatttatttt   12420
gtagttgaag tattttagaa agttggttgt ttagggtatt taattagtag aatggtggat   12480
aaaattattg tgttttgtt tttaagttat tttttgttag ttgagttttt ttaaaattaa   12540
gggagaatat taaatattta tttaatagaa ttttggtttt tttttggagg ttgtttatt    12600 ttggtgtgtt ttttatttt tttgtagata tttttatgg ataggagttt tattgatttt    12660
gttttttatg tttttaggt aattaaatag tttagtatt ttgtatttgg attgtttaat    12720
gatttttttt tttttttatt gattttattg gagtagaagg ttaaatatag gtatttattt   12780
ttatattttt taggttttt tatgtagata gagttgttat tattagtaga tggtgtttat    12840
aagagagata tggaaaagtg gaagaatgga aatagggatt tggagtggtg ttaaaaataa   12900
agaaagaggt ttttgaaagt tttttattta atatgattaa atatagaaga taaaagatgt   12960
aatttaatga ttaaggatag ggatatagtt ttgagaaaat tatagaagtg gaatgaatgt   13020
tttggatttt aaagaagagg gaatggaaat gtagttttga ggtagttaaa gttaataaag   13080 tttttgata tatttattgt agaaataaat gattatttt taatttaagg tttgtaaatt    13140
taggtgatta taggggtgag gtatggagtg gaaatgggta agagattaag tgggggtagt   13200
aatggttttg agtatataga tttaagggga gagattgttg tttggttaat gtttatgatt   13260
agttagttga aatatagatt tagtgttgtt agattttttg attttttgaa agaagttaga   13320
gattttatat ttagtgtaaa tagtttaatt tttaaattga gtaatttatt taaatatatt   13380
tatgtaattt atttaaatgt atttagagta tgtttgattt ttttttttgta tttttattta  13440 gttttagggg taattttaag gaaagtgatg tgtatatttg ttgtatttat gtagatggag   13500
gattattttt ttttttttaa taaaagatat tttataagg attgagtgtg gtataaagag   13560
tttgattttt agtatttaaa ttgagtagga aatttaaata tagaagattt ttttttgggt   13620 tatattttg gtttttttaa atgagatttg atttttttaga tattgataaa tattatatta  13680
ttgggttatg gtaaattttt aagtggattg atttaaaagt gtttaaaagt attttaggtg   13740
ttaaggaatt gttggtatgg agttttaaag gtgttttgt ataagaaata gaggtgttga    13800
ttatgtattt gatttataaa tattttttaa ggatatattt tgaatttggt aatgaagaaa   13860
tattgtggga attattaagt tgaataaagt attagttttg tttttttagaa gtttattgtt   13920 ttatagagga gattagatat gtttatagat aatttgaagt atatagtaat aaattatagg   13980
atgatttatt ttaagtataa agtgtatatt gttattatag tggtaattta ggttataatt   14040
tttaaatgta agagttttaa atattatttt tttttatttt agtgatatga aattatgtta   14100
gaatatttgt agaaagtttg aattagtaat tttaataata aatattgagt attgatatat   14160
tgtatattat tgagatttat tttatatata ttattttatt aattttatg attattttgg    14220 taagtattaa ttttttataat taagtagtga tagaaaatga ggtttagaga gatatagtat   14280
tttatttaaa gttatagaat ataagtagag aatgtagaat ttgtattttg ggttatttga   14340
tagtggagtt tagatttttta aaattaggtt tataaagatt ttttggaaaa aaagaaaaat   14400
aaaaaataga gaataaattt ttttgaagaa agtaggaaa ttattattta taagtataat    14460
taaagagaga tttttaattt ttttttttttt ttttttttg agatggagtt ttgtttttgtt   14520 gtttaggtgt aatttagtt tattgtaatt ttatttttt gggtttatgt tataaagaaa     14580
gtttttattt gattggtttg atttgattgt ttattagaat ataggttttt tagtagggtt   14640
```

```
aataagttat aatagttta gtgatataag ataaatataa attaataata aggttaattt       14700
agaattatta atatatgttt tttattgtga attattagtt ggtttataga tggaaaatat       14760
aagatatata atgtattagt ttaaaaaatg ttttttagag agtgtttaga attatagaat       14820
ttaaaaattt tgttttgaaa aggtttaatt tttattttaa aatatataaa gaaattaaat       14880
gtaaaaaaat taagagaaaa ggttttaatt aattaaatgt tgtataattt taagttttat       14940
ttatgtttaa gattagtttt gtaatttatg attaatttta gtattagttt gttttaatt       15000 taggtttgtt aaataatata gaattttttt tttaatgaag ttttttaggg ttttagttga       15060
aaaatatata ttagttagga tgttttaat tgtaaggaat aaaaagttat gattttattg       15120
ggtttaaata ataatgatat ttataattt atataaaatg aagtttaaag gtatggttta       15180
ttttaggttt aattttaag gatttatgtt ttgttttgt tgattttttt ttagttttat       15240
ttttagaggt attttattta tttatggatg taaaattttt ataatagttt tagtagaaag       15300
attttagtat gataatgttt agggaagaaa attgattatt tttttttttg tttttttttt       15360
aggatgaatt tattttttt agggatttt tattggagga agagattttt ttatatttta       15420
ttggttaaaa ttatattata tattgtttta aatttaatta ttggaaaagg gaatggtatt       15480
tttataattg atttaggata ttaggattat ttttgggtt ggggtttgat ttaggatttt       15540
ttaaagtatg tgattgaggg taggtattag aatggaatta gagttgtgtt agaaaggaga       15600
aatgtatggt tattatagaa tagttttaaa tgttattgag gagggtataa ttgtaaaaat       15660
taaataattt tttgttattt ttttgaagtt ggtatttga ttttagatg gttttttaat       15720 ataggttttt tttttttta ttattatagt tgttttgaaa tttgagttgg aagggaatat       15780
tttgagattt agattgttaa atgttttttt taaagttatg taataaatta aatggtaaag       15840
ttagggtagt ttttgattt agtatagggt atttttttt attttttatt tttgagattt       15900
tagaattgtt ggtattgttt taaaatttat ggtaagaatt ggttattttt gtaattaata       15960 ttttttata atatatttgt tttgtttgtt tagttagtta gaaattatat ggagttttg       16020 ttttaaaaag tttgttgaag ttttttattt ttgttttggt attatgtgta tgaattatta       16080
attggttttt ttttatttta tatttgatga agatgttttt tttttaatat tttttttat       16140 tgttttttat tttttttgt tttatttatg attagttgtt tgttttaaa tagattttgt       16200 ggttatttat tttttttgt gttagttttt atttattagt tatttgaatt gtggttttta       16260 ttgttttta tatagtttat ttatttgtgg ttgttatata tatttatatt gttatatgtt       16320
tttaaattgt attttggaat gattttggta atggttgtat tggatgagat ttaaattaat       16380
aattaaagta ttgagatagt ttttgttatt ataagttat ttttgttttt atagtttaag       16440
aggagttatt ttttttattt ttattattta atgtttaata ttattttat tatatataat       16500 gtataaaaag tatgtgattt atgatttatt ttaaatttga atgtttgtga tttattttgt       16560
gttttttttt attttaagg                                                  16579
```

<210> SEQ ID NO 19
<211> LENGTH: 16579
<212> TYPE: DNA
<213> ORGANISM: Artificial Sequence
<220> FEATURE:
<223> OTHER INFORMATION: chemically treated genomic DNA (Homo sapiens)

<400> SEQUENCE: 19

```
tttagaaatg aagaaaaata taaagtaaat tataagtatt taggtttaaa gtgggttata           60
aattatatgt tttttgtgta ttgtatgtaa taagggtagt attaagtatt aagtaataag         120
```

```
agtagaagaa gtagtttttt ttggattata aaaataggag taaatttgta atagtagaag     180 ttatttaat  gttttaatta ttagtttgaa ttttatttaa tgtagttatt attaaaatta     240
ttttagaata tagtttggga atatataata atgtggatgt gtgtgataat tataagtgag     300
taggttgtat gaagaataat agagattata gtttaagtaa ttagtggata ggagttggta     360
taaaaagaaa tgggtgatta taaagtttat ttagaaatag atagttgatt ataaatagag     420
taagagaaga tggggagtaa tagagaaaga tgttgaaaga aaggtatttt tattaagtgt     480
aaggtgagaa ggaattaatt ggtggtttat gtatataata ttaaaataga gaataaggat     540
tttggtaggt ttttaaagt  atagatttta tgtagttttt agttggttaa gtaaataaaa     600
taaatgtatt ataaggaggt gttaattata aaagtgatta gtttttgtta tgaatttaa      660 agtagtatta atagtttaa  agttttaaga gtaaagaatg aaagaaaata ttttgtattg     720
agttaagaaa ttgttttggt tttgttattt aatttattgt atgatttgg  aaaagatatt    780 taataattg  ggtttagaa  tgttttttt  tagtttaaat tttaaggtag ttataatgat    840
gaggaggaga agaatttgtg ttggggaatt atttagaaat taaagtgtta attttaaaag    900
aatggtaaaa gattatttgg ttttatagt  tgtgttttt  ttggtagtat ttagaattat    960
tttataatag ttatgtgttt tttttttta  atataatttt ggttttattt tagtgtttat   1020
ttttagttat atattttgga gaattttggg ttaaatttta gttaaggga  tgattttgat   1080 attttaagtt aattatagag gtattatttt tttttttaat gattggattt ggaatagtat   1140
ataatatagt tttggttagt gagatgtgag gggattttt  ttttagtga  agggttttg    1200 ggaaagatag atttattttg agaagagaat aaaggaagag gtggttagtt ttttttttg    1260 gatattatta tgttggaatt ttttgttgg  aattgttgta gggattttgt atttatgagt   1320
aagtgagata tttttggaaa tgaagttgag aaagaattag taaaggtaag gtgtaagttt   1380
ttaaggatta gatttagagt ggattatgtt tttgaatttt attttatatg agattataaa   1440
tgttattatt gtttaaattt aataaaattg tgattttttg ttttttatag ttgaaagtat   1500
tttaattggt atatatttt  tagttgggat tttgaaaaat tttattggaa aagaaatttt   1560
atattattta gtaaatttag attgaaaata agttaatgtt gaaattagtt ataaattata   1620
aaattgattt tgaatataaa tagggtttgg agttgtatag tatttaatta attaagattt   1680
ttttttttaa tttttttgta tttgattttt ttatatattt tgaaataaga attagatttt   1740
tttaaaataa aattttttaaa ttttataatt ttagatatt  tttgaagagt attttttaag   1800
ttaatatatt atatatttta tatttttat  ttatagatta attgataatt tataatgaaa   1860
aatatatgtt gataattta  aattaatttt attattagtt tgtatttatt ttatattatt   1920
agaattgtta tgatttgtta attttattgg aaagtttatg ttttagtaga taattaggtt   1980
ggattaatta aatagaaatt ttttttatgg tatgaatttg ggaggtggag gttgtagtga   2040
gttgagattg tgtttgggtg atagagtgag attttgtttt aaaaaaaaaa aaaaaaaga    2100 aattaaagat tttttttaa  ttatatttat aaataataat ttttattttt ttttaggaa    2160 aatttgtttt ttatttttta tttttttttt ttttaggaa  attttataa  gtttaatttt   2220 aaagtttgg  gttttattgt taaatagttt agaatgtaag ttttgtattt ttatttata    2280 ttttgtgatt ttgggtaaaa tattatattt tttaaatttt tatttttgt  tattatttag   2340 ttgtgaaaat tagtatttat tgaagtgatt ataggaattg ataaaataat gtatataaaa   2400
taaattttag tgatatataa tatattagta tttaatattt attattaaaa ttattaattt   2460
```

```
agattttttg tagatgtttt aatatagttt tatattatta agagtaaaaa gaatagtatt    2520
tggggttttt atatttgaaa attataattt aggttattat tatagtagta atatatattt    2580
tatgtttgga ataaattatt ttataattta ttgttatgta ttttaaatta tttgtaaata    2640
tgtttaattt tttttgtaga atagtaggtt tttggaaggt agagttagta ttttatttaa    2700
tttaataatt tttataatat ttttttattg ttaggtttag ggtatatttt tgaggaatgt    2760
ttgtagatta aatatatgat taatgttttt attttttatg tagaaatatt tttgaaattt    2820
tgtgttaata atttttaat atttgaaata tttttgaata ttttttgaatt agtttatttg    2880 aagatttatt atgatttaat aatatgatgt ttgttaatat ttagagagtt aaattttatt    2940
taaaaaaatt aaggtgtga tttaggaaag gatttttttgt atttgagttt tttatttaat    3000
ttaaatatta aaaattgaat ttttttgtgtt atatttaatt tttataaaag tgtttttttgt   3060 tggggagagg agaatggttt tttattttata taggtataat aagtatatgt attattttttt   3120 ttaagattat ttttaagatt aggtaagaat ataaggagga gattagatat gttttaaata    3180
tatttgaata agttgtataa atatgtttga ataagttatt taatttaaaa attagattgt    3240
ttatattaaa tataaaattt ttaattttttt ttaaaaaatt agaaggttta gtaatattaa    3300
gtttatattt tagttggttg attatgagta ttaattaagt agtagttttt tttttttaagt    3360 ttgtgtgttt aaggttatta ttgttttttat ttagttttttt attttattttt attttatgtt    3420 ttgttttttgt agtatttaa gtttgtaaat tttgaattaa aagatgatta tttattttta    3480
tagtaaatat attagagggt tttattgatt ttagttgttt tagaattgta tttttatttt    3540
tttttttttg gagtttaaga tgtttatttt attttttgtaa tttttttaag gttatgtttt    3600 tattttttggt tattaagtta tattttttgt tttttatgtt tgattatatt aaatggaaag    3660
tttttagaag tttttttttt tgtttttagt attattttaa atttttatttt ttattttttt    3720 attttttat gttttttttttta taagtattgt ttattagtga taataatttt gtttgtatgg    3780
aaagatttga gagatatgag agtgaatgtt tatatttagt ttttttatttt agtgaagtta    3840 atgagaaggg aagaaagtta ttgaataatt taggtatagg gtattgagat tgtttaattg    3900
tttgggagat ataaaagata aggttaatgg aattttttatt tatgagaaat gtttgtaggg    3960
aggataaggg atatattagg gatgggtagt ttttgagaga aagttaagat tttattaaat    4020
agatatttag tatttttttt tgattttggg gaagtttagt tgataagggg tgatttaagg    4080
atagagatat ggtggttttg tttattattt tgttaattag gtattttaga taattaattt    4140
tttaggatat tttagttata aagtggatgt aatgagtatt atatattata ttgtttattg    4200
gttttttttt atagaaagaa ttattgtata gtagagagaa attatgtgat ttaggtgtga    4260 aatttttatga atttatttta tataagtaat agtattatgt gaattttttga atttggatttt   4320 ggttaagttt ttttatattg ttgttttttta gtattttttt gttttttgtt tggtgaatttt   4380 ttttttttatt attttattta agatatattg tattttatttt ttttttttttat gttttattttt 4440 tattttagta tatattatta ttttgtatat gtgattggga attgttttttt tttatttatt    4500 atagtaaaag ttttaataga gtagttttttg atgttttgtt tattttttgta tttataatgt    4560 ttagaatatt tagtaaatat ttgttaaaag aatgaatata tatttatttt atataaattag    4620 atgtataata tatatttagt tttatttatt aattttttta tttagaatat aatatatttt    4680
ggagaatgtt ttaaattagt aaatataatt tttttatgtt attttttgata gttgtatagt    4740 ttttttattag gtggatatag taattttttat ttaaatggtt ttttatgatg agtttgttat    4800
attgttttta gatatttgtt tttagaagta atgttgtaaa gaatattttt gtttatttgt    4860
```

```
tttgggtgat attggtatta atatttattt atataataat gttgagaagt ggaattgttg    4920
aattaaagag tatatatatt ttttaaaaat ttttgataaa gaattaaaaa aaagtgattg    4980
ttaaattatt ttttgaagta gaggaattta tttattttta tataatagta tatgagagat    5040 ttagttttt  tataatttgg ttaatataaa tttgtattaa attttttaat tttattttg     5100 ttaggtatag tggtttatgt ttgtaatttt agtattttgg gaggttgagg tgggtgaatt    5160
atttgaggtt aggagtttaa gattaattgt tatggttaat atggtgaaat tttatttat    5220 taaaaatatg aaaattagtt aagtatggtg gtgggtgttt ataatttag ttattaggga    5280 ggttgatata ggagaattgt ttgaatttgg aaggtggagg ttgtagtgag ttgagattgt    5340
gttattgtat tttaatttga gtaatagatt ttattttaaa aaaaaaaaa aagaaaaaaa    5400 ttatttttt  ttgttatttt tttgattggt gaaaaaatgg tgtagtatat tattggtgtt    5460
ttaattatta tttatttaat tatagatgag gttgagtgat tttttttata atttaaaat    5520 tttatgtttt tttttgttat tatttgtata taattttgt ttatattttg atagatgtgg    5580 atttttaaa gttatttata aaagtttatg gaatattaag agttattagt ttttttgttt   5640
ttaaatgttg tagatgtttt ttaaatatat tatttgtttt tgtgtaattt ttatttagtt   5700
agatttatta gtatttttta gaatggtatt gggttttatg ttttgtttag aataggtttt   5760
tttattttta atttattttt tttaatttta tgatttttt ttattatttt gtaaaaagtt    5820
attttttata ttttatattt gatttatttt atattttttt taggatgaga aattaggtag   5880
agattgattt ttattttgta tggatttatt aattgttttg aaattattta ttgaataatt   5940
tttttttttt attgaatgtt taatttttatt ggagttaatt tttgtaattt gttttttgat  6000
taatgaaatt aaataatttt taaaataata tgtttttttt tgatttattt tatagattta   6060
gtagaaatta tatggtttgg gtaatgtagt tattattaaa attatagaat tagattaata   6120
tgaattttaa gatataatat attattattt tttttttgta tagttttta aagtatttat    6180 tttttttgatt tttataattg tatatttatt taatagatta tgatattaaa ggtttaaaag  6240
taatattttt gtttggtttt tttagttagt gagtttaatt taaattttt gattttaagt    6300 ttagtgttta ttttattata ttttaagtaa tattaaatta ataatttaat aataaaaga    6360 ttataattta ttaaatatgt ttattgtaaa atatgtaatt ttattttata gatataaata   6420 tttttaaaa tttttagaag aatgaggtag gatgtatata gatgtggaaa gtatatatat    6480 ttgtatttt ttatagttgg taaatttatt tagaggtgtg tttaggaaa tagaattgat     6540 atattaaata aagatttttt gtattgattt ttgaaatata attattttta atatatttaa   6600
tggtaagaat ttagtagtgt ttaaaaattt tgtatatata tatatatata tgtattttat   6660
atatatatat agatttttata tatatgtaat ttattaagtt taggttataa gaggaaattg  6720
gtaaaaattt attaattgaa atggagtttg gttaagatat ttatatttaa tttttttttt   6780
ttgattttaa attagggaga gtatatgttt tgtgttttt ggtaaaatat agatttatgt    6840
aataattagt atatttttt agattagagt aagtaatttt taataatgag tgtttgttag    6900
ttttaattgg ttttttttatg tgggtggtga aaaaatattt tattatagtt attaattttt   6960
ttttttaaaa gaattatgtg tttgagaag ttttgtttta ttagggta atatttatt       7020 ttaaatatag tgtttattga tgtttgttta tgaatgatgt taataaaaat gtttaaattt   7080
tattaggaaa ggagggttta gttgttagat tttgggagat agagtagtt gattttttgt    7140 tttttaaagg ttttgttatt taattaagtg attaattatt aattttaaag tatttaagtt   7200
```

```
taataatata ataaaagaga gaataatggg tagtattttt aatattaatt atggttattt    7260
ttggtttagt tgtttaggtt tttttttagt agaatttata agtgtataga tataggtatt    7320
ttggaatatt aaaggtattt tttttttagtt tgtaaatata gggaaaaaga agaaatttat   7380
atttgtaaat ttatgtaaat ttaggggggat tttttttaaa ttttgttttt ttgaaagtag   7440
gaaatataat ttaaaattaa ttttgttttt atttattaaa agaattaaaa ttttgaattt    7500
tgatataaat tttaaatgat tgttttgaat tttattttgt tttttattta attttttat    7560 aagaagatta aggattgtgg atttggtgtt ggaggaagta attgtttaat tatattggaa    7620
tttattggaa tttttttataa tattattgtg ggtagataat ataattttaa tatattttt    7680 tttttattta gagtttagaa taagaagtta gattttttgga gatttttttt ttgatgtatt   7740
gtttttaata ttttaagtt ataaattggg aattgttttt attttagaat attaattgtt     7800
gtttttattg gtatttttt attttatat tatatttata atatttttatt ttaggatttt    7860 atgtgaatat ttttaggatg ggtttggtga aattgttaag aagtgtttaa aataattagg    7920 ttatagttttt tagtagataa aaagaaaaag atgtggttgt tagttataga atttgaggtg    7980
atggaaaaga tttttaaaat ttagtttttt taatatgtag taaaatgggga ggatttaaaa    8040 tgtagtttta agaagtattg ttttgtttgt attaagtttt tttaggtttt tagtttagtt    8100
attttttaaa taggtgttga gtttttagtt tttgttaggt ttttgttaag gtttttttatt   8160 gaggtatagg aatttagttt atatttgtag tttttttatg tttgtttttta tgaaatttta    8220 ttagttttgt tgaatggtag tatttgttat tttaggtgaa tttttatgaa tagtttggaa    8280
tgaaattaat ttgttaattg attaagaatg ggttttagagg tgatttgaat gtatttaaaa    8340
agttaataaa tggaatatgg tataaagttt tattttttgg ataaaaagtt tgtttggagt    8400
aaattttaat tttttttttg ttttaaaata aagtatgat gttttttttta ttattttttaa    8460 gaagtaagta aaaataaaat aaaataaaat aaaatttaaa tagttttttta ataagagtgt    8520 ttagtgttgt ttggatggaa tttggggttag ttttagaagt agttggtttt gaattttggg    8580
ggtgaggtta tttggttttt ttggttaagt tgggttttgt ttttttttgtt ttgttttttat    8640 tggttttggt gggtggggggt tttggttgtg ttggttgttt gtgtggttgt attgtagtttt    8700 ttgagtttag gaagttatat ttgttttggt tgggagttga agtgttaatt tatgtggtgg    8760
ttggttaatt tagttgttgt ggggagtgtt tgttgtgggt ttttttttgg tgtgaggtga    8820
gtgagtgggg gtgggttttta gatttagttt ttttgggtgg ggttggatta ttttttgtttg    8880 tttagttttt ttttatttttt ttattttggt atgttttgt agttatattt gttgttgttg      8940
ggaaagggaa aagagtattt taaaatgagt tttgaaattt agatttaaat tttgaaatga    9000 attttttttgg tttgttttg gttgtttgaa tgttatttgt tttattttg tttttttttt      9060 tttttttttt ttttttatggt tttttttttt ttttttttt ttttttttt ttttttttt       9120 ttttttattgt ttgttttttt tttattttt tgttgatgt ttgttttgaa gttgaggaag      9180
tttaagtttt ggattaggag tttttttttt gtaaatttt ggggtgggggt tttattgttg     9240 ggtttaagtg gttatgggtt ttgagagtat ggtatgtgta ttatttttt taaagatgtt      9300 tagggtggtg tgtttagatt tttgaaattt ggttttattt tggttatgtg tgtttgttta     9360
ttaagtggtg aattggattt agggtgttgt gtgtgttta gttgatttgt gagaaggtat     9420 ttttgtatttt tgtatagatt aagatttttt tttagggttt tttaaatttt tagatgtatg    9480
ttgtagattg tggagtgtaa aatgaatgat ttaagggaaa attagggttt ttatttttg      9540 aatataaggt tgtgaaagat gtatgtttgg tttgggggggt ttgtttttt ttgtttgtgt     9600
```

```
gggattttttt tattaggggg tgtttatatt tgttgtaaaa ttttttaattt ttagatatttt    9660 aggttttgta agttttgtga gttgaattgg gggtagattt gaaggagtgt attgtttttt       9720
ttgttttttt tttttttgttg ttttggagta tgggaaaggt agggattttta tattagttat     9780 ttatttgtta gttgtgggggg aggggatgta aagttagag agagagaata gaggttggga      9840
gaggggaagg gaggtagaga agatggagat agagggagat ataaagatga ggaatgtgat      9900
ttagagagat tttgttgtgg gtgtgtgtgt ggtaggataa tttttttaggt gttgtgtaga     9960 tttttttttt ttttttgtagt atttttttagg gatatgtagg atttgttgag atgtagttgg   10020
attggagagt aaatagttta ggttatgata ttattttttt attttgtttt tttttgttta    10080
atatttagat tgttttatgt ttagtgatat agattgtggg ttagaataat ttggatgttt    10140 tagggtttgta tgtattaggg atgttgtttt atagtgtttta tgtttttgta ggatggtggg  10200
gtgttttagt tgaggatgtt ttttggggtt tttggtatat gtgtgtgttg ttgttgttag    10260
atttgttagt aaagttgttt aattagagtg gagaattagg agagggtggg gaatatgtaa    10320
ggaaatggag gatttttgta gtttgggtga gaggattgat ttagaggttt ttgatttggg    10380
tttttgagtt atttttgttt gtagtgtgtt ttgggtgttg gtttgtttgt tgagatggga    10440
gtgatagatt ttatttttatt ttttaggggtg agaaaaattg ttgtatattt ttgttgattt  10500
agaataggtt tttttttgttt aggggttttt tagattttttg tggggttttta ataattttat 10560 tttttatttt ttgttttttt tttgttggtt ttttttgtatt gtgtgtagga taaaagaatt   10620 tagggtgtt gggagagaat tgtgatagtt tttaagttgt taaagagata tggtggggat     10680 tttgtattttt ttttggttgg attttttttt agattgtttg tggtttgaag gggttaggtt   10740
tgtgtaaggt tttaggttgt ttgggtgttg ggttgtattg ttaggagttg tttgggagtg    10800
gttttttagg aatattaggt attgattata tattaggggt tgggaaatta ggtggtttgt    10860
attaaggtgg ttttggggat ttgtttgtgg taagttttgg tagttttttat ttaaattttt   10920 gttttgagtg tgttaagaat aataataata aaaaaattaa agtgttaaag gtttttttttt  10980 ttttttttagt ttaagaattt attattttttt tatgatttttt ttataatttta tttttttttt 11040 tttttttaatt ttgttagtta ttttattttt attttattttt gggttttttt tgtttgaatt  11100
ttttttaata ttaaggtttt tttgtatgtt tttttttaaa agtttttatg aaagttatttt   11160 gtattttttta agtgtttata ttttttttaat tttgttttat agttttttgtt tttaattaaa 11220 gttttttatt aattgttttt tttttttaag tttgtgggtt ttttttttata agtttttttgt  11280 ttttgttttt taagggggga ataaaagaaa tgtgattatt ttggaaggtg gtttattgta    11340
gtttgggggg aaaatttatt gtagtgttgt gtgattgggt ttggtgttgt ttaggtgggt    11400
tatataggaa gtgtggtggt ttggggaagg atgtggaggg tgtgggatgg tgttggaaga    11460
tgtgggagga tgtgggggttg gttgaagatt ttggttttag ttttttgttta taatatttaa   11520 tgttttttggt tgttgtgttt gtatgttggg agttttttttt tagaaaggtt tggggtagtt   11580
tgtttgtaag tttaaatgtg ggttgtgata tttattatta ttatattatt gtattgttag    11640
agttgaggag gagatttagt gagaagaagg aggagggaga ggaggagggt ttatttatag   11700
gttttaaaag tgttttgtag ttttagttat ttttaagagt ttaggtttgg aaagtaggtg    11760
gaggggtgga aagtagtttt tttgtgtttg tggtagggat tgtttgtttt ttttttttagg   11820 tatttttatt ttttggtgtt ttttttttgat aagaagtatt aattggtttg gggatagtag   11880
tgttttttat ttagggattt atttagtaat attgttttgt ttgtggaaat tattgttttt    11940
```

-continued

```
ttatttttt   tttattttta   ttttttttgtt   ttttgtgtag   ttagttttgg   gttaggggaa      12000
aggagttttt   aggttttag   ggggtaggtt   agtaatagat   aattgagtat   gattatttt       12060 ttttgggagt   atataaaatt   gtaaaattag   taaagaattt   ggttatagtg   tgtttatgtg      12120
tttatagagt   ttgttgttt   tattaaaggg   aagtgttagg   tttaaggttt   ttgttaattt      12180
gaaagagata   ttgagaaaat   gagatttttt   ggggatttag   agggaaagtg   taagaatttt      12240
ttattgtatt   tttagggaat   tgtttaatgg   ggagtttggt   tttaaaagat   tttggtaata      12300
aaaggttgga   taggaaattt   ttttaggtaa   attttttgtt   ggatttaaag   agaatattt       12360 ttttttgtta   taaattttt   tttatataag   tttagatttt   gtttttttg   tttttttttt        12420 ttttagttt   ttttaagtat   ttttgagtag   aatatttgat   aattttttg   agtaatagg         12480 attttttgga   agtattaatt   attttttatg   ttttttggaa   ataagattat   aattttttat      12540
gtgtatatgt   gattttttt   ttttagttag   gtttatttta   ttgtgtaaat   agtattaata      12600
tatggaagag   ttttttgtat   tgtgttataa   aagattttta   ataggatttt   atagagaaaa      12660
gggttaaata   gttgatataa   aggatttttg   tttttttaga   aaagagggat   tttggatttt      12720 ttttttttt    gaagttaagt   atgagtttat   ataataggaa   taaaataaat   ttaaggtgta      12780
tattagtata   atattaggga   tattagaatg   gatggtaaat   ttttttttt   atataaatat       12840 gaaagtattt   ttataatttt   tttttttgaa   gttttatttt   agaaaattat   attaaatata      12900
ggattttaaa   aatagtagtga  ttaaagatga   aagttaattt   tttttttaa   tttttttgat       12960 tagtttggtt   taaatttatg   ttttaaaatt   tttagtaatt   tagattttg   tatatgtgta       13020 tttataagat   ttttttata   ttttgtaatt   tgtaggtatt   tagtatggtt   attgattta       13080 agtgataaat   aggtagaaga   tttgttagga   taattttagt   ttttattatg   tgtatttttt      13140
attttttttg   ttatttatta   gttttttgta   gtaatataat   tgttagttat   attatttgga     13200
aattaatgtg   tttttgtagt   gaattattta   tttttagtaa   atttattgta   ttattatttt     13260
aaatattgaa   atttgatttt   attagatgtt   tagaatgata   gttatagagt   agaattagat      13320
tttaattttt   atgtataata   tgtaaataaa   ttaaggtgta   gaaagttatt   gttttaaagt      13380
tatataatta   atagtttagt   ggtttttta   gtgttaatta   tagtaatttt   agatttaaga      13440
ttgtttgatt   taggaatgga   gagaaataaa   ataaaatgaa   tgtttattga   aatatatatt      13500
ttagatatta   agatagattt   ttttgtgaaa   tattttaaga   tgtggatttg   tatttttatt      13560
tttaaatttg   agtaaattta   gttgagtttt   aaagagttta   agtaatttgt   ttaaggttat      13620
tttgtaagtg   atagatttgt   tagtttgaaa   agtttattat   ttttattttt   tttgtttttt     13680
tatgatatag   ttaagtaaaa   tttttaata   aaggagaatt   agattagaaa   taagtaatta       13740
atagtagatt   aatgtttatt   tttagggaaa   tgttaatagt   taatatttat   tataaataat      13800
gttatttgta   tataatggaa   tatgattgaa   agtgatgggt   tagatatttt   ttatatttg       13860 agatgttttt   atttatgttg   ttaaatttga   tttttttaatt   tttaaaatt   tttagttttt      13920 tttaatgtta   atagattta   taatatttga   ttaaatattt   ttataggata   aaggtatttt       13980
tttagggttg   atttaaggaa   ttagaatatg   tataatgttg   aaaagttta   aattgtttgt       14040 tttttttttt   ttttgatttg   taatattatt   atttagaaaa   ttaaatattt   ttttaggtta     14100
ttagataatt   aaaatgaaat   tatattttat   ggatattttt   ttttatttt   tagggtagat       14160 ttttttttt    agttgtttaa   aatggagaat   ggataaaaaa   gaaaaggaa   aatatattag       14220 ttatatttag   aatagagttt   atagttgtat   tattatttt   atgtaattgt   ttttaatgat       14280
ttttttttat   taagagaaag   aaaatgagag   agtatttatt   tttgatttt   taatgtttga       14340
```

```
taaaattatt agaagttttt gaatgggaaa atatatattt tttaggtttt ataattaaaa    14400
ttgtatttat ttgtttatta tatttaagta tgaattaaat agtaattaaa atattatttt    14460
gtgagttttt ttttaaatta tattttgta ttggggatat tttttgtgaa aatttaaga     14520 ttttaggtat aaataaagta agattttat ttataatgtt tgtgtttaaa agaaattata    14580
agttagaagt tatgtgtttt gttttttgt tttgattttg tttttgggaa tttggttgag    14640
tttaggggta gtaagttaat gatttggaga ggaaaggtgt agatggtaga tgtgttttta   14700
gggaatttta ttattttat ttaaatttt ttttgaggtt ttttaggatt atattttaga    14760
tttttttttt tttattgatt aggtgaagtg tttttagata tggtattatt tattgttgtt   14820
ttagggatga taagattta gttttattta aatttagaaa gagtttagtt ttaatttttt    14880
gatttgattg gttttaggta taattaagta aattattttt attggatgat atagtaatgt   14940
tatagattaa aaatgtattt ttaatttta aagatttgg aaaaggaag tttatttttt     15000 aagattgtgt tataatttt tttttaaata aaatattgta aattagggat agatatttta   15060
tttagtattt tgaatttttt ttggttttt aggaaaggta gaaatataag gttttttattg  15120 tttttttttt atttttaaaa aagaaatttt gtaaaaggta aagtgatggt ggtaaattta   15180 ttgtgttta atttgaagta tataaattgt tttgataaat taaatataga taaattttt   15240 tagaaagtta taaatatta gattttttt agatattaga tattgagttt ttgttttta    15300 attttaaat taaaatgtta tagtaaaata tttgttttaa taaatttttt ttttttttgt   15360
gttgtaaatg ttttgtttat ggttgagtag atttttttag aatttaattg aaagattatt   15420
tatattatga tagaattatg taagttaaag ttaagtttta atatggagtg atgggagagg   15480
ttgggttgtt gagaggagat gattttatta gtgagaagag aggttttttg agttggtttt   15540
taaggtagtt aaatggttta gtatatttgt atttattttg ggaggttgtt tggagtagag   15600
tattaaaaat gttattttt ttataaagaa aaagatgaag gtataaagaa tatagtttaa    15660
ttaaattgaa ttaagattg tattatttt atttttttt tagttatttt tttaaagttt     15720
tttttttttt ttttatagt ttgaaaaata taggttattt ttataaagta tttgtttgat   15780
tgaagtaaga taaattgaag agtttggttt ttgaatataa ggaagtggta gagattttag   15840
aattaatgag gtagggtgga atataatgta gaaggttttt taagaggtaa aattttgta    15900 gttgttgttt attttagtg attatttgtt tttatttatt taattagatt atagtgggat   15960
tgagataagg agtataatga aagttgttgt attgatggtg taaaagata tatggtatta    16020 ttaatgtttt tgtggtgagt aaaggtagaa tgtaagatag aaaataagga aatttttgtg   16080
ttgtaagaaa agtgtttagt atgggtatta attggtatgt agaagtagta agtatatatt   16140 ttattttat tttattgata aaagaattg taggattaat gtttgttttt attaaaatat     16200
gagaaattat atttttaattt tataaattaa aggttaaata tttgttgtaa taatttaaa   16260 aaaagagaa gatttgtaag atttagtaaa tattattat aaatagattg ttttaattt     16320 tttatatttt tttttaattt aataaaagtt tattgagtag ttttatgtg tattgttta    16380 gatagtaggt attatttaaa aaagtaataa ttatttttta tttttaagga gtttataatg   16440
tttttagaaa gaaattaatt tattggagta gttaaagtta taattgatt ataaaatgat    16500 tagtgaattt agaggaaaat tatatataaa tattttgtt tttattggtt ggtttagtta   16560
gatattattt taaaaaata                                                16579
```

<210> SEQ ID NO 20

<211> LENGTH: 3000
<212> TYPE: DNA
<213> ORGANISM: Artificial Sequence
<220> FEATURE:
<223> OTHER INFORMATION: chemically treated genomic DNA (Homo sapiens)

<400> SEQUENCE: 20

```
atatttaaat tgtatatttg gtttgtaata tattatatat ttaaaagaat tattattttt      60
ttgaatatta ttaatattaa taatagtatt atagtgatta agagtggatt taaataaagg     120
ttggtttgaa atttaggttt gttatttatt agtaagtttt taaaaatttt gagtttttag     180
ttttttttata tgtgaaatgg agaaaataaa tttgtaaaat taattaaatt tgtttattta     240
tattttttt tttagtgtat attaattggt attttttgtt aggttagaat gtgttttta       300
ttatgttta aatttgtttt gtgttaatttt tattgttaga atttttttta ttttgagaat      360
tagaaaagga aatattatgt ttggtaatgt ttatattttt taaaataaat tgtaggaaa      420
gaatatttag taagtgatga gagtagtaat gattgttttt attatttaa atttataata      480
ttattttttt tagagttttt taagtattgt agataatttt ttatttatta aaaataaat      540
tgtaattata agtatttagg gttgatattg tttttgaatt agatagtgtt tatattagtt     600
gtataagatt aatttaaagt agaggatgaa attttttttt tgaattttt ttagaatgta      660
atttagtgaa tatattaaaa ttaaattttt tttgaatggg agtaattttt atggattaat     720
ttgtaatttt ttagattata tttaaggtaa tgtagaggtt gttgtattat aggttttgtg     780
attagagatt attggatttg ttttttggaaa agttatttat gatttttttgg gttttggttt    840
ttttatttt tatattggtt taataatgat tattgtagag ttgttatgga agttaaatga      900
atttatgtat tataagtgat taatataatg attgatattt agtgatttat taataaatta     960
aaatatttat tattaatatg atagagaagg tgttgttaaa atagataata ggttttggga    1020
agaggtgatt aaatggatgt aaaatttatg gattgtttat tttgtttatt ttgttgtgt     1080
ttttggttg tggtatatat atgtgtgggt ataaaattgt aaattttatg tagttgtgta     1140
gtgtatgtgt agaaggttta gatatgaaat gttattttag taatgtgttt agagaagttt    1200
tgatgttgtt ttggaagtaa gttgttgttg tttgattttt gggtgttgg gatggatgtt     1260
tatatttgta tttagtagta ttggaagggg tttaggtttt ttgtagtata gtttattttt    1320
agattgttta gttttttata atatatattt ttatggaaaa gggtattttt ttttgttaga    1380
aaaagtgttt tagtttggtt tgggttggtt tttattttat gttgttgtaa gtaggtgaag    1440
ttttttttgt tttttttttt ggggtaagtg gaaaggagtt tggtagggggg tttgtagtgg    1500
tttgtatagg ggaattgggt agtgagagag tttttaggtaa ttttggggggt tgttttatag    1560
aagtaggtgg ggattgatag tggttttttg gtttagggag gagagtgtgg ttgtgggttt    1620
ttttttttag tttggaggtt gtagttgttt gagttggtttt gggtggggggt ggggtggggg    1680
tggtgtggag ggtatggaga ttatggtggt gttatttggg atatttaggg ttttgaggtt    1740
ttgggtggtt tttatgtgag attgtaaatt atgataatag gtagttattt gaggttaaat    1800
aaaaatggag tgggtttttt gtgtgttgtt gttttttgtg ttttggtgg ttttttttga    1860
ggttttggt ggtttatga gttgtagta gttggtggtg atgttgtttt tgttttattt      1920
ttttgtgtaa gtgtgaggtt gttggtagtg tggtgtatgt tttggttgtt tttggttttt    1980
gtgtaaaatt tttatttgt ttatgtgaag ttgttgttgt tttagagagg gggaaagagt     2040
tgtgggaaaa gttgggggagt gatgattgtg gtggttgggt gtgttttttt attttttttt    2100
ttttttttt tttttttgtt gtagtttgga gtttggtttt tttttttttt tttttttttt    2160
```

```
ttggagttgg tttttttttt tgttttgttt tttttttgtt tgtgtatgtt atttgttgtg      2220
gggtggttga agggatgtt tgtttttat tagaggtata gtgtgaaggg gaaattttga        2280
```

```
ttggagttgg tttttttttt tgttttgttt tttttttgtt tgtgtatgtt atttgttgtg     2220
gggtggttga agggatgtt  ttgtttttat tagaggtata gtgtgaaggg gaaattttga      2280
tattggaagg aatgagaata aatatttaat tatggatgta ttgaattgtg gttgggatag     2340
atattttggg aatttgaggt ggattgggtg atgaggtgag tgattttttt ttttaatttt     2400
tgttttaggg ttttgggg   agtttgagtt gagagaattt ttaaattttt tgggaaagtg     2460
tgtgaggttt tgttggggat gttgagtgtt gggtattgag gatgtgtagt tggatggtgt     2520
gtgggtgttt gtgttttttgg ggggtgtttg gaggttgggt gttttatgtt tgagggtttg    2580
ggttgtttgg attgtagtgg tgttttttgt tttagaagat gtttttaagt tttaagggtt     2640
ttttttgagt ttgtttgttt ttttttgggt tggtgtggag tttgtgtgta atggagttta     2700
tttagtagtt tagtgtgtgg ttttttattttg tattttgttt ttatttggta gaggtgtgag   2760 tattgggggtt tttttttatat tttttttatg atgtgtatta tttttttgatg atttttttaga 2820 tggtttaggt gtgaggatgt tgatttagag ttttttggag ggttataggt gtttgggttt     2880
ttttggtgtt gggtgtgtgt gtattttaaa ggtttgtgtt ttaattttta ggtattgatt     2940 gggttttta attgtggtga ttttattttta atagttttta tgtggtgtgg attgaatgtt     3000
```

<210> SEQ ID NO 21  
<211> LENGTH: 3000  
<212> TYPE: DNA  
<213> ORGANISM: Artificial Sequence  
<220> FEATURE:  
<223> OTHER INFORMATION: chemically treated genomic DNA (Homo sapiens)

<400> SEQUENCE: 21

```
gatatttagt ttatgttata taaaaattat taaagtggga ttgttgtagt tgaaaagttt      60
gattagtgtt tggagattag aatgtgagtt tttaaagtat atatgtatttt ggtattggga   120 aagtttaggt gtttgtgatt ttttgaagga ttttgggtta gtattttttgt gtttggatta    180 tttaggggggt tattagaaag taatatatgt tataagaaag atgtggggga gattttgatg    240
tttgtgtttt tgttaggtgg aagtgggggtg taggtagaag ttgtgtgttg gattgttgga    300
tgaattttgt tatgtgtagg ttttgtgttg attttggaag ggataggtag gtttggaagg     360 gattttttggg gtttggggat gtttttttagg gtagagagta ttgttgtggt ttgagtggtt   420
tgggttttta ggtgtgggggt atttggtttt taagtgttttt tggggatgt aggtgtttat    480 gtattgttta gttgtgtgtt tttagtattt agtgtttggt gtttttggtg gagttttgtg     540
tatttttttg gaaagtttgg gggtttttttt aatttaggtt ttttttgggag tttttggggtg  600 ggggttggaa aaggggtta tttattttgt tgtttggttt gttttgggtt tttgaagtgt      660
ttgttttagt tgtggtttag tgtgtttgta attaagtatt tatttttgtt ttttttagtg    720
ttgaagtttt tttttttgtgt tgtgtttttg gtgaaaatag gatatttttt ttggttatttt  780 tataataaat agtgtatata agtggggggag aagtgggggtg gagggagaag ttggttttga   840
gggggaggag gaaaggagag gagttaaaat tttggattgt gatagggggg aaaggagaag    900
aaaagaaaat gagagagtgt gtttagttgt tgtagttgtt attttttggt tttttttgta   960
gttttttttt tttttttaag gtagtgataa tttttatgtgg ataggatgga agttttgtgt   1020
ggaagttggg aatggttgga gtgtgtgttg tgttgttggt agtttgtat  ttgtgtaggg    1080 aggtggggtg ggggtgatgt tgttattggt tattgtgggt ttgtgaggtt gttggggggtt   1140 ttgggggagg ttgttaggga tgtgggggggt ggtggtgtgt ggggggattta ttttgtttttt 1200
```

```
atttgatttt gggtgattgt ttattgttat ggtttgtgat tttgtgtggg gattgtttag    1260
ggttttgggg ttttggatgt tttgggtggt gttgttgtaa tttttgtgtt ttttgtgttg    1320
tttttatttt gttttatttt gggttgattt gagtggttgt agtttttagg ttgaggggag    1380
ggatttgtga ttgtgttttt tttttgggt tggagagtta ttgttgattt ttatttgttt    1440 ttgtgggta gttttggaa ttgtttggaa ttttttgtt atttagtttt tttgtgtagg      1500
ttattgtggg ttttttgttg gattttttt tatttatttt aagggaggag ataaagggaa    1560 ttttgttat ttgtaataat gtgaaataaa aattaattta gattagattg gggtgttttt    1620
tttgatggga ggaaatattt tttttttgtgg agatatatgt tatgaaggat taagtggttt   1680
ggggataggt tgtgttgtga agggtttggg tttttttttag tgttgttggg tgtaggtata   1740
ggtatttgtt ttagatgttt aaaggttagg tagtaatgat ttattttaa ggtggtgtta    1800 gagttttttt aggtatattg ttgaaatgat attttgtgtt taagttttttt gtgtatgtat  1860 tatgtgatta tataggattt atgattttat atttatatgt gtgtatgtta taattagggg   1920
atatagtaaa ggtagatgga ataaataatt tataaatttt gtatttatttt aattattttt  1980 tttaaaaatt tattgtttat tttagtggta tttttttgt tatattgata ataaatgttt    2040
taatttattg ataaattatt gagtgttaat tattgtattg gttatttatg gtatatgagt   2100
ttatttaatt tttatgataa ttttatggtg gttattatta agttggtata aaagatgagg   2160
aaattaaagt ttaagaatt atgagtgatt tttttaaaga taaatttagt ggttttaat     2220 tataagtttt atgatataat aattttata ttattttagg tgtggtttaa gagattatag    2280 attaaatttgt agaaattatt tttatttaaa gaaagtttag ttttaatata tttattaagt  2340
tatgttttga aaaaggttta gaaaaaagat tttattttt atttttaggtt ggttttatgt   2400 aattgatatg agtattgttt aatttaaaag tagtattaat tttgaatatt tatggttata   2460 atttatttt taatgagtgg ggaattattt ataatgttta agaggtttta gaaaaggtgg    2520
tgttgtaaat ttaaaatgat aaaggtagtt gttgttgttt ttattattta ttgggtgttt   2580 tttttttgtag attttatttttg gagggtgtag gtattgttag gtataatgtt ttttttttg 2640 gtttttaagg tagaaagggt tttggtagtg gggttggtat aaagtggatt tggagtatgg   2700
ttgagagtat atttttggttt aatgaggaat gttagttaat atatattgga gagaaaaata  2760
tgaatggata gatttaatta attttgtaga ttttattttt ttattttata tgtgagaaaa   2820
ttaagggttt agaattttta gaagtttgtt aataaatggt agatttgagt tttaagttag   2880 ttttttattta agtttatttt tagttattgt gatgttatta ttagtattaa tggtatttag  2940
aaaaatagta atttttttaa atatgtaata tattataagt taaatatgta atttaaatgt   3000
```

<210> SEQ ID NO 22
<211> LENGTH: 1984
<212> TYPE: DNA
<213> ORGANISM: Artificial Sequence
<220> FEATURE:
<223> OTHER INFORMATION: chemically treated genomic DNA (Homo sapiens)
<220> FEATURE:
<221> NAME/KEY: unsure
<222> LOCATION: (9, 17, 18, 33, 41, 49, 50, 52, 54, 62, 80, 84, 127,
     157, 159)
<223> OTHER INFORMATION: unknown base
<220> FEATURE:
<221> NAME/KEY: unsure
<222> LOCATION: (175, 207..209, 214, 1181)
<223> OTHER INFORMATION: unknown base

<400> SEQUENCE: 22

```
agtttttagnt attattnnnta tttttattaa tgnttttggg nttataggnn gngntttttt    60
gnttaaatag tagttaatgn aggnatttta aaaggtatat tattttatat ttatttagtg    120
gttatgntat tatttaattt ttattataat tttgtgngnt tagtataatt tgtgntttta    180
ttttatttgt gaataaatgg aggtagnnnt ttgngtaatt tataagtaag tggtagattt    240
gggggttgtg tttagataat gtggttttag attttttgtt ttttttgtt ttttgttgta    300
ttttgattga gtttagttat ttattttttt aatatatatt aattgttgtt tttatgtttt    360
aggttttgtg ttagatgtta gaaatatatt tttatttatt ggattttggt atggtttatt    420
gtttagtgtt ttgttatgtt atgtgttata taatgtattt attttggtat ttagtttatg    480
gaaaataatg ttgaaagata ttgtatgtat gttttataa taaaattatg taatttatgt    540
ttttttttatt gttttggtta ttaggaagtt tttatttaaa ttagagtaaa tatattagaa    600
tttgggtttg ttatttagt ttgttgaatt ttttttttg gtttagattt tttattttgg    660
tttataaatt ttattgtata aatgtttttt attgtaaaat attttaaatt ttttttaagg    720
gaaggttgta tggaaatgat atagtaaggt ttttttttgta tttttttaga tttttattag    780
ggaaggtaga tttagatgtt ttttttattt ttagttttaa agtttttttat ttataaaatt    840
ttttaagtag tgattattgt tgttttgagt atttggaggt agtttagagt ttttgaaagg    900
taaaatttat atataaaaag aagttttttt tgatttagat tttagttttg gtgttagatg    960
tatatttgag gagtaggtgg ttagttagat ttttatttga gtagttaata aaatttattg   1020
tttttttaatg gaatttttttt tgtaagtttg aattgatttg ttattttttgt gatttgtgag   1080
atggtaggga agtattaaat attattatga tttgggttat agtggtggga aaaaaggaaa   1140
aaagaaaaaa aaaatttatt gttaagtttt gttaggtgta naaagggttg gaattgttgg   1200
ggttatttta tttgatttat tggaaataga gtggatttta ttaatatttt aataaagaga   1260
attttttttgt attaggttgg aagtggttgt tagtttttttg tgtaatttta tttttttggaa   1320
aagtggaatt agttggtatt gtttagtgtg atttgtgagg ttgagtttta atagtttaaa   1380
gaagtaaatg ggatgttatt tttgtggggt ttgttttttttg tgaggtgttt attttgtatt   1440
tgttatgtaa aatgagggag tgttaggaag gaatttgttt tgtaaagtta ttggtttttgg   1500
ttattagttt ttatttaatg tttttgtgat gttgttgttg atttatttgg gaagttggtt   1560
ggttggtgag gtagagtttt tttttaaagt ttggttttta tggaaaatat gtttagtgta   1620
gttgtgtgta tgaatgaaaa tgttgttggg tgtttttagt tggataaaat gtagttgaga   1680
attttgtttg ttttgtgtgt ttttttgttt taggtaggga agagggggttg ttgggtgtgt   1740
tttgtgttttt gtttttgtat ttggattgtt tggtatgggt agggtgaggg ggttttttggg   1800
gggttggggt ttttggttgt ggtggtgaag atagattggg gtttggtagg gaggttattt   1860
tgagtttaga gattttaggt attttttata tataggtttt tattttggtg tgtgtgtgtg   1920
tgtgtgtgtg tgtgtgtgtg tgtgtgtgtg tgtgtgtgtg tgtgtatgtt tgttaatggg   1980
agga                                                                1984
```

<210> SEQ ID NO 23
<211> LENGTH: 1984
<212> TYPE: DNA
<213> ORGANISM: Artificial Sequence
<220> FEATURE:
<223> OTHER INFORMATION: chemically treated genomic DNA (Homo sapiens)
<220> FEATURE:
<221> NAME/KEY: unsure
<222> LOCATION: (804, 1771, 1776..1778, 1810, 1826, 1828, 1858, 1901, 1905)

<223> OTHER INFORMATION: unknown base
<220> FEATURE:
<221> NAME/KEY: unsure
<222> LOCATION: (1923, 1931, 1933, 1935, 1936, 1944, 1952, 1967, 1968, 1976)
<223> OTHER INFORMATION: unknown base

<400> SEQUENCE: 23

```
ttttttttgtt aatgaatgta tatatatata tatatatata tatatatata tatatatata      60
tatatatgta tgtatgttag agtgggagtt tgtgtgtggg gggtgtttag gatttttggg     120
tttggaatga ttttttttatt gagttttgat ttgtttttgt tgttgtgatt ggaggttttg    180
attttttgaa agttttttta ttttgtttgt gttgggtgat ttgaatgtag aaatggggtg     240
tagagtgtgt ttggtagttt tttttttttta tttgggatag gagaatgtat agaatgagtg    300
gagttttttgg ttgtattttg tttgattaga agtgtttggt ggtgttttta tttatgtatg    360
tggttgtatt gagtatattt tttgtgggag ttaggttttg aggagaggtt ttgttttgtt    420
agttagttaa ttttttaaat agattagtag tagtattatg aaagtattgg gtagaggttg    480
atgattagga ttaatggttt tataagatgg attttttttt aatgtttttt tgttttgtat    540
ggtagatatg gggtgagtat tttgtgagga gtgagttttg tggaggtggt attttatttg    600
ttttttttgga ttgttggggt ttagttttat aaattatgtt gggtaatgtt agttgatttt   660
atttttttag agaatggaat tgtatggggg attggtggtt attttttagtt tagtgtaaaa    720
agattttttt tattaaaatg ttaataagat ttattttatt tttaataaat tagataaaat     780
ggttttagta gttttagttt tttntatgtt tggtaaggtt tggtagtgga tttttttttt     840
ttttttttttt ttttttttat tattgtggtt taagttatga tggtgtttgg tgtttttttg    900
ttatttttata aattataaag atgatagatt aatttgagtt tgtagaaaaa attttattaa    960
ggggtaatag attttattaa ttgtttaggt gagagtttga ttagttattt attttttaaa    1020
tgtgtatttg gtattaaagt tgggatttgg attggaagga attttttttttt gtatatggat  1080
tttatttttt agaagttttg aattattttt aggtatttag aatagtagta gttattgttt    1140
aagggatttt ataaatgggg ggttttggga ttgagggtaa gagggatatt taggtttgtt    1200
tttttttaata ggaatttaag aaaatgtagg gaagatttta ttgtattatt tttatgtagt   1260
tttttttttag aaagaattta aggtgtttta taataaagga tatttgtgta atagaattta   1320
tgaattaaaa tagaaaattt gggttagaag gaaaagttta gtaaattgaa atgataagtt    1380
taaattttaa tgtatttgtt ttgatttgga taagagtttt ttgatagtta aagtaataaa    1440
agaaatataa gttatatagt tttgttgtag aaatatgtat ataatgtttt ttagtattat    1500
ttttttatggg ttaaatattg gaataaatgt attatgtaat atgtaatata gtaggatatt    1560
gagtaatgga ttatgttaag atttagtgga tggggatgta ttttttagtat ttggtatagg   1620
gtttggaata tggagatagt aattagtgtg tgttaaagaa atagatggtt agatttaatt    1680
aagatgtagt agaaggtagg gaggggtaag gagtttggag ttatattgtt taggtatagt    1740
ttttggatttt gttatttatt tgtaaattat ntaaannntt gttttttattt gtttatagat  1800
aaaatgaaan tataaattgt attganttnta taaggttgtg gtgaggatta agtgatgnta   1860
taattattga ataaatataa agtgatgtgt ttttttaagat ntttntattg gttgttgttt   1920
ggntagaagg ntntnnttttg tggntttaag gntattgata aagatgnnag tgatgnttga   1980
agtt                                                                  1984
```

<210> SEQ ID NO 24

<211> LENGTH: 7833
<212> TYPE: DNA
<213> ORGANISM: Artificial Sequence
<220> FEATURE:
<223> OTHER INFORMATION: chemically treated genomic DNA (Homo sapiens)

<400> SEQUENCE: 24

```
gtttttggtg agatatgtgt tttataagtt ttaatggaga aaaatgtaag tatttattt       60
tttgaaattt ggttatttga gtaatgagaa aatagttatt ttttttagga tagtggtttt     120
taattatggt tatgtgtttt tttaggaaaa ttttaaaaat atatatatat taatgttttt     180
gtgttatttt tagggatttt aagtttttga atatgaattt tgtattagta tttttttaatt    240
atttaggtga ttgtgatgtg aaattatgat tgagtttttat tgttttaaga tgaaataaat    300
tttttttagt attgaaaatta taaatttaaa ttattaaaaat taattaaggg tatgggaatt   360
aataaggtat agggaagttt ttatattata aaattatttt tttaaattat agtttattgt     420
ttatatgtta tttgttattg tagaaaaggg tgaaaaaata gtaaatttaa ttattttttag    480
tttgaaaaat tatttagaaa tgaagatgat gattttgaaa tattgttaat attatttgat    540
ttataaataa tgttttaata tatttattat atattgatag atatttttt atatgaatat     600
tatatattaa aattaaggta ataatgtatt tagaatattt tatttatatt tatgtatttt    660
aagtaggtta gaaattaaga tatgagttat taagtatgag atgttaaggt gtggggttag    720
aaattatatt gtatttattt ttaataatt aatatatatt ttaatattat atatatttaa    780
ttttaatttg tatattttta attattttta attatgtgta taaatataag tatatatatt    840
tttatgtatt tatttattta tattttatt tattttattta tagggggat ttttttaaat    900
ttattattat taaattatat attttttattt taattttag aataagttta ggaggtaggt   960
attgttatta tttatatttt ataaatgagg aaattgttta tagttataaa gttattgtgt   1020
tagatatatt agaagtttaa tatatatttg gtgaatatat gtataaaaat agagagatag   1080
atatgtataa tagtttattt ttatattgag taaaagtttt taatttgttt tagaaatttt   1140
tttgtgaaaa ttgagtaaaa attgaggtat ttttttattt gttatatagg tataggtggt   1200
atttttattt tttaataagg atgaatattg aaatgtggat tttaaggttt aattttagat   1260
tttttgaatt tttgatagtg ggatttggaa tttgtttatt gttttaaagt ttttaagga    1320
atttatatga ttaattaggt ttagaaatta ttggatttta ttgttgaagt ttgagaatta   1380
aagtttgggt tttattgtgg ttttatagaa agggtaaatg aagtattatg gatagaattg   1440
atatgttttt agttagtttt ttttttaga agttaatagg tagtaatata gtagaaatta   1500
gtgatttatg ttttgtgttt tgaagttagg tagaaattta tagagtttta gtagtgttat   1560
tgatgagatt tgttttttgg ggtaagttgt tgatgttttt taaagttata ttttttttat   1620
ataaaatgag ataatatttt ttgttttata ggggtgtttt aaagattaaa taaaaataat   1680
atgttttatt ttatatggta taatgtttga tatttaagaa gtaaaggata tatttttattt  1740
ttattgaagt aattagaaag tatgaaatta tgaaggagat aagagttttg attggtagtg   1800
tatttttattt tttaggtttt atttatttat tttaaattat ttttgttgga gaataatttt   1860
taagtttttt atttaagttg tgagtaattt tatatttat aatgatgttt tttttatgag    1920
aaaaaaaaat gttttaagt tttttggaga aaatatattt gtattattt tattgaaaaa     1980
tttaataatt ggattttgtt tttttgtatt aatttagag tgtatatgtt ataaataaag    2040
tgttttagtt taagaagatt gaaagtaaat atggtatagt attttaaaat aagaattttg   2100
taaatatatg gtatgattgt gttatattat tagtaattat atgatatgta atgtaaagta   2160
```

```
tagtttatag atttaaattt aattttaata agtaaattga ttttgttttg ttggggaaaa   2220
gttaaagtat taatttaatt gttaatgtag ttttgtttat ttttttggta tttagtgata   2280
agtttaaata atgtatatat ttttatttat atatttagta atataatttt ttgtttaatg   2340
agtgatgttt ttttgttatt tggtggtgtt tgttagtttt agaatttgtt ttttggtggt   2400
attataatat taagtataga gtaagtgtaa taaaattgta gtatttttat tgaaaaggtt   2460
ttgttttaaa ttgttaata  atttaaagga ttttgtgga  agtaattgta tttgttaatt   2520
agttataatt agtaattaat ttttttggag ttttaattta ttttggtaa  aatgttttag   2580
gaagagtata tattattaga aagtatgtta aaaattatt  tagtagaaaa tttaaaaata   2640
gttttttttt gttaagaggt tttttaaaat tttatttata tagttaaatt ttgaaatttt   2700
agtaggtttt gttttattat tataattatt gtataaatat ttttaaggat tttgttttta   2760
gttttaagta tgatttattt ttataagttt gattagttat tatattagtt ttgttatgga   2820
aaatgatatg ttttttatttt ttgttgtaga gttgttaaat tttgatttat atttatgttg   2880
tttttttttgt tgaaagtttg tagtgaaaga aattttttaat ttttgtttt gtaatattag   2940
ttggtagttt tatttaatgg gtattttgtt tttttaaaga atttagttgt tttgtttaga   3000
agttgatttt ttgatgtttt taatgtttgg tttaattgat ttgttttaat ggagttttg    3060
ttggtgagga gtgagatgtt attgattaga atgttgggat ttgttgttta attgttagga   3120
gtgagagata ttgagattta gaatttttg  gaggtgggag gggagaggga tagttttgga   3180
tggaggtgga gatgtaagat aaagggatgg attttatata ggaaaaaaaa aaagattttg   3240
ttgaggtatt gaggtgttgt atgattatat ttttaaagg  agaagttaaa aagtaaggaa   3300
gtgggaggag gttggaggtt aaagtattta aaaggattat ttgggtataa tttgttttt    3360
tgttggtgtt tgtaaaggat agatagtttt gttttaaag  tatatgaatg ttttttttaa   3420
gtgattggga atggatatta attgtttgtt aaatgttatt aaatgttttt ttaaatttag   3480
gggatataga agagggggta taaaaggaga atttaaatag aaaaagggag gatttggagg   3540
tttttgaaag tggggggaga agaaggagga gggataatag agaggaatag agaaggagag   3600
tggagagaag ataaataaaa ataaaaatag gaattattga ataattatat attaaaaaga   3660
aagtttttt  ttatggggta tttaaaatat tgagattgta atagtgattt tggttatgga   3720
agaaagatgt tttttttttat ttttgttttt gaaagttttt ggttttgtta ttggtgatta   3780
aaatttatt  aggttaaaga gtgtgtttaa ttgtttgaag aatgtagtag atggaaggtg   3840
ggttttgtta tgttgtttgt ttttttgtt  ggagagaatg aaagaaatgt gtagagttag   3900
agattttgt  tgagttagat tttttttgt  tgttttaggt tattggttat ttggtaaaga   3960
tttgagtaag gaatgtaggg ttattgtttg ggttaataaa tggagtttgt ttttttttt    4020
ttggatgttg ttgtttggtt gatgttttg  gtaatttatt tgtggtgtat gtagaggagt   4080
tttttttttt tttttagatt attttgtttg attaatttga ttttttaaat atatttgatt   4140
gtattttta  ggtggatata ttaataggtt atggttgga  gaggagtggg tgatgaggag   4200
agggatttaa atttgtgaat gtttggttg  ggttggagtt gtgggggtt  tgggaggaga   4260
gagggggagaa gagagaagga aggagagtgt tgttgggat ggttgagttg ttttggtgag   4320
tagttttggg gttgtatgtt tttgtgggag atgttgttgt tgttttagg  ttggtaagag   4380
tggttttaat attattgttt tttattttt  ttttttgtaaa ttttagaga aatgttttg    4440
gtttttttgt tgtgatattt ttagtttgta ttttttttata gtttaggtgg tgtgtttttg   4500
```

```
tatgttggag tgttggttgt tagtaggatg ttttttttg tgttgatttg ttttttttg        4560 ttttgttgtt gttgttttt tgatatttt gttttatta tttttagttt ggagagatgt        4620
tatttagttg tggtttgtat ttgtggtttg gggttatgtg tggaagaggg gtgttagttt     4680
ggattttgtt tttggtaggg ggtgttttgg agtggagagt gaggtgaatg gtatatgagt     4740
gtgtgggtag tttattttga agtttgagtt ttttatttga gttatgtttt gtttagtttt     4800
atttgggtta gtgtttggtg agtgagttta tttgtggttt ttgtggttgt ttttttttg     4860 tattttgta tttatttgtt gattttttt ttttgggatt tgtatttgt tttattaatt        4920 agagtttgat tgttttttt tatgtgattt tgggtgggtt gaggatttgt tgttttttaa     4980
atgttagagg gatgtgggtg gtagagtttg agaggtggtt gttgggttgt ggggtgtttt     5040 gattttttt ttattttgtt tttttgggtt ttatttgttt gttttggat ttttgttttt     5100 ttttgtttt tggtttttta gagttttttt tttatggtag tagttttttg tgttttggt        5160 gtagttttt agtggatgat tttttgttt tggggttgag tttagttttt ggatgttgtt        5220 gaaattttg agattatgtg tgggtttggt tgttgttttt ttgttgggtg ttattgttat     5280
tgttgttgtt tttgttgttg ttgtttgtgg gatgtttagt agtttgttgt ttggttttg     5340 tgattttgtg ttttttggaa gttgtttgtt gttgtagagt tgtatgaatt agttatggtg     5400
ttgtgggagt ttttgtggta gtgtagtagt tggatatttt gtgagggttt tgttggttg     5460 ttgttgttgt ttgttatgtt atttattgta gtttgtttgg tgaagtttgt tgttttttt     5520 attttttaa gtgattgtta aatgttatt ggttggaatt gttttggtaa gtttagaatt     5580
tttgtttttg atttttaat tttgtagaag aatatgtgta tttagtatag attagtttat     5640
tttagtgtgt tttttagtt ttttatttt tattgttta gattttaat attatttatt       5700 tttatttaga gaaataaggg gaattgttgt aggtttggggg gtgaggggtg gttttgggat    5760
gggtagaaag tgtaggtgta gtaggaaatt tttgtatgtt tgtgtttata ttggagttgt     5820
gaggattttg agaaatatta aatgggatgg ttttttgggt ttattgttt gaaagagtat     5880 taattttagg ggaaatattg aaatagaagt tttgttatta ttaaagaaaa aagttttatt     5940
aggatgagga agaaataatt ttatgagaaa gaatagtga gaaagtaata aattaaatgg     6000
tgattgtagg ggaattgttg atttttggta aaggtgttat gaggttgtat tggtttttg     6060 ttgaagatta ggttatatag attttagagg agttgggttt taatagaatt ttttttttt      6120 ttttttttt tttttttt ttttttttt ttttttatt tatttatttt tttttttttt         6180
ttattttttt tttttagg tggtaaaaga tattggtttt gtagtttaga tatgttttt       6240 tttttgtttt tttaagtttt aaggtagtat aggggagttg agaaaagaa tattttgtgg     6300 gtttttagg ttggagtggg tatgattgag gttggttagg ttttatgtag gtgagttgag     6360
ggtggaattg attttagtgg gtgttgattt ttttatttt ggataggttt ttgtggagtg     6420
ggttaggtat tttttttgtt tgttgggtt ttttagatt ttgatggtga atgtttggta     6480
ggttttgttt tgttgaagtt ttttaattaa atagggttag aggatgggag ttgttgtatt     6540
tttagttggt atagtatttg gtttgatagt ttgtagtata gggtgtatgt aatttttat      6600 ttttgtgaa tataatttg ttgtagtaa atttggtttt gaataaagtg ttttttaaag        6660
atgtatataa gttgaagtgt atgtaatttt agagaggagg gaatgattaa ttgtaattta     6720
gggtgaaagt ttgtatagtt tttagttatt attgatgtaa atgttaaaag gaaaattatt     6780
atgtattatt ttaatttatt ttttataaag ataagttgag atatgtaatt ttattagatt     6840
tgggttaata gattgttttt tttttggta gttttaaat ttggtatttt aataaaattt       6900
```

-continued

```
aatatgtttt tataattttt tgatttatgt gtatatgtgt gttgttttg aaagaataag    6960 ttttattttg ttattgttta attatttttt agatgttta ttatggtaat aattatgagt    7020
ttgtaaaaat aattttga aatgttgatg gttttgtagt ttaatataga ttggtttgtt    7080 ttattttag ttttgtatt gttttaggaa ataattaatt taaatgtgaa gttgatattt    7140
gtaattaaga aattatatat ttattagata ttttaaggg gattgtataa attaaagaga    7200
ataaattggt tttgtagata ggttgttaag aatttggtat tttgttttta ttttgttaa    7260 tttagaggtg attaattttt atttgagtta aatagattat tatagaaaat attgtgtttg    7320
tttattttta ttattgaggt tttgtttttt ttttgtttgg atatatttta aataaggggt    7380
tgttttagtt gttgaagtaa aagaataatt aaagatgggg aaatggtaaa agggtattta    7440
gagattatta ttagtttttt tttaaaatgt ggagttttgt ggttataaat attgtttatt    7500
taatgagtaa aaaataaaaa taaaaaaaaa ataggaagta aatgttaagt ttttatttat    7560
tattgttagt attaatgtaa gttttaaaaa atagtattat tagaaaagga tattaaagga    7620
gaattgatta gaaaagaatt gtggaaaatg gaaatgaata ttgattattt aattagattt    7680
tgaggttatt agtagatagt gattttgtag tatagttata gttgttggat ttaaaattta    7740
ggataagtat tttaaagttt taaagtagtg ttttttttg ttaaaaattt gtaagatgtt    7800
ttaatgattg gagtgttttt tttgaatttg agg                               7833
```

<210> SEQ ID NO 25
<211> LENGTH: 7833
<212> TYPE: DNA
<213> ORGANISM: Artificial Sequence
<220> FEATURE:
<223> OTHER INFORMATION: chemically treated genomic DNA (Homo sapiens)

<400> SEQUENCE: 25

```
ttttaaattt aaagagaata ttttagttat taaaatattt tatagattt taataaaaaa     60 aagtattatt ttgaagttt aaaatatttg ttttaaattt taaatttaat aattatagtt    120
gtattgtaag gttattgttt attgataatt ttaaaattta gttaagtgat taatatttgt    180 ttttatttt tataatttt ttttagttaa ttttttttta gtattttttt ttgatagtgt    240
tattttttaa agtttgtgtt aatattgata gtggtgaatg aaagtttaat atttgttttt    300 tgttttttt ttattttat tttttgttta ttaggtggat aatatttatg attataaaat    360
tttatatttt ggaaaagagt tagtgatgat ttttgaatat tttttatta ttttttatt    420 tttaattgtt ttttgtttt aatgattgaa ataattttt atttgaaatg tatttagata    480
aagaggaaat aaagttttaa taataaagat aaataggtat agtgtttttt gtgatggttt    540
gtttggttta aatgaagatt gattattttt aagttaatag gggtggaagt ggggtgttaa    600 gttttgata atttatttgt aaaattagtt tatttttttt agtttatgta gtttttttta    660
aaatatttgg taaatatgta attttttgat tgtaaatgtt aatttatat ttaagttagt    720 tatttttaa aataatgtaa gggttaggaa tgaagtaaat tagtttgtgt tggattataa    780
agttattaat attttaaaa attgttttg taggtttata attattatta taataaagta    840
tttaaaaagt gattaggtaa tagtaaagtg aaatttattt ttttaaaaat aatatatatg    900
tatgtatgaa ttaagaagtt atagaaatat gttgagtttt attaaaatgt taaatttaga    960
aattgttaaa aaagagaata atttattgat ttaaatttaa tagggttgta tatttaatt    1020 tgtttttgta aaggataaat tagaatgatg tataataatt ttttttttgg tatttatatt   1080
```

```
agtaataatt aggaattata taggttttta ttttgagtta tagttggtta ttttttttt      1140
tttaaagtta tatatatttt agtttatata tatttttgaa agatatttta tttagagtta      1200
gatttaatta tagtaaaatt atatttatag aagatgaaaa attatatata ttttatatta      1260
taggttgtta aattgaatgt tatgttagtt aggagtgtag taatttttat tttttggttt      1320
tatttaatta ggaagtttta gtagagtgaa gtttgttaag tgtttgttgt tagaatttga      1380
aggaatttga gtgagtaaga agagtgtttg atttattttta tagaagtttg tttagaaatg      1440
gaggagttag tgtttattga agttggtttt gttttggtt tgtttatatg gagtttgatt       1500
agttttagtt atgtttattt tggtttggga gatttgtaaa gtgttttttt ttttaatttt      1560
tttgtattat tttgaagttt agggaagtaa agagaggggt atatttggat tgtaaaatta     1620
atgttttttg ttgtttagga gagaaggaa tgagagagag agagagatag atagatagag       1680
agagagagag agagagagag agagagagag agagagagag agaaatttta ttgaaattta      1740
gttttttttag aatttgtgtg atttggtttt taatgggaga ttagtgtgat tttatggtat     1800
ttttgttagg aattagtgat ttttttgtag ttattatttg atttattgtt ttttttgttta    1860
ttttttttta taaagttatt tttttttttat tttagtaaga tttttttttt taatgatgat     1920
aaagttttg ttttagtgtt tttttagga ttggtgtttt tttaaaatag tgaatttaga        1980
aaattatttt gtttaatatt ttttaaaatt tttgtagttt taatgtaagt gtaagtatgt      2040
aaaggtttt tgttatatttt gtatttttg tttatttag aattatttt tatttttggg         2100
tttgtaatag ttttttttgt tttttggat agaggtgggt ggtattaggg gtttagggta      2160
gtaggaggtg aggggttgag gaggtgtgtt agggtaggtt ggtttgtgtt ggatatgtgt     2220
gttttttgt ggagttaaag ggttggggat ggggttttg gatttattag agtaattta        2280
gttggtgggt gtttggtagt tatttaagga ggtagggaaa gtagtgagtt ttattgggtg     2340
ggttatgatg agtagtatga tgggtagtag tagtagttag taaaagtttt tgtaaagtgt     2400
ttagttgttg tattgttgtg gggattttta tagtattatg attagtttgt gtaattttgt     2460
agtagtaaat ggttttgag gaatataggga ttgtgggggt gggtagtgg gttattgagt      2520
attttgtgga tggtggtagt agaggtgtg gtggtgtag tggtatttgg tggggaagta       2580
gtagttaaat ttgtgtatga ttttgagagt tttagtaata tttagggatt gggtttagtt     2640
ttggagtgag agggttgttt gttgagaagt tgtgttggag atgtgggaag ttgttgttat     2700
aaggagggag ttttgggaag ttggaggata ggaggagatg ggagtttagg ggtagatgag     2760
tggagtttga ggaggtaggg tggagggaga gttaaggtgt tttgtagttt ggtagttgtt     2820
ttttgagttt tgttgtttgt atttttttgg tgtttgggaa gtagtaggtt tttagtttgt     2880
ttggggttat gtgggaagag gtagttgggt tttgattggt ggagtaggat gtaggttttg     2940
ggagggaggg gttgatgagt aggtgtaagg atgtaaggag gaggtggttg tggaagttat     3000
agatgggttt gtttgttagg tgttggtttg agtggggtta ggtggggtat ggtttaaatg     3060
agaagtttgg gtttttagggt gggttatttg tatatttata tattatttgt tttatttttt    3120
gttttaggat gttttttatt gaaggtgggg tttggattag tgtttttttt ttgtgtgtga     3180
ttttgggttg tgagtgtggg ttgtggttgg gtggtgtttt tttgagttgg agatggtggg     3240
ggtggaggtg ttagaggagt agtagtagta gggtagagag gggtgagttg gtgtgggaga     3300
gggtgttttt ttggtgattg gtgttttagt gtgtgggagt gtgttgttta ggttgtaggg     3360
ggatgtaggt tgggaatgtt gtggtggaga ggttagggat gttttttttag ggattatag    3420
gaaagagggt gagaggtgat ggtgttagaa ttgttttttgt tgatttggaa gtaatagtag    3480
```

```
tattttttat aagagtgtgt aattttaagg ttgtttgttg aggtagttta gttattttgg    3540
taggtgtttt tttttttttt tttttttttt tttttttttt ttaggtttttt tgtagttttg    3600 atttagttta agtgtttgta ggtttgaatt tttttttttta ttatttgttt ttttttagtt    3660
tgtagtttat tagtgtgttt atttgggagg tgtggttaga tgtgtttgga aggttagatt    3720
ggttgggata agtggtttga gagaaagaga aaggttttttt tgtatatgtt gtgggtgggt    3780
tgttgggagt attggttggg tagtggtgtt tgggaagggg agagtgggtt ttatttgttg    3840
gtttaggtag tgattttgtg ttttttattt gggttttttgt tggatggttg gtgatttggg    3900
gtgatgagag aaggtttaat ttggtaggag ttttttggttt tgtgtgtttt ttttatttttt    3960 tttagtggga agggtaaatg gtatagtggg atttgttttt tgtttgttgt attttttagg    4020
tagttagata tattttttag tttaatggaa ttttagttgt tagtaatggg attaagagtt    4080
tttggggata agggtggaga ggaatatttt ttttttatga ttggggttat tattgtagtt    4140
ttagtgtttt ggatgtttta tagggaagag ttttttttttt ggtgtgtgat tatttagtga    4200
tttttgtttt tgttttttgtt tattttttttt tgttttttttt ttttatttttt ttttttgttat    4260 tttttttttt tttttttttt ttgttttttaa aagtttttgg attttttttt tttttatttta    4320 aattttttttt ttgtgttttt tttttgtgt ttttgaatt taggagagta tttgataata    4380
tttaataggt aattagtgtt tattttttaat tatttaaaag aggtatttat atattttgaa    4440
aatgggatta tttattttttt gtagatatta gtagaaaaat aaattgtatt tgagtaattt    4500
ttttaagtat tttaattttt aatttttttt tatttttttg ttttttaatt tttttttttga    4560 gagatgtgat tgtgtagtat tttagtgttt taatgaaatt tttttttttt ttttgtgtga    4620 aatttattttt tttatttttat attttttgttt ttgtttgaga ttgttttttttt ttttttttat    4680 ttttaaagat ttttgaatt tagtgttttt tatttttggt aattaagtag tagatttttag    4740 tattttagtt ggtggtattt tgttttttat tgatgaagat tttattaaaa tagattaatt    4800
agattagatg ttggaggtat tagaaaattg gttttttagat agagtagtta aattttttaa    4860
ggaaatagaa tatttattag atagagttgt taattaatat tgtaaaataa ggaattagaa    4920
attttttttg ttataggttt ttagtagaga aggtaatata aatatagatt aagatttaat    4980
aattttatag tagagaatga gaatatgtta ttttttatag taaggttggt gtggtaatta    5040
attaggttta tgaaaataag ttatgtttga aattaaaggt aaagttttta aaagtgttta    5100
tgtagtaatt atgataatga aataggattt gttaggattt tagagtttgg ttatgtaagt    5160 agaatttag agaattttttt agtagaggaa aattgttttt gaattttttg ttaagtaaat    5220
ttttggtata tttttttaata atatatgttt tttttaagat gttttgttaa agtaagtta    5280 aaatttttaaa ggagttaatt attggttgta attggttaat aaatgtggtt gttttttatag    5340 aggtttttta aattattaaa tagtttgaag taaagttttt ttaatgggaa tgttgtaatt    5400
ttgttgtatt tattttgtat ttagtgttat agtgttatta agaaataaat tttgaaattg    5460
gtaagtatta ttaagtggta gaagaatatt atttattgag tagagaattg tattattgaa    5520
tatgtaaata aaaatatata tattatttag atttgttatt aggtattaaa gaagtagata    5580
agattgtatt agtaattgga ttagtgtttt aattttttttt tagtaaggta aaattagttt    5640
atttattaga attaaattta agtttatgaa ttgtattttg tattgtgtat tatatgattg    5700
ttagtaatat gatataatta tattatgtat ttgtaaaatt tttattttaa aatattatat    5760
tatatttatt tttaattttt ttgagttaga atattttatt tgtggtatat atattttaga    5820
```

```
attgatgtag aggagtagag tttagttgtt agatttttta gtagaaatag tgtagatata   5880
ttttttttag aaaatttaag aatatttttt tttttatgg aaagaatatt attataaagt    5940
gtgagattat ttatagttta agtaggggt tgggagtta ttttttaata agaatagttt     6000
aagataaata aatgaatttg ggaaaataag atatattgtt aattagaatt tttattttt    6060
ttatgatttt atatttttg attgttttaa taaaggtaag atgtattttt tgttttttag    6120
gtgttaggta ttgtgttatg taggatagaa tatgttattt ttatttaatt tttaaaatat   6180
ttttatgaga taaagaatat tattttattt tatataaag gaatatggtt ttgaaagtat    6240
taggtaattt gttttaagaa ataaattttg ttagtgatat tgttgggatt ttgtgaaatt   6300
ttgtttgatt ttagagtata agatataagt tattaatttt tgttgtattg ttgtttgtta   6360
gttttttgaga gggaaatta attgggaatg tattagttttt gtttatgata ttttatttgt   6420
ttttttttgtg gagttgtagt aaggtttaaa ttttaatttt taaattttgg taataagatt  6480
tagtgatttt tgaatttggt tgattatatg aattttttga gaaattttga ataatagat    6540
aaattttaag ttttattatt agggatttag aaaatttgga gttgggtttt gggatttata   6600
ttttaatatt tattttttgtt ggagaagtaa ggtattattt atattatat gataaatgaa   6660
aggatatttt gattttttgtt tagttttttat agagaggtt ttgagatagg ttaaaagttt  6720
ttatttagtg taaagatgag ttgttgtata tgtttgtttt tttgttttta tgtatatgtt   6780
tattaaatat gtattaagtt tttaatatgt ttgatatagt aattttgtga ttgtagataa   6840
ttttttttatt tgtaaaatgt gagtaataat aatatttgtt ttttgggttt gttttaaaga  6900
ttaaaataaa aatgtatggt ttaatggtag tggatttggg gggattttt atataaataa    6960
gtgaatggag gtatgaataa ataaatatat aaagatgtgt gtatttatat ttatatatat   7020
aattaaaaat agttaaagat gtataaatta aagttaaatg tatgtgatat tgaagtatat   7080
gttgattatt gataatgaag tatagtataa ttttttaattt tatattttaa tatttttata   7140
ttaataattt atatttttaat ttttagttta tttaagatat atagatatag atagaatgtt  7200
ttaaatgtat tattgtttta gttttaatgt ataatattta tatgaaaaag tatttattag   7260
tgtgtagtaa atgtattaga atattatta taggttaaat gatattgata atgttttaga   7320
gttgttattt ttatttttgg ataatttttt aaattgagag taattaaatt tgttatttt    7380
ttatttttt ttataatggt aaataatata taaataatga gttgtgattt aaagaaataa    7440
ttttataatg taaaagtttt tttatgtttt attgattttt atgttttaa ttaattttgg    7500
tagtttaagt ttgtgatttt agtgttgagg aaagtttatt ttatttaga gtagtggggt    7560
ttagttatga ttttatatta taattatttg gataattaaa gaatattgat gtagagtttg   7620
tatttaaaga tttggaattt ttagaagtga tatagaagta ttggtatata tatattttta   7680
aagttttttt ggagaaatat atagttatga ttgagaatta ttgttttggg gaaagtgatt   7740
atttttttat tatttaaata gttaagttttt aggaggtaaa atatttatat ttttttttat  7800
taaaattgt aaaatatata ttttattaaa gat                                 7833
```

<210> SEQ ID NO 26
<211> LENGTH: 22
<212> TYPE: DNA
<213> ORGANISM: Artificial Sequence
<220> FEATURE:
<223> OTHER INFORMATION: 0002044:2092P22

<400> SEQUENCE: 26
ggataggagt tgggattaag at                                            22

<210> SEQ ID NO 27
<211> LENGTH: 22
<212> TYPE: DNA
<213> ORGANISM: Artificial Sequence
<220> FEATURE:
<223> OTHER INFORMATION: 0002044:2462O22

<400> SEQUENCE: 27
aaatcttttt caacaccaaa at                                              22

<210> SEQ ID NO 28
<211> LENGTH: 21
<212> TYPE: DNA
<213> ORGANISM: Artificial Sequence
<220> FEATURE:
<223> OTHER INFORMATION: 0002064:1038P21

<400> SEQUENCE: 28
ggaagaggtg attaaatgga t                                               21

<210> SEQ ID NO 29
<211> LENGTH: 19
<212> TYPE: DNA
<213> ORGANISM: Artificial Sequence
<220> FEATURE:
<223> OTHER INFORMATION: 0002064:1224O19

<400> SEQUENCE: 29
cccaaaaatc aaacaacaa                                                  19

<210> SEQ ID NO 30
<211> LENGTH: 22
<212> TYPE: DNA
<213> ORGANISM: Artificial Sequence
<220> FEATURE:
<223> OTHER INFORMATION: 0002383:1287P22

<400> SEQUENCE: 30
tttgtattag gttggaagtg gt                                              22

<210> SEQ ID NO 31
<211> LENGTH: 22
<212> TYPE: DNA
<213> ORGANISM: Artificial Sequence
<220> FEATURE:
<223> OTHER INFORMATION: 0002383:1529O22

<400> SEQUENCE: 31
cccaaataaa tcaacaacaa ca                                              22

<210> SEQ ID NO 32
<211> LENGTH: 21
<212> TYPE: DNA
<213> ORGANISM: Artificial Sequence
<220> FEATURE:
<223> OTHER INFORMATION: 0002393:1127P21

<400> SEQUENCE: 32
ttgtttgggt taataaatgg a                                               21

<210> SEQ ID NO 33
<211> LENGTH: 20
<212> TYPE: DNA
<213> ORGANISM: Artificial Sequence
<220> FEATURE:

```
<223> OTHER INFORMATION: 0002393:138IO20

<400> SEQUENCE: 33
cttctctctt ctcccctctc                                              20

<210> SEQ ID NO 34
<211> LENGTH: 21
<212> TYPE: DNA
<213> ORGANISM: Artificial Sequence
<220> FEATURE:
<223> OTHER INFORMATION: MSP PRIMER CALCITONIN

<400> SEQUENCE: 34
aggttatcgt cgtgcgagtg t                                            21

<210> SEQ ID NO 35
<211> LENGTH: 24
<212> TYPE: DNA
<213> ORGANISM: Artificial Sequence
<220> FEATURE:
<223> OTHER INFORMATION: MSP PRIMER CALCITONIN

<400> SEQUENCE: 35
tcactcaaac gtatcccaaa ccta                                         24

<210> SEQ ID NO 36
<211> LENGTH: 26
<212> TYPE: DNA
<213> ORGANISM: Artificial Sequence
<220> FEATURE:
<223> OTHER INFORMATION: MSP PRIMER VERSICAN

<400> SEQUENCE: 36
tgggattaag attttcggtt agtttc                                       26

<210> SEQ ID NO 37
<211> LENGTH: 23
<212> TYPE: DNA
<213> ORGANISM: Artificial Sequence
<220> FEATURE:
<223> OTHER INFORMATION: MSP PRIMER VERSICAN

<400> SEQUENCE: 37
cactacaacg ctacgcgact aaa                                          23

<210> SEQ ID NO 38
<211> LENGTH: 21
<212> TYPE: DNA
<213> ORGANISM: Artificial Sequence
<220> FEATURE:
<223> OTHER INFORMATION: MSP PRIMER TPEF

<400> SEQUENCE: 38
tttttttttc ggacgtcgtt g                                            21

<210> SEQ ID NO 39
<211> LENGTH: 20
<212> TYPE: DNA
<213> ORGANISM: Artificial Sequence
<220> FEATURE:
<223> OTHER INFORMATION: MSP PRIMER TPEF

<400> SEQUENCE: 39
cctctacata cgccgcgaat                                              20
```

-continued

```
<210> SEQ ID NO 40
<211> LENGTH: 20
<212> TYPE: DNA
<213> ORGANISM: Artificial Sequence
<220> FEATURE:
<223> OTHER INFORMATION: MSP PRIMER EYA4

<400> SEQUENCE: 40
cggagggtac ggagattacg                                            20

<210> SEQ ID NO 41
<211> LENGTH: 15
<212> TYPE: DNA
<213> ORGANISM: Artificial Sequence
<220> FEATURE:
<223> OTHER INFORMATION: MSP PRIMER EYA4

<400> SEQUENCE: 41
cgacgacgcg cgaaa                                                 15

<210> SEQ ID NO 42
<211> LENGTH: 26
<212> TYPE: DNA
<213> ORGANISM: Artificial Sequence
<220> FEATURE:
<223> OTHER INFORMATION: MSP PRIMER HCADHERIN

<400> SEQUENCE: 42
gacggatttt tttttaacgt tttttc                                     26

<210> SEQ ID NO 43
<211> LENGTH: 22
<212> TYPE: DNA
<213> ORGANISM: Artificial Sequence
<220> FEATURE:
<223> OTHER INFORMATION: MSP PRIMER HCADHERIN

<400> SEQUENCE: 43
aaataaaata ccacctccgc ga                                         22

<210> SEQ ID NO 44
<211> LENGTH: 25
<212> TYPE: DNA
<213> ORGANISM: Artificial Sequence
<220> FEATURE:
<223> OTHER INFORMATION: HM PRIMER EYA4

<400> SEQUENCE: 44
ggtgattgtt tattgttatg gtttg                                      25

<210> SEQ ID NO 45
<211> LENGTH: 23
<212> TYPE: DNA
<213> ORGANISM: Artificial Sequence
<220> FEATURE:
<223> OTHER INFORMATION: HM PRIMER EYA4

<400> SEQUENCE: 45
cccctcaacc taaaaactac aac                                        23

<210> SEQ ID NO 46
<211> LENGTH: 23
<212> TYPE: DNA
<213> ORGANISM: Artificial Sequence
<220> FEATURE:
<223> OTHER INFORMATION: HM PRIMER CALCITONIN
```

```
<400> SEQUENCE: 46
ggatgtgaga gttgttgagg tta                                          23

<210> SEQ ID NO 47
<211> LENGTH: 24
<212> TYPE: DNA
<213> ORGANISM: Artificial Sequence
<220> FEATURE:
<223> OTHER INFORMATION: HM PRIMER CALCITONIN

<400> SEQUENCE: 47
acacacccaa acccattact atct                                         24

<210> SEQ ID NO 48
<211> LENGTH: 21
<212> TYPE: DNA
<213> ORGANISM: Artificial Sequence
<220> FEATURE:
<223> OTHER INFORMATION: TPEF FORWARD PRIMER

<400> SEQUENCE: 48
ggacgttttt tatcgaaggc g                                            21

<210> SEQ ID NO 49
<211> LENGTH: 15
<212> TYPE: DNA
<213> ORGANISM: Artificial Sequence
<220> FEATURE:
<223> OTHER INFORMATION: TPEF BACKWARD PRIMER

<400> SEQUENCE: 49
gccacccaac cgcga                                                   15

<210> SEQ ID NO 50
<211> LENGTH: 18
<212> TYPE: DNA
<213> ORGANISM: Artificial Sequence
<220> FEATURE:
<223> OTHER INFORMATION: 0002044:2183A188

<400> SEQUENCE: 50
atgtgattcg tttgggta                                                18

<210> SEQ ID NO 51
<211> LENGTH: 18
<212> TYPE: DNA
<213> ORGANISM: Artificial Sequence
<220> FEATURE:
<223> OTHER INFORMATION: 0002044:2183B188

<400> SEQUENCE: 51
atgtgatttg tttgggta                                                18

<210> SEQ ID NO 52
<211> LENGTH: 18
<212> TYPE: DNA
<213> ORGANISM: Artificial Sequence
<220> FEATURE:
<223> OTHER INFORMATION: 0002044:2194A186

<400> SEQUENCE: 52
gggtaacgtc gaatttag                                                18

<210> SEQ ID NO 53
<211> LENGTH: 18
```

```
<212> TYPE: DNA
<213> ORGANISM: Artificial Sequence
<220> FEATURE:
<223> OTHER INFORMATION: 0002044:2194B186

<400> SEQUENCE: 53
gggtaatgtt gaatttag                                                 18

<210> SEQ ID NO 54
<211> LENGTH: 18
<212> TYPE: DNA
<213> ORGANISM: Artificial Sequence
<220> FEATURE:
<223> OTHER INFORMATION: 0002044:2324A187

<400> SEQUENCE: 54
aaaaattcgc gagtttag                                                 18

<210> SEQ ID NO 55
<211> LENGTH: 18
<212> TYPE: DNA
<213> ORGANISM: Artificial Sequence
<220> FEATURE:
<223> OTHER INFORMATION: 0002044:2324B187

<400> SEQUENCE: 55
aaaaatttgt gagtttag                                                 18

<210> SEQ ID NO 56
<211> LENGTH: 18
<212> TYPE: DNA
<213> ORGANISM: Artificial Sequence
<220> FEATURE:
<223> OTHER INFORMATION: 0002064:1101A188

<400> SEQUENCE: 56
tatatatacg tgtgggta                                                 18

<210> SEQ ID NO 57
<211> LENGTH: 18
<212> TYPE: DNA
<213> ORGANISM: Artificial Sequence
<220> FEATURE:
<223> OTHER INFORMATION: 0002064:1101B188

<400> SEQUENCE: 57
tatatatatg tgtgggta                                                 18

<210> SEQ ID NO 58
<211> LENGTH: 18
<212> TYPE: DNA
<213> ORGANISM: Artificial Sequence
<220> FEATURE:
<223> OTHER INFORMATION: 0002064:1147A188

<400> SEQUENCE: 58
agtgtatgcg tagaaggt                                                 18

<210> SEQ ID NO 59
<211> LENGTH: 18
<212> TYPE: DNA
<213> ORGANISM: Artificial Sequence
<220> FEATURE:
<223> OTHER INFORMATION: 0002064:1147B188

<400> SEQUENCE: 59
```
agtgtatgtg tagaaggt                                               18

<210> SEQ ID NO 60
<211> LENGTH: 18
<212> TYPE: DNA
<213> ORGANISM: Artificial Sequence
<220> FEATURE:
<223> OTHER INFORMATION: 0002064:1156A188

<400> SEQUENCE: 60
tttagatacg aaatgtta                                               18

<210> SEQ ID NO 61
<211> LENGTH: 18
<212> TYPE: DNA
<213> ORGANISM: Artificial Sequence
<220> FEATURE:
<223> OTHER INFORMATION: 0002064:1156B188

<400> SEQUENCE: 61
tttagatatg aaatgtta                                               18

<210> SEQ ID NO 62
<211> LENGTH: 18
<212> TYPE: DNA
<213> ORGANISM: Artificial Sequence
<220> FEATURE:
<223> OTHER INFORMATION: 0002064:1222A188

<400> SEQUENCE: 62
aagtaagtcg ttgttgtt                                               18

<210> SEQ ID NO 63
<211> LENGTH: 18
<212> TYPE: DNA
<213> ORGANISM: Artificial Sequence
<220> FEATURE:
<223> OTHER INFORMATION: 0002064:1222B188

<400> SEQUENCE: 63
aagtaagttg ttgttgtt                                               18

<210> SEQ ID NO 64
<211> LENGTH: 18
<212> TYPE: DNA
<213> ORGANISM: Artificial Sequence
<220> FEATURE:
<223> OTHER INFORMATION: 0002383:1279A188

<400> SEQUENCE: 64
gaagtggtcg ttagtttt                                               18

<210> SEQ ID NO 65
<211> LENGTH: 19
<212> TYPE: DNA
<213> ORGANISM: Artificial Sequence
<220> FEATURE:
<223> OTHER INFORMATION: 0002383:1279B188

<400> SEQUENCE: 65
gaagtggttg ttagttttt                                              19

<210> SEQ ID NO 66
<211> LENGTH: 18
<212> TYPE: DNA
<213> ORGANISM: Artificial Sequence

```
<220> FEATURE:
<223> OTHER INFORMATION: 0002383:1346A188

<400> SEQUENCE: 66
ttgtttagcg tgatttgt                                              18

<210> SEQ ID NO 67
<211> LENGTH: 18
<212> TYPE: DNA
<213> ORGANISM: Artificial Sequence
<220> FEATURE:
<223> OTHER INFORMATION: 0002383:1346B188

<400> SEQUENCE: 67
ttgtttagtg tgatttgt                                              18

<210> SEQ ID NO 68
<211> LENGTH: 18
<212> TYPE: DNA
<213> ORGANISM: Artificial Sequence
<220> FEATURE:
<223> OTHER INFORMATION: 0002383:1475A188

<400> SEQUENCE: 68
aaggaattcg ttttgtaa                                              18

<210> SEQ ID NO 69
<211> LENGTH: 18
<212> TYPE: DNA
<213> ORGANISM: Artificial Sequence
<220> FEATURE:
<223> OTHER INFORMATION: 0002383:1475B188

<400> SEQUENCE: 69
aaggaatttg ttttgtaa                                              18

<210> SEQ ID NO 70
<211> LENGTH: 18
<212> TYPE: DNA
<213> ORGANISM: Artificial Sequence
<220> FEATURE:
<223> OTHER INFORMATION: 0002383:1524A188

<400> SEQUENCE: 70
aatgttttcg tgatgttg                                              18

<210> SEQ ID NO 71
<211> LENGTH: 18
<212> TYPE: DNA
<213> ORGANISM: Artificial Sequence
<220> FEATURE:
<223> OTHER INFORMATION: 0002383:1524B188

<400> SEQUENCE: 71 aatgttttg tgatgttg                                               18

<210> SEQ ID NO 72
<211> LENGTH: 18
<212> TYPE: DNA
<213> ORGANISM: Artificial Sequence
<220> FEATURE:
<223> OTHER INFORMATION: 0002393:1223A188

<400> SEQUENCE: 72
atttgtttcg attaattt                                              18
```

```
<210> SEQ ID NO 73
<211> LENGTH: 18
<212> TYPE: DNA
<213> ORGANISM: Artificial Sequence
<220> FEATURE:
<223> OTHER INFORMATION: 0002393:1223B188

<400> SEQUENCE: 73
atttgttttg attaattt                                                 18

<210> SEQ ID NO 74
<211> LENGTH: 18
<212> TYPE: DNA
<213> ORGANISM: Artificial Sequence
<220> FEATURE:
<223> OTHER INFORMATION: 0002393:1294A188

<400> SEQUENCE: 74
ataggttacg ggttggag                                                 18

<210> SEQ ID NO 75
<211> LENGTH: 18
<212> TYPE: DNA
<213> ORGANISM: Artificial Sequence
<220> FEATURE:
<223> OTHER INFORMATION: 0002393:1294B188

<400> SEQUENCE: 75
ataggttatg ggttggag                                                 18

<210> SEQ ID NO 76
<211> LENGTH: 18
<212> TYPE: DNA
<213> ORGANISM: Artificial Sequence
<220> FEATURE:
<223> OTHER INFORMATION: 0002393:1332A186

<400> SEQUENCE: 76
aatttgcgaa cgtttggg                                                 18

<210> SEQ ID NO 77
<211> LENGTH: 18
<212> TYPE: DNA
<213> ORGANISM: Artificial Sequence
<220> FEATURE:
<223> OTHER INFORMATION: 0002393:1332B186

<400> SEQUENCE: 77
aatttgtgaa tgtttggg                                                 18

<210> SEQ ID NO 78
<211> LENGTH: 25
<212> TYPE: DNA
<213> ORGANISM: Artificial Sequence
<220> FEATURE:
<223> OTHER INFORMATION: Calcitonin ML probe

<400> SEQUENCE: 78
cgaatctctc gaacgatcgc atcca                                         25

<210> SEQ ID NO 79
<211> LENGTH: 32
<212> TYPE: DNA
<213> ORGANISM: Artificial Sequence
<220> FEATURE:
<223> OTHER INFORMATION: Versican ML probe
```

```
<400> SEQUENCE: 79
tcgacgttac ccaaacgaat cacataaaaa ac                              32

<210> SEQ ID NO 80
<211> LENGTH: 22
<212> TYPE: DNA
<213> ORGANISM: Artificial Sequence
<220> FEATURE:
<223> OTHER INFORMATION: TPEF ML probe

<400> SEQUENCE: 80
aattaccgaa aacatcgacc ga                                         22

<210> SEQ ID NO 81
<211> LENGTH: 29
<212> TYPE: DNA
<213> ORGANISM: Artificial Sequence
<220> FEATURE:
<223> OTHER INFORMATION: EYA4 ML probe

<400> SEQUENCE: 81 cgaaaccta aatatcccga ataacgccg                                   29

<210> SEQ ID NO 82
<211> LENGTH: 24
<212> TYPE: DNA
<213> ORGANISM: Artificial Sequence
<220> FEATURE:
<223> OTHER INFORMATION: HCadherin ML probe

<400> SEQUENCE: 82
gctcctcgcg aaatactcac cccg                                       24

<210> SEQ ID NO 83
<211> LENGTH: 25
<212> TYPE: DNA
<213> ORGANISM: Artificial Sequence
<220> FEATURE:
<223> OTHER INFORMATION: Calcitonin HM probe

<400> SEQUENCE: 83
acctccgaat ctctcgaacg atcgc                                      25

<210> SEQ ID NO 84
<211> LENGTH: 25
<212> TYPE: DNA
<213> ORGANISM: Artificial Sequence
<220> FEATURE:
<223> OTHER INFORMATION: EYA4 HM probe

<400> SEQUENCE: 84
aaaattacga cgacgccacc cgaaa                                      25

<210> SEQ ID NO 85
<211> LENGTH: 28
<212> TYPE: DNA
<213> ORGANISM: Artificial Sequence
<220> FEATURE:
<223> OTHER INFORMATION: Calcitonin HM blocker

<400> SEQUENCE: 85
tgttgaggtt atgtgtaatt gggtgtga                                   28

<210> SEQ ID NO 86
```

```
<211> LENGTH: 26
<212> TYPE: DNA
<213> ORGANISM: Artificial Sequence
<220> FEATURE:
<223> OTHER INFORMATION: EYA4 HM blocker

<400> SEQUENCE: 86
aaactacaac cactcaaatc aaccca                                              26

<210> SEQ ID NO 87
<211> LENGTH: 25
<212> TYPE: DNA
<213> ORGANISM: Artificial Sequence
<220> FEATURE:
<223> OTHER INFORMATION: EYA4 HM blocker

<400> SEQUENCE: 87
gttatggttt gtgattttgt gtggg                                               25

<210> SEQ ID NO 88
<211> LENGTH: 18
<212> TYPE: DNA
<213> ORGANISM: Artificial Sequence
<220> FEATURE:
<223> OTHER INFORMATION: 0002044:2096A188

<400> SEQUENCE: 88
aagattttcg gttagttt                                                       18

<210> SEQ ID NO 89
<211> LENGTH: 18
<212> TYPE: DNA
<213> ORGANISM: Artificial Sequence
<220> FEATURE:
<223> OTHER INFORMATION: 0002044:2096B188

<400> SEQUENCE: 89
aagatttttg gttagttt                                                       18

<210> SEQ ID NO 90
<211> LENGTH: 22
<212> TYPE: DNA
<213> ORGANISM: Artificial Sequence
<220> FEATURE:
<223> OTHER INFORMATION: TPEF ML PROBE

<400> SEQUENCE: 90
acccgaaatc acgcgcgaaa aa                                                  22

<210> SEQ ID NO 91
<211> LENGTH: 25
<212> TYPE: DNA
<213> ORGANISM: Artificial Sequence
<220> FEATURE:
<223> OTHER INFORMATION: control primer

<400> SEQUENCE: 91
tggtgatgga ggaggtttag taagt                                               25

<210> SEQ ID NO 92
<211> LENGTH: 27
<212> TYPE: DNA
<213> ORGANISM: Artificial Sequence
<220> FEATURE:
<223> OTHER INFORMATION: control primer

<400> SEQUENCE: 92
```

| | |
|---|---|
| aaccaataaa acctactcct cccttaa | 27 |

<210> SEQ ID NO 93
<211> LENGTH: 30
<212> TYPE: DNA
<213> ORGANISM: Artificial Sequence
<220> FEATURE:
<223> OTHER INFORMATION: control probe

<400> SEQUENCE: 93

| | |
|---|---|
| accaccaccc aacacacaat aacaaacaca | 30 |

<210> SEQ ID NO 94
<211> LENGTH: 20
<212> TYPE: DNA
<213> ORGANISM: Homo Sapiens

<400> SEQUENCE: 94

| | |
|---|---|
| ccttagtccc tacctctgct | 20 |

<210> SEQ ID NO 95
<211> LENGTH: 21
<212> TYPE: DNA
<213> ORGANISM: Homo Sapiens

<400> SEQUENCE: 95

| | |
|---|---|
| ctcatttaca cacacccaaa c | 21 |

<210> SEQ ID NO 96
<211> LENGTH: 26
<212> TYPE: DNA
<213> ORGANISM: Artificial Sequence
<220> FEATURE:
<223> OTHER INFORMATION: primer

<400> SEQUENCE: 96

| | |
|---|---|
| tggataggag ttgggattaa gatttt | 26 |

<210> SEQ ID NO 97
<211> LENGTH: 33
<212> TYPE: DNA
<213> ORGANISM: Artificial Sequence
<220> FEATURE:
<223> OTHER INFORMATION: primer

<400> SEQUENCE: 97

| | |
|---|---|
| cttattacaa tttaaaaaaa aaattcacta caa | 33 |

<210> SEQ ID NO 98
<211> LENGTH: 39
<212> TYPE: DNA
<213> ORGANISM: Artificial Sequence
<220> FEATURE:
<223> OTHER INFORMATION: blocker

<400> SEQUENCE: 98

| | |
|---|---|
| aaattcacta caacactaca caactaaatt caacattac | 39 |

<210> SEQ ID NO 99
<211> LENGTH: 32
<212> TYPE: DNA
<213> ORGANISM: Artificial Sequence
<220> FEATURE:
<223> OTHER INFORMATION: Probe

<400> SEQUENCE: 99
ttttcgtatt tttttcggg ttattacgtt tt    32

<210> SEQ ID NO 100
<211> LENGTH: 25
<212> TYPE: DNA
<213> ORGANISM: Artificial Sequence
<220> FEATURE:
<223> OTHER INFORMATION: Probe

<400> SEQUENCE: 100
atgtgattcg tttgggtaac gtcga    25

<210> SEQ ID NO 101
<211> LENGTH: 27
<212> TYPE: DNA
<213> ORGANISM: Artificial Sequence
<220> FEATURE:
<223> OTHER INFORMATION: primer

<400> SEQUENCE: 101
gtagggttat tgtttgggtt aataaat    27

<210> SEQ ID NO 102
<211> LENGTH: 30
<212> TYPE: DNA
<213> ORGANISM: Artificial Sequence
<220> FEATURE:
<223> OTHER INFORMATION: primer

<400> SEQUENCE: 102
taaaaaaaaa aaaaaaactc ctctacatac    30

<210> SEQ ID NO 103
<211> LENGTH: 29
<212> TYPE: DNA
<213> ORGANISM: Artificial Sequence
<220> FEATURE:
<223> OTHER INFORMATION: blocker

<400> SEQUENCE: 103
aactcctcta catacaccac aaataaatt    29

<210> SEQ ID NO 104
<211> LENGTH: 22
<212> TYPE: DNA
<213> ORGANISM: Artificial Sequence
<220> FEATURE:
<223> OTHER INFORMATION: Probe

<400> SEQUENCE: 104
cgaaaacatc gaccgaacaa cg    22

<210> SEQ ID NO 105
<211> LENGTH: 25
<212> TYPE: DNA
<213> ORGANISM: Artificial Sequence
<220> FEATURE:
<223> OTHER INFORMATION: Probe

<400> SEQUENCE: 105
gtccgaaaaa aaaaaaacga actcc    25

<210> SEQ ID NO 106
<211> LENGTH: 33

```
<212> TYPE: DNA
<213> ORGANISM: Artificial Sequence
<220> FEATURE:
<223> OTHER INFORMATION: Forward Primer

<400> SEQUENCE: 106
gttagttagt taatttttta aatagattag tag                                    33

<210> SEQ ID NO 107
<211> LENGTH: 27
<212> TYPE: DNA
<213> ORGANISM: Artificial Sequence
<220> FEATURE:
<223> OTHER INFORMATION: Reverse Primer

<400> SEQUENCE: 107
caaaaaaaca aataaaatac cacctcc                                           27

<210> SEQ ID NO 108
<211> LENGTH: 30
<212> TYPE: DNA
<213> ORGANISM: Artificial Sequence
<220> FEATURE:
<223> OTHER INFORMATION: Blocker

<400> SEQUENCE: 108
cctccacaaa actcactcct cacaaaatac                                        30

<210> SEQ ID NO 109
<211> LENGTH: 29
<212> TYPE: DNA
<213> ORGANISM: Artificial Sequence
<220> FEATURE:
<223> OTHER INFORMATION: LC Probe

<400> SEQUENCE: 109
tttcgttttg tatggtagat acggggtga                                         29

<210> SEQ ID NO 110
<211> LENGTH: 36
<212> TYPE: DNA
<213> ORGANISM: Artificial Sequence
<220> FEATURE:
<223> OTHER INFORMATION: LC Probe

<400> SEQUENCE: 110
attaatggtt ttataagacg gattttttt taacgt                                  36
```

METHOD AND NUCLEIC ACIDS FOR THE ANALYSIS OF COLON CELL PROLIFERATIVE DISORDERS

CROSS-REFERENCE TO RELATED APPLICATIONS

This application is a continuation of U.S. patent application Ser. No. 10/506,089, which is the United States nationalization pursuant to 35 U.S.C. § 371 of International application number PCT/EP2003/002034, filed 27 Feb. 2003 and published 4 Sep. 2003 as WO 2003/072820, which claims priority to European Application EP 02004551.4, filed 27 Feb. 2002, both of which are incorporated by reference herein in their entireties.

FIELD OF THE INVENTION

Aspects of the invention relate generally to cellular proliferative disorders (e.g., cancer) and genomic DNA methylation, and more particularly to modified and genomic sequences, to oligonucleotides and/or PNA-oligomers for detecting the cytosine methylation state of genomic DNA, as well as to methods for ascertaining genetic and/or epigenetic parameters of genes for use in the differentiation, diagnosis, prognosis, treatment and/or monitoring of cellular proliferative disorders (e.g., cancer) including colon cell proliferative disorders (e.g., adenocarcinomas, polyps, squamous cell cancers, carcinoid tumours, sarcomas and lymphomas), or the predisposition to colon cell proliferative disorders.

BACKGROUND

Colon cancer is the fourth leading cause of cancer mortality in men and women. The 5-year survival rate is 61% over all stages with early detection being a prerequisite for curative therapy of the disease. Up to 95% of all colorectal cancers are adenocarcinomas of varying differentiation grades.

Sporadic colon cancer develops in a multistep process starting with the pathological transformation of normal colonic epithelium to an adenoma which consecutively progresses to invasive cancer. The progression rate of colonic adenomas is currently predicted based on their histological appearance, location, degree of spread and extent of bowel involvement. For example, tubular-type benign adenomas rarely progress to malignant tumours, whereas villous benign adenomas, particularly if larger than 2 cm in diameter, have a significant malignant potential.

During progression from benign proliferative lesions to malignant neoplasms several genetic and epigenetic alterations are known to occur. Somatic mutation of the APC gene seems to be one of the earliest events in 75 to 80% of colorectal adenomas and carcinomas. Activation of K-RAS is thought to be a critical step in the progression towards a malignant phenotype. Consecutively, mutations in other oncogenes as well as alterations leading to inactivation of tumor suppressor genes accumulate.

Aberrant DNA methylation within CpG islands is among the earliest and most common alterations in human cancers leading to abrogation or overexpression of a broad spectrum of genes. In addition, abnormal methylation has been shown to occur in CpG rich regulatory elements in intronic and coding parts of genes for certain tumours. In contrast to the specific hypermethylation of tumour suppressor genes, an overall hypomethylation of DNA can be observed in tumour cells. This decrease in global methylation can be detected early, far before the development of frank tumour formation. Also, correlation between hypomethylation and increased gene expression was reported for many oncogenes. In colon cancer, aberrant DNA methylation constitutes one of the most prominent alterations and inactivates many tumour suppressor genes such as p14ARF, p16INK4a, THBS1, MINT2, and MINT31 and DNA mismatch repair genes such as hMLH1.

In the molecular evolution of colorectal cancer, DNA methylation errors have been suggested to play two distinct roles. In normal colonic mucosa cells, methylation errors accumulate as a function of age or as time-dependent events predisposing these cells to neoplastic transformation. For example, hypermethylation of several loci could be shown to be already present in adenomas, particularly in the tubulovillous and villous subtype. At later stages, increased DNA methylation of CpG islands plays an important role in a subset of tumours affected by the so called CpG island methylator phenotype (CIMP). Most CIMP+ tumours, which constitute about 15% of all sporadic colorectal cancers, are characterized by micro satellite instability (MIN) due to hypermethylation of the hMLH1 promoter and other DNA mismatch repair genes. By contrast, CIMP– colon cancers evolve along a more classic genetic instability pathway (CIN), with a high rate of p53 mutations and chromosomal changes.

However, the molecular subtypes do not only show varying frequencies regarding molecular alterations. According to the presence of either micro satellite instability or chromosomal aberrations, colon cancer can be subclassified into two classes, which also exhibit significant clinical differences. Almost all MIN tumours originate in the proximal colon (ascending and transversum), whereas 70% of CIN tumours are located in the distal colon and rectum. This has been attributed to the varying prevalence of different carcinogens in different sections of the colon. Methylating carcinogens, which constitute the prevailing carcinogen in the proximal colon have been suggested to play a role in the pathogenesis of MIN cancers, whereas CIN tumours are thought to be more frequently caused by adduct-forming carcinogens, which occur more frequently in distal parts of the colon and rectum. Moreover, MIN tumours have a better prognosis than do tumours with a CIN phenotype and respond better to adjuvant chemotherapy.

The identification of markers for the differentiation of colon carcinoma as well as for early detection are main goals of current research.

The alpha-calcitonin gene encodes a small family of peptides: calcitonin, katacalcin, and calcitonin gene-related peptide (CGRP). Calcitonin is concerned with skeletal integrity, the secretion of calcitonin is, in part, oestrogen dependent, and it appears likely that a postmenopausal decline in calcitonin secretion is a factor in the development of postmenopausal osteoporosis.

Investigation of the Calcitonin gene has revealed that hypermethylation of the promoter region of the gene is present in neoplastic cells of several cancer types, particularly acute leukemias. The major part of said research was carried out using methylation sensitive enzyme based methods, this identified the general phenomenon of hypermethylation within the promoter and first exon regions of the gene in multiple types of cancers. However said methods do not allow for a targeted analysis of selected CpG positions. The observations of hypermethylation were enabled only by the assumption of comethylation within the region. Comethylation is a phenomenon whereby methylation of one CpG position is taken as indicative of methylation of all CpG positions within the region. Examples of research carried out using restriction enzyme based methods include the following:

Hiltunen M O, Koistinaho J, Alhonen L, Myohanen S, Marin S, Kosma V M, Paakkonen M, Janne J. Hypermethylation of the WT1 and calcitonin gene promoter regions at chromosome 11p in human colorectal cancer. Br J Cancer. 1997; 76(9):1124-30.

Silverman A L, Park J G, Hamilton S R, Gazdar A F, Luk G D, Baylin S B. Abnormal methylation of the calcitonin gene in human colonic neoplasms. Cancer Res. 1989 Jul. 1; 49(13):3468-73.

The gene "Versican," (NM_004385) also known as CSPG2 encodes a large chondroitin sulfate proteoglycan. This gene is known to exhibit aberrant methylation patterns and conflicting opinions on this matter have been published. For instance Adany R and Iozzo R V. ("Altered methylation of versican proteoglycan gene in human colon carcinoma." Biochem Biophys Res Commun 1990 Sep. 28; 171(3):1402-13) observed a correlation between hypomethylation and colonic neoplasms. However, more recently Issa et. al. ("Accelerated Age-related CpG Island Methylation in Ulcerative Colitis," Cancer Research 61, 3573-3577, May 1, 2001) described an observed hypermethylation of dysplastic mucosa as compared to non-UC control mucosa (58% versus 31%, P=0.01) or compared with adjacent uninvolved mucosa (58% versus 35%, P=0.06). Therefore it would seem that although aberrant methylation of this gene has been observed in colorectal cell proliferative disorders, the characterisation of this aberrant methylation is as yet not obvious and it would appear that the commonly held assumption of co-methylation does not hold in the case of this gene.

The gene TPEF (also known as TMEFF2) NM_016192 encodes a transmembrane protein containing EGF and follistatin domains. It was initially identified on the basis of its methylation properties by Jones et. al. ("The Gene for a Novel Transmembrane Protein Containing Epidermal Growth Factor and Follistatin Domains Is Frequently Hypermethylated in Human Tumor Cells," Cancer Research 60, 4907-4912, Sep. 1, 2000). It was therein shown that the 5' region of the gene contained a CpG island, a 3' region of which was shown to exhibit significant hypermethylation in tumor cell lines. Although significant said observation was carried out by means of arbitrarily primed PCR, a methodology that is not suitable for application in a clinical or diagnostic setting.

EYA4 is the most recently identified member of the vertebrate Eya (eyes-absent) gene family, a group of four transcriptional activators that interact with other proteins in a conserved regulatory hierarchy to ensure normal embryologic development. The EYA4 gene is mapped to 6q22.3 and encodes a 640 amino acid protein. The structure of EYA4 conforms to the basic pattern established by EYA1-3, and includes a highly conserved 271 amino acid C-terminus called the eya-homologous region (eyaHR; alternatively referred to as the eya domain or eya homology domain 1) and a more divergent proline-serine-threonine (PST)-rich (34-41%) transactivation domain at the N-terminus. EYA proteins interact with members of the SIX and DACH protein families during early embryonic development. Mutations in the EYA4 gene are responsible for postlingual, progressive, autosomal dominant hearing loss at the DFNA10 locus (Wayne S, Robertson N G, DeClau F, Chen N, Verhoeven K, Prasad S, Tranebjarg L, Morton C C, Ryan A F, Van Camp G, Smith R J: Mutations in the transcriptional activator EYA4 cause late-onset deafness at the DFNA10 locus. Hum Mol Genet 2001 Feb. 1; 10(3):195-200 with further references). A link between the Methylation of Cytosine positions in the EYA 4 gene and cancer has not yet been established.

The cadherins are a family of cell surface glycoproteins responsible for selective cell recognition and adhesion. Several family members, including CDH1 (E-cadherin) and CDH13 (H-cadherin, NM_001257) are located on the long arm of chromosome 16, while another gene cluster resides on the short arm of chromosome 5. The chromosomal locations of several of the cadherins are sites of frequent loss of heterozygosity in many tumor types. Deletions of 16q are frequent in breast, lung, and other carcinomas. Loss of expression of cadherins has been described in many epithelial cancers, and it may play a role in tumour cell invasion and metastasis CDH13 expression is diminished in breast and lung cancers. In ovarian tumours, the combination of deletion and aberrant methylation has been reported to inactivate CDH13. Aberrant methylation of CDH13 has also been reported in lung cancers.

5-methylcytosine is the most frequent covalent base modification in the DNA of eukaryotic cells. It plays a role, for example, in the regulation of the transcription, in genetic imprinting, and in tumorigenesis. Therefore, the identification of 5-methylcytosine as a component of genetic information is of considerable interest. However, 5-methylcytosine positions cannot be identified by sequencing since 5-methylcytosine has the same base pairing behaviour as cytosine. Moreover, the epigenetic information carried by 5-methylcytosine is completely lost during PCR amplification.

A relatively new and currently the most frequently used method for analysing DNA for 5-methylcytosine is based upon the specific reaction of bisulfite with cytosine which, upon subsequent alkaline hydrolysis, is converted to uracil which corresponds to thymidine in its base pairing behaviour. However, 5-methylcytosine remains unmodified under these conditions. Consequently, the original DNA is converted in such a manner that methylcytosine, which originally could not be distinguished from cytosine by its hybridisation behaviour, can now be detected as the only remaining cytosine using "normal" molecular biological techniques, for example, by amplification and hybridisation or sequencing. All of these techniques are based on base pairing which can now be fully exploited. In terms of sensitivity, the prior art is defined by a method which encloses the DNA to be analysed in an agarose matrix, thus preventing the diffusion and renaturation of the DNA (bisulfite only reacts with single-stranded DNA), and which replaces all precipitation and purification steps with fast dialysis (Olek A, Oswald J, Walter J. A modified and improved method for bisulphite based cytosine methylation analysis. Nucleic Acids Res. 1996 Dec. 15; 24(24):5064-6). Using this method, it is possible to analyse individual cells, which illustrates the potential of the method. However, currently only individual regions of a length of up to approximately 3000 base pairs are analysed, a global analysis of cells for thousands of possible methylation events is not possible. However, this method cannot reliably analyse very small fragments from small sample quantities either. These are lost through the matrix in spite of the diffusion protection.

An overview of the further known methods of detecting 5-methylcytosine may be gathered from the following review article: Rein, T., DePamphilis, M. L., Zorbas, H., Nucleic Acids Res. 1998, 26, 2255.

To date, barring few exceptions (e.g., Zeschnigk M, Lich C, Buiting K, Doerfler W, Horsthemke B. A single-tube PCR test for the diagnosis of Angelman and Prader-Willi syndrome based on allelic methylation differences at the SNRPN locus. Eur J Hum Genet. 1997 March-April; 5(2): 94-8) the bisulfite technique is only used in research. Always, however, short, specific fragments of a known gene are amplified subsequent to a bisulfite treatment and either completely sequenced (Olek A, Walter J. The pre-implantation ontogeny of the H19 methylation imprint. Nat Genet. 1997 November; 17(3):275-6) or individual cytosine positions are detected by a primer extension reaction (Gonzalgo M L, Jones P A. Rapid quantitation of methylation differences at specific sites using methylation-sensitive single nucleotide primer extension (Ms-SNuPE). Nucleic Acids Res. 1997 Jun. 15; 25(12):2529-31, WO 95/00669) or by enzymatic digestion (Xiong Z, Laird P W. COBRA: a sensitive and quantitative DNA methylation assay. Nucleic Acids Res. 1997 Jun. 15; 25(12):2532-4). In addition, detection by hybridization has also been described (Olek et al., WO 99/28498).

Further publications dealing with the use of the bisulfite technique for methylation detection in individual genes are: Grigg G, Clark S. Sequencing 5-methylcytosine residues in genomic DNA. Bioessays. 1994 June; 16(6):431-6, 431; Zeschnigk M, Schmitz B, Dittrich B, Buiting K, Horsthemke B, Doerfler W. Imprinted segments in the human genome: different DNA methylation patterns in the Prader-Willi/Angelman syndrome region as determined by the genomic sequencing method. Hum Mol Genet. 1997 March; 6(3): 387-95; Feil R, Charlton J, Bird A P, Walter J, Reik W. Methylation analysis on individual chromosomes: improved protocol for bisulphite genomic sequencing. Nucleic Acids Res. 1994 Feb. 25; 22(4):695-6; Martin V, Ribieras S, Song-Wang X, Rio M C, Dante R. Genomic sequencing indicates a correlation between DNA hypomethylation in the 5' region of the pS2 gene and its expression in human breast cancer cell lines. Gene. 1995 May 19; 157(1-2):261-4; WO 97/46705 and WO 95/15373.

An overview of the Prior Art in oligomer array manufacturing can be gathered from a special edition of Nature Genetics (Nature Genetics Supplement, Volume 21, January 1999), published in January 1999, and from the literature cited therein.

Fluorescently labeled probes are often used for the scanning of immobilized DNA arrays. The simple attachment of Cy3 and Cy5 dyes to the 5'-OH of the specific probe are particularly suitable for fluorescence labels. The detection of the fluorescence of the hybridized probes may be carried out, for example via a confocal microscope. Cy3 and Cy5 dyes, besides many others, are commercially available.

Matrix Assisted Laser Desorption Ionisation Mass Spectrometry (MALDI-TOF) is a very efficient development for the analysis of biomolecules (Karas M, Hillenkamp F. Laser desorption ionisation of proteins with molecular masses exceeding 10,000 daltons. Anal Chem. 1988 Oct. 15; 60(20): 2299-301). An analyte is embedded in a light-absorbing matrix. The matrix is evaporated by a short laser pulse thus transporting the analyte molecule into the vapor phase in an unfragmented manner. The analyte is ionised by collisions with matrix molecules. An applied voltage accelerates the ions into a field-free flight tube. Due to their different masses, the ions are accelerated at different rates. Smaller ions reach the detector sooner than bigger ones.

MALDI-TOF spectrometry is excellently suited to the analysis of peptides and proteins. The analysis of nucleic acids is somewhat more difficult (Gut I G, Beck S. DNA and Matrix Assisted Laser Desorption Ionisation Mass Spectrometry. Current Innovations and Future Trends. 1995, 1; 147-57). The sensitivity to nucleic acids is approximately 100 times worse than to peptides and decreases disproportionally with increasing fragment size. For nucleic acids having a multiply negatively charged backbone, the ionisation process via the matrix is considerably less efficient. In MALDI-TOF spectrometry, the selection of the matrix plays an eminently important role. For the desorption of peptides, several very efficient matrixes have been found which produce a very fine crystallisation. There are now several responsive matrixes for DNA, however, the difference in sensitivity has not been reduced. The difference in sensitivity can be reduced by chemically modifying the DNA in such a manner that it becomes more similar to a peptide. Phosphorothioate nucleic acids in which the usual phosphates of the backbone are substituted with thiophosphates can be converted into a charge-neutral DNA using simple alkylation chemistry (Gut I G, Beck S. A procedure for selective DNA alkylation and detection by mass spectrometry. Nucleic Acids Res. 1995 Apr. 25; 23(8):1367-73). The coupling of a charge tag to this modified DNA results in an increase in sensitivity to the same level as that found for peptides. A further advantage of charge tagging is the increased stability of the analysis against impurities which make the detection of unmodified substrates considerably more difficult.

Genomic DNA is obtained from DNA of cell, tissue or other test samples using standard methods. This standard methodology is found in references such as Sambrook, Fritsch and Maniatis eds., Molecular Cloning: A Laboratory Manual, 1989.

DETAILED DESCRIPTION

The invention provides a method for the analysis of biological samples for features associated with the development of colon cell proliferative disorders, characterised in that the nucleic acid of at least one member of the group comprising Versican, TPEF, H-Cadherin, Calcitonin and EYA4 is/are contacted with a reagent or series of reagents capable of distinguishing between methylated and non methylated CpG dinucleotides within the genomic sequence of interest.

The genes that form the basis of the present invention may also be used to form a "gene panel," i.e. a collection comprising the particular genetic sequences of the present invention and/or their respective informative methylation sites. The formation of gene panels allows for a quick and specific analysis of specific aspects of breast cancer treatment. The gene panel(s) as described and employed in this invention can be used with surprisingly high efficiency for the improved diagnosis, treatment and monitoring of colon cell proliferative disorders.

The invention provides significant improvements over the state of the art in that there are currently no markers used to detect colorectal cancer from body fluid samples. Current methods used to detect and diagnose colon cell proliferative disorders include colonoscopy, sigmoidoscopy, and fecal occult blood colon cancer. In comparison to these methods, the disclosed invention is much less invasive than colonoscopy, and as, if not more sensitive than sigmoidoscopy and FOBT. Compared to the previous descriptions of these markers in the literature, the described invention provides significant advantages in terms of sensitivity and specificity due to the advantageous combination of using a gene panel and highly sensitive assay techniques.

The present invention makes available a method for ascertaining genetic and/or epigenetic parameters of genomic DNA. The method is for use in the improved diagnosis, treatment and monitoring of colon cell proliferative disorders, more specifically by enabling the improved identification of and differentiation between subclasses of said disorder and the genetic predisposition to said disorders. The invention presents improvements over the state of the art in that it enables a highly specific classification of colon carcinomas, thereby allowing for improved and informed treatment of patients.

In one aspect of the invention, the disclosed matters provides novel nucleic acid sequences useful for the analysis of methylation within said gene, other aspects provide novel uses of the gene and the gene product as well as methods, assays and kits directed to detecting, differentiating and distinguishing colon cell proliferative disorders. The method and nucleic acids according to the invention may be used for the analysis of colon cell proliferative disorders taken form the group comprising adenocarcinomas, polyps, squamous cell cancers, carcinoid tumours, sarcomas and lymphomas.

In one embodiment the method discloses the use of one or more genes selected from the group comprising Versican, TPEF, H-Cadherin, Calcitonin and EYA4 as markers for the differentiation, detection and distinguishing of colon cell proliferative disorders. Said use of the gene may be enabled by means of analysis of the methylation status of one or more genes selected from the group comprising Versican, TPEF, H-Cadherin, Calcitonin and EYA4 and their promoter or regulatory elements.

The objective of the invention may be achieved by analysis of the methylation state of the CpG dinucleotides within one or more of the genomic sequence according to SEQ ID NOS:1 to SEQ ID NO:5 and sequences complementary thereto. SEQ ID NOS:1 to SEQ ID NO:5 disclose the nucleic acid sequences of the genes from the group consisting of Versican, TPEF, H-Cadherin, Calcitonin and EYA4 and their promoter and regulatory elements, wherein said fragment comprises CpG dinucleotides exhibiting a disease specific methylation pattern. Due to the degeneracy of the genetic code, the sequence as identified in SEQ ID NOS:1 to SEQ ID NO:5 should be interpreted so as to include all substantially similar and equivalent sequences upstream of the promoter region of a gene which encodes a polypeptide with the biological activity of that encoded by the genes Versican, TPEF, H-Cadherin, Calcitonin and EYA4.

In a preferred embodiment of the method, the objective of the invention is achieved by analysis of a nucleic acid comprising a sequence of at least 18 bases in length according to one of SEQ ID NOS:6 to SEQ ID NO:25 and sequences complementary thereto.

The sequences of SEQ ID NOS:6 to SEQ ID NO:25 provide modified versions of the nucleic acid according to SEQ ID NOS:1 to SEQ ID NO:5, wherein the conversion of said sequence results in the synthesis of a nucleic acid having a sequence that is unique and distinct from SEQ ID NOS:1 to SEQ ID NO:5 as follows. (see also the following TABLE 1): SEQ ID NOS:1 to SEQ ID NO:5, sense DNA strand of Versican, TPEF, H-Cadherin, Calcitonin and EYA4 and their promoter and regulatory elements; SEQ ID NOS:6 to SEQ ID NO:15, converted SEQ ID NOS:1 to SEQ ID NO:5 and complementary sequences, wherein "C" or "T," but "CpG" remains "CpG" (i.e., corresponds to case where all "C" residues of CpG dinucleotide sequences are methylated and are thus not converted); SEQ ID NOS:16 to SEQ ID NO:25, converted SEQ ID NOS:1 to SEQ ID NO:5 and complementary sequences, wherein "C" converted to "T" for all "C" residues, including those of "CpG" dinucleotide sequences (i.e., corresponds to case where, for SEQ ID NOS:1 to SEQ ID NO:5, all "C" residues of CpG dinucleotide sequences are unmethylated);

TABLE 1

Description of SEQ ID NO: 1 to SEQ ID NO: 25

| SEQ ID NO | Relationship to SEQ ID NO 1 to SEQ ID NO 5 | Nature of cytosine base conversion |
| --- | --- | --- |
| SEQ ID NOS: 1 to SEQ ID NO: 5 | Sense strand (Versican, TPEF, H-Cadherin, Calcitonin and EYA4 including promoter and regulatory elements) | None; untreated sequence |
| SEQ ID NOS: 6 to 15 | Converted methylated strand | "C" to "T," but "CpG" remains "CpG" (all "C" residues of CpGs are methylated) |
| SEQ ID NOS: 16 to 25 | Converted sense strand | "C" to "T" for all "C" residues (all "C" residues of CpGs are unmethylated) |

Significantly, heretofore, the nucleic acid sequences and molecules according to SEQ ID NOS:6 to SEQ ID NO:25 were not implicated in or connected with the ascertainment of colon cell proliferative disorders.

The described invention further disclose an oligonucleotide or oligomer for detecting the cytosine methylation state within pretreated DNA, according to SEQ ID NOS:6 to SEQ ID NO:25. Said oligonucleotide or oligomer comprising a nucleic acid sequence having a length of at least nine (9) nucleotides which hybridizes, under moderately stringent or stringent conditions (as defined herein above), to a pretreated nucleic acid sequence according to SEQ ID NOS:6 to SEQ ID NO:25 and/or sequences complementary thereto.

Thus, the present invention includes nucleic acid molecules (e.g., oligonucleotides and peptide nucleic acid (PNA) molecules (PNA-oligomers)) that hybridise under moderately stringent and/or stringent hybridisation conditions to all or a portion of the sequences of SEQ ID NOS:6 to SEQ ID NO:25, or to the complements thereof. The hybridising portion of the hybridising nucleic acids is typically at least 9, 15, 20, 25, 30 or 35 nucleotides in length. However, longer molecules have inventive utility, and are thus within the scope of the present invention.

Preferably, the hybridising portion of the inventive hybridising nucleic acids is at least 95%, or at least 98%, or 100% identical to the sequence, or to a portion thereof of SEQ ID NOS:6 to SEQ ID NO:25, or to the complements thereof.

Hybridising nucleic acids of the type described herein can be used, for example, as a primer (e.g., a PCR primer), or a diagnostic and/or prognostic probe or primer. Preferably, hybridisation of the oligonucleotide probe to a nucleic acid sample is performed under stringent conditions and the probe is 100% identical to the target sequence. Nucleic acid duplex or hybrid stability is expressed as the melting temperature or Tm, which is the temperature at which a probe dissociates from a target DNA. This melting temperature is used to define the required stringency conditions.

For target sequences that are related and substantially identical to the corresponding sequence of SEQ ID NOS:1 to SEQ ID NO:5 (such as allelic variants and SNPs), rather than identical, it is useful to first establish the lowest temperature at which only homologous hybridisation occurs with a particular concentration of salt (e.g., SSC or SSPE). Then, assuming that 1% mismatching results in a 1° C. decrease in the Tm, the temperature of the final wash in the hybridisation reaction is reduced accordingly (for example, if sequences having >95% identity with the probe are sought, the final wash temperature is decreased by 5° C.). In practice, the change in Tm can be between 0.5° C. and 1.5° C. per 1% mismatch.

Examples of inventive oligonucleotides of length X (in nucleotides), as indicated by polynucleotide positions with reference to, e.g., SEQ ID NOS:1 to SEQ ID NO:5, include those corresponding to sets of consecutively overlapping oligonucleotides of length X, where the oligonucleotides within each consecutively overlapping set (corresponding to a given X value) are defined as the finite set of Z oligonucleotides from nucleotide positions:

n to (n+(X−1));

where n=1, 2, 3, . . . (Y−(X−1));

where Y equals the length (nucleotides or base pairs) of SEQ ID NOS:1 to SEQ ID NO:5;

where X equals the common length (in nucleotides) of each oligonucleotide in the set (e.g., X=20 for a set of consecutively overlapping 20-mers); and where the number (Z) of consecutively overlapping oligomers of length X for a given SEQ ID NO of length Y is equal to Y−(X−1). For example Z=2,785−19=2, 766 for either sense or antisense sets of SEQ ID NOS:1 to SEQ ID NO:5, where X=20.

Preferably, the set is limited to those oligomers that comprise at least one CpG, TpG or CpA dinucleotide.

The present invention encompasses, for each of SEQ ID NOS:6 to SEQ ID NO:25 (sense and antisense), multiple consecutively overlapping sets of oligonucleotides or modified oligonucleotides of length X, where, e.g., X=9, 10, 17, 20, 22, 23, 25, 27, 30 or 35 nucleotides.

The oligonucleotides or oligomers according to the present invention constitute effective tools useful to ascertain genetic and epigenetic parameters of the genomic sequence corresponding to SEQ ID NOS:1 to SEQ ID NO:5. Preferred sets of such oligonucleotides or modified oligonucleotides of length X are those consecutively overlapping sets of oligomers corresponding to SEQ ID NOS:1 to SEQ ID NO:25 (and to the complements thereof). Preferably, said oligomers comprise at least one CpG, TpG or CpA dinucleotide. Included in these preferred sets are the preferred oligomers corresponding to SEQ ID NOS:11 to SEQ ID NO:15.

Particularly preferred oligonucleotides or oligomers according to the present invention are those in which the cytosine of the CpG dinucleotide (or the thymine of the TpG or the adenosine of the CpA dinucleotide) sequences is within the middle third of the oligonucleotide; that is, where the oligonucleotide is, for example, 13 bases in length, the CpG, TpG or CpA dinucleotide is positioned within the fifth to ninth nucleotide from the 5′-end.

The oligonucleotides of the invention can also be modified by chemically linking the oligonucleotide to one or more moieties or conjugates to enhance the activity, stability or detection of the oligonucleotide. Such moieties or conjugates include chromophores, fluorophors, lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567,810, 5,574,142, 5,585, 481, 5,587,371, 5,597,696 and 5,958,773. The probes may also exist in the form of a PNA (peptide nucleic acid) which has particularly preferred pairing properties. Thus, the oligonucleotide may include other appended groups such as peptides, and may include hybridization-triggered cleavage agents (Krol et al., *BioTechniques* 6:958-976, 1988) or intercalating agents (Zon, *Pharm. Res.* 5:539-549, 1988). To this end, the oligonucleotide may be conjugated to another molecule, e.g., a chromophore, fluorophor, peptide, hybridisation-triggered cross-linking agent, transport agent, hybridisation-triggered cleavage agent, etc.

The oligonucleotide may also comprise at least one art-recognised modified sugar and/or base moiety, or may comprise a modified backbone or non-natural internucleoside linkage.

The oligomers according to the present invention are normally used in so called "sets" which in one embodiment contain at least one oligomer for analysis of each of the CpG dinucleotides of a genomic sequence comprising SEQ ID NOS:1 to SEQ ID NO:5 and sequences complementary thereto or to their corresponding CG, TG or CA dinucleotide within the pretreated nucleic acids according to SEQ ID NOS:6 to SEQ ID NO:25 and sequences complementary thereto. Preferred is a set which contains at least one oligomer for each of the CpG dinucleotides within one or more genes selected from the group comprising Versican, TPEF, H-Cadherin, Calcitonin and EYA4 and their promoter and regulatory elements in both the pretreated and genomic versions of each gene, SEQ ID NOS:1 to SEQ ID NO:25 respectively. However, it is anticipated that for economic or other factors it may be preferable to analyse a limited selection of the CpG dinucleotides within said sequences and the contents of the set of oligonucleotides should be altered accordingly. Therefore, the present invention moreover relates to a set of at least 4 oligonucleotides and/or PNA-oligomers used for detecting the cytosine methylation state in pretreated genomic DNA (SEQ ID NOS:6 to SEQ ID NO:25 and sequences complementary thereto) and genomic DNA (SEQ ID NOS:1 to SEQ ID NO:5 and sequences complementary thereto). These probes enable diagnosis and/ or therapy of genetic and epigenetic parameters of cell proliferative disorders. The set of oligomers may also be used for detecting single nucleotide polymorphisms (SNPs) in pretreated genomic DNA (SEQ ID NOS:6 to SEQ ID NO:25, and sequences complementary thereto) and genomic DNA (SEQ ID NOS:1 to SEQ ID NO:5, and sequences complementary thereto).

Moreover, the present invention makes available a set of at least two oligonucleotides which can be used as so-called "primer oligonucleotides" for amplifying DNA sequences of one of SEQ ID NOS:6 to SEQ ID NO:25 and sequences complementary thereto, or segments thereof.

In the case of the sets of oligonucleotides according to the present invention, it is preferred that at least one and more preferably all members of the set of oligonucleotides is bound to a solid phase.

According to the present invention, it is preferred that an arrangement of different oligonucleotides and/or PNA-oligomers (a so-called "array") made available by the present invention is present in a manner that it is likewise bound to a solid phase. This array of different oligonucleotide- and/or PNA-oligomer sequences can be characterized in that it is arranged on the solid phase in the form of a rectangular or hexagonal lattice. The solid phase surface is preferably composed of silicon, glass, polystyrene, aluminium, steel, iron, copper, nickel, silver, or gold. However, nitrocellulose as well as plastics such as nylon which can exist in the form of pellets or also as resin matrices may also be used.

Therefore, a further subject matter of the present invention is a method for manufacturing an array fixed to a carrier material for analysis in connection with cell proliferative disorders, in which method at least one oligomer according to the present invention is coupled to a solid phase. Methods for manufacturing such arrays are known, for example, from U.S. Pat. No. 5,744,305 by means of solid-phase chemistry and photolabile protecting groups.

A further subject matter of the present invention relates to a DNA chip for the analysis of cell proliferative disorders. DNA chips are known, for example, in U.S. Pat. No. 5,837,832.

The present invention further provides a method for conducting an assay in order to ascertain genetic and/or epigenetic parameters of one or more genes selected from the group comprising Versican, TPEF, H-Cadherin, Calcitonin and EYA4 and their promoter and regulatory elements. Most preferably the assays according to the following method are used in order to detect methylation within one or more genes selected from the group comprising Versican, TPEF, H-Cadherin, Calcitonin and EYA4 wherein said methylated nucleic acids are present in a solution further comprising an excess of background DNA, wherein the background DNA is present in between 100 to 1000 times the concentration of the DNA to be detected. Said method comprises contacting a nucleic acid sample obtained from a subject with at least one reagent or a series of reagents, wherein said reagent or series of reagents, distinguishes between methylated and non-methylated CpG dinucleotides within the target nucleic acid.

Preferably, said method comprises the following steps: In the first step, a sample of the tissue to be analysed is obtained. The source may be any suitable source, preferably, the source of the sample is selected from the group consisting of histological slides, biopsies, paraffin-embedded tissue, bodily fluids, stool, blood, serum, plasma, urine, sputum and combinations thereof. Preferably, the source is biopsies, bodily fluids, urine, or blood.

The DNA is then isolated from the sample. Extraction may be by means that are standard to one skilled in the art, including the use of detergent lysates, sonification and vortexing with glass beads. Once the nucleic acids have been extracted, the genomic double stranded DNA is used in the analysis.

In the second step of the method, the genomic DNA sample is treated in such a manner that cytosine bases which are unmethylated at the 5'-position are converted to uracil, thymine, or another base which is dissimilar to cytosine in terms of hybridisation behavior. This will be understood as "pretreatment" herein.

The above described treatment of genomic DNA is preferably carried out with bisulfite (hydrogen sulfite, disulfite) and subsequent alkaline hydrolysis which results in a conversion of non-methylated cytosine nucleobases to uracil or to another base which is dissimilar to cytosine in terms of base pairing behaviour. Enclosing the DNA to be analysed in an agarose matrix, thereby preventing the diffusion and renaturation of the DNA (bisulfite only reacts with single-stranded DNA), and replacing all precipitation and purification steps with fast dialysis (Olek A, et al., A modified and improved method for bisulfite based cytosine methylation analysis, *Nucleic Acids Res.* 24:5064-6, 1996). It is further preferred that the bisulfite treatment is carried out in the presence of a radical trap or DNA denaturing agent.

In the third step of the method, fragments of the pretreated DNA are amplified. Wherein the source of the DNA is free DNA from serum, or DNA extracted from paraffin it is particularly preferred that the size of the amplificate fragment is between 100 and 200 base pairs in length, and wherein said DNA source is extracted from cellular sources (e.g. tissues, biopsies, cell lines) it is preferred that the amplificate is between 100 and 350 base pairs in length. It is particularly preferred that said amplificates comprise at least one 20 base pair sequence comprising at least three CpG dinucleotides. Said amplification is carried out using sets of primer oligonucleotides according to the present invention, and a preferably heat-stable polymerase. The amplification of several DNA segments can be carried out simultaneously in one and the same reaction vessel, in one embodiment of the method preferably two or more fragments are amplified simultaneously. Typically, the amplification is carried out using a polymerase chain reaction (PCR). The set of primer oligonucleotides includes at least two oligonucleotides whose sequences are each reverse complementary, identical, or hybridise under stringent or highly stringent conditions to an at least 18-base-pair long segment of the base sequences of SEQ ID NO 6 to SEQ ID NO 25 and sequences complementary thereto.

In an alternate embodiment of the method, the methylation status of preselected CpG positions within the nucleic acid sequences comprising SEQ ID NOS:6 to SEQ ID NO:25 may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primers pairs contain at least one primer which hybridizes to a bisulfite treated CpG dinucleotide. Therefore, the sequence of said primers comprises at least one CpG, TpG or CpA dinucleotide. MSP primers specific for non-methylated DNA contain a "T" at the 3' position of the C position in the CpG. Preferably, therefore, the base sequence of said primers is required to comprise a sequence having a length of at least 18 nucleotides which hybridizes to a pretreated nucleic acid sequence according to SEQ ID NOS:6 to SEQ ID NO:25 and sequences complementary thereto, wherein the base sequence of said oligomers comprises at least one CpG, TpG or CpA dinucleotide. In this embodiment of the method according to the invention it is particularly preferred that the MSP primers comprise between 2 and 5 CpG, TpG or CpA dinucleotides. It is further preferred that said dinucleotides are located within the 3' half of the primer e.g. wherein a primer is 18 bases in length the specified dinucleotides are located within the first 9 bases form the 3' end of the molecule. In addition to the CpG, TpG or CpA dinucleotides it is further preferred that said primers should further comprise several bisulfite converted bases (i.e. cytosine converted to thymine, or on the hybridizing strand, guanine converted to adenosine). In a further preferred embodiment said primers are designed so as to comprise no more than 2 cytosine or guanine bases.

In one embodiment of the method the primers may be selected from the group consisting of SEQ ID NOS:34 to SEQ ID NO:49, SEQ ID NOS:96, 97, 101, 102, 106 and SEQ ID NO:107.

The fragments obtained by means of the amplification can carry a directly or indirectly detectable label. Preferred are labels in the form of fluorescence labels, radionuclides, or detachable molecule fragments having a typical mass which can be detected in a mass spectrometer. Where said labels are mass labels, it is preferred that the labelled amplificates have a single positive or negative net charge, allowing for better detectability in the mass spectrometer. The detection may be carried out and visualised by means of, e.g., matrix assisted laser desorption/ionisation mass spectrometry (MALDI) or using electron spray mass spectrometry (ESI).

Matrix Assisted Laser Desorption/Ionization Mass Spectrometry (MALDI-TOF) is a very efficient development for the analysis of biomolecules (Karas & Hillenkamp, *Anal Chem.*, 60:2299-301, 1988). An analyte is embedded in a light-absorbing matrix. The matrix is evaporated by a short laser pulse thus transporting the analyte molecule into the vapour phase in an unfragmented manner. The analyte is ionised by collisions with matrix molecules. An applied voltage accelerates the ions into a field-free flight tube. Due to their different masses, the ions are accelerated at different rates. Smaller ions reach the detector sooner than bigger ones. MALDI-TOF spectrometry is well suited to the analysis of peptides and proteins. The analysis of nucleic acids is somewhat more difficult (Gut & Beck, *Current Innovations and Future Trends*, 1:147-57, 1995). The sensitivity with respect to nucleic acid analysis is approximately 100-times less than for peptides, and decreases disproportionally with increasing fragment size. Moreover, for nucleic acids having a multiply negatively charged backbone, the ionisation process via the matrix is considerably less efficient. In MALDI-TOF spectrometry, the selection of the matrix plays an eminently important role. For the desorption of peptides, several very efficient matrixes have been found which produce a very fine crystallisation. There are now several responsive matrixes for DNA, however, the difference in sensitivity between peptides and nucleic acids has not been reduced. This difference in sensitivity can be reduced, however, by chemically modifying the DNA in such a manner that it becomes more similar to a peptide. For example, phosphorothioate nucleic acids, in which the usual phosphates of the backbone are substituted with thiophosphates, can be converted into a charge-neutral DNA using simple alkylation chemistry (Gut & Beck, *Nucleic Acids Res.* 23: 1367-73, 1995). The coupling of a charge tag to this modified DNA results in an increase in MALDI-TOF sensitivity to the same level as that found for peptides. A further advantage of charge tagging is the increased stability of the analysis against impurities, which makes the detection of unmodified substrates considerably more difficult.

In a particularly preferred embodiment of the method the amplification of step three is carried out in the presence of at least one species of blocker oligonucleotides. The use of such blocker oligonucleotides has been described by Yu et al., *BioTechniques* 23:714-720, 1997. The use of blocking oligonucleotides enables the improved specificity of the amplification of a subpopulation of nucleic acids. Blocking probes hybridised to a nucleic acid suppress, or hinder the polymerase mediated amplification of said nucleic acid. In one embodiment of the method blocking oligonucleotides are designed so as to hybridise to background DNA. In a further embodiment of the method said oligonucleotides are designed so as to hinder or suppress the amplification of unmethylated nucleic acids as opposed to methylated nucleic acids or vice versa.

Blocking probe oligonucleotides are hybridised to the bisulfite treated nucleic acid concurrently with the PCR primers. PCR amplification of the nucleic acid is terminated at the 5' position of the blocking probe, such that amplification of a nucleic acid is suppressed where the complementary sequence to the blocking probe is present. The probes may be designed to hybridize to the bisulfite treated nucleic acid in a methylation status specific manner. For example, for detection of methylated nucleic acids within a population of unmethylated nucleic acids, suppression of the amplification of nucleic acids which are unmethylated at the position in question would be carried out by the use of blocking probes comprising a "TpG" at the position in question, as opposed to a "CpG." In one embodiment of the method the sequence of said blocking oligonucleotides should be identical or complementary to molecule is complementary or identical to a sequence at least 18 base pairs in length selected from the group consisting of SEQ ID NOS:6 to SEQ ID NO:25, preferably comprising one or more CpG, TpG or CpA dinucleotides. In one embodiment of the method the sequence of said oligonucleotides is selected from the group consisting SEQ ID NOS:85 to SEQ ID NO:87, SEQ ID NOS:98, 103 and SEQ ID NO:108, and sequences complementary thereto.

For PCR methods using blocker oligonucleotides, efficient disruption of polymerase-mediated amplification requires that blocker oligonucleotides not be elongated by the polymerase. Preferably, this is achieved through the use of blockers that are 3'-deoxyoligonucleotides, or oligonucleotides derivatized at the 3' position with other than a "free" hydroxyl group. For example, 3'-O-acetyl oligonucleotides are representative of a preferred class of blocker molecule.

Additionally, polymerase-mediated decomposition of the blocker oligonucleotides should be precluded. Preferably, such preclusion comprises either use of a polymerase lacking 5'-3' exonuclease activity, or use of modified blocker oligonucleotides having, for example, thioate bridges at the 5'-terminii thereof that render the blocker molecule nuclease-resistant. Particular applications may not require such 5' modifications of the blocker. For example, if the blocker- and primer-binding sites overlap, thereby precluding binding of the primer (e.g., with excess blocker), degradation of the blocker oligonucleotide will be substantially precluded. This is because the polymerase will not extend the primer toward, and through (in the 5'-3' direction) the blocker—a process that normally results in degradation of the hybridized blocker oligonucleotide.

A particularly preferred blocker/PCR embodiment, for purposes of the present invention and as implemented herein, comprises the use of peptide nucleic acid (PNA) oligomers as blocking oligonucleotides. Such PNA blocker oligomers are ideally suited, because they are neither decomposed nor extended by the polymerase.

In one embodiment of the method, the binding site of the blocking oligonucleotide is identical to, or overlaps with that of the primer and thereby hinders the hybridisation of the primer to its binding site. In a further preferred embodiment of the method, two or more such blocking oligonucleotides are used. In a particularly preferred embodiment, the hybridisation of one of the blocking oligonucleotides hinders the hybridisation of a forward primer, and the hybridisation of another of the probe (blocker) oligonucleotides hinders the hybridisation of a reverse primer that binds to the amplificate product of said forward primer.

In an alternative embodiment of the method, the blocking oligonucleotide hybridises to a location between the reverse and forward primer positions of the treated background DNA, thereby hindering the elongation of the primer oligonucleotides.

It is particularly preferred that the blocking oligonucleotides are present in at least 5 times the concentration of the primers.

In the fourth step of the method, the amplificates obtained during the third step of the method are analysed in order to ascertain the methylation status of the CpG dinucleotides prior to the treatment.

In embodiments where the amplificates were obtained by means of MSP amplification and/or blocking oligonucleotides, the presence or absence of an amplificate is in itself indicative of the methylation state of the CpG positions covered by the primers and or blocking oligonucleotide, according to the base sequences thereof. All possible known molecular biological methods may be used for this detection, including, but not limited to gel electrophoresis, sequencing, liquid chromatography, hybridisations, real time PCR analysis or combinations thereof. This step of the method further acts as a qualitative control of the preceding steps.

In the fourth step of the method amplificates obtained by means of both standard and methylation specific PCR are further analysed in order to determine the CpG methylation status of the genomic DNA isolated in the first step of the method. This may be carried out by means of based-based methods such as, but not limited to, array technology and probe based technologies as well as by means of techniques such as sequencing and template directed extension.

In one embodiment of the method, the amplificates synthesised in step three are subsequently hybridised to an array or a set of oligonucleotides and/or PNA probes. In this context, the hybridisation takes place in the following manner: the set of probes used during the hybridisation is preferably composed of at least 2 oligonucleotides or PNA-oligomers; in the process, the amplificates serve as probes which hybridise to oligonucleotides previously bonded to a solid phase; the non-hybridised fragments are subsequently removed; said oligonucleotides contain at least one base sequence having a length of at least 9 nucleotides which is reverse complementary or identical to a segment of the base sequences specified in the SEQ ID NOS:2 to SEQ ID NO:5; and the segment comprises at least one CpG, TpG or CpA dinucleotide.

In a preferred embodiment, said dinucleotide is present in the central third of the oligomer. For example, wherein the oligomer comprises one CpG dinucleotide, said dinucleotide is preferably the fifth to ninth nucleotide from the 5'-end of a 13-mer. One oligonucleotide exists for the analysis of each CpG dinucleotide within the sequence according to SEQ ID NOS:1 to SEQ ID NO:5, and the equivalent positions within SEQ ID NOS:6 to SEQ ID NO:25. Said oligonucleotides may also be in the form of peptide nucleic acids. The non-hybridised amplificates are then removed. The hybridised amplificates are detected. In this context, it is preferred that labels attached to the amplificates are identifiable at each position of the solid phase at which an oligonucleotide sequence is located. In one embodiment of the method said oligonucleotides may be selected from the group comprising SEQ ID NOS:50-77, and SEQ ID NOS:88 and 89.

In yet a further embodiment of the method, the genomic methylation status of the CpG positions may be ascertained by means of oligonucleotide probes that are hybridised to the bisulfite treated DNA concurrently with the PCR amplification primers (wherein said primers may either be methylation specific or standard).

A particularly preferred embodiment of this method is the use of fluorescence-based Real Time Quantitative PCR (Heid et al., *Genome Res.* 6:986-994, 1996; also see U.S. Pat. No. 6,331,393). There are two preferred embodiments of utilising this method. One embodiment, known as the TaqMan™ assay employs a dual-labelled fluorescent oligonucleotide probe. The TaqMan™ PCR reaction employs the use of a nonextendible interrogating oligonucleotide, called a TaqMan™ probe, which is designed to hybridise to a GpC-rich sequence located between the forward and reverse amplification primers. The TaqMan™ probe further comprises a fluorescent "reporter moiety" and a "quencher moiety" covalently bound to linker moieties (e.g., phosphoramidites) attached to the nucleotides of the TaqMan™ oligonucleotide. Hybridised probes are displaced and broken down by the polymerase of the amplification reaction thereby leading to an increase in fluorescence. For analysis of methylation within nucleic acids subsequent to bisulfite treatment, it is required that the probe be methylation specific, as described in U.S. Pat. No. 6,331,393, (hereby incorporated by reference in its entirety) also known as the MethylLight™ assay. The second preferred embodiment of this technology is the use of dual-probe technology (Lightcycler™), each carrying donor or recipient fluorescent moieties, hybridisation of two probes in proximity to each other is indicated by an increase or fluorescent amplification primers. Both these techniques may be adapted in a manner suitable for use with bisulfite treated DNA, and moreover for methylation analysis within CpG dinucleotides. In one embodiment of the method the sequence of said probe oligonucleotides may be selected from the group comprising SEQ ID NOS:78-84, 90, 99, 100, 104, 105, 109 and SEQ ID NO:110.

In a further preferred embodiment of the method, the fourth step of the method comprises the use of template-directed oligonucleotide extension, such as MS-SNuPE as described by Gonzalgo & Jones, *Nucleic Acids Res.* 25:2529-2531, 1997. In said embodiment it is preferred that the Ms-SNuPE primer is identical or complementary to a sequence at least nine but preferably no more than twenty five nucleotides in length of one or more of the sequences taken from the group of SEQ ID NOS:2 to SEQ ID NO:5.

In yet a further embodiment of the method, the fourth step of the method comprises sequencing and subsequent sequence analysis of the amplificate generated in the third step of the method (Sanger F., et al., *Proc Natl Acad Sci USA* 74:5463-5467, 1977).

Additional embodiments of the invention provide a method for the analysis of the methylation status of genomic DNA according to the invention (SEQ ID NOS:1 to SEQ ID NO:5) without the need for pretreatment.

In the first step of such additional embodiments, the genomic DNA sample is isolated from tissue or cellular sources. Preferably, such sources include cell lines, histological slides, body fluids, or tissue embedded in paraffin. Extraction may be by means that are standard to one skilled in the art, including but not limited to the use of detergent lysates, sonification and vortexing with glass beads. Once the nucleic acids have been extracted, the genomic double-stranded DNA is used in the analysis.

In a preferred embodiment, the DNA may be cleaved prior to the treatment, and this may be by any means standard in the state of the art, in particular with methylation-sensitive restriction endonucleases.

In the second step, the DNA is then digested with one or more methylation sensitive restriction enzymes. The digestion is carried out such that hydrolysis of the DNA at the restriction site is informative of the methylation status of a specific CpG dinucleotide.

In the third step, which is optional but a preferred embodiment, the restriction fragments are amplified. This is preferably carried out using a polymerase chain reaction, and said amplificates may carry suitable detectable labels as discussed above, namely fluorophore labels, radionuclides and mass labels.

In the final step the amplificates are detected. The detection may be by any means standard in the art, for example, but not limited to, gel electrophoresis analysis, hybridisation analysis, incorporation of detectable tags within the PCR products, DNA array analysis, MALDI or ESI analysis.

The present invention enables diagnosis and/or prognosis of events which are disadvantageous to patients or individuals in which important genetic and/or epigenetic parameters within the Versican, TPEF, H-Cadherin, Calcitonin and EYA4 and their promoter or regulatory elements may be used as markers. Said parameters obtained by means of the present invention may be compared to another set of genetic and/or epigenetic parameters, the differences serving as the basis for a diagnosis and/or prognosis of events which are disadvantageous to patients or individuals.

Specifically, the present invention provides for diagnostic and/or prognostic cancer assays based on measurement of differential methylation of Versican, TPEF, H-Cadherin, Calcitonin and/or EYA4 CpG dinucleotide sequences. Preferred gene sequences useful to measure such differential methylation are represented herein by SEQ ID NOS:1 to SEQ ID NO:25. Typically, such assays involve obtaining a tissue sample from a test tissue, performing an assay to measure the methylation status of at least one of the inventive Versican, TPEF, H-Cadherin, Calcitonin and/or EYA4 specific CpG dinucleotide sequences derived from the tissue sample, relative to a control sample, and making a diagnosis or prognosis based thereon.

In particular preferred embodiments, inventive oligomers are used to assess Versican, TPEF, H-Cadherin, Calcitonin and/or EYA4 specific CpG dinucleotide methylation status, such as those based on SEQ ID NOS:1 to SEQ ID NO:25, including the representative preferred oligomers corresponding to SEQ ID NOS: ALL OLIGOS, or arrays thereof, as well as a kit based thereon are useful for the diagnosis and/or prognosis of cancer and/or other prostate cell proliferative disorders.

The present invention moreover relates to a diagnostic agent and/or therapeutic agent for the diagnosis and/or therapy colon cell proliferative disorders, the diagnostic agent and/or therapeutic agent being characterised in that at least one primer or probe based on SEQ ID NOS:1 to SEQ ID NO:25 is used for manufacturing it, possibly together with suitable additives and ancillary agents.

Moreover, an additional aspect of the present invention is a kit comprising, for example: a bisulfite-containing reagent as well as at least one oligonucleotide whose sequences in each case correspond, are complementary, or hybridise under stringent or highly stringent conditions to a 18-base long segment of the sequences SEQ ID NOS:1 to SEQ ID NO:5. Said kit may further comprise instructions for carrying out and evaluating the described method. In a further preferred embodiment, said kit may further comprise standard reagents for performing a CpG position-specific methylation analysis, wherein said analysis comprises one or more of the following techniques: MS-SNuPE, MSP, MethyLight, HeavyMethyl™, COBRA, and nucleic acid sequencing. However, a kit along the lines of the present invention can also contain only part of the aforementioned components.

Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridisation oligo; control hybridisation oligo; kinase labelling kit for oligo probe; and radioactive nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Typical reagents (e.g., as might be found in a typical MethyLight-based kit) for MethyLight analysis may include, but are not limited to: PCR primers for specific gene (or methylation-altered DNA sequence or CpG island); TaqMan® probes; optimized PCR buffers and deoxynucleotides; and Taq polymerase.

Typical reagents (e.g., as might be found in a typical Ms-SNuPE-based kit) for Ms-SNuPE analysis may include, but are not limited to: PCR primers for specific gene (or methylation-altered DNA sequence or CpG island); optimised PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

Typical reagents (e.g., as might be found in a typical MSP-based kit) for MSP analysis may include, but are not limited to: methylated and unmethylated PCR primers for specific gene (or methylation-altered DNA sequence or CpG island), optimized PCR buffers and deoxynucleotides, and specific probes.

Definitions

The term "CpG island" refers to a contiguous region of genomic DNA that satisfies the criteria of (1) having a frequency of CpG dinucleotides corresponding to an "Observed/Expected Ratio">0.6, and (2) having a "GC Content">0.5. CpG islands are typically, but not always, between about 0.2 to about 1 kb in length.

The term "methylation state" or "methylation status" refers to the presence or absence of 5-methylcytosine ("5-mCyt") at one or a plurality of CpG dinucleotides within a DNA sequence. Methylation states at one or more particular palindromic CpG methylation sites (each having two CpG CpG dinucleotide sequences) within a DNA sequence include "unmethylated," "fully-methylated" and "hemi-methylated."

The term "hemi-methylation" or "hemimethylation" refers to the methylation state of a palindromic CpG methylation site, where only a single cytosine in one of the two CpG dinucleotide sequences of the palindromic CpG methylation site is methylated (e.g., 5'-CC$^M$GG-3' (top strand): 3'-GGCC-5' (bottom strand)).

The term "hypermethylation" refers to the average methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

The term "hypomethylation" refers to the average methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

The term "microarray" refers broadly to both "DNA microarrays," and "DNA chip(s)," as recognised in the art, encompasses all art-recognized solid supports, and encompasses all methods for affixing nucleic acid molecules thereto or synthesis of nucleic acids thereon.

"Genetic parameters" are mutations and polymorphisms of genes and sequences further required for their regulation. To be designated as mutations are, in particular, insertions, deletions, point mutations, inversions and polymorphisms and, particularly preferred, SNPs (single nucleotide polymorphisms).

"Epigenetic parameters" are, in particular, cytosine methylations. Further epigenetic parameters include, for example, the acetylation of histones which, however, cannot be directly analysed using the described method but which, in turn, correlate with the DNA methylation.

The term "bisulfite reagent" refers to a reagent comprising bisulfite, disulfite, hydrogen sulfite or combinations thereof, useful as disclosed herein to distinguish between methylated and unmethylated CpG dinucleotide sequences.

The term "Methylation assay" refers to any assay for determining the methylation state of one or more CpG dinucleotide sequences within a sequence of DNA.

The term "MS.AP-PCR" (Methylation-Sensitive Arbitrarily-Primed Polymerase Chain Reaction) refers to the art-recognised technology that allows for a global scan of the genome using CG-rich primers to focus on the regions most likely to contain CpG dinucleotides, and described by Gonzalgo et al., *Cancer Research* 57:594-599, 1997.

The term "MethyLight" refers to the art-recognised fluorescence-based real-time PCR technique described by Eads et al., *Cancer Res.* 59:2302-2306, 1999.

The term "HeavyMethyl" assay, in the embodiment thereof implemented herein, refers to a HeavyMethyl™ MethylLight assay, which is a variation of the MethylLight assay, wherein the MethylLight assay is combined with methylation specific blocking probes covering CpG positions between the amplification primers.

The term "Ms-SNuPE" (Methylation-sensitive Single Nucleotide Primer Extension) refers to the art-recognised assay described by Gonzalgo & Jones, *Nucleic Acids Res.* 25:2529-2531, 1997.

The term "MSP" (Methylation-specific PCR) refers to the art-recognized methylation assay described by Herman et al. *Proc. Natl. Acad. Sci. USA* 93:9821-9826, 1996, and by U.S. Pat. No. 5,786,146.

The term "COBRA" (Combined Bisulfite Restriction Analysis) refers to the art-recognized methylation assay described by Xiong & Laird, *Nucleic Acids Res.* 25:2532-2534, 1997.

The term "hybridisation" is to be understood as a bond of an oligonucleotide to a complementary sequence along the lines of the Watson-Crick base pairings in the sample DNA, forming a duplex structure.

"Stringent hybridisation conditions," as defined herein, involve hybridising at 68° C. in 5×SSC/5×Denhardt's solution/1.0% SDS, and washing in 0.2×SSC/0.1% SDS at room temperature, or involve the art-recognised equivalent thereof (e.g., conditions in which a hybridisation is carried out at 60° C. in 2.5×SSC buffer, followed by several washing steps at 37° C. in a low buffer concentration, and remains stable). Moderately stringent conditions, as defined herein, involve including washing in 3×SSC at 42° C., or the art-recognised equivalent thereof. The parameters of salt concentration and temperature can be varied to achieve the optimal level of identity between the probe and the target nucleic acid. Guidance regarding such conditions is available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

"Background DNA" as used herein refers to any nucleic acids which originate from sources other than colon cells.

EXAMPLES

The following examples describe the analysis of the methylation status of the genes EYA 4, Calcitonin, TPEF, H-Cadherin and Versican in healthy and sick colon cell proliferative disorder samples. The initial link between said genes and colon cell proliferative disorders was initially carried by means of hybridisation analysis as described in examples 13 onwards. The genes EYA 4, Calcitonin, TPEF, H-Cadherin and Versican were then selected from the larger set of genes analysed in said examples, and the correlation between methylation status and colon cell proliferative disorder states was validated by analysis of samples using other methylation analysis techniques, namely the MSP-MethyLight and HeavyMethyl MethyLight assays. Please note that the term 'MethyLight' is used to describe real time PCR analysis of bisulfite treated DNA using probes of both the Taqman single probe) and Lightcycler (dual probe) technologies.

Example 1

Analysis of methylation within colon cancer using an MSP-MethyLight assay (EYA4) DNA was extracted from 33 colon adenocarcinoma samples and 43 colon normal adjacent tissues using a Qiagen extraction kit. The DNA from each sample was treated using a bisulfite solution (hydrogen sulfite, disulfite) according to the agarose-bead method (Olek et al 1996). The treatment is such that all non methylated cytosines within the sample are converted to thymidine. Conversely, 5-methylated cytosines within the sample remain unmodified.

The methylation status was determined with a MSP-MethyLight assay designed for the CpG island of interest and a control fragment from the beta actin gene (Eads et al., 2001). The CpG island assay covers CpG sites in both the primers and the Taqman style probe, while the control gene does not. The control gene is used as a measure of total DNA concentration, and the CpG island assay (methylation assay) determines the methylation levels at that site.

Methods:

The EYA4 gene CpG island assay was performed using the following primers and probes: Forward Primer: CGGAGGGTACGGAGATTACG (SEQ ID NO:40); Reverse Primer: CGACGACGCGCGAAA (SEQ ID NO:41); and Probe: CGAAACCCTAAATATC-CCGAATAACGCCG (SEQ ID NO:81). The corresponding control assay was performed using the following primers and probes: Primer: TGGTGATGGAGGAGGTTTAG-TAAGT (SEQ ID NO:91); Primer: AACCAATAAAAC-CTACTCCTCCCTTAA (SEQ ID NO:92); and Probe: ACCACCACCCAACACACAATAACAAACACA (SEQ ID NO:93). The reactions were run in triplicate on each DNA sample with the following assay conditions: Reaction solution: (900 nM primers; 300 nM probe; 3.5 mM Magnesium Chloride; 1 unit of taq polymerase; 200 µM dNTPs; of DNA, in a final reaction volume of 20 µl); Cycling conditions: (95° C. for 10 minutes; then 50 cycles of: 95° C. for 15 seconds; 60° C. for 1 minute).

The data was analysed using a PMR calculation previously described in the literature (Eads et al 2001). Results.

Results.

Figure 1:
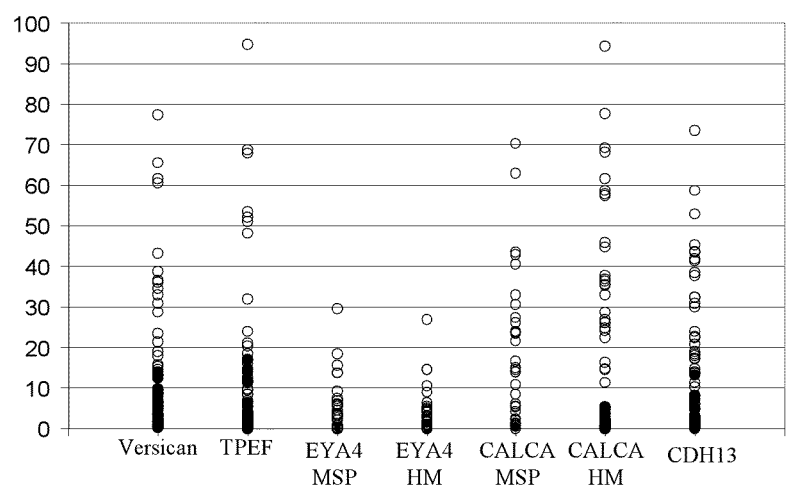
FIG. 1 shows the level of methylation determined by different MSP MethyLight assays and HeavyMethyl MethyLight assays. The Y-axis shows the degree of methylation. Tumor samples are represented by white points, and normal colon tissue samples by black points. A significantly higher degree of methylation was observed in tumor samples than in healthy tissue samples.
Figure 2:
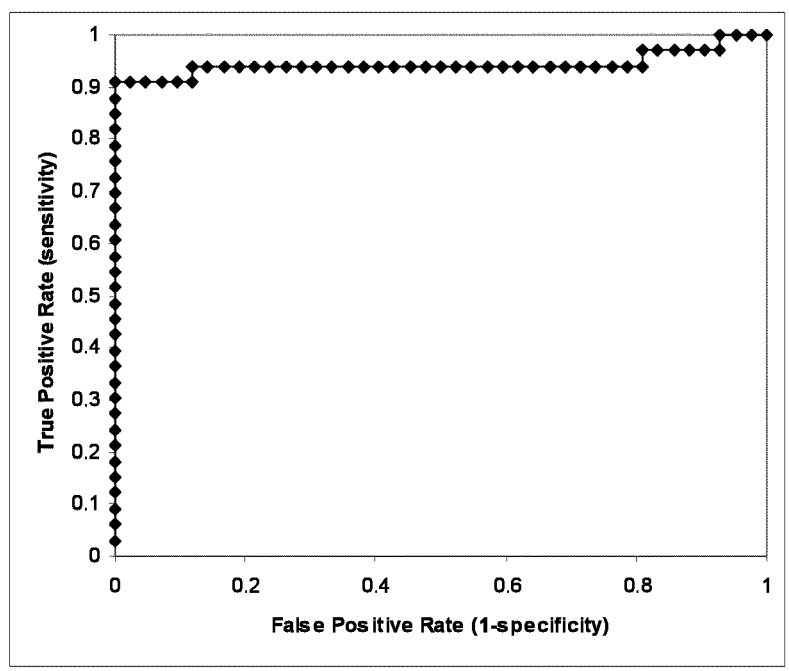
FIG. 2 shows the Receiver Operating Characteristic curve (ROC curve) of the EYA4-MSP-Methyl-Light-Assay for adenocarcinomas according to Example 1. The AUC for the MSP-Methyl-Light-Assay is: 0.94.

The mean PMR for normal samples was 0.15, with a standard deviation of 0.18. The mean PMR for tumour samples was 17.98, with a standard deviation of 18.18. The overall difference in methylation levels between tumour and normal samples is significant in a t-test (p=0.00000312). The results are shown in FIG. 1. A Receiver Operating Characteristic curve (ROC curve) of the assay was also determined. A ROC is a plot of the true positive rate against the false positive rate for the different possible cut-points of a diagnostic test. It shows the tradeoff between sensitivity and specificity depending on the selected cutpoint (any increase in sensitivity will be accompanied by a decrease in specificity). The area under an ROC curve (AUC) is a measure for the accuracy of a diagnostic test (the larger the area the better, optimum is 1, a random test would have a ROC curve lying on the diagonal with an area of 0.5; for reference: J. P. Egan. Signal Detection Theory and ROC Analysis, Academic Press, New York, 1975). The AUC for the MSP-Methyl-Light-Assay is: 0.94 (FIG. 2).

Example 2

Methylation within colon cancer was analysed using a EYA4-HeavyMethyl MethyLight assay. The same DNA samples were also used to analyse methylation of the CpG island with a HeavyMethyl MethyLight (or HM MethyLight) assay, also referred to as the HeavyMethyl assay. The methylation status was determined with a HM MethyLight assay designed for the CpG island of interest and the same control gene assay described above. The CpG island assay covers CpG sites in both the blockers and the Taqman style probe, while the control gene does not.

Methods.

The CpG island assay (methylation assay) was performed using the following primers and probes:

```
                                          (SEQ ID NO: 44)
   Forward Primer: GGTGATTGTTTATTGTTATGGTTTG;

(SEQ ID NO: 45)
   Reverse Primer: CCCCTCAACCTAAAAACTACAAC;

(SEQ ID NO: 87)
   Forward Blocker: GTTATGGTTTGTGATTTTGTGTGGG;

(SEQ ID NO: 86)
   Reverse Blocker: AAACTACAACCACTCAAATCAACCCA;
   and (SEQ ID NO: 84)
   Probe: AAAATTACGACGACGCCACCCGAAA.
```

The reactions were each run in triplicate on each DNA sample with the following assay conditions:

Reaction Solution:

(400 nM primers; 400 nM probe; 10 µM both blockers; 3.5 mM magnesium chloride; 1×ABI Taqman buffer; 1 unit of ABI TaqGold polymerase; 200, µM dNTPs; and 7 µl of DNA, in a final reaction volume of 20 µl);

Cycling conditions: (95° C. for 10 minutes); (95° C. for 15 seconds, 64° C. for 1 minute (2 cycles)); (95° C. for 15 seconds, 62° C. for 1 minute (2 cycles); (95° C. for 15 seconds, 60° C. for 1 minute (2 cycles)); and (95° C. for 15 seconds, 58° C. for 1 minute, 60° C. for 40 seconds (41 cycles)).

Results.

The mean PMR for normal samples was 1.12 with a standard deviation of 1.45. The mean PMR for tumour samples was 38.23 with a standard deviation of 33.22. The overall difference in methylation levels between tumour and normal samples is significant in a t-test (p=0.000000326). The results are shown in FIG. 1.

Figure 3:
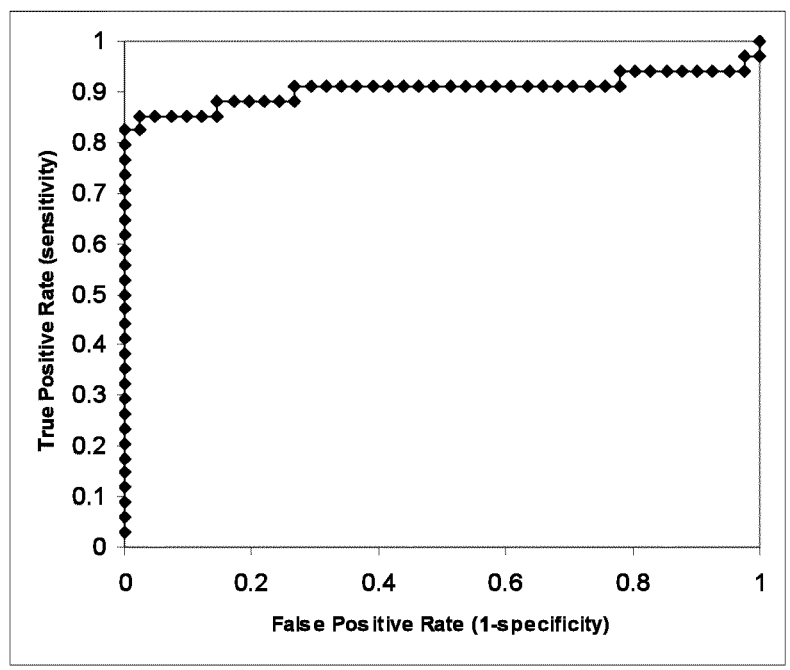
FIG. 3 shows the Receiver Operating Characteristic curve (ROC curve) of the EYA4-HM-Methyl-Light-Assay for Adenocarcinoma according to Example 2. The AUC for the HM-Methyl-Light-Assay is: 0.91.

A ROC curve of the assay was also determined. The AUC for the MSP-Methyl-Light-Assay is 0.91 (FIG. 3).

Figure 4:
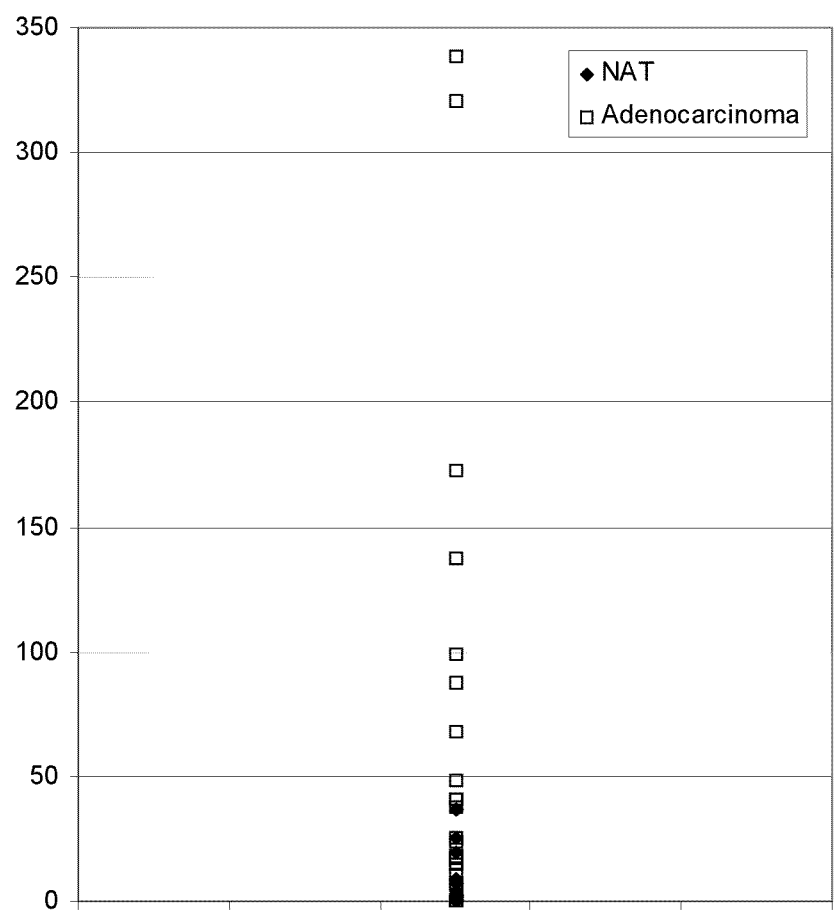
FIG. 4 shows the level of methylation determined by a EYA4-HeavyMethyl MethyLight™ assay according to example 2, testing an additional set of colon samples (25 adenocarcinoma, 33 normals, and 13 adenomas). The Y-axis shows the degree of methylation within the region of the EYA4 gene investigated. Adenocarcinoma samples are represented by white squares, and normal colon tissue samples by black diamonds. A significantly higher degree of methylation was observed in tumor samples than in healthy tissue samples. The level of significance as measured using a t-test was 0.00424.
Figure 5:
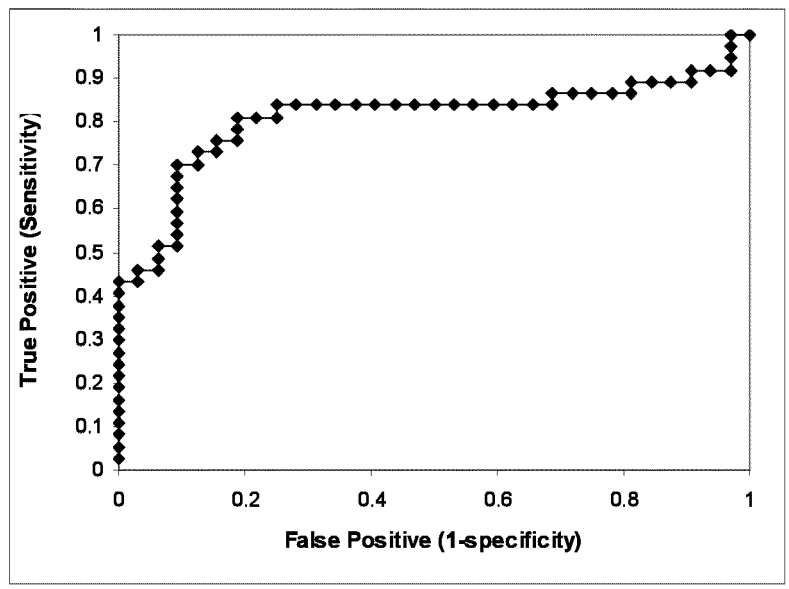
FIG. 5 shows the Receiver Operating Characteristic curve (ROC curve) of the EYA4-HM-Methyl-Light-Assay for Adenocarcinoma and Adenoma according to Example 2 (additional sets of samples). The area under an ROC curve (AUC) is a measure for the accuracy of a diagnostic test. The AUC for the HM-Methyl-Light-Assay is 0.81.
Figure 6:
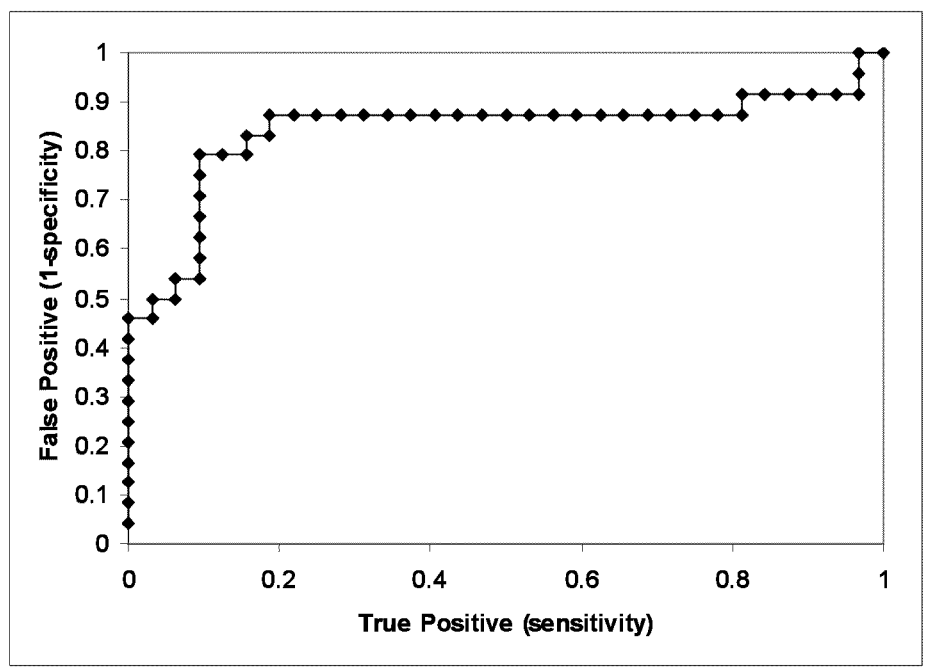
FIG. 6 shows the Receiver Operating Characteristic curve (ROC curve) of the EYA4-HM-Methyl-Light-Assay for Adenocarcinoma only according to Example 2 (additional sets of samples). The area under an ROC curve (AUC) is a measure for the accuracy of a diagnostic test. The AUC for the HM-Methyl-Light-Assay is: 0.844.
Figure 7:
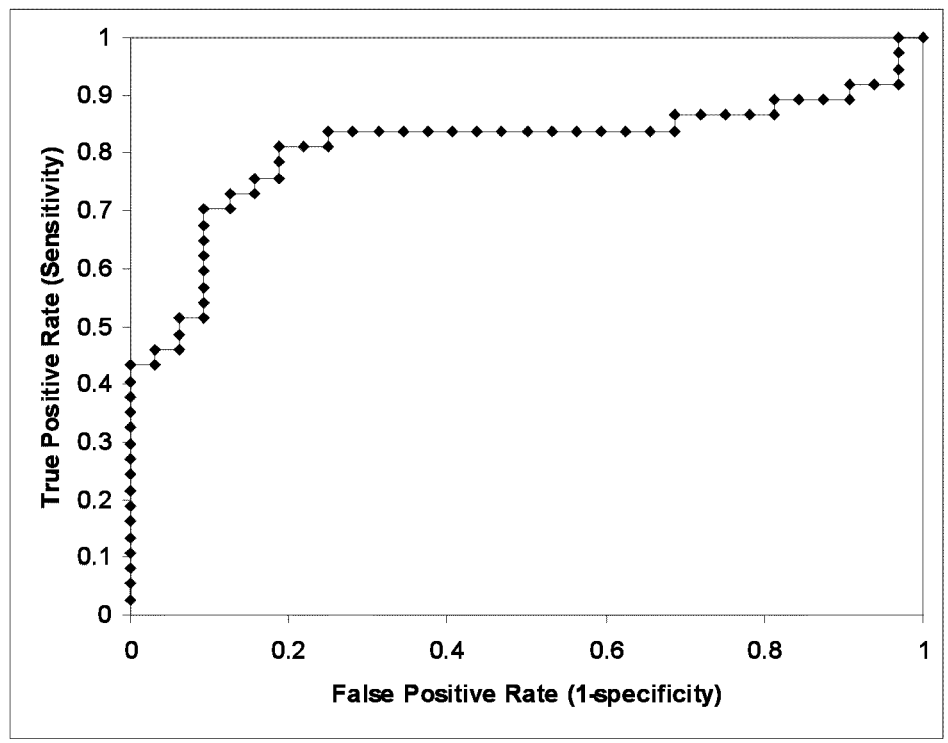
FIG. 7 shows the Receiver Operating Characteristic curve (ROC curve) of the EYA4-HM-Methyl-Light-Assay for Adenenomas according to Example 2 (additional sets of samples). The area under an ROC curve (AUC) is a measure for the accuracy of a diagnostic test. The AUC for the HM-Methyl-Light-Assay is: 0.748.

The assay was tested on an additional set of colon samples (25 adenocarcinoma, 33 normals, and 13 adenomas). The results showed a significant difference again (FIG. 4). The ROC are shown in FIG. 5-7.

Figure 22:
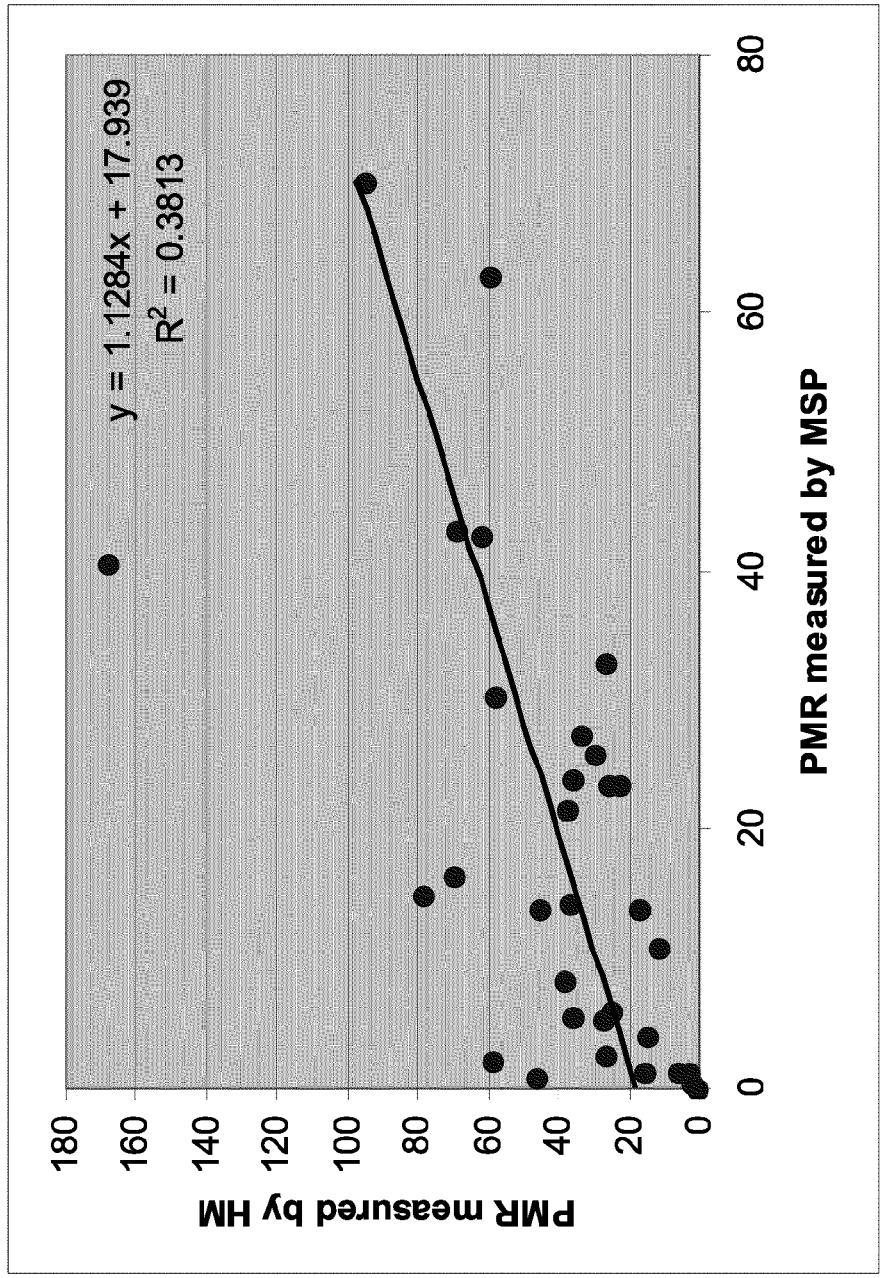
FIG. 22 shows the regression plot of the percentage methylation within the EYA 4 gene calculated in each sample using the MSP and HeavyMethyl variants of the MethyLight assay.

The MSP and HeavyMethyl variants of the MethyLight assay were determined to be equivalent for the analysis of methylation in the gene EYA4, FIG. 22 shows the regression plot of the percentage methylation detected in each sample using the two methods.

Example 3

Figure 8:
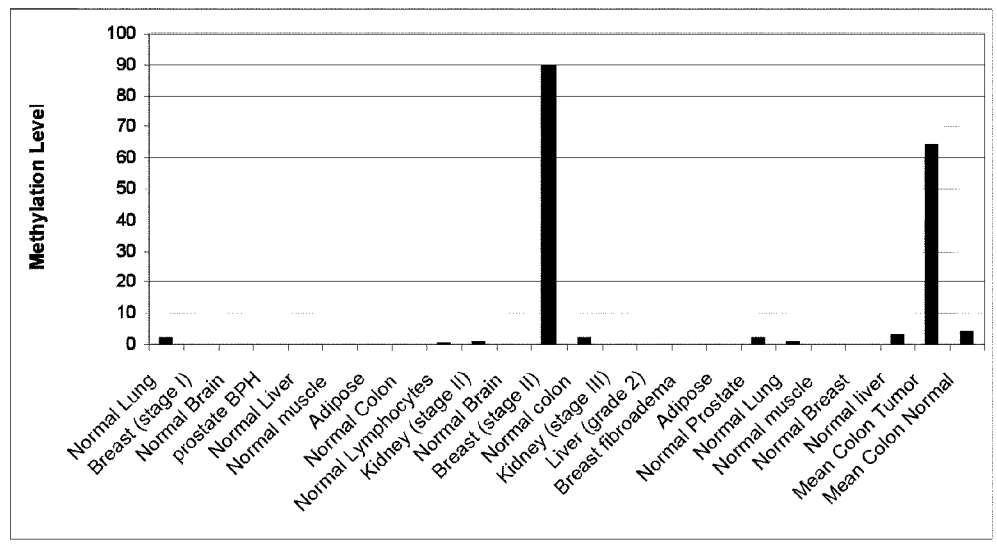
FIG. 8 shows the level of methylation in different tumor and healthy tissues determined by a EYA4-HeavyMethyl MethyLight™ assay according to example 3. The Y-axis shows the degree of methylation within the region of the EYA4 gene investigated. Besides the colon cancer samples only one of the two breast cancer tissues were methylated.
Figure 9:
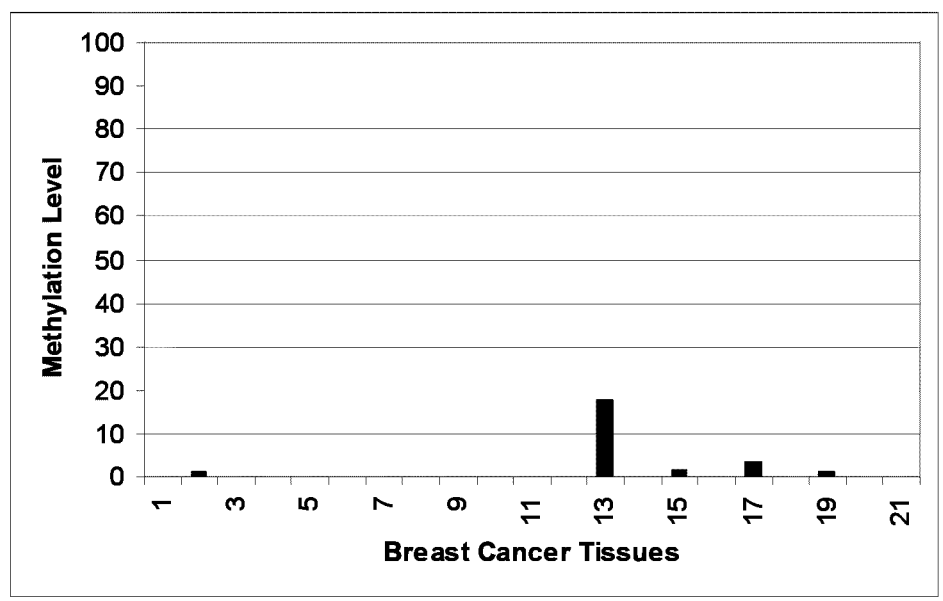
FIG. 9 shows the level of methylation in different breast cancer tissues determined by a EYA4-HeavyMethyl MethyLight™ assay according to example 3. Only one was methylated.

The EYA4-HeavyMethyl-MethyLight-assay was also tested against a panel of other tissues (FIG. 8). Besides the colon cancer samples only one of the two breast cancer tissues were methylated. However, on a panel of 21 additional breast tumours (different stages), only one was methylated (FIG. 9). So the marker is specific for colon tumour samples. All primers, probes, blockers and reaction conditions were identical to those used in the analysis of the colon cancer samples (Example 2).

Example 4

Figure 10:
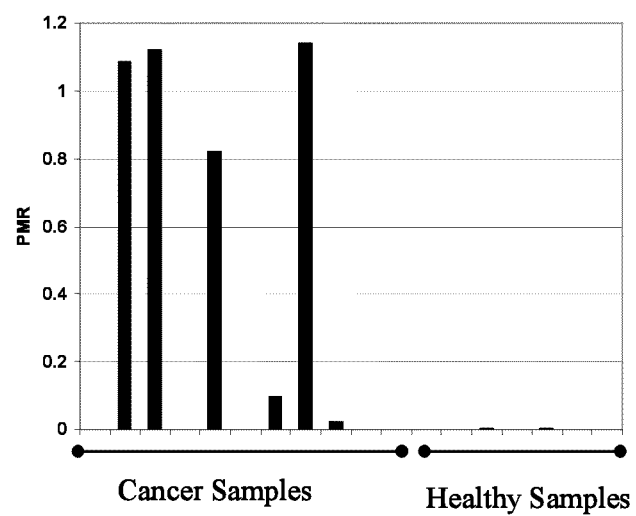
FIG. 10 shows the level of methylation in serum samples determined by a EYA4-HeavyMethyl MethyLight™ assay according to example 4. The Y-axis shows the degree of methylation within the region of the EYA4 gene investigated.

Twelve of the colon tissues analysed by real-time PCR also had paired serum taken before surgery. We extracted DNA from 1 ml of that serum using a Qiagen UltraSens DNA extraction kit, bisulfite treated the DNA sample, and ran the EYA4-HeavyMethyl-MethyLight-assay on those samples. The control gene did not amplify for three of the cancer serum samples and three of the normal serum samples, so we can conclude that the sample preparation did not work in these cases. In the other cases, there was evidence of higher methylation in the cancer samples than the normal samples (FIG. 10).

Example 5

Analysis of methylation within colon cancer using a Calcitonin-MSP-MethyLight Assay The colon cancer samples described in Example 1 were also analysed using a Calcitonin-MSP-MethyLight Assay, with a Taqman® style probe. The sample preparation was carried out as described above (Example 1) The assay was performed using the following primers and probes:

```
Primer: AGGTTATCGTCGTGCGAGTGT;       (SEQ ID NO: 34)

Primer: TCACTCAAACGTATCCCAAACCTA;    (SEQ ID NO: 35)
and

Probe: CGAATCTCTCGAACGATCGCATCCA.    (SEQ ID NO: 78)
```

The corresponding control assay was performed as described above (Example 1).

The reactions were run in triplicate on each DNA sample with the following assay conditions:

Reaction Solution:

(900 nM primers; 300 nM probe; 3.5 mM Magnesium Chloride; 1 unit of taq polymerase; 200 µM dNTPs; 7 µl of DNA, in a final reaction volume of 20 µl);

Cycling Conditions:

(95° C. for 10 minutes; 95° C. for 15 seconds; 67° C. for 1 minute (3 cycles)); (95° C. for 15 seconds, 64° C. for 1 minute (3 cycles)); (95° C. for 15 seconds, 62° C. for 1 minute (3 cycles)); and (95° C. for 15 seconds, 60° C. for 1 minute (40 cycles)).

The data was analysed using a PMR calculation previously described in the literature (Eads et al 2001).

Results.

Figure 11:
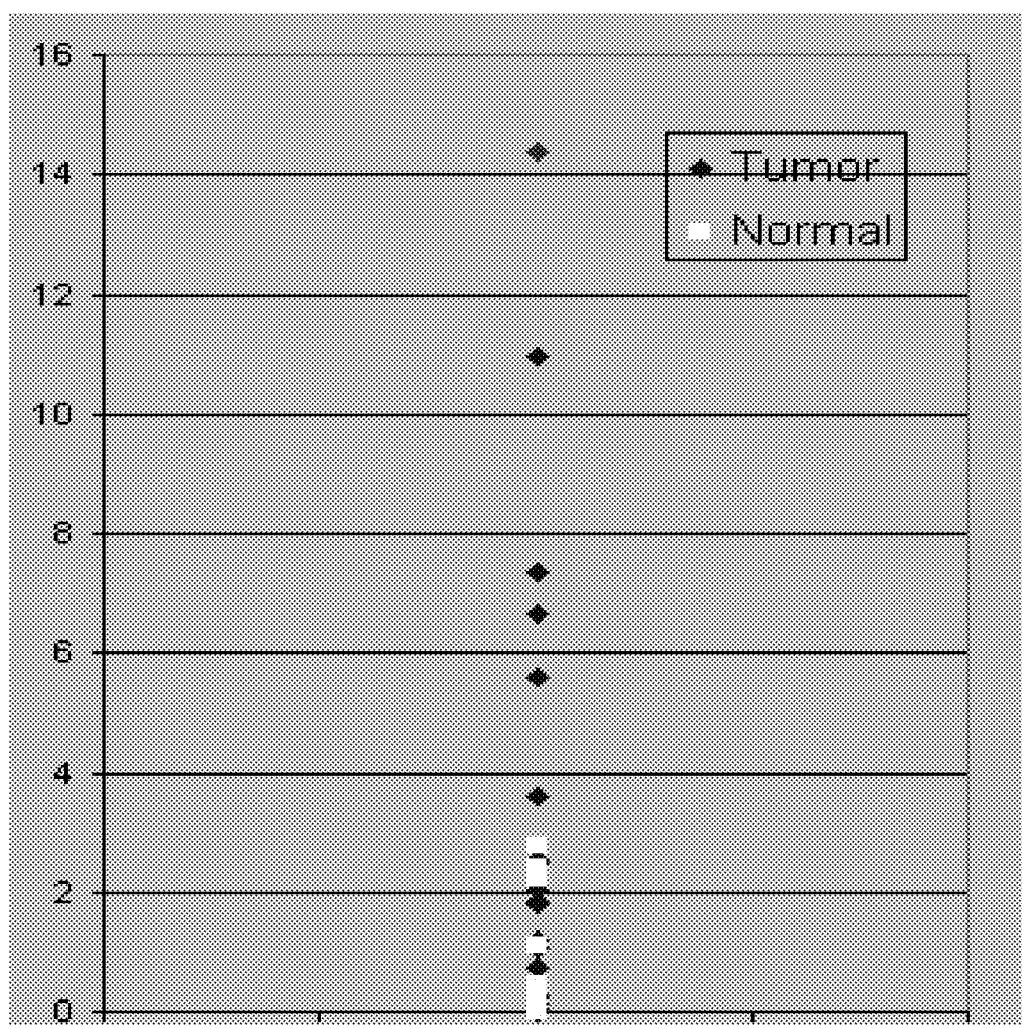
FIG. 11 shows the Receiver Operating Characteristic curve (ROC curve) of the Calcitonin-MSP-Methyl-Light-Assay according to Example 5. The area under an ROC curve (AUC) is a measure for the accuracy of a diagnostic test. The AUC for the HM-Methyl-Light-Assay is: 0.85.

The mean PMR for normal samples was 0.19, with a standard deviation of 0.79. None of the normal samples was greater than 2 standard deviations about the normal mean, while 18 of 33 tumour samples reached this level of methylation. The overall difference in methylation levels between tumour and normal samples is significant in a t-test (p=0.002). The results are shown in FIG. 1. Significantly, the tumour samples are substantially hypermethylated relative to normal control tissue. A ROC curve of the assay was also determined. The AUC for the MSP-Methyl-Light-Assay is 0.80 (FIG. 11).

Example 6

Methylation within colon cancer was analysed using a Calcitonin-HeavyMethyl MethyLight assay. The same DNA samples were also used to analyse methylation of the Calcitonin-CpG island with a HeavyMethyl MethyLight assay using a Taqman® style probe (see Example 2).

The CpG island assay (methylation assay) was performed using the following primers and probes:

```
                                              (SEQ ID NO: 46)
Primer: GGATGTGAGAGTTGTTGAGGTTA;

(SEQ ID NO: 47)
Primer: ACACACCCAAACCCATTACTATCT;

(SEQ ID NO: 83)
Probe: ACCTCCGAATCTCTCGAACGATCGC;
and (SEQ ID NO: 85)
Blocker: TGTTGAGGTTATGTGTAATTGGGTGTGA.
```

The reactions were each run in triplicate on each DNA sample with the following assay conditions:

Reaction Solution:

(300 nM primers; 450 nM probe; 3.5 mM magnesium chloride; 2 units of taq polymerase; 400 µM dNTPs, 5 µM blocker; and 7 µl of DNA, in a final reaction volume of 20 µl);

Cycling Conditions:

(95° C. for 10 minutes); (95° C. for 15 seconds, 67° C. for 1 minute (3 cycles)); (95° C. for 15 seconds, 64° C. for 1 minute (3 cycles); (95° C. for 15 seconds, 62° C. for 1 minute (3 cycles)); and (95° C. for 15 seconds, 60° C. for 1 minute (40 cycles)).

The corresponding control assay was performed as described above (Example 2).

Results.

Figure 12:
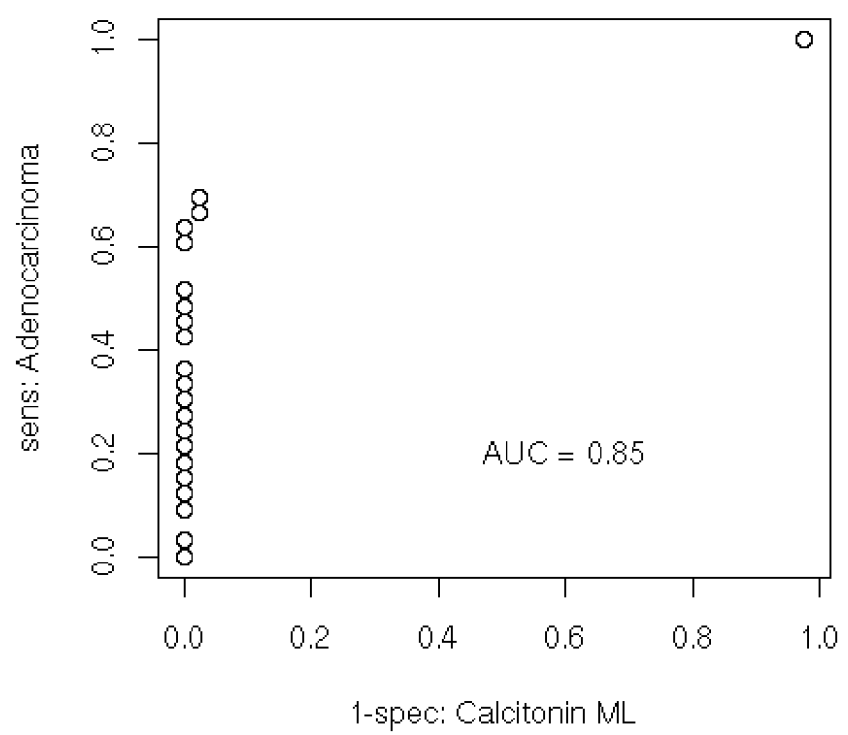
FIG. 12 shows the ROC curve of the Calcitonin-HM-Methyl-Light-Assay according to Example 6. The AUC is: 0.81.

The mean PMR for normal samples was 0.13 with a standard deviation of 0.58. None of the normal samples was greater than 2 standard deviations about the normal mean, while 19 of 33 tumour samples reached this level of methylation. The overall difference in methylation levels between tumour and normal samples is significant in a t-test (p=0.0004). The results are shown in FIG. 1. A ROC curve of the assay was also determined. The AUC for the HM-Methyl-Light-Assay is 0.84 (FIG. 12).

Figure 21:
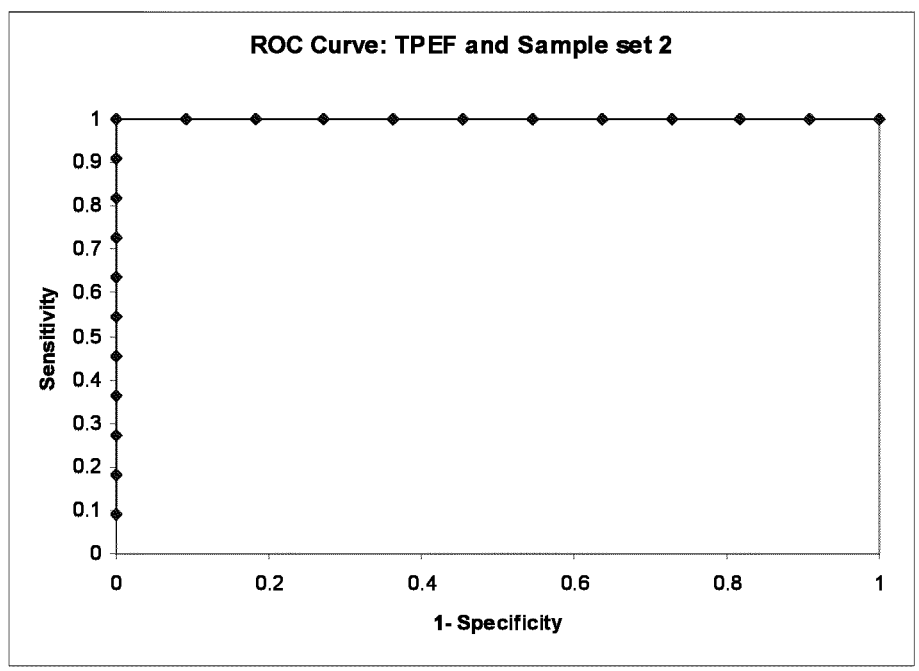
FIG. 21 shows the ROC curve of a combined EYA4-Calcitonin-Heavymethyl-MethylLight-Assay according to Example 6. The AUC is: 0.97.

In order to estimate the sensitivity and specificity of a real time assay analysing a gene panel comprising the genes Calcitonin and EYA 4, the ROC of said assay was in sillico determined by combining the ROCs of the 2 genes (as described above) using a logistics model. The AUC of said curve (FIG. 21) is 0.97.

Figure 23:
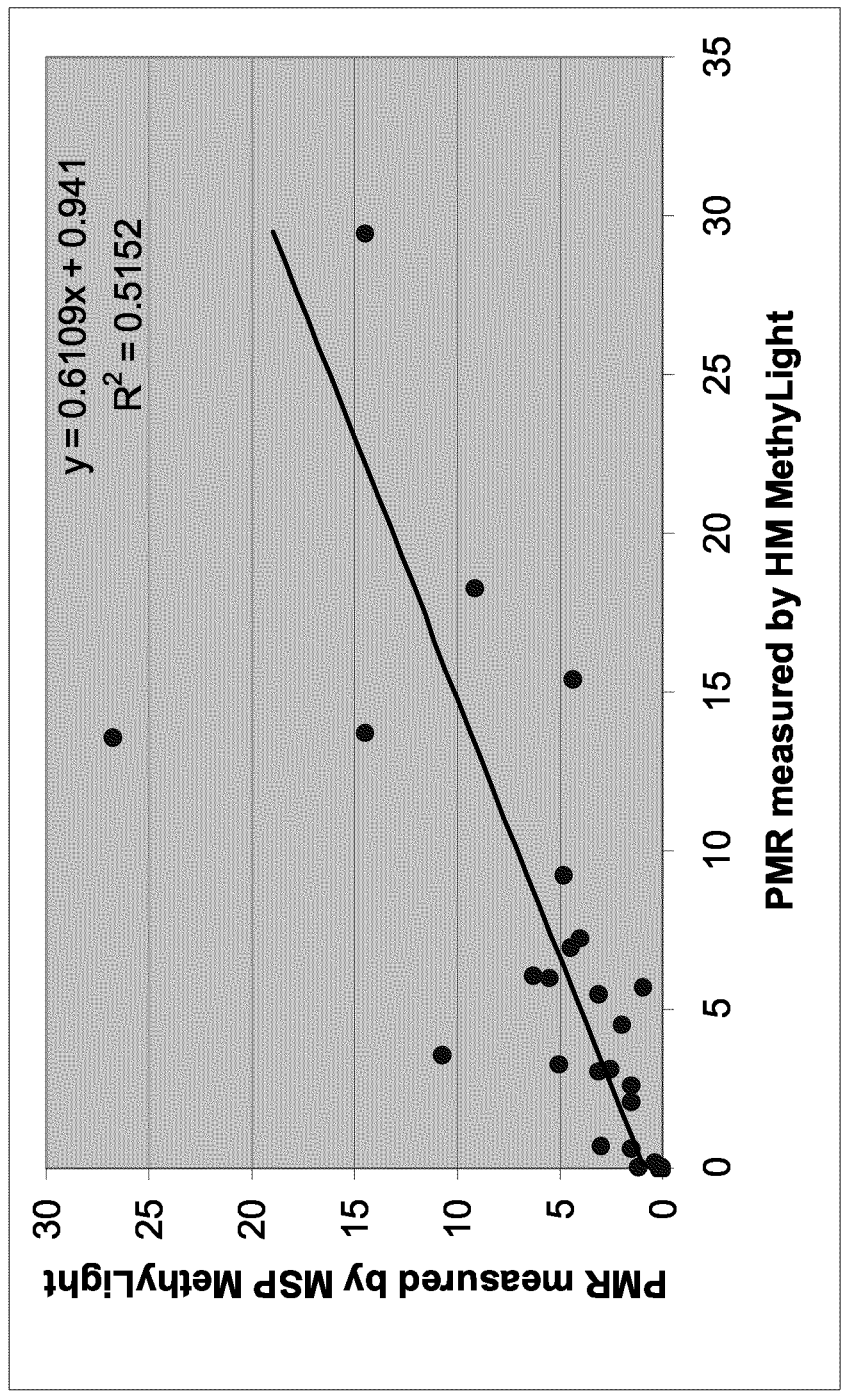
FIG. 23 shows the regression plot of the percentage methylation within the Calcitonin gene calculated in each sample using the MSP and HeavyMethyl variants of the MethyLight assay.

The MSP and HeavyMethyl variants of the MethyLight assay were determined to be equivalent for the analysis of methylation in the gene Calcitonin, FIG. 23 shows the regression plot of the percentage methylation detected in each sample using the two methods.

Example 7

Serum analysis with Calcitonin-HM MethyLight assay. Twelve of the colon tissues analysed by real-time PCR also had paired serum taken before surgery. DNA was extracted from 1 ml of that serum using a Qiagen UltraSens® DNA extraction kit, the DNA sample was bisulfite treated, and the HeavyMethyl-MethyLight-assay was run on those samples (see Example 3). Calcitonin was not methylated in all tumours, but of the five patients with the highest levels of methylation in the tumoursect methylation was detected in the serum of four of them. In contrast, no methylation was detected in any of the 11 serum samples taken from healthy donors.

Example 8

Identification of the methylation status of a CpG site within the Calcitonin Gene. A fragment of the upstream region of the calcitonin gene (SEQ ID NO:1) was amplified by PCR using the primers CCTTAGTCCCTACCTCTGCT (SEQ ID NO:94) and CTCATTTACACACACCCAAAC (SEQ ID NO:95). The resultant amplificate, 378 bp in length, contained an informative CpG at position 165. The amplificate DNA was digested with the methylation sensitive restriction endonuclease Nar I; recognition motif GGCGCC. Hydrolysis by said endonuclease is blocked by methylation of the CpG at position 165 of the amplificate. The digest was used as a control.

Genomic DNA was isolated from the samples using the DNA WIZZARD® DNA isolation kit (PROMEGA™). Each sample was digested using Nar I according to manufacturer's recommendations (New England Biolabs).

About 10 ng of each genomic digest was then amplified using PCR primers CCTTAGTCCCTACCTCTGCT (SEQ ID NO:94) and CTCATTTACACACACCCAAAC (SEQ ID NO:95). The PCR reactions were performed using a thermocycler (Eppendorf GmbH) using 10 ng of DNA, 6 pmole of each primer, 200 µM of each dNTP, 1.5 mM MgCl$_2$ and 1 U of HOTSTART®Taq (Qiagen AG). The other conditions were as recommended by the Taq polymerase manufacturer.

Using the above mentioned primers, gene fragments were amplified by PCR performing a first denaturation step for 14 min at 96° C., followed by 30-45 cycles (step 2: 60 sec at 96° C., step 3: 45 sec at 52° C., step 4: 75 sec at 72° C.) and a subsequent final elongation of 10 min at 72° C. The presence of PCR products was analysed by agarose gel electrophoresis.

PCR products were detectable, with Nar I-hydrolyzed DNA isolated wherein the tissue in question contained upmethylated DNA, when step 2 to step 4 of the cycle program were repeated 34, 37, 39, 42 and 45 fold. In contrast, PCR products were only detectable with Nar I-hydrolysed DNA isolated from downmethylated tissue when steps 2 to step 4 of the cycle program were repeated 42- and 45-fold.

Example 9

Analysis of methylation within colon cancer using a Versican-MSP-MethyLight Assay. The colon cancer samples described in Example 1 were also analysed using a Versican-MSP-MethyLight Assay with a TAQMAN® style probe. The sample preparation was carried out as described above (Example 1) The assay was performed using the following primers and probes:

```
Forward Primer: TGGGATTAAGATTTTCGGTTAGTTTC;     (SEQ ID NO: 36)

Reverse Primer: CACTACAACGCTACGCGACTAAA;        (SEQ ID NO: 37)
and

Probe: TCGACGTTACCCAAACGAATCACATAAAAAAC        (SEQ ID NO: 79)
```

The corresponding control assay was performed as described above (Example 1). The reactions were run in triplicate on each DNA sample with the following assay conditions:

Reaction Solution:
(900 nM primers; 300 nM probe; 3.5 mM magnesium chloride; 1 units of taq polymerase; 200 µM dNTPs, 5 µM blocker; and 7 µl of DNA, in a final reaction volume of 20 µl);

Cycling Conditions:
95° C. for 10 minutes; (95° C. for 15 seconds, 60° C. for 1 minute) 50 cycles.

The data was analysed using a PMR calculation previously described in the literature (Eads et al 2001).

Results.

Figure 13:
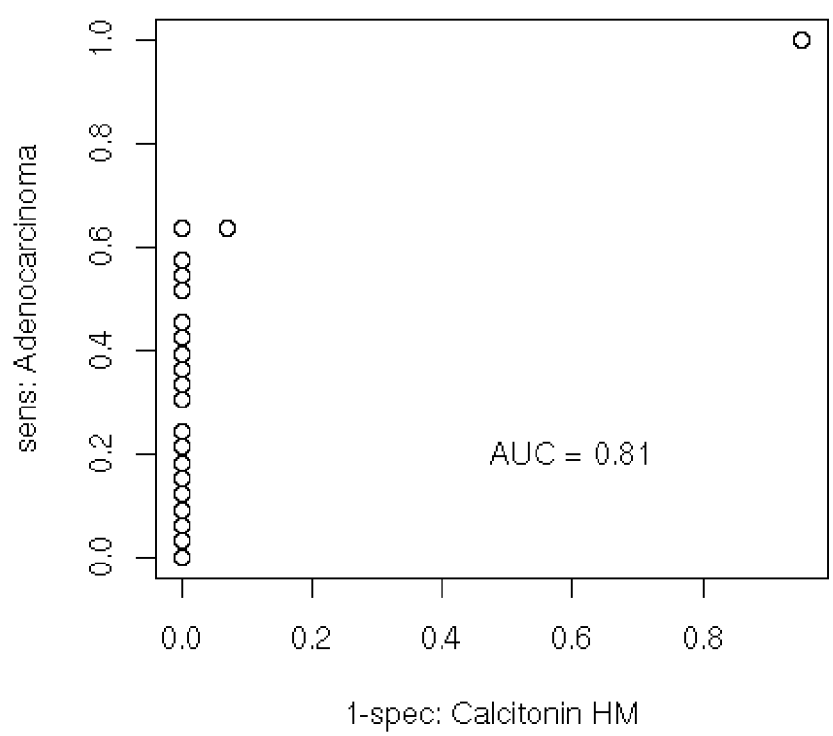
FIG. 13 shows the ROC curve of the Versican-MSP-Methyl-Light-Assay according to Example 9. The AUC is: 0.84.

The results are shown in FIG. 1. The mean PMR for normal samples was 3.93, with a standard deviation of 3.57. The mean PMR for tumour samples was 23.06, with a standard deviation of 20.23. The overall difference in methylation levels between tumour and normal samples is significant in a t-test (p=0.000003063). The ROC curve of the assay is shown in FIG. 13. The AUC is 0.84.

This was further confirmed using a Versican-HeavyMethyl MethyLight assay, using dual LIGHTCYCLER™ probes.

Methods.

The CpG island assay (methylation assay) was performed using the following primers and probes:

| | | |
|---|---|---|
| Forward Primer: | TGGATAGGAGTTGGGATTAAGATTTT | (SEQ ID NO: 96); |
| Reverse Primer: | CTTATTACAATTTAAAAAAAAATTCACTACAA | (SEQ ID NO: 97); |
| Blocker: | AAATTCACTACAACACTACACAACTAAATTCAACATTAC | (SEQ ID NO: 98); |
| Probe: | TTTTCGTATTTTTTTTCGGGTTATTACGTTTT-Fluor | (SEQ ID NO: 99); and |
| Probe: | LC640-ATGTGATTCGTTTGGGTAACGTCGA-Phos | (SEQ ID NO: 100). |

The reactions were each run in triplicate on each DNA sample with the following assay conditions:

Reaction Conditions:
500 nM primers;
10 uM blocker; and
250 nM probes.
LightCycler FastStart Hybridization Probes Mix
4 mM Magnesium Chloride.
Cycling Profile:
95° C. denaturation for 10 minutes; and
50 cycles: 95° C. 10 seconds, 57° C. 30 seconds, 72° C. 20 seconds.

Example 10

Analysis of methylation within colon cancer using a TPEF-MSP-MethyLight Assay. The colon cancer samples described in Example 1 were also analysed using a TPEF-MSP-MethyLight Assay with a TAQMAN® style probe. The sample preparation was carried out as described above (Example 1) The assay was performed using the following primers and probes:

```
Forward Primer: TTTTTTTTTCGGACGTCGTTG;         (SEQ ID NO: 38)

Reverse Primer: CCTCTACATACGCCGCGAAT;          (SEQ ID NO: 39)
and

Probe: AATTACCGAAAACATCGACCGA.                 (SEQ ID NO: 80)
```

The reactions were run in triplicate on each DNA sample with the following assay conditions:

Reaction Solution:
(900 nM primers; 300 nM probe; 3.5 mM magnesium chloride; 1 units of taq polymerase; 200 µM dNTPs, 5 µM blocker; and 7 µl of DNA, in a final reaction volume of 2 µl).

Cycling Conditions:
95° C. for 10 minutes; (95° C. for 15 seconds, 60° C. for 1 minute) 50 cycles.

The corresponding control assay was performed as described above (Example 1). The data was analysed using a PMR calculation previously described in the literature (Eads et al 2001).

Results.

Figure 14:
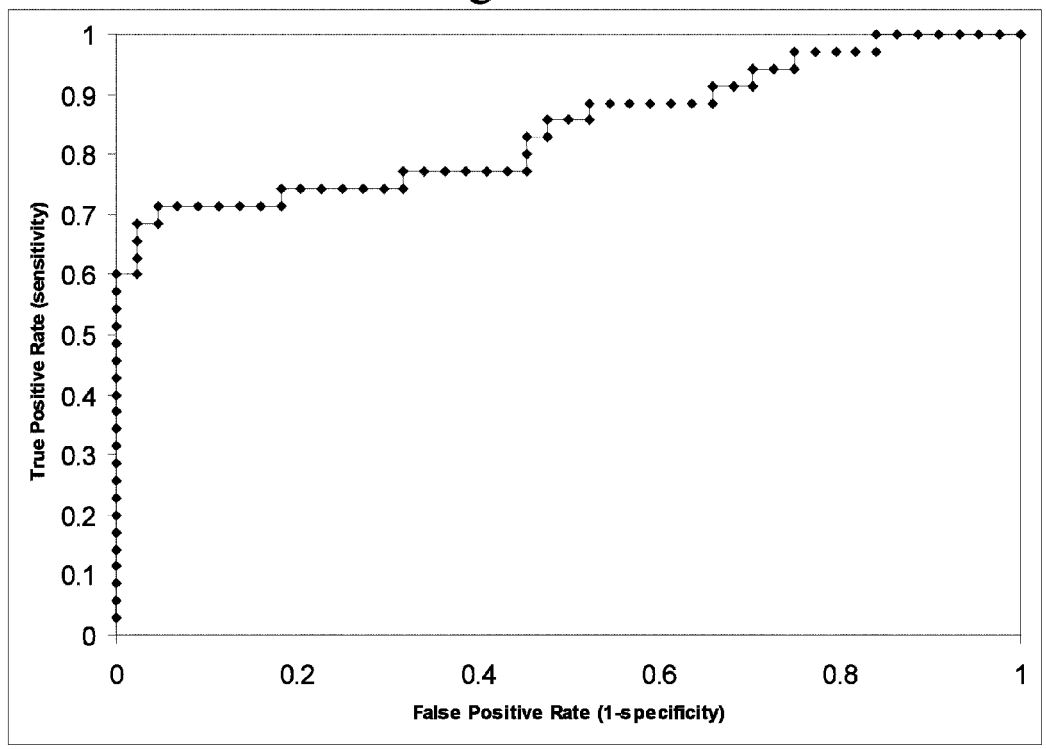
FIG. 14 shows the ROC curve of the TBEF-MSP-Methyl-Light-Assay according to Example 10. The AUC is: 0.80.

The results are shown in FIG. 1. The mean PMR for normal samples was 3.04, with a standard deviation of 4.21. The mean PMR for tumour samples was 21.38, with a standard deviation of 24.08. The overall difference in methylation levels between tumour and normal samples is significant in a t-test (p=0.0000101973). The ROC curve of the assay is shown in FIG. 14. The AUC is 0.80.

This was further confirmed using a TPEF-HeavyMethyl MethyLight assay (using dual labeled LIGHTCYCLER™ probes.

Methods.

The CpG island assay (methylation assay) was performed using the following primers and probes:

```
Forward Primer: GTAGGGTTATTGTTTGGGTTAATAAAT;   (SEQ ID NO: 101)

Reverse Primer: TAAAAAAAAAAAAAAAACTCCTCTACATAC; (SEQ ID NO: 102)

Blocker: AACTCCTCTACATACACCACAAATAAATT;        (SEQ ID NO: 103)

Probe: CGAAAACATCGACCGAACAACG-Fluor;           (SEQ ID NO: 104)
and
```

-continued

```
                                           (SEQ ID NO: 105)
  Probe: LC640-GTCCGAAAAAAAAAAAAACGAACTCC-Phos.
```

The reactions were each run in triplicate on each DNA sample with the following assay conditions:
Reaction Conditions:
  Forward primer: 600 nM;
  Reverse primer: 300 nM;
  Blocker: 10 uM;
  Probes: 500 nM;
  Taq polymerase: 0.1 U/ul;
  dNTPs: 0.2 mM each;
  Magnesium Chloride: 4 mM;
  BSA: 0.25 mg/ml; and
  Roche buffer with no MgCl: 1×.
Cycling Conditions:
  95° C. denaturation for 10 minutes; and
  50 cycles: 95° C. for 10 seconds, 57° C. for 25 seconds, 72° C. for 10 seconds.

Example 11

Analysis of methylation within colon cancer using a TPEF-MSP-MethyLight Assay. An additional assay for TPEF was tested on colon samples. The assay was tested on two sets of tissues, each with 12 colon adenocarcinomas and 12 normal adjacent tissue samples.

The sample preparation was carried out as described above (Example 1). The assay was performed using the following primers and probes:

```
                                            (SEQ ID NO: 48)
  Forward Primer: GGACGTTTTTTATCGAAGGCG;

(SEQ ID NO: 49)
  Reverse Primer: GCCACCCAACCGCGA;
  and (SEQ ID NO: 90)
  Probe: ACCCGAAATCACGCGCGAAAAA.
```

The reactions were run in triplicate on each DNA sample with the following assay conditions:
Reaction Solution:
  (900 nM primers; 300 nM probe; 3.5 mM magnesium chloride; 1 units of taq polymerase; 200 μM dNTPs, 5 μM blocker; and 7 μl of DNA, in a final reaction volume of 20 μl).
Cycling Conditions:
  95° C. for 10 minutes; (95° C. for 15 seconds, 60° C. for 1 minute) 50 cycles.

The corresponding control assay was performed as described above (Example 1).

Figure 19:
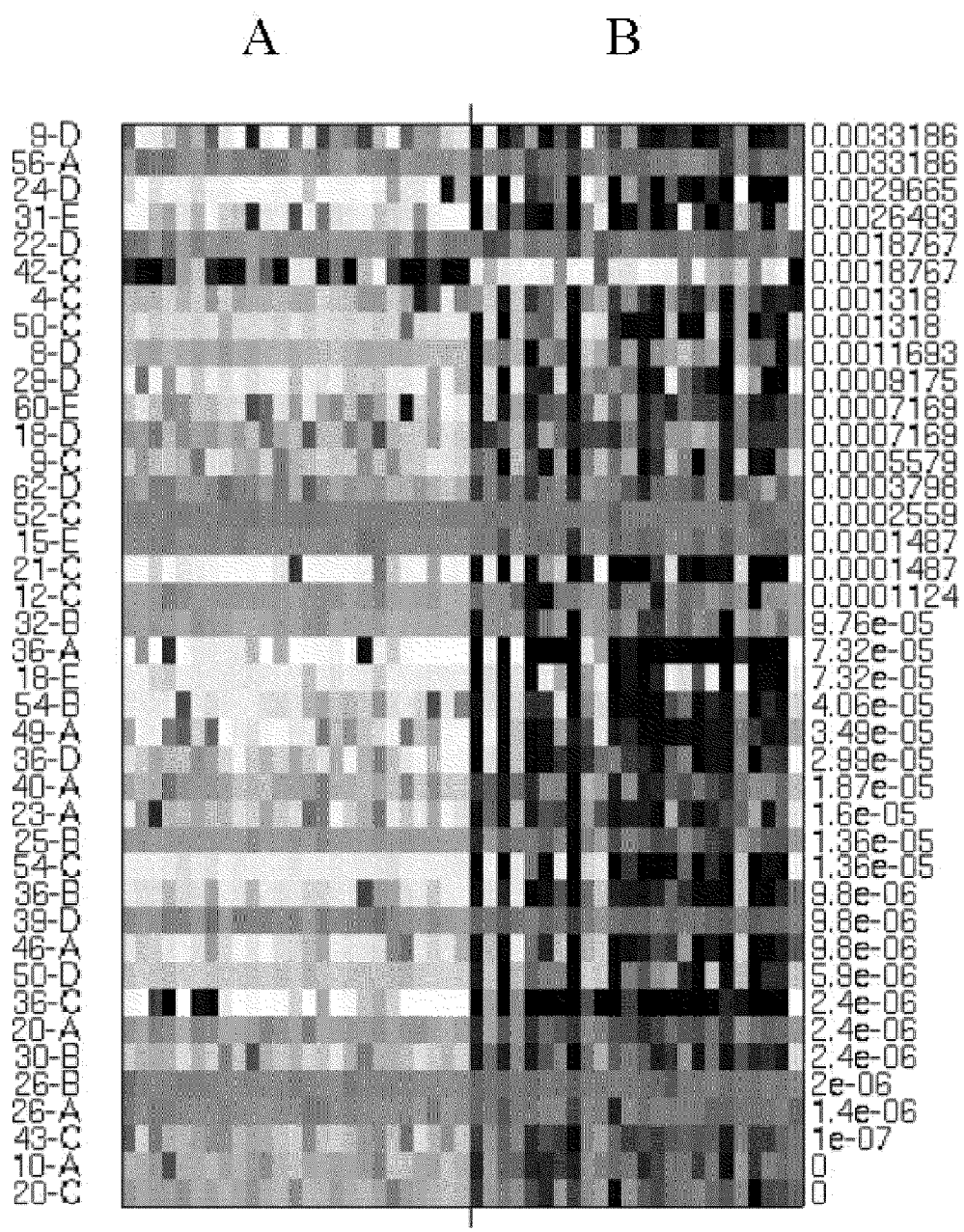
FIG. 19 shows the ROC curve of the TPEF-MSP-Methyl-Light-Assay according to Example 11 (first sample set). The AUC is: 0.93.
Figure 20:
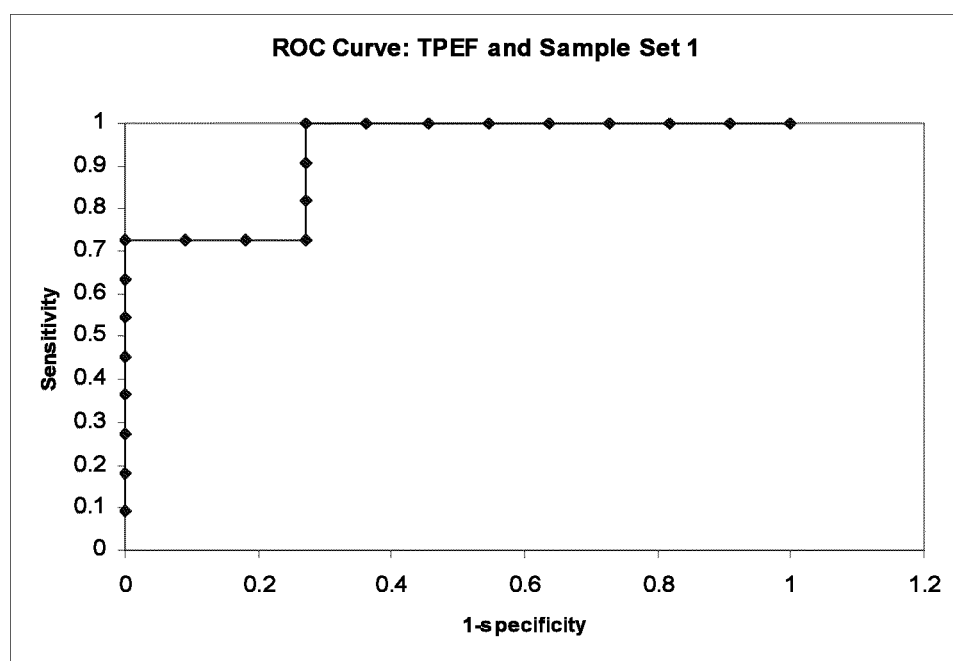
FIG. 20 shows the ROC curve of the TPEF-MSP-Methyl-Light-Assay according to Example 11 (second sample set). The AUC is: 1.

The data was analysed using a PMR calculation previously described in the literature (Eads et al 2001). In both cases, TPEF was significantly more methylated in the cancer samples. The ROC curves of the assays are shown in FIG. 19-20. The AUC are 0.93 and 1.

Example 12

Analysis of methylation within colon cancer using a H Cadherin-MSP-MethyLight Assay.

The colon cancer samples described in Example 1 were also analysed using a H Cadherin-MSP-MethyLight Assay.

The sample preparation was carried out as described above (Example 1). The assay was performed using the following primers and probes:

```
                                            (SEQ ID NO: 42)
  Forward Primer: GACGGATTTTTTTTTAACGTTTTTC;

(SEQ ID NO: 43)
  Reverse Primer: AAATAAAATACCACCTCCGCGA;
  and (SEQ ID NO: 82)
  Probe: GCTCCTCGCGAAATACTCACCCCG
```

The reactions were run in triplicate on each DNA sample with the following assay conditions:
Reaction Solution:
  (900 nM primers; 300 nM probe; 3.5 mM magnesium chloride; 1 units of taq polymerase; 200 μM dNTPs, 5 μM blocker; and 7 μl of DNA, in a final reaction volume of 20 μl).
Cycling Conditions:
  95° C. for 10 minutes; (95° C. for 15 seconds, 60° C. for 1 minute) 50 cycles.

The corresponding control assay was performed as described above (Example 1). The data was analysed using a PMR calculation previously described in the literature (Eads et al 2001).

Results.

Figure 15:
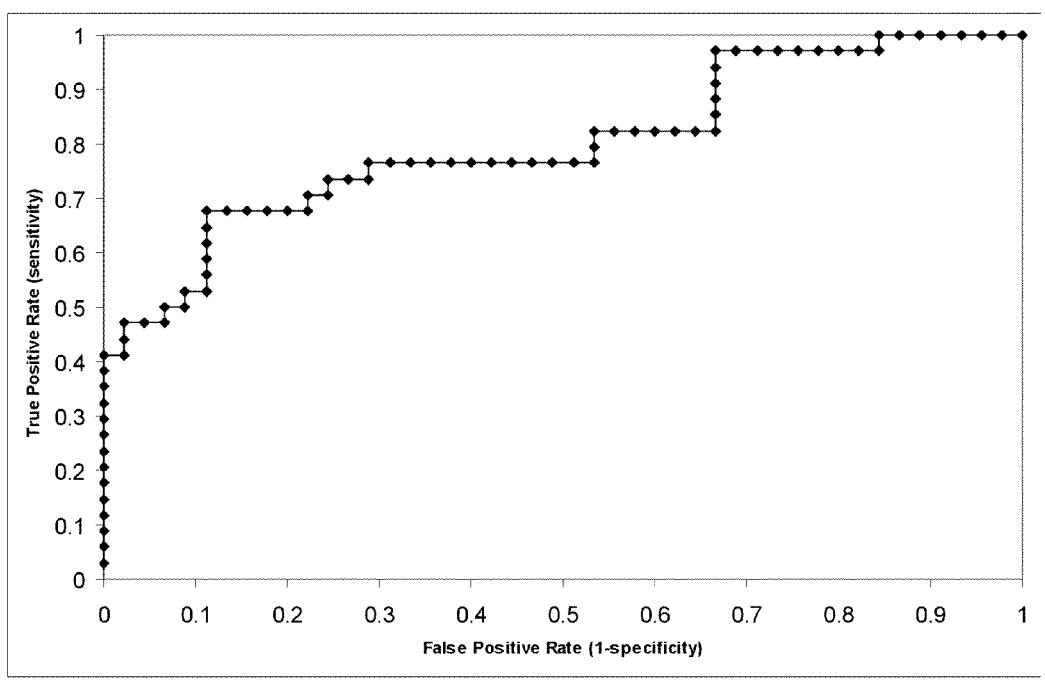
FIG. 15 shows the ROC curve of the Cadherin-MSP-Methyl-Light-Assay according to Example 12. The AUC is: 0.94.

The results are shown in FIG. 1. The mean PMR for normal samples was 2.25, with a standard deviation of 2.42. The mean PMR for tumour samples was 25.67, with a standard deviation of 17.57. The overall difference in methylation levels between tumour and normal samples is significant in a t-test (p=0.00000000118). The ROC curve of the assay is shown in FIG. 15. The AUC is 0.94.

This was further confirmed using a H Cadherin-HeavyMethyl MethyLight assay, using dual Lightcycler probes using Lightcycler style dual probe technology.

Methods.

The CpG island assay (methylation assay) was performed using the following primers and probes:

```
                                              (SEQ ID NO: 106)
  Forward Primer: GTTAGTTAGTTAATTTTTTAAATAGATTAGTAG;

(SEQ ID NO: 107)
  Reverse Primer: CAAAAAAACAAATAAAATACCACCTCC;

(SEQ ID NO: 108)
  Blocker: CCTCCACAAAACTCACTCCTCACAAAATAC;

(SEQ ID NO: 109)
  Probe: red640 TTTCGTTTTGTATGGTAGATACGGGGTGA-
  phosphate;
  and (SEQ ID NO: 110)
  Probe: ATTAATGGTTTTATAAGACGGATTTTTTTTAACGT-
  fluorescine.
```

The reactions were each run in triplicate on each DNA sample with the following assay conditions:
Reaction Conditions:
  Forward primer: 600 nM;
  Reverse primer: 300 nM;
  Blocker: 10 uM;
  Probes: 500 nM;
  Taq polymerase: 0.1 U/ul;

dNTPs: 0.2 mM each;
Magnesium Chloride: 4 mM;
BSA: 0.25 mg/ml; and
Roche buffer with no MgCl: 1×.
Cycling Conditions:
95° C. denaturation for 10 minutes; and
50 cycles: 95° C. for 10 seconds, 57° C. for 25 seconds, 72° C. for 10 seconds.

Example 13

Multiplex-PCR of colon cancer samples. In the first step the genomic DNA was isolated from the cell samples using the WIZZARD™ kit from (Promega). The isolated genomic DNA from the samples are treated using a bisulfite solution (hydrogen sulfite, disulfite). The treatment is such that all non methylated cytosines within the sample are converted to thiamine, conversely 5-methylated cytosines within the sample remain unmodified. The treated nucleic acids were then amplified using multiplex PCRs, amplifying 8 fragments per reaction with Cy5 fluorescently labelled primers. PCR primers used are described in Table 1. PCR conditions were as follows.
Reaction Solution:
10 ng bisulfite treated DNA;
3.5 mM MgCl2;
400 µM dNTPs;
2 pmol each primer; and
1 U Hot Star Taq (Qiagen).
Forty cycles were carried out as follows. Denaturation at 95° C. for 15 min, followed by annealing at 55° C. for 45 sec., primer elongation at 65° C. for 2 min. A final elongation at 65° C. was carried out for 10 min.

All PCR products from each individual sample were then hybridised to glass slides carrying a pair of immobilised oligonucleotides for each CpG position under analysis. Each of these detection oligonucleotides was designed to hybridise to the bisulphite converted sequence around one CpG site which was either originally unmethylated (TG) or methylated (CG). See Table 2 for further details of all hybridisation oligonucleotides used (both informative and non-informative). Hybridisation conditions were selected to allow the detection of the single nucleotide differences between the TG and CG variants.

A 5 µl volume of each multiplex PCR product was diluted in 10×Ssarc buffer (10×Ssarc:230 ml 20×SSC, 180 ml sodium lauroyl sarcosinate solution 20%, dilute to 1000 ml with dH2O). The reaction mixture was then hybridised to the detection oligonucleotides as follows. Denaturation at 95° C., cooling down to 10° C., hybridisation at 42° C. overnight followed by washing with 10×Ssarc and dH$_2$O at 42° C.

Fluorescent signals from each hybridised oligonucleotide were detected using genepix scanner and software. Ratios for the two signals (from the CG oligonucleotide and the TG oligonucleotide used to analyse each CpG position) were calculated based on comparison of intensity of the fluorescent signals.

Figure 16:
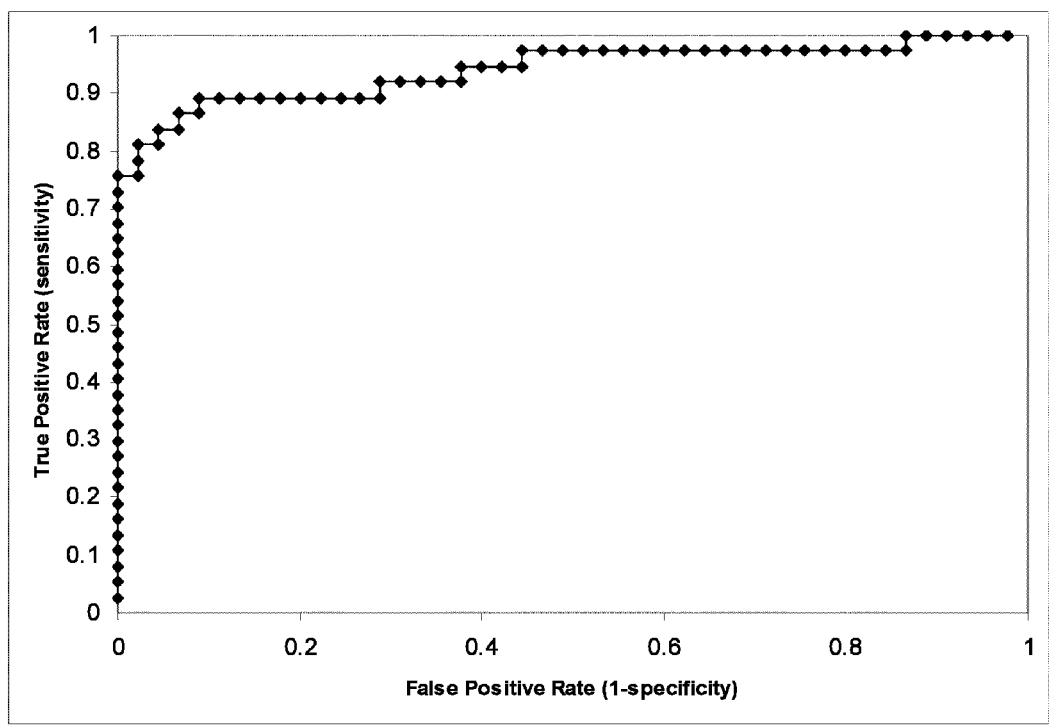
FIG. 16 shows the differentiation of healthy tissue from non healthy tissue wherein the non healthy specimens are obtained from either colon adenoma or colon carcinoma tissue (Example 13). The evaluation is carried out using informative CpG positions from 27 genes. Informative CpG positions from the genes Versican, TPEF, EYA4 and H-Cadherin are further described in Table 3.
Figure 17:
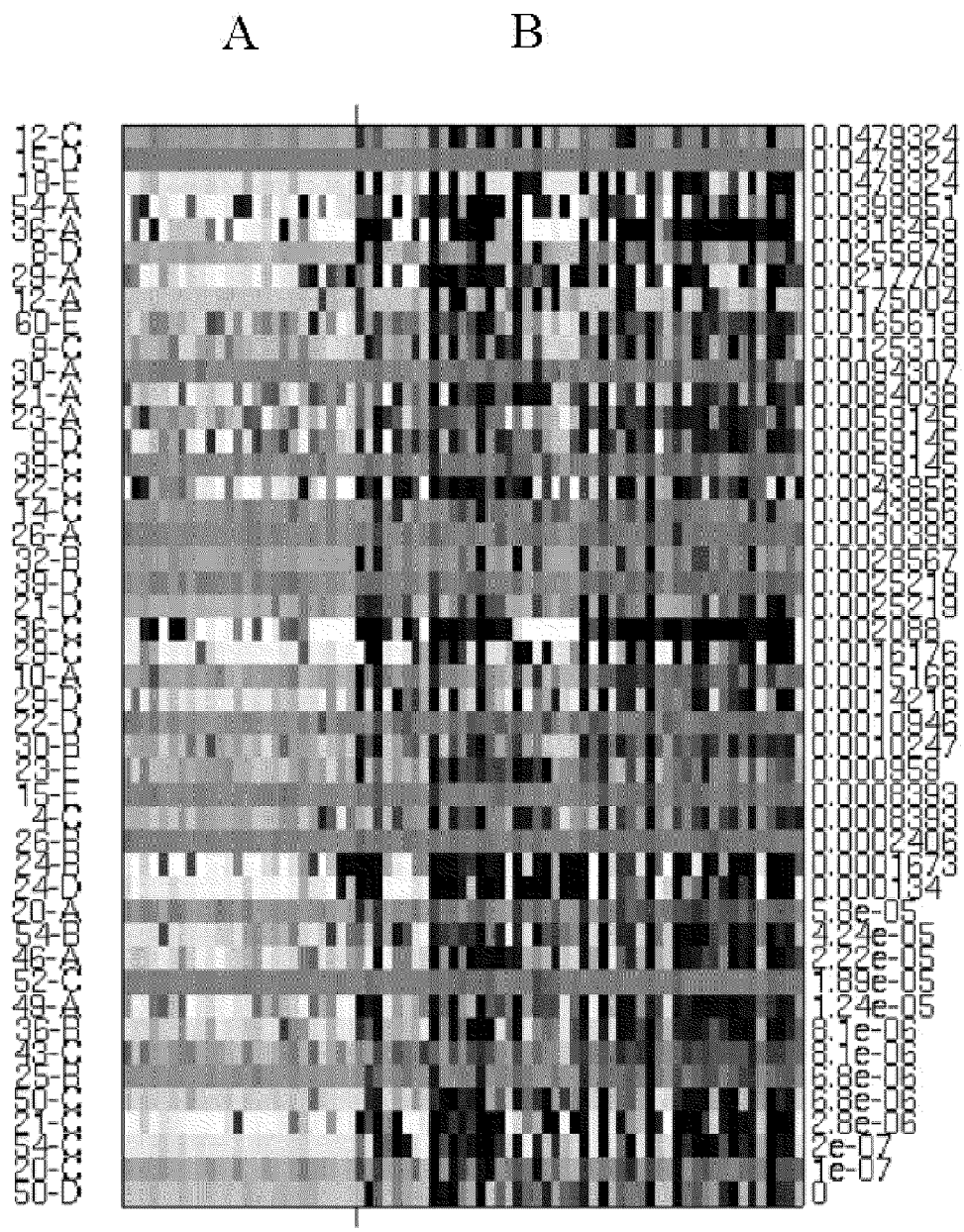
FIG. 17 shows the differentiation of healthy tissue from carcinoma tissue using informative CpG positions from 15 genes (Example 13). Informative CpG positions from the genes Versican, TPEF, EYA4 and H-Cadherin are further described in Table 4.
Figure 18:
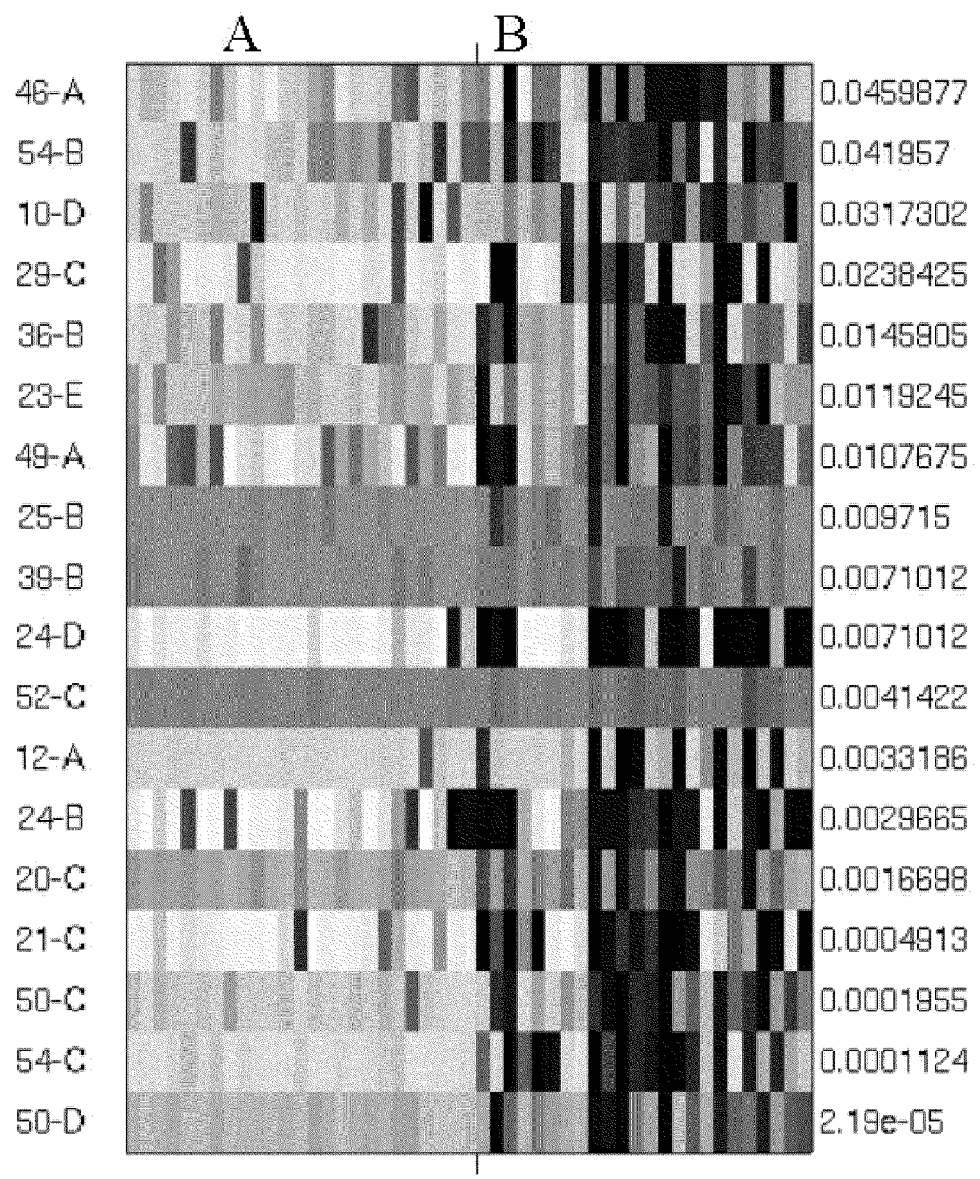
FIG. 18 shows the differentiation of healthy tissue from adenoma tissue using informative CpG positions from 40 genes (Example 13). Informative CpG positions from the genes Versican, TPEF, EYA4 and H-Cadherin are further described in Table 5.

The data was then sorted into a ranked matrix (as shown in FIGS. 16 to 18) according to CpG methylation differences between the two classes of tissues, using an algorithm. The most significant CpG positions are at the bottom of the matrix with significance decreasing towards the top. Black indicates total methylation at a given CpG position, white represents no methylation at the particular position, with degrees of methylation represented in gray, from light (low proportion of methylation) to dark (high proportion of methylation). Each row represents one specific CpG position within a gene and each column shows the methylation profile for the different CpGs for one sample. On the left side a CpG and gene identifier is shown this may be cross referenced with the accompanying tables (Table 1 to 6) in order to ascertain the gene in question and the detection oligomer used. On the right side p values for the individual CpG positions are shown. The p values are the probabilities that the observed distribution occurred by chance in the data set.

For selected distinctions, we trained a learning algorithm (support vector machine, SVM). The SVM (as discussed by F. Model, P. Adorjan, A. Olek, C. Piepenbrock, Feature selection for DNA methylation based cancer classification. Bioinformatics. 2001 June; 17 Suppl 1:S157-64) constructs an optimal discriminant between two classes of given training samples. In this case each sample is described by the methylation patterns (CG/TG ratios) at the investigated CpG sites. The SVM was trained on a subset of samples of each class, which were presented with the diagnosis attached. Independent test samples, which were not shown to the SVM before were then presented to evaluate, if the diagnosis can be predicted correctly based on the predictor created in the training round. This procedure was repeated several times using different partitions of the samples, a method called crossvalidation. Note that all rounds are performed without using any knowledge obtained in the previous runs. The number of correct classifications was averaged over all runs, which gives a good estimate of our test accuracy (percent of correct classified samples over all rounds).

Tables

TABLE 1

PCR primers and products

| Gene | Primers | Amplificate length |
|---|---|---|
| Versican (SEQ ID NO: 2) | GGATAGGAGTTGGGATTA AGAT AAATCTTTTTCAACACCA AAAT | 414 |
| EYA4 (SEQ ID NO: 3) | GGAAGAGGTGATTAAATG GAT CCCAAAAATCAAACAACAA | 226 |
| H-Cadherin (SEQ ID NO: 4) | TTTGTATTAGGTTGGAAGT GGT CCCAAATAAATCAACAAC AACA | 286 |
| TPEF (SEQ ID NO: 5) | TTGTTTGGGTTAATAAATG GA CTTCTCTCTTCTCCCCTCTC | 295 |

TABLE 2

Hybridisation oligonucleotides

| Gene | Oligomer sequence |
|---|---|
| Versican (SEQ ID NO: 2) | AAGATTTTCGGTTAGTTT (SEQ ID NO: 88) |
| Versican (SEQ ID NO: 2) | AAGATTTTTGGTTAGTTT (SEQ ID NO: 89) |

TABLE 2-continued

Hybridisation oligonucleotides

| Gene | Oligomer sequence |
|---|---|
| Versican (SEQ ID NO: 2) | ATGTGATTCGTTTGGGTA (SEQ ID NO: 50) |
| Versican (SEQ ID NO: 2) | ATGTGATTTGTTTGGGTA (SEQ ID NO: 51) |
| Versican (SEQ ID NO: 2) | GGGTAACGTCGAATTTAG (SEQ ID NO: 52) |
| Versican (SEQ ID NO: 2) | GGGTAATGTTGAATTTAG (SEQ ID NO: 53) |
| Versican (SEQ ID NO: 2) | AAAAATTCGCGAGTTTAG (SEQ ID NO: 54) |
| Versican (SEQ ID NO: 2) | AAAAATTTGTGAGTTTAG (SEQ ID NO: 55) |
| EYA4 (SEQ ID NO: 3) | TATATATACGTGTGGGTA (SEQ ID NO: 56) |
| EYA4 (SEQ ID NO: 3) | TATATATATGTGTGGGTA (SEQ ID NO: 57) |
| EYA4 (SEQ ID NO: 3) | AGTGTATGCGTAGAAGGT (SEQ ID NO: 58) |
| EYA4 (SEQ ID NO: 3) | AGTGTATGTGTAGAAGGT (SEQ ID NO: 59) |
| EYA4 (SEQ ID NO: 3) | TTTAGATACGAAATGTTA (SEQ ID NO: 60) |
| EYA4 (SEQ ID NO: 3) | TTTAGATATGAAATGTTA (SEQ ID NO: 61) |
| EYA4 (SEQ ID NO: 3) | AAGTAAGTCGTTGTTGTT (SEQ ID NO: 62) |
| EYA4 (SEQ ID NO: 3) | AAGTAAGTTGTTGTTGTT (SEQ ID NO: 63) |
| H-Cadherin (SEQ ID NO: 4) | GAAGTGGTCGTTAGTTTT (SEQ ID NO: 64) |
| H-Cadherin (SEQ ID NO: 4) | GAAGTGGTTGTTAGTTTTT (SEQ ID NO: 65) |
| H-Cadherin (SEQ ID NO: 4) | TTGTTTAGCGTGATTTGT (SEQ ID NO: 66) |
| H-Cadherin (SEQ ID NO: 4) | TTGTTTAGTGTGATTTGT (SEQ ID NO: 67) |
| H-Cadherin (SEQ ID NO: 4) | AAGGAATTCGTTTTGTAA (SEQ ID NO: 68) |
| H-Cadherin (SEQ ID NO: 4) | AAGGAATTTGTTTTGTAA (SEQ ID NO: 69) |
| H-Cadherin (SEQ ID NO: 4) | AATGTTTTCGTGATGTTG (SEQ ID NO: 70) |
| H-Cadherin (SEQ ID NO: 4) | AATGTTTTTGTGATGTTG (SEQ ID NO: 71) |
| TPEF (SEQ ID NO: 5) | ATTTGTTTCGATTAATTT (SEQ ID NO: 72) |
| TPEF (SEQ ID NO: 5) | ATTTGTTTTGATTAATTT (SEQ ID NO: 73) |
| TPEF (SEQ ID NO: 5) | ATAGGTTACGGGTTGGAG (SEQ ID NO: 74) |

TABLE 2-continued

Hybridisation oligonucleotides

| Gene | Oligomer sequence |
|---|---|
| TPEF (SEQ ID NO: 5) | ATAGGTTATGGGTTGGAG (SEQ ID NO: 75) |
| TPEF (SEQ ID NO 5) | AATTTGCGAACGTTTGGG |
| TPEF (SEQ ID NO: 5) | AATTTGTGAATGTTTGGG |

TABLE 3

Oligonucleotides used in differentiation between colon adenomas or carcinoma tissue and healthy colon tissue.

| Gene | Oligo: |
|---|---|
| H-Cadherin (SEQ ID NO: 4) | AATGTTTTCGTGATGTTG (SEQ ID NO: 70) |
| H-Cadherin (SEQ ID NO: 4) | AATGTTTTTGTGATGTTG (SEQ ID NO: 71) |
| TPEF (SEQ ID NO: 5) | AATTTGCGAACGTTTGGG (SEQ ID NO: 76) |
| TPEF (SEQ ID NO: 5) | AATTTGTGAATGTTTGGG (SEQ ID NO: 77) |
| Versican (SEQ ID NO: 2) | GGGTAACGTCGAATTTAG (SEQ ID NO: 52) |
| Versican (SEQ ID NO: 2) | GGGTAATGTTGAATTTAG (SEQ ID NO: 53) |
| H-Cadherin (SEQ ID NO: 4) | AAGGAATTCGTTTTGTAA (SEQ ID NO: 68) |
| H-Cadherin (SEQ ID NO: 4) | AAGGAATTTGTTTTGTAA (SEQ ID NO: 69) |
| TPEF (SEQ ID NO: 5) | ATAGGTTACGGGTTGGAG (SEQ ID NO: 74) |
| TPEF (SEQ ID NO: 5) | ATAGGTTATGGGTTGGAG (SEQ ID NO: 75) |
| EYA4 (SEQ ID NO: 3) | AAGTAAGTCGTTGTTGTT (SEQ ID NO: 62) |
| EYA4 (SEQ ID NO: 3) | AAGTAAGTTGTTGTTGTT (SEQ ID NO: 63) |
| EYA4 (SEQ ID NO: 3) | AGTGTATGCGTAGAAGGT (SEQ ID NO: 58) |
| EYA4 (SEQ ID NO: 3) | AGTGTATGTGTAGAAGGT (SEQ ID NO: 59) |
| Versican (SEQ ID NO: 2) | AAAAATTCGCGAGTTTAG (SEQ ID NO: 54) |
| Versican (SEQ ID NO: 2) | AAAAATTTGTGAGTTTAG (SEQ ID NO: 55) |
| Versican (SEQ ID NO: 2) | AAGATTTTCGGTTAGTTT (SEQ ID NO: 88) |
| Versican (SEQ ID NO: 2) | AAGATTTTTGGTTAGTTT (SEQ ID NO: 89) |
| TPEF (SEQ ID NO: 5) | ATTTGTTTCGATTAATTT (SEQ ID NO: 72) |

TABLE 3-continued

Oligonucleotides used in differentiation between colon adenomas or carcinoma tissue and healthy colon tissue.

| Gene | Oligo: |
|---|---|
| TPEF (SEQ ID NO: 5) | ATTTGTTTTGATTAATTT (SEQ ID NO: 73) |

TABLE 4

OLIGONUCLEOTIDES USED IN DIFFERENTIATION BETWEEN COLON CARCINOMA TISSUE AND HEALTHY COLON TISSUE.

| Gene | Oligo: |
|---|---|
| H-Cadherin (SEQ ID NO: 4) | AATGTTTTCGTGATGTTG (SEQ ID NO: 70) |
| H-Cadherin (SEQ ID NO: 4) | AATGTTTTTGTGATGTTG (SEQ ID NO: 71) |
| TPEF (SEQ ID NO: 5) | AATTTGCGAACGTTTGGG (SEQ ID NO: 76) |
| TPEF (SEQ ID NO: 5) | AATTTGTGAATGTTTGGG (SEQ ID NO: 77) |
| H-Cadherin (SEQ ID NO: 4) | AAGGAATTCGTTTTGTAA (SEQ ID NO: 68) |
| H-Cadherin (SEQ ID NO: 4) | AAGGAATTTGTTTTGTAA (SEQ ID NO: 69) |
| Versican (SEQ ID NO: 2) | GGGTAACGTCGAATTTAG (SEQ ID NO: 52) |
| Versican (SEQ ID NO: 2) | GGGTAATGTTGAATTTAG (SEQ ID NO: 53) |
| EYA4 (SEQ ID NO: 3) | AGTGTATGCGTAGAAGGT (SEQ ID NO: 58) |
| EYA4 (SEQ ID NO: 3) | AGTGTATGTGTAGAAGGT (SEQ ID NO: 59) |
| EYA4 (SEQ ID NO: 3) | AAGTAAGTCGTTGTTGTT (SEQ ID NO: 62) |
| EYA4 (SEQ ID NO: 3) | AAGTAAGTTGTTGTTGTT (SEQ ID NO: 63) |
| TPEF (SEQ ID NO: 5) | ATAGGTTACGGGTTGGAG (SEQ ID NO: 74) |
| TPEF (SEQ ID NO: 5) | ATAGGTTATGGGTTGGAG (SEQ ID NO: 75) |

TABLE 5

Oligonucleotides used in differentiation between colon adenoma tissue and healthy colon tissue.

| H-Cadherin (SEQ ID NO: 4) | AATGTTTTCGTGATGTTG (SEQ ID NO: 70) |
|---|---|
| H-Cadherin (SEQ ID NO: 4) | AATGTTTTTGTGATGTTG (SEQ ID NO: 71) |
| TPEF (SEQ ID NO: 5) | AATTTGCGAACGTTTGGG (SEQ ID NO: 76) |
| TPEF (SEQ ID NO: 5) | AATTTGTGAATGTTTGGG (SEQ ID NO: 77) |

TABLE 5-continued

Oligonucleotides used in differentiation between colon adenoma tissue and healthy colon tissue.

| TPEF (SEQ ID NO: 5) | ATAGGTTACGGGTTGGAG (SEQ ID NO: 74) |
|---|---|
| TPEF (SEQ ID NO: 5) | ATAGGTTATGGGTTGGAG (SEQ ID NO: 75) |
| Versican (SEQ ID NO: 2) | GGGTAACGTCGAATTTAG (SEQ ID NO: 52) |
| Versican (SEQ ID NO: 2) | GGGTAATGTTGAATTTAG (SEQ ID NO: 53) |
| H-Cadherin (SEQ ID NO: 4) | AAGGAATTCGTTTTGTAA (SEQ ID NO: 68) |
| H-Cadherin (SEQ ID NO: 4) | AAGGAATTTGTTTTGTAA (SEQ ID NO: 69) |
| EYA4 (SEQ ID NO: 3) | AAGTAAGTCGTTGTTGTT (SEQ ID NO: 62) |
| EYA4 (SEQ ID NO: 3) | AAGTAAGTTGTTGTTGTT (SEQ ID NO: 63) |
| EYA4 (SEQ ID NO: 3) | AGTGTATGCGTAGAAGGT (SEQ ID NO: 58) |
| EYA4 (SEQ ID NO: 3) | AGTGTATGTGTAGAAGGT (SEQ ID NO: 59) |
| Versican (SEQ ID NO: 2) | AAAAATTCGCGAGTTTAG (SEQ ID NO: 54) |
| Versican (SEQ ID NO: 2) | AAAAATTTGTGAGTTTAG (SEQ ID NO: 55) |

TABLE 6

Genes analysed according to FIGS. 16 to 18

| Number in Figures | Gene name |
|---|---|
| Healthy vs Non-Healthy | |
| 50-D | H-CADHERIN |
| 20-C | CD44 |
| 54-C | TPEF (=TMEFF2; =HPP1) |
| 21-C | VERSICAN |
| 50-C | H-CADHERIN |
| 25-B | GSTP1 |
| 43-C | TGFBR2 |
| 36-B | N33 |
| 49-A | CAV1 |
| 52-C | PTGS2 |
| 46-A | TP73 |
| 54-B | TPEF (=TMEFF2; =HPP1) |
| 20-A | CD44 |
| 24-D | EYA4 |
| 24-B | EYA4 |
| 26-B | GTBP/MSH6 |
| 4-C | EGR4 |
| 15-E | CDH1 |
| 23-E | EGFR |
| 30-B | LKB1 |
| 22-D | DAPK1 |
| 29-D | IGF2 |
| 10-A | HLA-F |
| 29-C | IGF2 |
| 36-C | N33 |
| 21-D | VERSICAN |
| 39-D | PTEN |
| 32-B | MLH1 |
| 26-A | GTBP/MSH6 |

TABLE 6-continued

Genes analysed according to FIGS. 16 to 18

| Number in Figures | Gene name |
|---|---|
| 14-C | CALCA |
| 22-C | DAPK1 |
| 39-C | PTEN |
| 9-D | WT1 |
| 23-A | EGFR |
| 21-A | VERSICAN |
| 30-A | LKB1 |
| 9-C | WT1 |
| 60-E | ESR1 |
| 12-A | APC |
| 29-A | IGF2 |
| 8-D | MYOD1 |
| 36-A | N33 |
| 54-A | TPEF (=TMEFF2; =HPP1) |
| 18-E | CDKN2a |
| 15-D | CDH1 |
| 12-C | APC |
| Healthy vs Carcinoma | |
| 50-D | H-CADHERIN |
| 54-C | TPEF (=TMEFF2; =HPP1) |
| 50-C | H-CADHERIN |
| 21-C | VERSICAN |
| 20-C | CD44 |
| 24-B | EYA4 |
| 12-A | APC |
| 52-C | PTGS2 |
| 24-D | EYA4 |
| 39-B | PGR |
| 25-B | GSTP1 |
| 49-A | CAV1 |
| 23-E | EGFR |
| 36-B | N33 |
| 29-C | IGF2 |
| 10-D | HLA-F |
| 54-B | TPEF (=TMEFF2; =HPP1) |
| 46-A | TP73 |
| Healthy vs Adenoma | |
| 20-C | CD44 |
| 10-A | HLA-F |
| 43-C | TGFBR2 |
| 26-A | GTBP/MSH6 |
| 26-B | GTBP/MSH6 |
| 30-B | LKB1 |
| 20-A | CD44 |
| 36-C | N33 |
| 50-D | H-CADHERIN |
| 46-A | TP73 |
| 39-D | PTEN |
| 36-B | N33 |
| 54-C | TPEF (=TMEFF2; =HPP1) |
| 25-B | GSTP1 |
| 23-A | EGFR |
| 40-A | RARB |
| 36-D | N33 |
| 49-A | CAV1 |
| 54-B | TPEF (=TMEFF2; =HPP1) |
| 18-E | CDKN2a |
| 36-A | N33 |
| 32-B | MLH1 |
| 12-C | APC |
| 21-C | VERSICAN |
| 15-E | CDH1 |
| 52-C | PTGS2 |
| 62-D | RASSF1 |
| 9-C | WT1 |
| 18-D | CDKN2a |
| 60-E | ESR1 |
| 29-D | IGF2 |
| 8-D | MYOD1 |
| 50-C | H-CADHERIN |
| 4-C | EGR4 |
| 42-C | S100A2 |
| 22-D | DAPK1 |
| 31-E | MGMT |
| 24-D | EYA4 |
| 56-A | CEA |
| 9-D | WT1 |
| 7-E | GPIb beta |
| 14-C | CALCA |
| 52-D | PTGS2 |
| 8-B | MYOD1 |
| 24-B | EYA4 |
| 21-D | VERSICAN |
| 38-C | PGR |
| 58-A | PCNA |
| 34-D | MSH3 |
| 9-B | WT1 |
| 35-B | MYC |
| 27-C | HIC-1 |
| 52-B | PTGS2 |
| 23-E | EGFR |
| 30-A | LKB1 |
| 29-C | IGF2 |
| 39-C | PTEN |
| 13-D | BCL2 |
| 5-B | AR |
| 15-D | CDH1 |
| Carcinoma vs Adenoma | |
| 18-B | CDKN2a |
| 7-E | GPIb beta |

The invention claimed is:

1. A method for detecting cytosine methylation of one or more CpG dinucleotides in an EYA4 gene, or a fragment thereof, in genomic DNA in a sample from a human subject, the method comprising:
   a) isolating genomic DNA comprising an EYA4 gene from the biological sample from the human subject;
   b) chemically modifying the genomic DNA comprising the EYA4 gene, or a fragment thereof, to convert non-methylated cytosine bases to uracil by treating the genomic DNA with bisulfite, thereby producing modified genomic DNA comprising a modified EYA4 gene, or a fragment thereof;
   c) amplifying the modified genomic DNA comprising the modified EYA4 gene, or the fragment thereof, with an amplification enzyme and at least a forward primer and a reverse primer, each primer comprising a contiguous sequence at least 16 nucleotides in length that is complementary to a contiguous sequence of at least 16 nucleotides of a sequence selected from the group consisting of SEQ ID NOs: 10, 11, 20 and 21, or complements thereof, to produce one or more amplificates, wherein the one or more amplificates comprise the one or more CpG dinucleotides; and
   d) detecting the cytosine methylation of the one or more CpG dinucleotides in the EYA4 gene or the fragment thereof by determining the presence of the one or more amplificates.

2. The method of claim 1, wherein in step a) the biological sample is selected from the group consisting of histological slides, biopsies, paraffin-embedded tissue, bodily fluid, stool, blood, serum, plasma, urine, sputum, and combinations thereof.

3. The method of claim 1, wherein treating in step b) is subsequent to embedding the genomic DNA comprising the EYA4 gene, or the fragment thereof, in agarose.

4. The method of claim 1, wherein step b) comprises treating the genomic DNA comprising the EYA4 gene, or the fragment thereof, with bisulfite in the presence of at least one of a DNA denaturing agent or a radical scavenger.

5. The method of claim 1, wherein amplifying in step c) comprises use of at least one method selected from the group consisting of: use of a heat-resistant DNA polymerase as the amplification enzyme; use of a polymerase lacking 5'-3' exonuclease activity; use of a polymerase chain reaction (PCR); generation of an amplificate nucleic acid molecule carrying a detectable label; and combinations thereof.

6. The method of claim 5, wherein the detectable label is selected from the group consisting of: fluorescent labels; radionuclides or radiolabels; amplificate mass labels detectable in a mass spectrometer; detachable amplificate fragment mass labels detectable in a mass spectrometer; amplificate, and detachable amplificate fragment mass labels having a single-positive or single-negative net charge detectable in a mass spectrometer; and combinations thereof.

7. The method of claim 6, wherein detecting in step d) comprises use of mass spectrometry for detecting the one or more amplificates or detecting detachable amplificate fragment mass labels carried by the one or more amplificates.

8. The method of claim 1, wherein amplifying in step c) comprises amplifying two or more different portions of the modified EYA4 gene or the fragment thereof.

9. The method of claim 1, wherein one or more of the at least two primers comprise sequences selected from the group consisting of SEQ ID NOs: 40, 41, 44, and 45.

10. The method of claim 1, wherein one or more of the at least two primers comprise one or more CpG, TpG or CpA dinucleotides.

11. The method of claim 10, wherein one or more of the at least two primers comprise between 2 to 5 CpG, TpG or CpA dinucleotides.

12. The method of claim 10, wherein the one or more CpG, TpG or CpA dinucleotides are located within the half of the primer that terminates at the 3' end of the primer.

13. The method of claim 1, wherein the one or more amplificates obtained in step c) comprise at least one 20 base pair sequence that comprises 3 or more CpG, TpG or CpA dinucleotides.

14. The method of claim 1, further comprising in step c) hybridizing at least one nucleic acid molecule or peptide nucleic acid molecule at least 18 base pairs in length to the one or more amplificates, the at least one nucleic acid molecule or peptide nucleic acid molecule comprising one or more CpG, TpG or CpA dinucleotides, and wherein the sequence of the at least one nucleic acid molecule or peptide nucleic acid molecule is complementary or identical to at least 18 base pairs of a sequence selected from the group consisting of SEQ ID NOs: 10, 11, 20 and 21, and complements thereof, and wherein said nucleic acid molecule or peptide nucleic acid molecule suppresses amplification of the one or more amplificates to which it is hybridized.

15. The method according to claim 14, wherein the sequence of the at least one nucleic acid molecule or peptide nucleic acid molecule is selected from the group consisting of SEQ ID NOs: 85, 86, 87, 98, 103, and 108, and complements thereof.

16. The method of claim 14, wherein amplification of DNA that was unmethylated prior to treatment of step b) is suppressed.

17. The method of claim 14, wherein the at least one nucleic acid molecule or peptide nucleic acid molecule is in each case modified at the 5'-end thereof to preclude degradation by an enzyme having a 5'-3' exonuclease activity.

18. The method of claim 14, wherein the at least one nucleic acid molecule or peptide nucleic acid molecule in each case lacks a 3' hydroxyl group.

19. The method of claim 14, wherein the amplification enzyme is a polymerase lacking 5'-3' exonuclease activity.

20. The method of claim 14, wherein the binding site of the at least one nucleic acid molecule or peptide nucleic acid molecule is identical to, or overlaps with, one of the at least two primers and thereby hinders hybridization of the primer to its binding site.

21. The method of claim 14, wherein the at least one nucleic acid molecule or peptide nucleic acid molecule is at least two nucleic acid molecules or peptide nucleic acid molecules, and wherein the binding sites of the at least two nucleic acid molecules or peptide nucleic acid molecules are identical to, or overlap with those of the at least two primers, and thereby hinder hybridization of the at least two primers to their binding site.

22. The method of claim 21, wherein hybridization of at least one of the nucleic acid molecules or peptide nucleic acid molecules hinders hybridization of a forward primer, and the hybridization of at least one of the nucleic acid molecules or peptide nucleic acid molecules hinders the hybridization of a reverse primer that binds to the elongation product of said forward primer.

23. The method of claim 14, wherein the at least one nucleic acid molecule or peptide nucleic acid molecule hybridizes between the binding sites of the forward and reverse primers.

24. The method of claim 1, wherein step c) comprises hybridization of at least one nucleic acid molecule or peptide nucleic acid molecule in each case comprising a contiguous sequence at least 9 nucleotides in length comprising one or more CpG, TpG or CpA dinucleotides and wherein the sequence of the molecule is complementary or identical to at least 9 nucleotides of a sequence selected from the group consisting of SEQ ID NOs:10, 11, 20 and 21.

25. The method of claim 24, wherein the at least one nucleic acid molecule or peptide nucleic acid molecule is bound to a solid phase.

26. The method of claim 25, wherein a plurality of the nucleic acid molecules or peptide nucleic acid molecules are bound to a solid phase in the form of a nucleic acid or peptide nucleic acid array selected from the group consisting of linear arrays, hexagonal arrays, rectangular arrays, and combinations thereof.

27. The method of claim 24, wherein the sequence of the at least one nucleic acid molecule or peptide nucleic acid molecule is selected from the group consisting SEQ ID NOs: 84, 86, 87, and complements thereof.

28. The method according to claim 24, wherein the at least one nucleic acid molecule or peptide nucleic acid molecule is fluorescently labelled, and wherein detection thereof is by either an increase or a decrease in fluorescence or fluorescence polarization.

29. The method according to claim 24, wherein the hybridization of the at least one nucleic acid molecule or peptide nucleic acid molecule is detectable by fluorescence resonance energy transfer, and wherein the detection is by either an increase or a decrease in fluorescence.

30. The method of claim 1, wherein determining the presence of the one or more amplificates comprises sequencing the one or more amplificates.

31. The method of claim 1, wherein step c) further comprises: hybridizing at least one nucleic acid molecule comprising a contiguous sequence at least 9 nucleotides in length that is complementary to a sequence selected from the group consisting of SEQ ID NOs: 10, 11, 20 and 21, and complements thereof; and extending the at least one hybridized nucleic acid molecule by at least one nucleotide.

32. The method of claim 1, wherein the biological sample has a background DNA concentration between 100 to 1000 fold excess of the concentration of the genomic DNA comprising the EYA4 gene or the fragment thereof.

33. The method of claim 1, wherein the at least two primers used in step c) are methylation-specific primers and the methylation status of the EYA4 gene or portion thereof is determined based on detecting the presence or absence of the one or more amplificates generated by the methylation-specific primers.

34. The method of claim 1, wherein the subject has colorectal cancer.

35. The method of claim 1, wherein the biological sample is blood, plasma or serum.

* * * * *